US012691100B2

(12) United States Patent
Tate et al.

(10) Patent No.: US 12,691,100 B2
(45) Date of Patent: Jul. 28, 2026

(54) NMT INHIBITOR TREATMENT OF A SENESCENCE-ASSOCIATED DISEASE OR DISORDER OF THE LIVER

(71) Applicants: Imperial College Innovations Limited, London (GB); United Kingdom Research and Innovation, Swindon (GB)

(72) Inventors: Edward Tate, London (GB); Wouter Kallemeijn, London (GB); Jesus Gil, London (GB); Domhnall McHugh, London (GB)

(73) Assignees: IMPERIAL COLLEGE INNOVATIONS LIMITED, London (GB); UNITED KINGDOM RESEARCH AND INNOVATION, Swindon (GB)

( * ) Notice: Subject to any disclaimer, the term of this patent is extended or adjusted under 35 U.S.C. 154(b) by 1057 days.

(21) Appl. No.: 17/736,576

(22) Filed: May 4, 2022

(65) Prior Publication Data

US 2022/0280484 A1 Sep. 8, 2022

Related U.S. Application Data

(63) Continuation-in-part of application No. PCT/GB2021/052833, filed on Nov. 2, 2021.

(30) Foreign Application Priority Data

Nov. 2, 2020 (GB) ..................................... 2017367

(51) Int. Cl.

| | |
|---|---|
| ***A61K 31/416*** | (2006.01) |
| ***A61K 31/4353*** | (2006.01) |
| ***A61K 31/496*** | (2006.01) |
| ***A61P 1/16*** | (2006.01) |
| ***A61P 11/00*** | (2006.01) |
| ***A61P 35/00*** | (2006.01) |

(52) U.S. Cl.

CPC ........ *A61K 31/416* (2013.01); *A61K 31/4353* (2013.01); *A61K 31/496* (2013.01); *A61P 1/16* (2018.01); *A61P 11/00* (2018.01); *A61P 35/00* (2018.01)

(58) Field of Classification Search

None

See application file for complete search history.

(56) References Cited

U.S. PATENT DOCUMENTS

| | | | |
|---|---|---|---|
| 10,759,804 | B2 | 9/2020 | Bell et al. |
| 11,135,218 | B2 | 10/2021 | Berthiaume et al. |
| 2018/0208990 | A1 | 7/2018 | Berthiaume et al. |
| 2019/0010555 | A1 | 1/2019 | Berthiaume et al. |
| 2020/0339586 | A1 | 10/2020 | Bell et al. |
| 2022/0023294 | A1 | 1/2022 | Berthiaume et al. |
| 2022/0064158 | A1 | 3/2022 | Tate et al. |
| 2022/0071960 | A1 | 3/2022 | Tate et al. |
| 2024/0350481 | A1 * | 10/2024 | Berthiaume ............ A61P 37/00 |

FOREIGN PATENT DOCUMENTS

| | | | | |
|---|---|---|---|---|
| WO | WO 00/37464 | A1 | 6/2000 | |
| WO | WO 2008/076965 | A1 | 6/2008 | |
| WO | WO 2010/026365 | A1 | 3/2010 | |
| WO | WO 2013/083991 | A1 | 6/2013 | |
| WO | WO 2017/001812 | A1 | 1/2017 | |
| WO | WO 2017/011907 | A1 * | 1/2017 | ............... C12Q 1/68 |
| WO | WO 2020/128473 | A1 | 6/2020 | |
| WO | WO 2020/128475 | A1 | 6/2020 | |
| WO | WO2021/008512 | A1 * | 1/2021 | ........... C07D 403/12 |
| WO | WO 2022/058745 | A1 | 3/2022 | |
| WO | WO 2022/082306 | A1 | 4/2022 | |
| WO | WO 2022/090746 | A1 | 5/2022 | |

OTHER PUBLICATIONS

Anonymous, CAS SciFinder entry for substance RN: 1215010-55-1 (also known as compound DDD 85646) accessed on Aug. 13, 2025.*

Beauchamp et al., "Targeting N-myristoylation for therapy of B-cell lymphomas," Nature Communications (2020), 11, 5348, pp. 1-16. https://doi.org/10.1038/s41467-020-18998-1.

Gorgoulis et al., "Cellular Senescence: Defining a path forward," Cell (2019), vol. 179, pp. 813-827.

Herranz, N. and Gill, J., "Mechanisms and functions of cellular senescense," The Journal of Clinical Investigation (Apr. 2018), vol. 128, No. 4, pp. 1238-1246.

International Search Report dated Apr. 14, 2022, in PCT/GB2021/052833.

Lueg et al., "N-myristoyltransferase inhibition is syntheic lethal in MYC-deregulated cancers," bioRxiv (2021), pp. 1-2511.

Sieben et al., "Two-step senescence-focused cancer therapies," Trends Cell Bio. (Sep. 2018), vol. 28, No. 9, pp. 723-737.

Wang et al., "Inducing and exploiting vulnerabilities for the treatment of liver cancer," Nature (Oct. 2019), vol. 574, No. 7777, pp. 268-272.

Written Opinion of the International Searching Authority issued Apr. 14, 2022, PCT/GB2021/052833.

* cited by examiner

*Primary Examiner* — Brian J Davis

(74) *Attorney, Agent, or Firm* — Birch, Stewart, Kolasch & Birch, LLP

(57) ABSTRACT

The present invention provides a method of prophylaxis or treatment of a senescence-associated disease or disorder by administering to a subject in need thereof, a therapeutically effective amount of a NMT inhibitor.

13 Claims, 50 Drawing Sheets

Specification includes a Sequence Listing.

HFD+NMTi HFD+vehicle

HFD+NMTi HFD+vehicle

NMT INHIBITOR TREATMENT OF A SENESCENCE-ASSOCIATED DISEASE OR DISORDER OF THE LIVER

CROSS REFERENCE TO RELATED APPLICATIONS

This application is a Continuation-in-Part of PCT International Application No. PCT/GB2021/052833, filed on Nov. 2, 2021, which claims priority under 35 U.S.C. 119 (a) to Patent Application No. 2017367.0, filed in the United Kingdom on Nov. 2, 2020, all of which are hereby expressly incorporated by reference into the present application.

TECHNICAL FIELD

The invention relates to compounds and pharmaceutical compositions containing such compounds for use in the prophylaxis or treatment of a senescence-associated disease or disorder, and to related methods and uses.

STATEMENT OF FUNDING

The project leading to this application has received funding from the European Union's Horizon 2020 research and innovation programme under the Marie Sklodowska-Curie grant agreement No. 752165.

BACKGROUND TO THE INVENTION

Senescence

Senescence is a cellular programme that can be induced by multiple stresses such as replicative exhaustion, oncogenes, irradiation or chemotherapeutic drugs (Gorgoulis, Adams et al. 2019). In addition, some targeted anti-cancer drugs such as CDK4/6 inhibitors (e.g. palbociclib) or Aurora kinase inhibitors (e.g. alisertib) also trigger senescence (Wang, Leite de Oliveira et al. 2017, Wagner and Gil 2020). Senescent cells enter into a stable cell cycle arrest that avoids the replication of preneoplastic, damaged and old cells. In addition, senescent cells undergo a number of phenotypic changes, including chromatin reorganization, metabolic reprogramming, induction of lysosomal b-galactosidase activity (referred as senescence-associated β-galactosidase or SA-β-Gal) and secretion of a plethora of factors, mainly pro-inflammatory that collectively are referred as the senescence-associated secretory phenotype (SASP) (Herranz and Gil 2018).

Molecular Mechanisms of Senescence

The stable growth arrest characteristic of senescence depends of the activation of the p16/Rb and p53/p21 tumour suppressor pathways. As a result, the cyclin dependent kinase inhibitors (CDKI) $p16^{INK4a}$ and $p21^{Cip1}$ are induced. This inhibits CDK activity, resulting in Rb hypophosphorylation and a G1 growth arrest. $p16^{INK4a}$ is specifically induced during senescence and it is often used as to identify senescent cells alone or in combination with other markers such as SA-β-Gal activity, formation of senescence-associated heterochromatin foci (SAHF) and others (Gorgoulis, Adams et al. 2019). The SASP is induced by independent pathways that eventually converge into epigenetic changes (such as superenhancer remodelling) and the activation of transcription factors such as NF-kB and CEBPb (Herranz and Gil 2018).

Senescence and Disease

Senescent cells are present in cancerous tissues (e.g. preneoplastic lesions, chemotherapy or irradiated tumours and in the tumour microenvironment) (Sieben, Sturmlechner et al. 2018). They are also associated with fibrotic lesions (e.g. in the liver, kidney, heart or pancreas) (Krizhanovsky, Yon et al. 2008) and accumulate in old tissues (Krishnamurthy, Torrice et al. 2004). Importantly, work in the last decade has shown that senescent cells are associated with multiple pathologies, including neurological (Brain aneurysm, Alzheimer's and Parkinson), pulmonary (IPF, COPD or cystic fibrosis), ophthalmological (e.g. cataracts, glaucoma, macular degeneration), musculoskeletal (e.g. sarcopenia, disc degeneration, osteoarthritis), cardiovascular (e.g. atherosclerosis, cardiac fibrosis, aorta aneurysm), renal (e.g. kidney disease, transplant complications) and others such as diabetes, mucositis, hypertension and OMF (Munoz-Espin and Serrano 2014). While acute induction of senescence is tumour suppressive (Collado, Gil et al. 2005) and limits fibrosis (Krizhanovsky, Yon et al. 2008), the aberrant accumulation of senescent cells during ageing and disease is detrimental. There is not a single explanation for why the build-up of senescent cells is detrimental. The prevalent hypothesis is that pro-inflammatory factors produces by senescent cells interfere with tissue homeostasis. Overall, it is thought that senescent cells are an underlying cause of ageing and disease and might be responsible of the problems associated with many age-related pathologies, including cancer.

The Benefits of Eliminating Senescent Cells

Unequivocal evidence for the negative effects associated with senescence (and conversely the benefits of selectively killing senescent cells) was produced by work from the van Deursen lab (Baker, Wijshake et al. 2011, Baker, Childs et al. 2016). They took advantage of a transgenic mouse (called INK-ATTAC) that expresses an inducible form of caspase 8 on senescent cells (using the promoter for $p16^{INK4a}$) Activation of this inducible form of caspase 8 (by treatment with a small molecule that cause its dimerization) allows for the selective killing of senescent cells. Experiments carried out with the INK-ATTAC mice has shown that the selective clearance of senescent cells increases lifespan and improves healthspan by attenuating multiple age-related pathologies (e.g. delayed tumorigenesis, attenuated atherosclerosis and age-related deterioration of kidney, fat and heart). Similar results have been in part replicated in 3MR mice, another mouse model that allows for the selective killing of senescent cells (Demaria, Ohtani et al. 2014). The elimination of senescent cells does not have important side effects besides delaying wound healing if the senescent cells are eliminated during the healing process (Baker, Wijshake et al. 2011, Demaria, Ohtani et al. 2014).

Senolytic Drugs

These genetic proof-of-concept studies established the rationale for searching for drugs that selectively eliminate senescent cells (so-called senolytics). Several senolytic compounds have been identified to date, including cardiac glycosides (Guerrero, Herranz et al. 2019), HSP90 inhibitors (Fuhrmann-Stroissnigg, Ling et al. 2017), dasatinib and quercetin (Zhu et al., 2015) and Bcl2-family inhibitors such as ABT263 and ABT737 (Ovadya and Krizhanovsky 2018). Currently BCl2 family inhibitors are the most widely used senolytics and they have been shown to be effective in killing a range of senescent cells in vivo and reproducing the effects observed upon genetic elimination of senescent cells (Ovadya and Krizhanovsky 2018). However, Bcl2 inhibitors such as ABT-263 causes significant neutropenia and thrombocytopenia (Wilson, O'Connor et al. 2010). Due to the important side-effects that the current 'gold standard' senolytic compounds present, there is a need to identify further compounds with senolytic properties that could be better suited for clinical use.

N-Myristoyl Transferase (NMT) Inhibitors

N-myristoyl transferase (NMT) is a monomeric enzyme, which is ubiquitous in eukaryotes. NMT catalyses an irreversible co-translational transfer of myristic acid (a saturated 14-carbon fatty acid) from myristoyl-Coenzyme A (myr-CoA) to a protein substrate containing an N-terminal glycine with formation of an amide bond (Farazi, T. A., G. Waksman, and J. I. Gordon, J. Biol. Chem., 2001. 276(43): p. 39501-39504).

There are two types of human NMT, human NMT1 (HsNMT1) and human NMT2 (HsNMT2). Inhibition of human NMT has been suggested as a target for treating or preventing various diseases or disorders, for example hyperproliferative disorders (cancers, e.g. human colorectal cancer, gallbladder carcinoma, brain tumours, and lymphomas such as B-cell lymphoma) (Resh M D. 1993. Biochern. Biophys. Acta 1115, 307-22; Berthiaume L G, Beuachamp E, WO2017/011907). As NMT plays a key role in protein trafficking, mediation of protein-protein interactions, stabilization of protein structures and signal transduction in living systems, inhibition of the NMT enzyme has the potential to disrupt multi-protein pathways. This is an attractive characteristic which could allow NMT inhibitors to be useful in a variety of indications, such as in the prophylaxis or treatment of senescence-associated diseases and disorders, such as the diseases and disorders described herein.

Compounds active as inhibitors of NMT have previously been disclosed, see for example WO00/37464 (Roche), WO2010/026365 (University of Dundee), WO2013/083991 (Imperial Innovations Limited), WO2017/001812 (Imperial Innovations Limited), WO2020/128473 (Imperial College Innovations Limited), and WO2020/128475 (Imperial College Innovations Limited).

SUMMARY OF THE INVENTION

The present invention relates to a NMT inhibitor for use in the prophylaxis or treatment of a senescence-associated disease or disorder.

The present invention further provides the use of a NMT inhibitor in the manufacture of a medicament for the prophylaxis or treatment of a senescence-associated disease or disorder.

The present invention also provides a method of prophylaxis or treatment of a senescence-associated disease or disorder by administering to a subject in need thereof, a therapeutically effective amount of a NMT inhibitor. A "therapeutically effective amount" in this context means an amount of the NMT inhibitor sufficient to be effective in therapy e.g. in the treatment of cancer or other senescence-associated disease or disorder.

The present invention also provides a pharmaceutical composition comprising a NMT inhibitor for use in the prophylaxis or treatment of a senescence-associated disease or disorder, optionally wherein the composition comprises one or more therapeutic agents and/or one or more pharmaceutically acceptable excipients.

Suitably the senescence-associated disease or disorder is selected from a metabolic disease, an inflammatory or autoimmune disease or disorder, a cardiovascular disease or disorder, a pulmonary disease or disorder, a neurological disease or disorder, an eye disease or disorder, and a dermatological disease or disorder.

Suitably the senescence-associated disease or disorder is cancer, wherein said cancer comprises senescent cells.

Suitably the senescence-associated disease or disorder is one or more side effects of chemotherapy or radiotherapy, wherein said chemotherapy or radiotherapy induce senescence.

Suitably the senescence-associated disease or disorder is precancerous lesions.

The present invention also provides a NMT inhibitor for use in prolonging the lifespan of a subject.

The present invention also provides a NMT inhibitor for use as a vaccine adjuvant.

The senolytic activity of the NMT inhibitors of the invention is demonstrated with reference to the accompanying examples, and is described in more detail below.

Studies by the Applicant in IMR90 E:RAS cells have demonstrated that the NMT inhibitors described herein can eliminate senescent cells. In particular, the NMT inhibitors of the invention resulted in a selective reduction of senescent (but not normal) cell numbers and are therefore candidate senolytic compounds. Further experiments indicated that the NMT inhibitors of the invention are capable of selectively killing cells which have been induced to senescence by oncogene-induced senescence (FIGS. 1A-C).

Additionally, the Applicant has demonstrated that the senolytic effect of the NMT inhibitors is also observed in cells which have been induced to senescence upon treatment with chemotherapeutic agents, such as bleomycin, doxorubicin, etoposide and cisplatin (see FIGS. 2A to 9C).

Additionally, treatment of NMT inhibitors caused Golgi dispersal in senescent cells (FIGS. 10A-B) and leads to enrichment of transcriptional signatures for Golgi transport in senescent cells (FIG. 11). Furthermore, the Applicant has found that treatment with NMT inhibitors results in intracellular accumulation of cytokines and induces the unfolded protein response in senescent cells (FIGS. 12A-C) and leads to enrichment of transcriptional signatures for UPR in senescent cells (FIG. 14). Treatment of senolytic cells with Kira6, an inhibitor of the UPR protein IRE1, eliminated the senolytic activity of the NMT inhibitors (FIGS. 15A-B).

The Applicant has also investigated whether the NMT inhibitors are capable of eliminating senescent cells in vivo. In a first experiment, treatment of mice with an NMT inhibitor resulted in reduced numbers of senescent cells when to compared to vehicle treated mice (FIGS. 16A-E). In a second experiment, mice whose liver hepatocytes had been induced to senescence by oncogene-induced-senescence were treated with an NMT inhibitor (FIGS. 17A-C). In further experiments, treatment with a NMT inhibitor resulted in reduced accumulation of lipids in the liver with mice (FIG. 18A, and also led to reduced glucose levels in the blood (FIGS. 18B-C). In further experiments, treatment of old mice with a NMT inhibitor (FIG. 19) resulted in lower levels of ALT, amylase and glucose in blood (FIGS. 20A-C), which are markers of liver or pancreatic damage. In further experiments, mice fed with a high fat diet were treated with a NMT inhibitor (FIG. 21). Mice treated with a NMT inhibitor showed lower levels of suPAR, suggesting that treatment with a NMT inhibitor reduces the levels of senescent cells. Treatment of mice with a NMT inhibitor normalized the levels of ALT, ALP and albumin in blood (FIGS. 22B-D). In further experiments, treatment with a NMT inhibitor partially normalized liver fibrosis in mice fed with a high fat diet (FIG. 23), reduced liver senescence (FIGS. 24A-C), reduced accumulation of lipids (FIG. 24D) and collagen markers of senescence (FIGS. 24E-G) in the liver. In further experiments, treatment with a NMT inhibitor and a chemotherapeutic agent reduced the tumor size in mice inoculated with HCT116 cells (FIGS. 25, 26A and 26B). In further experiments utilizing a model of pulmonary fibrosis (FIG. 27), treatment with a NMT inhibitor reduced the accumulation of hydroxyproline (FIG. 28A) and other markers of pulmonary fibrosis (collagen, pro-fibrotic factors, matrix metalloproteinases, CXCL5 and a-SMA; FIGS. 28B-I).

The results from these experiments indicate that the NMT inhibitors of the invention are capable of eliminating senescent cells in vivo and are expected to be useful in the prophylaxis or treatment of senescence-associated diseases and disorders.

SEQUENCE LISTING

SEQ ID NO: 1—Forward primer for Actin b in mice
SEQ ID NO: 2—Reverse primer for Actin b in mice
SEQ ID NO: 3—Forward primer for Col3a1 in mice
SEQ ID NO: 4—Reverse primer for Col3a1 in mice
SEQ ID NO: 5—Forward primer for Col6a3 in mice
SEQ ID NO: 6—Reverse primer for Col6a3 in mice
SEQ ID NO: 7—Forward primer for CXCL5 in mice
SEQ ID NO: 8—Reverse primer for CXCL5 in mice
SEQ ID NO: 9—Forward primer for MMP3 in mice
SEQ ID NO: 10—Reverse primer for MMP3 in mice
SEQ ID NO: 11—Forward primer for MMP12 in mice
SEQ ID NO: 12—Reverse primer for MMP12 in mice
SEQ ID NO: 13—Forward primer for Tgf-β in mice
SEQ ID NO: 14—Reverse primer for Tgf-β in mice
SEQ ID NO: 15—Forward primer for Pai-1 in mice
SEQ ID NO: 16—Reverse primer for Pai-1 in mice
SEQ ID NO: 17—Forward primer for α-SMA in mice
SEQ ID NO: 18—Reverse primer for α-SMA in mice
SEQ ID NO: 19—Forward primer for Hprt in mice
SEQ ID NO: 20—Reverse primer for Hprt in mice
SEQ ID NO: 21—Forward primer for Col1a1 in mice
SEQ ID NO: 22—Reverse primer for Col1a1 in mice
SEQ ID NO: 23—Forward primer for Col4a1 in mice
SEQ ID NO: 24—Reverse primer for Col4a1 in mice

DETAILED DESCRIPTION OF THE INVENTION

Figure 1A:
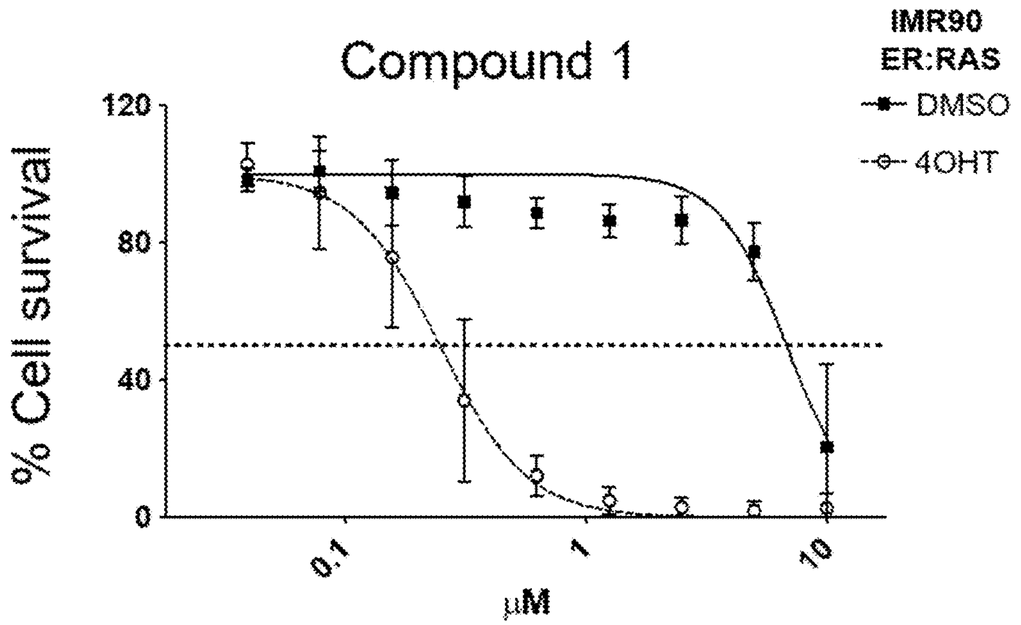
FIGS. 1A-C: Illustrate that Compounds 1 to 3 selectively eliminate IMR90 ER:RAS cells undergoing oncogene-induced senescence over non-senescent cells (DMSO control).

The term "hydrocarbyl" used herein will be understood to mean any compound straight or branched chain saturated, unsaturated or partially unsaturated hydrocarbon groups. Suitable examples of "hydrocarbyl" groups may include, for example, "alkyl", "alkenyl", "alkynyl" and/or "haloalkyl" groups, each of which are as defined hereinbelow.

The term "alkyl" used herein will be understood to mean straight and branched chain saturated hydrocarbon groups. Examples of "alkyl" groups include methyl, ethyl, n-propyl, iso-propyl, n-butyl, t-butyl, i-butyl, sec-butyl, pentyl and hexyl groups. Among unbranched alkyl groups, there are preferred methyl, ethyl, n-propyl, iso-propyl, n-butyl groups. Among branched alkyl groups, there may be mentioned t-butyl, i-butyl, 1-ethylpropyl and 1-ethylbutyl groups.

The term "$C_{m-n}$" or "(m-nC) group" used alone or as a prefix, refers to any group having m to n carbon atoms.

As used herein, the term "alkenyl" means both straight and branched chain unsaturated hydrocarbon groups with at least one carbon carbon double bond. Examples of alkenyl groups include ethenyl, propenyl, butenyl, pentenyl and hexenyl. Preferred alkenyl groups include ethenyl, 1-propenyl, 2-propenyl and but-2-enyl.

As used herein, the term "alkynyl" means both straight and branched chain unsaturated hydrocarbon groups with at least one carbon carbon triple bond. Examples of alkynyl groups include ethynyl, propynyl, butynyl, pentynyl and hexynyl. Preferred alkynyl groups include ethynyl, 1-propynyl and 2-propynyl.

As used herein, the term "carbocyclyl" (or "carbocycle") is intended to mean any 3- to 13-membered carbon ring system, which may be saturated, partially unsaturated, or aromatic. The carbon ring system may be monocyclic or contain more than one ring (e.g. the ring system may be bicyclic). Examples of monocyclic saturated carbocycles include cyclopropyl, cyclobutyl, cyclopentyl, cyclohexyl, cycloheptyl, cyclooctyl. Examples of bicyclic saturated carbocycles include bicyclooctane, bicyclononane, bicyclodecane (decalin) and bicyclooctane. A further example of a saturated carbocycle is adamantane. Examples of monocyclic non-saturated carbocycles include cyclobutene, cyclopentene, cyclopentadiene, cyclohexene. Examples of aromatic carbocycles include phenyl and naphthyl. Further examples of aromatic carbocycles include tetrahydronaphthyl (tetralin) and indane.

As used herein, the term "cycloalkyl" means a saturated group in a ring system. A cycloalkyl group can be monocyclic or bicyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo [2.2.1]hept-2-yl. Preferably, the cycloalkyl group is monocyclic.

As used herein, the term "halogen" or "halo" means fluorine, chlorine, bromine or iodine. Fluorine, chlorine and bromine are particularly preferred.

As used herein, the term "haloalkyl" means an alkyl group having a halogen substituent, the terms "alkyl" and "halogen" being understood to have the meanings outlined above. Similarly, the term "dihaloalkyl" means an alkyl group having two halogen substituents and the term "trihaloalkyl" means an alkyl group having three halogen substituents. Examples of haloalkyl groups include fluoromethyl, chloromethyl, bromomethyl, fluoromethyl, fluoropropyl and fluorobutyl groups; examples of dihaloalkyl groups include difluoromethyl and difluoroethyl groups; examples of trihaloalkyl groups include trifluoromethyl and trifluoroethyl groups.

As used herein, the term "heterocyclyl" (or heterocycle) means an aromatic or a non-aromatic cyclic group of carbon atoms wherein from one to four of the carbon atoms is/are replaced by one or more heteroatoms independently selected from nitrogen, oxygen or sulfur. A heterocyclyl (or heterocycle) group may, for example, be monocyclic or bicyclic. In a bicyclic heterocyclyl (or heterocycle) group there may be one or more heteroatoms in each ring, or only in one of the rings. A heteroatom may be S, O or N, and is preferably O or N.

Examples of monocyclic non-aromatic heterocyclyl (or heterocycle) include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl.

Examples of monocyclic aromatic heterocyclyl (or heterocycle) groups include furanyl, thienyl, pyrrolyl, oxazolyl, thiazolyl, imidazolyl, oxadiazolyl, thiadiazolyl, pyridyl, triazolyl, triazinyl, tetrazolyl, pyridazyl, isothiazolyl, isoxazolyl, pyrazinyl, pyrazolyl and pyrimidinyl.

Examples of bicyclic aromatic heterocyclyl groups (or heterocycle) include quinoxalinyl, quinazolinyl, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridiyl, pyridopyrimidinyl, isoquinolinyl and benzodroxazole. Further examples of bicyclic aromatic heterocyclyl groups include those in which one of the rings is aromatic and the other is non-aromatic, such as dihydrobenzofuranyl, indanyl, indolinyl, isoindolinyl, tetrahydroisoquinolinyl, tetrahydroquinolyl and benzoazepanyl.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups, it is to be understood that this definition includes all substituents being chosen from one of the specified groups or the substituents being chosen from two or more of the specified groups.

As used herein, the term "senolytic" refers to a compound that selectively (preferentially or to a greater degree) destroys, kills, removes, or facilitates selective destruction of senescent cells, i.e. the compound destroys or kills a senescent cell in a biologically, clinically, and/or statistically significant manner compared with its capability to destroy or kill a non-senescent cell. The senolytic compound is used in an amount and for a time sufficient to selectively kill established senescent cells, but which is insufficient to kill non-senescent cells in a clinically significant or biologically significant manner.

In certain embodiments, the senolytic compounds described herein alter at least one signaling pathway in a manner that induces (initiates, stimulates, triggers, activates, promotes) and results in death of the senescent cell. A senolytic compound may alter one or more signaling pathways in a senescent cell by interacting with one or more target proteins, which results in removing or reducing suppression of a cell death pathway, such as an apoptotic pathway. For example, contacting or exposing a senescent cell to a senolytic compound may restore the cell's mechanisms and pathways for initiating apoptosis.

The present application provides a NMT inhibitor for use in the prophylaxis or treatment of a senescence-associated disease or disorder, such as the diseases and disorders described herein.

The present invention further provides the use of a NMT inhibitor in the manufacture of a medicament for the prophylaxis or treatment of a senescence-associated disease or disorder, such as the diseases and disorders described herein.

The present invention also provides a method of prophylaxis or treatment of a senescence-associated disease or disorder, such as the diseases and disorders described herein, by administering to a subject in need thereof, a therapeutically effective amount of a NMT inhibitor. A "therapeutically effective amount" in this context means an amount of the NMT inhibitor sufficient to be effective in therapy e.g. in the treatment of cancer or other senescence-associated disease or disorder.

The present invention also provides a pharmaceutical composition comprising a NMT inhibitor for use in the prophylaxis or treatment of a senescence-associated disease or disorder, such as the diseases and disorders described herein, optionally wherein the composition comprises one or more therapeutic agents and/or one or more pharmaceutically acceptable excipients.

Therapeutic Applications

The present invention relates to NMT inhibitors for use in the prophylaxis or treatment of a senescence-associated disease or disorder, such as the diseases or disorders described herein.

The term "treatment" or "treating" as used herein includes the control, mitigation, reduction, or modulation of the disease state or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

As used herein, senescence-associated disorders or diseases include disorders or diseases associated with, or caused by cellular senescence. In particular, the senescence-associated disorders or diseases are caused by cellular senescence i.e. cellular senescence pathogenesis is responsible for the diseased state of the subject.

Senescent cells can be detected by techniques and procedures known in the art. For example, the presence of senescent cells can be analyzed by histochemical or immunohistochemical techniques that detect the senescence marker, SA-beta galactosidase (SA-β-gal) (Dimri et al, Proc. Natl. Acad. Sci. USA 92: 9363-9367 (1995); see also methods described in WO 2015/116735). Alternatively, senescent cells can be detected by the presence of the senescent cell-associated polypeptide p16, as determined by known immunochemical methods, for example, immunoblotting analysis. Expression of pl6 mRNA in a cell can be measured by a variety of techniques, including quantitative PCR. Senescence cell associated polypeptides can be detected using known assays, for example, a Luminex array assay (Coppe et al, PLoS Biol 6: 2853-68 (2008)).

The presence of senescent cells can also be determined by detecting other senescent cell-associated molecules, such as cytokines, chemokines, expressed and secreted growth factors, proteases, cell-related metabolites, reactive oxygen species, and other molecules that stimulate inflammation and/or other biological effects. Examples of senescent cell-associated molecules include those that comprise the senescence-associated secretory phenotype (SASP), senescent-messaging secretome, and DNA damage secretory program (DDSP).

In one embodiment, the senescence-associated disease or disorder is selected from a metabolic disease, an inflammatory or autoimmune disease or disorder, a cardiovascular disease or disorder, a pulmonary disease or disorder, a neurological disease or disorder, an eye disease or disorder, and a dermatological disease or disorder.

Cancer

In one embodiment the senescence-associated disease or disorder is cancer, wherein said cancer comprises senescent cells. Suitably, the cells of the cancer have been induced into senescence by treatment with a chemotherapeutic agent or radiotherapy. In one embodiment, the chemotherapeutic agent is selected from aphidicolin, bleomycin, carboplatin, docetaxel, cisplatin, cyclophosphamide, 5-fluorouracil diaziquone, epigallocatechin gallate, etoposide, hydroxyurea, K858, lovastatin, MLN4924, pyrithione, resveratrol, retinols, TPA, PEP005, PEP008 and VO—OHpic.

In one embodiment, the chemotherapeutic agent is a CDK4/6 inhibitor, such as ribociclib, abemaciclib, SHR6390, trilaciclib, lerociclib, palbociclib, PF-06873600, FCN-437c, BPI-16350, XZP-3287, HS-10342 and CS3002. In another embodiment, the chemotherapeutic agent is an aurora kinase inhibitor, such as barasertib, alisertib, danusertib, AT9283, PF-03814735, MLN8054 and AMG 900. In another embodiment, the chemotherapeutic agent is a Topo I or Topo II inhibitor, such as irinotecan, topotecan, camptothecin, diflomotecan, lamellarin D, etoposide, teniposide, doxorubicin, daunorubicin, mitoxantrone, amsacrine, ellipticines, aurintricarboxylic acid, and HU-331.

In one embodiment, the chemotherapeutic agent is bleomycin, doxorubicin, etoposide, palbociclib or cisplatin. In one embodiment, the chemotherapeutic agent is cisplatin.

K858 is the codename for the compound of the following formula:

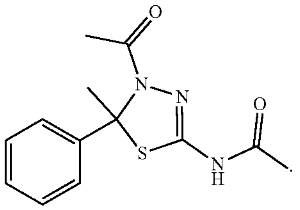

MLN4924 is the codename for the compound of the following formula:

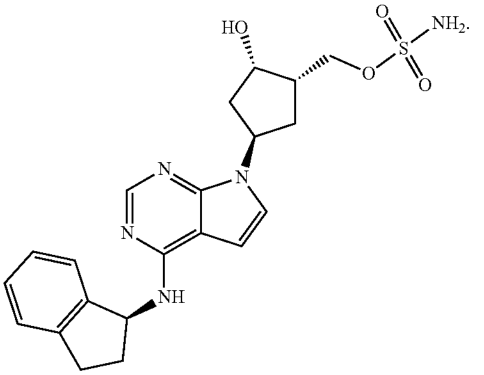 [SMILES: NS(=O)(=O)OC[C@@H]1C[C@@H](n2ccc3c(N[C@H]4CCc5ccccc54)ncnc32)C[C@@H]1O]

TPA is the codename for 12-O-tetradecanoylphorbol-13-acetate, which has the following formula:

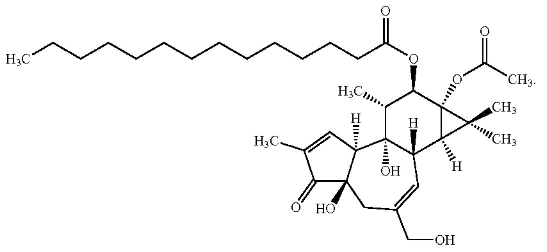

PEP005 is the codename for ingenol mebutate, which has the following formula:

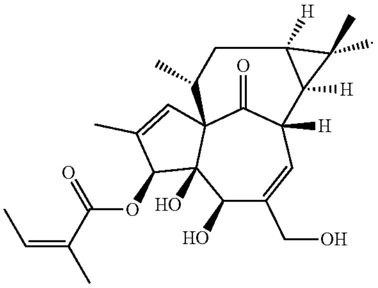

PEP008 is the codename for 20-O-acetyl-ingenol-3-angelate, which has the following formula:

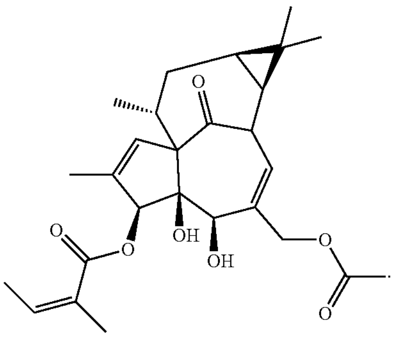

VO—OHpic has the following formula:

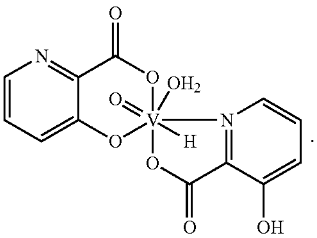

SHR6390 is the codename for the compound with the following formula:

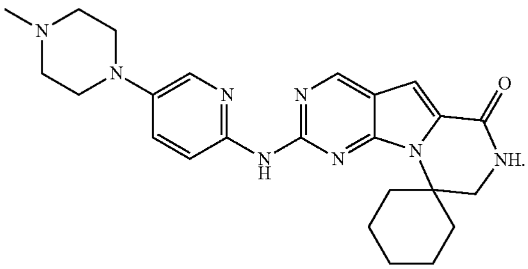 [SMILES: CN1CCN(c2ccc(Nc3ncc4cc5n(c4n3)C3(CCCCC3)CNC5=O)nc2)CC1]

PF-06873600 is the codename for the compound with the following formula:

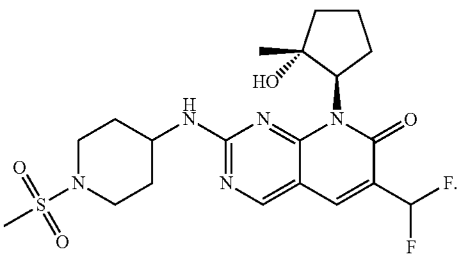 [SMILES: C[C@@]1(O)CCC[C@H]1n1c(=O)c(C(F)F)cc2cnc(NC3CCN(S(C)(=O)=O)CC3)nc21]

BPI-16350 is the codename for the compound with the following formula:

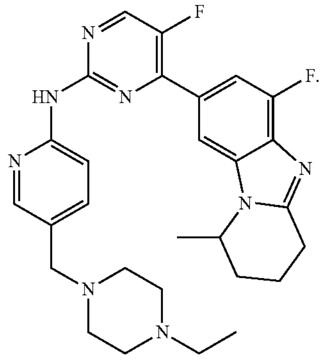 [SMILES: CCN1CCN(Cc2ccc(Nc3ncc(F)c(-c4cc(F)c5nc6n(c5c4)C(C)CCC6)n3)nc2)CC1]

AT9283 is the codename for the compound with the following formula:

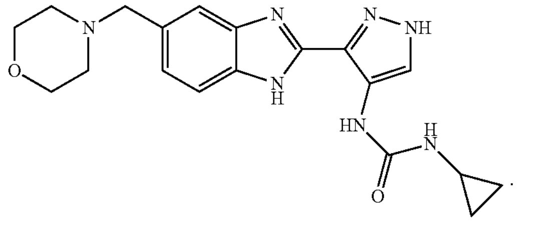 [SMILES: O=C(Nc1c[nH]nc1-c1nc2cc(CN3CCOCC3)ccc2[nH]1)NC1CC1]

PF-03814735 is the codename for the compound with the following formula:

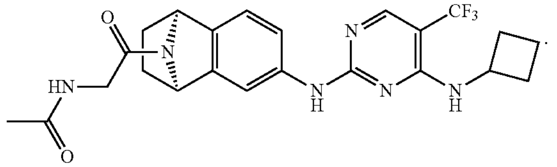 [SMILES: CC(=O)NCC(=O)N1[C@@H]2CC[C@H]1c1ccc(Nc3ncc(C(F)(F)F)c(NC4CCC4)n3)cc12]

MLN8054 is the codename for the compound with the following formula:

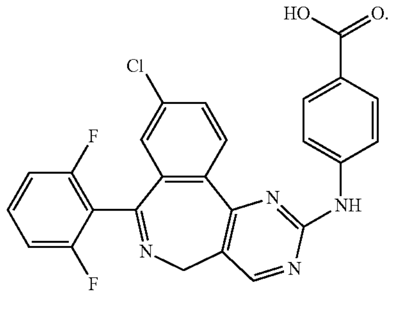 [SMILES: O=C(O)c1ccc(Nc2ncc3c(n2)-c2ccc(Cl)cc2C(c2c(F)cccc2F)=NC3)cc1]

AMG 900 is the codename for the compound with the following formula:

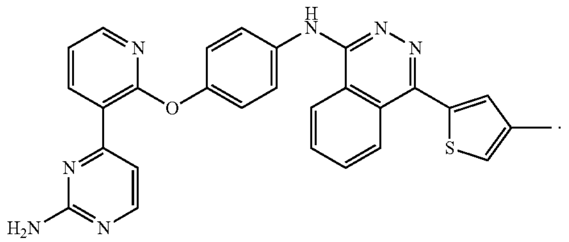 [SMILES: Cc1csc(-c2nnc(Nc3ccc(Oc4ncccc4-c4ccnc(N)n4)cc3)c3ccccc23)c1]

HU-331 is the codename for the compound with the following formula:

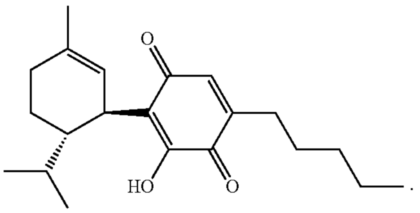 [SMILES: CCCCCC1=CC(=O)C([C@@H]2C=C(C)CC[C@H]2C(C)C)=C(O)C1=O]

FCN-437c, XZP-3287, HS-10342 and CS3002 are codenames for compounds whose chemical structures have not been publicly disclosed.

In one embodiment, the chemotherapeutic agent or radiotherapy is administered in an amount which induces senescence (a "senescence-inducing amount"). A senescence-inducing amount may be less than a therapeutically effective amount e.g. between 5% to 90% of the therapeutically effective amount, such as at the higher end of this range e.g. between 75% and 90% of the therapeutically effective amount, or between 50% and 75% of the therapeutically effective amount, or between 40% and 60% of the therapeutically effective amount, or between 50% and 70% of the therapeutically effective amount, or at the lower end of this range e.g. between 20% and 40% of the therapeutically effective amount, or between 5% and 20% of the therapeutically effective amount, or between 10% and 20% of the therapeutically effective amount, or between 5% and 10% of the therapeutically effective amount. A "therapeutically effective amount" in this context means an amount of the chemotherapeutic agent or radiotherapy sufficient to be effective in therapy e.g. in the treatment of cancer. Thus, in one embodiment, the chemotherapeutic agent or radiotherapy is administered in an amount which induces senescence and which is less than a therapeutically effective amount.

In one embodiment, the cancer is a recurrent cancer or a metastatic cancer.

Although cellular senescence suppresses tumorigenesis early in life, studies have shown that it may promote cancer in aged organisms (Krtolica et al; PNAS, Oct. 9, 2001, Vol 98, No 21, 12072-12077). Oncogene-induced senescence is classically considered a tumour defense barrier. However, several studies have shown that under certain circumstances, senescent cells may favour tumour progression because of their secretory phenotype (Angelini et al; Cancer Res 73(1), 1 Jan. 2013, 450-458).

In one embodiment, the senescence-associated disease or disorder is one or more side effects of chemotherapy or radiotherapy, wherein said chemotherapy or radiotherapy induce senescence. Suitably, the one or more side effects are selected from weight loss, endocrine changes, hormone imbalance, changes in hormone signaling, cardiotoxicity, changes in body composition, a reduced ability to be physically active, gastrointestinal toxicity, nausea, vomiting, constipation, anorexia, diarrhea, peripheral neuropathy, fatigue, malaise, low physical activity, hematological toxicity, anemia, hepatotoxicity, alopecia, pain, infection, mucositis, fluid retention, dermatological toxicity, rashes, dermatitis, hyperpigmentation, urticaria, photosensitivity, nail changes, and mouth, gum and throat problems.

In one embodiment, the NMT inhibitors of the invention can be used in the treatment of chronic or long-term chemotherapy-induced or radiotherapy-induced side effects, wherein said side-effects induce senescence. Certain toxic effects can appear long after treatment and can result from damage to an organ or system by the therapy. Organ dysfunction, for example, neurological, pulmonary, cardiovascular, and endocrine dysfunction, can be observed in subjects who were treated for cancers during childhood. Chronic or late toxic side effects that occur in subjects who received chemotherapy or radiation therapy include, for example, cardiomyopathy, congestive heart disease, inflammation, early menopause, osteoporosis, infertility, impaired cognitive function, peripheral neuropathy, secondary cancers, cataracts and other vision problems, hearing loss, chronic fatigue, reduced lung capacity, and lung disease.

In one embodiment, the senescence-associated disease or disorder is precancerous lesions. Senescent cells exist in premalignant tumours, but not in malignant ones. In this regard, it is understood that a substantial number of cells in premalignant tumours undergo oncogene-induced senescence, but that cells in malignant tumours are unable to do this owing to the loss of oncogene-induced senescence effectors such as $p16^{INK4a}$ or p53 (Collado et al; Nature, Vol 436, August 2005, page 642).

Metabolic Diseases

Senescent cells are understood to play a role in metabolic diseases, such as obesity and type 2 diabetes. Senescence in beta cells has been proposed as a mechanism contributing to type 1 diabetes (Thompson et al., Cell Metab. 2019 May 7; 29(5):1045-1060.e10.). Studies have shown that fat tissue from obese mice showed induction of the senescence markers SA-β-Gal, p53, and p21 (Tchkonia et al, Aging Cell 9:667-684 (2010); Minamino et al, Nat. Med. 15: 1082-1087 (2009)). Induction of senescent cells in obesity has potential clinical implications because pro-inflammatory SASP components are also believed to contribute to type 2 diabetes. A similar pattern of up-regulation of senescence markers and SASP components are associated with diabetes, both in mice and in humans. Accordingly, the NMT inhibitors described herein have potential applications in treating or preventing type 2 diabetes, obesity and metabolic syndrome.

Therefore in one embodiment, the senescence-associated disease or disorder is a metabolic disease. Suitably, the metabolic disease is selected from diabetes, diabetic ulcer, metabolic syndrome, and obesity.

Inflammatory and Autoimmune Diseases and Disorders

Chronic inflammation is thought to be the main age-related factor associated with osteoarthritis. In combination with aging, joint overuse and obesity appear to promote osteoarthritis. By selectively killing senescent cell, the NMT inhibitors of the invention can reduce or inhibit loss or erosion of proteoglycan layers in a joint, reduce inflammation in the affected joint, and promote production of collagen. Removal of senescent cells causes a reduction in the amount of inflammatory cytokines, such as IL-6, produced in a joint and inflammation is reduced. Subjects with herniated discs exhibit elevated presence of cell senescence in the blood and in vessel walls (Roberts et al. (2006) Eur. Spine J. 15 Suppl 3: S312-316).

Senescence in bone marrow mesenchymal stem cells has been proposed as a mechanism contributing to systemic lupus erythematosus (SLE) (Gao et al., Curr Rheumatol Rep. 2019 Jan. 14; 21(2):1.). Senescence in globumerular cells has been proposed as a mechanism contributing to lupus nephritis (Yang et al., Med Sci Monit. 2018 Sep. 28; 24:6882-6891.).

Therefore in one embodiment, the senescence-associated disease or disorder is an inflammatory or autoimmune disease or disorder. Suitably, the autoimmune disease or disorder disease or disorder is selected from osteoarthritis, osteoporosis, oral mucositis, inflammatory bowel disease, kyphosis, herniated intervertebral disc, systemic lupus erythematosus and lupus nephritis.

Vaccine Adjuvantation

A subset of B cells, termed age-associated B cells (ABCs) have been shown to be closely associated with immune senescence (Mehr et al., Aging (Albany NY). 2011 April; 3(4):438-43; Frasca et al., Exp Gerontol. 2018 Jul. 1; 107:55-58; Ma et al., Frontiers in Immunology, 10, 2019, 318). Use of NMTi to directly remove senescent B-cells leading to improved antibody response to vaccinations and infectious agents e.g. among the older population. In addition, use of NMTi should remove senescent cells of other cell types (e.g macrophages, NK cells, even CD4 T cells and neutrophils) and be expected to lead to reduction of paracrine induction of further B-cell senescence and therefore restore the B-cell immune response.

Therefore, in one embodiment the invention provides a NMT inhibitor for use in stimulating a beneficial immune response (e.g. an antibody response) and provides a method of stimulating a beneficial immune response (e.g. an antibody response). in a subject by administering an NMT inhibitor to said subject. In one embodiment, the invention provides a NMT inhibitor for use in adjuvanting an immune response and provides a method of adjuvanting an immune response in a subject by administering an NMT inhibitor to said subject. Thus, the NMT inhibitor may be administered in combination with a vaccine, such as a vaccine composition comprising an antigen derived from a pathogen (e.g. an infectious agent) or a cancer (or nucleic acid encoding the same). In one embodiment, the invention provides a NMT inhibitor for use as a vaccine adjuvant and provides a method of adjuvanting an immune response to a vaccine in a subject by administering an NMT inhibitor to said subject together with said vaccine. The vaccine and the NMT inhibitor may be administered simultaneously, sequentially or separately. In an embodiment the NMT inhibitor is administered prior to the vaccine. In an embodiment the NMT inhibitor is administered at the same time as the vaccine. In an embodiment the NMT inhibitor is administered after the vaccine. The effect of the NMT inhibitor is believed to involve the killing of senescent immune cells, particularly senescent B-cells (such as ABCs) in the subject.

Cardiovascular Diseases and Disorders

Cellular senescence has a critical role in cardiovascular diseases (Minamino et al., Front Cardiovasc Med. 2018 Mar. 5; 5:18). Cellular senescence of endothelial cells contributes to heart failure with preserved ejection fraction (Craenenbroeck et al., Circ Heart Fail. 2017 June; 10(6):e003806). Senescent endothelial cells, vascular smooth muscle cells and foamy macrophages are found in atherosclerotic plaque, and the elimination of senescent cells contributes ameliorates atherosclerosis (Bennett et al., Circulation. 2015 Nov. 17; 132(20):1909-19; van Deursen et al. Science. 2016 Oct.

28; 354(6311):472-477. The elimination of senescent cells also improves survival and recovery in aged mice following acute myocardial infarction (Richardson et al., Aging Cell. 2019 June; 18(3):e12945).

In one embodiment, the senescence-associated disease or disorder is a cardiovascular disease or disorder. Suitably, the cardiovascular disease or disorder is selected from atherosclerosis, angina, arrhythmia, cardiomyopathy, congestive heart failure, coronary artery disease, carotid artery disease, endocarditis, coronary thrombosis, myocardial infarction, hypertension, aortic aneurysm, cardiac diastolic dysfunction, hypercholesterolemia, hyperlipidemia, mitral valve prolapse, peripheral vascular disease, cardiac stress resistance, cardiac fibrosis, brain aneurysm, and stroke.

Pulmonary Diseases and Disorders

COPD is a lung disease defined by persistently poor airflow resulting from the breakdown of lung tissue (emphysema) and the dysfunction of the small airways (obstructive bronchiolitis). Pulmonary fibrosis is a chronic and progressive lung disease characterized by stiffening and scarring of the lung, which may lead to respiratory failure, lung cancer, and heart failure. The NMT inhibitors of the invention can also be used for treating a subject who is aging and has loss (or degeneration) of pulmonary function (i.e., declining or impaired pulmonary function compared with a younger subject) and/or degeneration of pulmonary tissue.

Fibrosis is a pathological condition whereby tissue accumulates ECM proteins such as collagen, resulting in tissue scarification, usually in response to damage. Senescence appears to have both beneficial and detrimental roles during fibrosis and wound healing. Secretion of MMPs, which occurs as part of the SASP, could help in the resolution of fibrotic plaques (Craig et al., 2015). Conversely, fibroblasts and tissues isolated from IPF patients display increased levels of SA-β-Gal staining and p21CIP1, suggesting a link with senescence (Yanai et al., 2015; Schafer et al., 2017). The detrimental nature of senescence in IPF was recently demonstrated using senolytics. Elimination of senescent fibroblasts in a mouse model of lung fibrosis reduced expression of profibrotic SASP components and improved pulmonary function (Schafer et al., 2017).

Cellular senescence has been found to be critical in the pathogenesis of several chronic lung disease, including COPD and IPF (Barnes et al., 2019).

Therefore, in one embodiment, the senescence-associated disease or disorder is a pulmonary disease or disorder. Suitably, the pulmonary disease or disorder is selected from pulmonary fibrosis, idiopathic pulmonary fibrosis (IPF), chronic obstructive pulmonary disease (COPD), asthma, cystic fibrosis, emphysema, bronchiectasis and age-related loss of pulmonary function.

Neurological Diseases and Disorders

Parkinson's disease (PD) is a disabling condition of the brain characterized by slowness of movement (bradykinesia), shaking, stiffness, postural instability and loss of balance. Many of these symptoms are due to the loss of certain nerves in the brain, which results in a lack of dopamine. Senescence of dopamine-producing neurons is thought to contribute to the observed cell death in PD through the production of reactive oxygen species (Cohen et al, J. Neural Transm. Suppl. 19:89-103(1983)).

Alzheimer's disease (AD) is a neurodegenerative disease that shows a slow progressive mental deterioration with failure of memory, disorientation, and confusion, leading to profound dementia. As the disease progresses, impaired judgment, confusion, behavioral changes, disorientation, and difficulty in walking and swallowing occur. Age is the single greatest predisposing risk factor for developing AD, which is the leading cause of dementia in the elderly (Hebert, et al., Arch. Neurol. 60:1119-1122 (2003)). Early clinical symptoms show remarkable similarity to mild cognitive impairment.

Senescent cells have been linked to neurodegenerative diseases including Parkinson's and Alzheimer's disease, and pathologies in which chronic inflammation causes tissue degeneration (Petersen et al., J Clin Invest. 2018 Apr. 2; 128(4):1208-1216). It has been shown that senescent cell markers are present in astrocytes on mouse models of Parkinson's disease. Moreover, the elimination of senescent cells restores neurogenesis and improves motor function in these mice (Andersen et al, Cell Rep. 2018 Jan. 23; 22(4): 930-940). Senolytic therapy also alleviates senescence in Aβ-associated oligodendrocyte progenitor cells, resulting in an improvement of the cognitive deficits associated with an Alzheimer's disease mouse model (Mattson et al., Nat Neurosci. 2019 May; 22(5):719-728). The elimination of senescent cells has been also shown to restore neurogenesis and alleviate anxiety-like behaviors (Jurk et al., Cell Metab. 2019 May 7; 29(5):1061-1077.e8).

Mild Cognitive Impairment (MCI) is a brain-function syndrome involving the onset and evolution of cognitive impairments beyond those expected based on age and education of the individual, but which are not significant enough to interfere with the individual's daily activities. MCI is an aspect of cognitive aging that is considered to be a transitional state between normal aging and the dementia into which it may convert (Pepeu, Dialogues in Clinical Neuroscience 6:369-377, 2004). MCI that primarily affects memory is known as "amnestic MCI", which is frequently seen as prodromal stage of Alzheimer's disease. MCI that affects thinking skills other than memory is known as "non-amnestic MCI."

MND is a group of progressive neurological disorders that destroy motor neurons, the cells that control voluntary muscle activities such as speaking, walking, breathing and swallowing. Examples of MNDs include Amyotrophic Lateral Sclerosis (ALS), also known as Lou Gehrig's Disease, progressive bulbar palsy, pseudobulbar palsy, primary lateral sclerosis, progressive muscular atrophy, lower motor neuron disease, and spinal muscular atrophy (SMA) (e.g., SMA1 also called Werdnig-Hoffmann Disease, SMA2, SMA3 also called Kugelberg-Welander Disease, and Kennedy's disease), post-polio syndrome, and hereditary spastic paraplegia. Cells associated with other pathologies such as amyotrophic lateral sclerosis (ALS) showed an increase in cellular senescence, suggesting that senescence plays roles in ALS (Butler-Browne et al., Amyotroph Lateral Scler. 2011 July; 12(4):264-71).

Therefore, in one embodiment, the senescence-associated disease or disorder is a neurological disease or disorder. Suitably, the neurological disease or disorder is selected from Alzheimer's disease, Parkinson's disease, Huntington's disease, dementia, mild cognitive impairment, macular degeneration, and motor neuron dysfunction.

Eye Diseases and Disorders

Multiple ocular diseases such as Age-related macular degeneration (AMD), Wet AMD, Glaucoma, Experimental ocular hypertension Cataracts, Retinal microaneurysm, Fuchs endothelial dystrophy (FED) Birdshot Uveitis, Diabetic retinopathy and Hyperglycemia-induced retinal microangiopathy have been linked with cellular senescence (Kannan et al., Oxid Med Cell Longev. 2020 Mar. 9; 2020:2583601 and references therein). Senescent cells have been shown to have a causal role in retinopathies, that can be ameliorated by senescent cell removal (Sapieha et al., Science. 2020 Aug. 21; 369(6506):eaay5356.).

In one embodiment, the senescence-associated disease or disorder is an eye disease or disorder. Suitably, the eye disease or disorder is selected from macular degeneration, glaucoma, cataracts, presbyopia, and vision loss. Macular degeneration is a neurodegenerative disease that causes the loss of photoreceptor cells in the central part of retina, called the macula.

Dermatological Diseases and Disorders

Cellular senescence is linked to lupus (PMID: Looney et al., Curr Rheumatol Rep. 2019 Jan. 14; 21(2):1; Cheng et al., Cell Signal. 2012 December; 24(12):2307-14). Other skin-related diseases such as vitiligo and melasma have also been associated with cellular senescence (Picardo et al., Ageing Res Rev. 2020 January; 57:100981). Nevi are known to be enriched in preneoplastic senescent cells (Peeper et al., Nature. 2005 Aug. 4; 436(7051):720-4).

In one embodiment, the senescence-associated disease or disorder is dermatological disease or disorder. Suitably, the dermatological disease or disorder is selected from eczema, psoriasis, hyperpigmentation, nevi, rashes, atopic dermatitis (a form of eczema and associated with inflammation), urticaria, diseases and disorders related to photosensitivity or photoaging, rhytides (wrinkles due to aging), pruritis (linked to diabetes and aging), dysesthesia (a chemotherapy side effect linked to diabetes and multiple sclerosis), eczematous eruptions (often observed in aging patients and linked to side effects of certain drugs), eosinophilic dermatosis (linked to certain kinds of hemotologic cancers), reactive neutrophilic dermatosis (associated with underlying diseases such as inflammatory bowel syndrome), pemphigus, pemphigoid, immunobullous dermatosis (autoimmune blistering of skin) fibrohistocytic proliferations of skin, cutaneous lymphomas, and cutaneous lupus. Late onset lupus may be linked to decreased (i.e., reduced) function of T-cell and B-cells and cytokines (immunosenescence) associated with aging.

Aging-Related Diseases and Disorders

Cirrhosis is the pathological outcome from liver fibrosis and nonalcoholic fatty liver disease, which in turn is a result of hepatic steatosis, the abnormal accumulation of lipids in hepatocytes (Pellicoro et al., 2014; Hardy et al., 2016). Senescence is associated with liver fibrosis (Kim et al., 2013) and cirrhosis (Wiemann et al., 2002). The risk of developing nonalcoholic fatty liver disease increases with age (Hardy et al., 2016) and is predicted by the presence of senescent hepatocytes (Pellicoro et al., 2014). The elimination of senescent cells using INK-ATTC mice reduces liver fat accumulation (Ogrodnik et al., 2017). The role of senescence in the liver is complex, however, because knocking out p53 or p16INK4a increases liver fibrosis (Krizhanovsky et al., 2008). Moreover, senescent hepatic stellate cells down-regulate collagen and up-regulate MMPs and cytokines that could remodel fibrotic plaques and recruit macrophages (Krizhanovsky et al., 2008). Senescence has been shown to drive age-dependent hepatic steatosis in a way that improves after senolytic treatment (Ogrodnik et al., 2017).

Aged individuals often display a reduced glomerular filtration rate and cortical volume that can result in glomerulosclerosis and nephron atrophy, both of which are associated with increased expression of p16INK4a and p53 (Melk et al., 2003, 2004). Senescence has detrimental effects in most renal diseases analyzed (Sturmlechner et al., 2017). Ablation of senescent cells protects against glomerulosclerosis and improves kidney function in aged mice (Baker et al., 2016).

Cellular senescence drives age-dependent hepatic steatosis and eliminating senescent cells reduce steatosis (Jurk et al., Nat Commun. 2017 Jun. 13; 8:15691). Senescence is an underlying condition that is causative to age- and obesity-related liver steatosis and it is associated with Non-alcoholic fatty liver disease (NAFLD) (Jurk et al., Cell Stress. 2017 Sep. 19; 1(1):70-72.).

Therefore in one embodiment, the senescence-associated disease or disorder is an aging-related disease or disorder. Suitably, the aging-related disease or disorder is selected from renal disease, renal failure, chronic kidney disease, frailty, hearing loss, muscle fatigue, skin conditions, skin wound healing, liver fibrosis, non-alcoholic fatty liver disease, hepatic steatosis, pancreatic fibrosis, oral submucosa fibrosis, and sarcopenia. Suitably, the aging-related disease or disorder is selected from renal disease, renal failure, chronic kidney disease, frailty, hearing loss, muscle fatigue, skin conditions, skin wound healing, non-alcoholic fatty liver disease, hepatic steatosis, pancreatic fibrosis, oral submucosa fibrosis, and sarcopenia.

Prolongation of Lifespan

In one embodiment the invention provides a NMT inhibitor for use in the prolonging the lifespan of a subject and provides a method of prolonging the lifespan of a subject by administering an NMT inhibitor to said subject. Suitably, the NMT inhibitor reduces the number of senescent cells in the subject.

Pharmaceutical Compositions

For use in therapy, the NMT inhibitors of the invention are usually administered as a pharmaceutical composition. The invention also provides a pharmaceutical composition comprising a NMT inhibitor (such as a compound of formula (I), formula (II), formula (III) or formula (IV), or a pharmaceutically acceptable salt and/or solvate thereof) for use in the prophylaxis or treatment of a senescence-associated disease or disorder, optionally wherein the composition comprises one or more therapeutic agents and/or one or more pharmaceutically acceptable excipients.

The NMT inhibitor may be administered by any convenient method, e.g. by oral, parenteral, buccal, sublingual, nasal, rectal, intrathecal or transdermal administration, and the pharmaceutical compositions adapted accordingly.

NMT inhibitors which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, *arachis* oil or sesame oil. Alternatively, the solution can be lyophilised and then reconstituted with a suitable solvent just prior to administration.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. In one embodiment the composition is in unit dose form such as a tablet, capsule or ampoule.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Suitably the compounds of the invention are administered topically to the lung or nose, particularly, topically to the lung. Thus, in an embodiment there is provided a pharmaceutical composition comprising one or more NMT inhibitors of the invention optionally in combination with one or more topically acceptable diluents or carriers.

Suitable compositions for pulmonary or intranasal administration include powders, liquid solutions, liquid suspensions, nasal drops comprising solutions or suspensions or pressurised or non-pressurised aerosols.

Topical administration to the nose or lung may be achieved by use of a non-pressurised formulation such as an aqueous solution or suspension. Such formulations may be administered by means of a nebuliser e.g. one that can be hand-held and portable or for home or hospital use (i.e. non-portable). An example device is a RESPIMAT inhaler. The formulation may comprise excipients such as water, buffers, tonicity adjusting agents, pH adjusting agents, viscosity modifiers, surfactants and co-solvents (such as ethanol). Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

According to one specific aspect of the invention there is provided a pharmaceutical composition comprising one or more NMT inhibitors of the invention in particulate form suspended in an aqueous medium. The aqueous medium typically comprises water and one or more excipients selected from buffers, tonicity adjusting agents, pH adjusting agents, viscosity modifiers and surfactants.

Topical administration to the nose or lung may also be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a dry-powder formulation. A dry powder formulation will contain the NMT inhibitor of the disclosure in finely divided form, typically with an MMD of 1-10 μm or a $D_{50}$ of 0.5-10 μm e.g. around 1-5 μm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. an MMD of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Example dry powder delivery systems include SPINHALER, DISKHALER, TURBOHALER, DISKUS, SKYEHALER, ACCUHALER and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

The NMT inhibitors of the invention might also be administered topically to another internal or external surface (e.g. a mucosal surface or skin) or administered orally. The compounds of the invention may be formulated conventionally for such routes of administration.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Pharmaceutical or veterinary composition as described above can be prepared by bringing the agent into association with the carrier, for example by admixture.

In general, the formulations are prepared by uniformly and intimately bringing into association the agent with liquid carriers or finely divided solid carriers or both, and then if necessary shaping the product.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The NMT inhibitors of the invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when agents of the present invention are administered in accordance with the present invention. The NMT inhibitors of the invention, which may have good bioavailability, may be tested in one of several biological assays to determine the concentration of a compound which is required to have a given pharmacological effect.

Combination Therapies

The NMT inhibitors as defined herein may be applied as a sole therapy or be administered in combination with one or more chemotherapeutic agents, or may be administered in combination with a chemotherapeutic agent or radiotherapy. In particular, the NMT inhibitors of the invention are expected to be useful in the treatment of cancers comprising senescent cells, wherein senescence is induced with an appropriate chemotherapeutic agent and/or radiotherapy and the resulting senescent cells are eliminated or reduced by administration of a NMT inhibitor.

Therefore, in one embodiment the invention provides a NMT inhibitor for use in combination with a chemotherapeutic agent or radiotherapy in the treatment of a cancer comprising senescent cells, wherein the NMT inhibitor and the chemotherapeutic agent or radiotherapy are administered simultaneously, sequentially or separately.

Such conjoint treatment may be achieved by way of the simultaneous, sequential or separate dosing of the NMT inhibitor and the chemotherapeutic agent or radiotherapy. Such combination products may employ the NMT inhibitors of the present invention within any suitable dosage range, such as the dosage range described herein. The chemotherapeutic agent or radiotherapy may be employed within their approved dosage ranges. Suitably, the chemotherapeutic agent or radiotherapy are employed in a therapeutically effective amount. A "therapeutically effective amount" in this context means an amount of the chemotherapeutic agent or radiotherapy sufficient to be effective in therapy e.g. in the treatment of cancer.

Therefore, in one embodiment the invention provides a NMT inhibitor, or a pharmaceutically acceptable salt and/or solvate thereof, for use in combination with a chemotherapeutic agent or radiotherapy in the treatment of a cancer comprising senescent cells, wherein the NMT inhibitor and the chemotherapeutic agent or radiotherapy are administered simultaneously, sequentially or separately. In a most suitable embodiment the NMT inhibitor is administered after the chemotherapeutic agent or radiotherapy. In an embodiment the NMT inhibitor is administered at the same time as the chemotherapeutic agent or radiotherapy. In an embodiment the NMT inhibitor is administered prior to the chemotherapeutic agent or radiotherapy.

Suitably, the chemotherapeutic agent is selected from aphidicolin, bleomycin, carboplatin, docetaxel, cisplatin, cyclophosphamide, 5-fluorouracil diaziquone, epigallocatechin gallate, etoposide, hydroxyurea, K858, lovastatin, MLN4924, pyrithione, resveratrol, retinols, TPA, PEP005, PEP008 and VO—OHpic.

Suitably, the chemotherapeutic agent is a CDK4/6 inhibitor, such as ribociclib, abemaciclib, SHR6390, trilaciclib, lerociclib, palbociclib, PF-06873600, FCN-437c, BPI-16350, XZP-3287, HS-10342 and CS3002. In another embodiment, the chemotherapeutic agent is an aurora kinase inhibitor, such as barasertib, alisertib, danusertib, AT9283, PF-03814735, MLN8054 and AMG 900. In another embodiment, the chemotherapeutic agent is a Topo I or Topo II inhibitor, such as irinotecan, topotecan, camptothecin, diflomotecan, lamellarin D, etoposide, teniposide, doxorubicin, daunorubicin, mitoxantrone, amsacrine, ellipticines, aurintricarboxylic acid, and HU-331.

Suitably, the chemotherapeutic agent is selected from bleomycin, doxorubicin, etoposide and palbociclib. Suitably, the chemotherapeutic agent is selected from bleomycin, doxorubicin, etoposide, palbociclib and cisplatin. Suitably, the chemotherapeutic agent is cisplatin.

It will be understood that references to treatment with a chemotherapeutic agent or radiotherapy include references to treatment with one or more chemotherapeutic agents (e.g. one or more of the chemotherapeutic agents referred to herein) or indeed with a combination of one or more chemotherapeutic agents and radiotherapy.

When a patient is to be treated with bleomycin, it may be administered in a therapeutically effective amount or a senescence-inducing amount. A therapeutically effective amount of bleomycin may vary between 1 to 50 $mg/m^2$ of body surface area, such as 15 to 25 $mg/m^2$ of body surface area, depending on which disease or disorder is to be treated. Initially a higher dose may be used, such as 10 to 20 $mg/m^2$ of body surface area, followed by a reduced dose of 1 to 5 $mg/m^2$ of body surface area. A senescence-inducing amount of bleomycin may be less than a therapeutically effective amount e.g. a percentage of the therapeutically effective amount as defined above.

When a patient is to be treated with doxorubicin, it may be administered in a therapeutically effective amount or a senescence-inducing amount. A therapeutically effective amount of doxorubicin may vary between 1 to 100 $mg/m^2$ of body surface area, such as 20 to 80 $mg/m^2$ of body surface area, for example 40-60 $mg/m^2$ of body surface area, depending on which disease or disorder is to be treated. Initially a higher dose may be used, such as 60 to 75 $mg/m^2$ of body surface area followed by a reduced dose of 30-60 $mg/m^2$ of body area, such as 40 $mg/m^2$ of body area. A senescence-inducing amount of doxorubicin may be less than a therapeutically effective amount e.g. a percentage of the therapeutically effective amount as defined above.

When a patient is to be treated with etoposide, it may be administered in a therapeutically effective amount or a senescence-inducing amount. A therapeutically effective amount of etoposide may vary between 50 to 150 $mg/m^2$ of body surface area, such as 50 to 100 $mg/m^2$ of body surface area, such as 100 to 150 $mg/m^2$ of body surface area, depending on which disease or disorder is to be treated. Initially a higher dose may be used, such as 100 to 150 $mg/m^2$ of body surface area, for example 120 $mg/m^2$ of body surface area. A senescence-inducing amount of etoposide may be less than a therapeutically effective amount e.g. a percentage of the therapeutically effective amount as defined above.

When a patient is to be treated with palbociclib, it may be administered in a therapeutically effective amount or a senescence-inducing amount. A therapeutically effective amount of palbociclib may vary between 50 mg to 150 mg, such as between 75 mg to 125 mg, for example 100 mg, depending on which disease or disorder is to be treated. Initially a higher dose may be used, such as 100 mg to 150 mg, such as 125 mg followed by a reduced dose of 50 to 100 mg, such as 100 mg. A senescence-inducing amount of palbociclib may be less than a therapeutically effective amount e.g. a percentage of the therapeutically effective amount as defined above.

When a patient is to be treated with cisplatin, it may be administered in a therapeutically effective amount or a senescence-inducing amount. A therapeutically effective amount of cisplatin may vary between 20 to 100 $mg/m^2$ of body surface area, such as 50 to 100 $mg/m^2$ of body surface area, such as 50 to 75 $mg/m^2$ of body surface area, such as 20 to 50 $mg/m^2$ of body area, for example 40 to 60 $mg/m^2$ of body surface area, depending on which disease or disorder is to be treated. A senescence-inducing amount of cisplatin may be less than a therapeutically effective amount e.g. a percentage of the therapeutically effective amount as defined above.

When a patient is to be treated with radiotherapy, it may be administered in a therapeutically effective amount or a senescence-inducing amount. A therapeutically effective amount of radiotherapy may vary between 5 Gy ("Gray") to 80 Gy, such as between 60 Gy to 80 Gy, such as between 50 Gy to 60 Gy, such as between 40 Gy to 60 Gy, such as between 30 Gy to 50 Gy, such as between 25 Gy to 40 Gy, such as between 20 Gy to 30 Gy, such as between 10 Gy to 25 Gy, such as between 5 Gy to 15 Gy, such as between 5 Gy to 10 Gy, depending on which disease or disorder is to be treated. It will be understood that the therapeutically effective amount refers to the total dose of radiotherapy administered during a course of treatment e.g. a 60 Gy total dose may be administered in 30 fractions (smaller doses) over a 6 week period. The number of fractions and the length of radiotherapy will both vary depending on which disease or disorder is to be treated. A senescence-inducing amount of radiotherapy may be less than a therapeutically effective amount e.g. a percentage of the therapeutically effective amount as defined above.

Other chemotherapeutic agents may be administered according to established dosages or dosages that may be determined by the skilled person.

The combined use of an NMT inhibitor and chemotherapeutic agent may have the beneficial effect of reducing the dose of the chemotherapeutic agent capable of achieving a therapeutic effect. Radiotherapy may be administered according to established dosages or dosages that may be determined by the skilled person.

The combined use of an NMT inhibitor and radiotherapy may have the beneficial effect of reducing the dose of the radiotherapy capable of achieving a therapeutic effect.

Therefore, in one embodiment the invention provides a NMT inhibitor, or a pharmaceutically acceptable salt and/or solvate thereof, for use in combination with a chemotherapeutic agent or radiotherapy in the treatment of a cancer comprising senescent cells, wherein the NMT inhibitor and the chemotherapeutic agent are administered simultaneously, sequentially or separately, and wherein the dosage of said chemotherapeutic agent or radiotherapy is reduced in comparison with that used in the absence of the NMT inhibitor.

N-Myristoyl Transferase (NMT) Inhibitors

The phrase "NMT inhibitor of the invention" means those compounds which display activity as inhibitors of the human N-myristoyl transferases (NMT) which are disclosed herein, both generically and specifically. Furthermore, the term "NMT inhibitor" as used herein will be understood to cover any species which binds to NMT and inhibits its activity. In particular, the NMT inhibitors of the invention are inhibitors of human NMT. Human NMT is suitably HsNMT1 hence the NMT inhibitors of the invention are suitable inhibitors of HsNMT1. The inhibitors may act as competitive inhibitors, or partial competitive inhibitors. The inhibitor may bind to NMT at the myr-CoA binding pocket or at the peptide binding pocket (or inhibit NMT through another mechanism). The NMT inhibitor of the present invention preferably bind and inhibit NMT through the peptide binding pocket.

Suitably, the NMT inhibitors for use in the present invention are compounds which display activity as inhibitors of N-myristoyl transferase (NMT). Suitable compounds which display activity as inhibitors of NMT are known in the art. Non-limiting examples of suitable NMT inhibitors are described in, for example, WO00/37464 (Roche), WO2010/026365 (University of Dundee), WO2013/083991 (Imperial Innovations Limited), WO2017/001812 (Imperial Innovations Limited), WO2020/128473 (Imperial College Innovations Limited), and WO2020/128475 (Imperial College Innovations Limited), the entire contents of which are incorporated herein by reference.

In a particular embodiment, the NMT inhibitor for use in the present invention is a compound of formula (I), formula (II), formula (III) or formula (IV) as defined herein, or a pharmaceutically acceptable salt and/or solvate thereof. For the avoidance of doubt, this embodiment of the present invention also encompass all sub-formulae of formula (I), formula (II), formula (III) and formula (IV) as described herein, such as formulae (IA*, IA, IA*, IA", IA^, IA^^^, IA^^ or IIIa).

In particular embodiments, the NMT inhibitor for use in the present invention is a compound of formula (I), or a pharmaceutically acceptable salt and/or solvate thereof.

In particular embodiments, the NMT inhibitor for use in the present invention is a compound of formula (II), or a pharmaceutically acceptable salt and/or solvate thereof.

In particular embodiments, the NMT inhibitor for use in the present invention is a compound of formula (III), or a pharmaceutically acceptable salt and/or solvate thereof.

In particular embodiments, the NMT inhibitor for use in the present invention is a compound of formula (IV), or a pharmaceutically acceptable salt and/or solvate thereof.

NMT Inhibitors of Formula (I)

As outlined above, in certain embodiments the NMT inhibitor is a compound of formula (I):

(I)

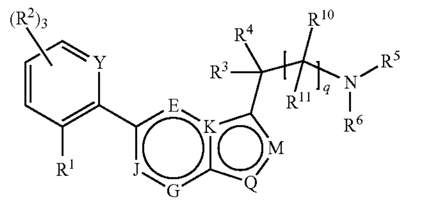

wherein:

Y is selected from the group consisting of —CH—, —C($R^2$)— and —N—;

$R^1$ is a group of formula —X-L-A;

X represents —O—;

L represents —$(CH_2)_m$—;

m is 1, 2 or 3;

A is a 6-10-membered aromatic carbocycle or a 5-10-membered aromatic heterocycle, said aromatic carbocycle or heterocycle being optionally substituted with 1, 2, or 3 substituents each independently selected from the group consisting of —F, —Cl, —Br, —$OCH_3$, —$OCF_3$, —CN, —$C_{1-6}$alkyl optionally substituted by up to 3 halogen, hydroxyl, or —$OC_{1-4}$alkyl groups, —S(O)$C_{1-4}$alkyl, —$S(O)_2C_{1-4}$alkyl, —C(O)N$(R^9)_2$, —C(O)N($R^{13}$)$C_{1-4}$alkylO$C_{1-4}$alkyl, —C(O)N($C_{1-4}$alkylO$C_{1-4}$alkyl$)_2$, —CH—$_2$C(O)N$(R^9)_2$, —$CH_2$C(O)N($R^{13}$)$C_{1-4}$alkylO$C_{1-4}$alkyl, —$CH_2$C(O)N($C_{1-4}$alkylO$C_{1-4}$alkyl$)_2$, —$S(O)_2$NH$C_{1-4}$alkyl, —$S(O)_2$N($C_{1-4}$alkyl$)_2$, —NH$C_{1-4}$alkyl, —N($C_{1-4}$alkyl$)_2$, —NHC(O)$C_{1-4}$alkyl, —NHC(O)$CF_3$, —NHS$(O)_2C_{1-4}$alkyl, $CH_2N(R^{13})_2$, $CH_2N(R^{13})$C(O)$C_{1-4}$alkyl, $CH_2N(R^{13})S(O)_2C_{1-4}$alkyl, —$CH_2S(O)_2C_{1-4}$alkyl, and $CO_2H$;

s is 0, 1, 2, or 3;

each $R^2$ is independently selected from the group consisting of —F, —C, —Br, —$OCH_3$, —$OCF_3$, —CN, —$C_{1-4}$alkyl optionally substituted by up to 3 halogen or hydroxyl groups, —S(O)$C_{1-4}$alkyl, —$S(O)_2C_{1-4}$alkyl, —$S(O)_2$NH$C_{1-4}$alkyl, —$S(O)_2$N($C_{1-4}$alkyl$)_2$, qj—NH$C_{1-4}$alkyl, —N($C_{1-4}$alkyl$)_2$, —NHC(O)$C_{1-4}$alkyl, —NHC(O)$CF_3$, and —NHS$(O)_2C_{1-4}$alkyl;

q is 0 or 1;

$R^3$ is hydrogen or methyl; $R^4$ is hydrogen or methyl;

$R^5$ is hydrogen or $C_{1-6}$alkyl optionally substituted by up to 3 —F, —C, —Br, —OH, —$OCH_3$, —$OCF_3$ or —CN groups; $R^6$ is hydrogen or $C_{1-6}$alkyl optionally substituted by up to 3 —F, —C, —Br, —OH, —$OCH_3$, —$OCF_3$ or —CN groups; or the $R^5$ and $R^6$ groups and the N they are bonded to form a 4 to 7 membered non-aromatic heterocycle, the heterocycle optionally comprising 1 or 2 further heteroatoms selected from N, O and S, optionally substituted by up to 3 —F, —C, —Br, —OH, —$OCH_3$, —$OCF_3$ or —CN groups;

when present $R^{10}$ is hydrogen or methyl;

when present $R^{11}$ is hydrogen or methyl;

or the $R^3$ group and the $R^5$ group and the intervening atoms form a 3 to 7 membered non-aromatic heterocycle composed of the intervening atoms and bond, or the intervening atoms and —$(CHR^a)_r$—; or the $R^{10}$ group and the $R^5$ group and the intervening atoms form a 3 to 7 membered non-aromatic heterocycle composed of the intervening atoms and —$(CHR^a)_r$;

r is 1, 2, 3, 4 or 5; $R^a$ is hydrogen or methyl;

each $R^7$ is independently selected from the group consisting of hydrogen, halogen, $C_{1-4}$alkoxy, and $C_{1-4}$alkyl optionally substituted with 1, 2 or 3 halogens; and $R^8$ is selected from the group selected from hydrogen and $C_{1-4}$alkyl;

each $R^9$ is independently selected from the group consisting of hydrogen and $C_{1-4}$alkyl, or two $R^9$ groups and the N they are bonded to form a 4 to 7 membered non-aromatic heterocycle, the heterocycle optionally comprising 1 or 2 further heteroatoms selected from N, O and S;

each $R^{13}$ is independently selected from the group consisting of hydrogen and $C_{1-4}$alkyl; and wherein i) E, J and G are each C($R^7$), K is carbon, Q is N($R^8$), and M is nitrogen;

ii) E, J and G are each C($R^7$), and K, Q and M are each nitrogen; or iii) E, J, G and M are each C($R^7$), and K and Q are each nitrogen;

or a pharmaceutically acceptable salt and/or solvate thereof.

NMT inhibitors of formula (I) are further described in WO2017/001812. It will be understood that suitable and preferred NMT inhibitors of formula (I) of the present invention may include any of the compounds (generic or specific) disclosed in WO2017/001812.

In one preferred embodiment, E, J, G and M are each C($R^7$), and K and Q are each nitrogen.

In one embodiment, A is an aromatic carbocycle or heterocycle selected from the group consisting of phenyl, pyridinyl, quinolinyl, imidazolyl, benzimidazolyl, pyrazolyl, thiazolyl, 1,2,3-triazolyl and 1,2,4-triazolyl, said aromatic carbocycle or heterocycle being optionally substituted with 1, 2, or 3 groups independently selected from the group consisting of —$C_{1-4}$alkyl, wherein each —$C_{1-4}$alkyl is optionally substituted by up to 3 halogen, hydroxyl or —$OC_{1-4}$alkyl groups; —C(O)N$(R^9)_2$; —CH—$_2$C(O)N$(R^9)_2$; —C(O)N($R^{13}$)$C_{1-4}$alkylO$C_{1-4}$alkyl; —$CH_2N(R^{13})_2$, and $CH_2N(R^{13})S(O)_2C_{1-4}$alkyl; preferably A is selected from the group consisting of optionally substituted pyrazolyl and thiazolyl.

In one embodiment, Y is —CH— or —C($R^2$)—, preferably Y is CH.

In one embodiment, m is 1 or 2.

In one embodiment, $R^7$ is hydrogen or methyl, and/or $R^8$ is hydrogen or methyl.

In one preferred embodiment, A is substituted with 1, 2, or 3 substituents, and at least one of the substituents is C(O)N$(R^9)_2$.

In one preferred embodiment, the compound has the formula (IA*), (IA) or (IA*):

(IA*)

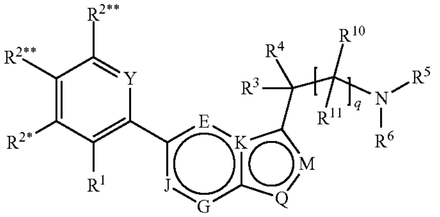

(IA**)

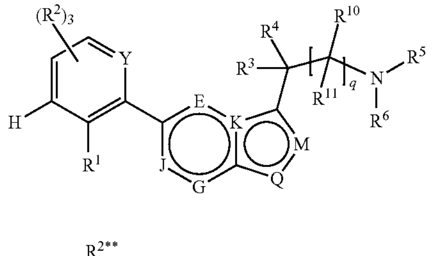

(IA***)

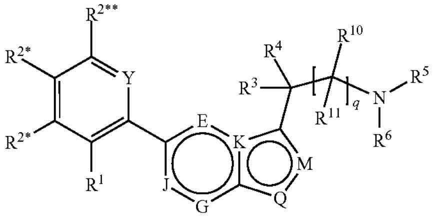

wherein each $R^{2*}$ is independently selected from the group consisting of —F, —Cl, —Br, —$OCH_3$, —$OCF_3$, —CN, —$C_{1-4}$alkyl optionally substituted by up to 3 halogen or hydroxyl groups, —$S(O)C_{1-4}$alkyl, —$S(O)_2C_{1-4}$alkyl, —$S(O)_2NHC_{1-4}$alkyl, —$S(O)_2N(C_{1-4}alkyl)_2$, —$NHC_{1-4}$alkyl, —$N(C_{1-4}alkyl)_2$, —$NHC(O)C_{1-4}$ alkyl, —$NHC(O)CF_3$, and —$NHS(O)_2C_{1-4}$alkyl; and $R^{2**}$ is selected from the group consisting of —H, —F, —Cl, —Br, —$OCH_3$, —$OCF_3$, —CN, —$C_{1-4}$alkyl optionally substituted by up to 3 halogen or hydroxyl groups, —$S(O)C_{1-4}$alkyl, —$S(O)_2C_{1-4}$alkyl, —$S(O)_2NHC_{1-4}$alkyl, —$S(O)_2N(C_{1-4}alkyl)_2$, —$NHC_{1-4}$alkyl, —$N(C_{1-4}alkyl)_2$, —$NHC(O)C_{1-4}$alkyl, —$NHC(O)CF_3$, and —$NHS(O)_2C_{1-4}$alkyl; and wherein s is 0, 1 or 2.

In one preferred embodiment, s is 0, 1, 2 or 3 (preferably 1 or 2, more preferably 2), and, where present, each $R^2$ is independently selected from the group consisting of —F, —Cl, —Br, —$OCH_3$, —$OCF_3$, —CN, and —$C_{1-4}$alkyl optionally substituted by up to 3 halogen or hydroxyl groups.

In one preferred embodiment, A is an optionally substituted 4-pyrazolyl, such as a 4-pyrazolyl optionally substituted by up to 3 substituents independently selected from the group consisting of —$C_{1-4}$alkyl, wherein each —$C_{1-4}$alkyl is optionally substituted by up to 3 halogen, hydroxyl or —$OC_{1-4}$alkyl groups; —$C(O)N(R^9)_2$, —$CH_2C(O)N(R^9)_2$, —$CH_2C(O)N(R^9)_2$, —$C(O)N(R^{13})C_{1-4}alkylOC_{1-4}$alkyl, —$CH_2N(R^{13})_2$, and $CH_2N(R^{13})S(O)_2C_{1-4}$alkyl and $CH_2N(R^{13})S(O)_2C_{1-4}$alkyl; and $R^9$ where present is each selected from the group consisting of hydrogen and —$C_{1-4}$alkyl, or two $R^9$ groups and the N they are bonded to form a 4 to 7 membered non-aromatic heterocycle, the heterocycle optionally comprising 1 or 2 further heteroatoms selected from N, O and S; more preferably A is 4-pyrazolyl optionally substituted by up to 3 groups selected from —$C_{1-4}$alkyl; —$CH_2OC_{1-4}$alkyl, $CF_2H$, $CF_3$, $C(O)N(Me)_2$, —C(O)-1-pyrazole; and —C(O)-4-morpholine.

In one embodiment, the compound has the formula (IA"):

(IA″)

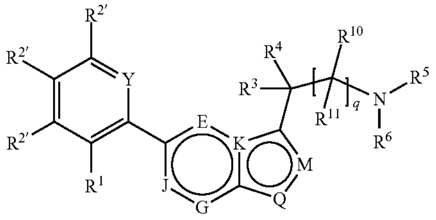

and wherein:

Y is selected from the group consisting of —CH—, —$C(R^{2'})$— and —N—;

X represents —O—; L is —$(CH_2)_m$—; m is 1, 2 or 3;

each $R^{2'}$ is independently selected from the group consisting of hydrogen, fluorine, chlorine, —CN and methyl; $R^3$ is hydrogen or methyl; $R^4$ is hydrogen or methyl;

$R^5$ is hydrogen or methyl; $R^6$ is hydrogen or methyl;

when present $R^{10}$ is hydrogen or methyl;

when present $R^{11}$ is hydrogen or methyl;

or the $R^3$ group and the $R^5$ group and the intervening atoms form a 3 to 7 membered non-aromatic heterocycle composed of the intervening atoms and bond, or the intervening atoms and —$(CHR^a)_r$—;

or the $R^{10}$ group and the $R^5$ group and the intervening atoms form a 3 to 7 membered non-aromatic heterocycle composed of the intervening atoms and —$(CHR^a)_r$—;

r is 1, 2, 3, 4 or 5; $R^a$ is hydrogen or methyl;

$R^7$ where present is hydrogen or methyl; and $R^8$ where present is hydrogen or methyl.

In one embodiment, the compound has the formula (IA^)

(IA^)

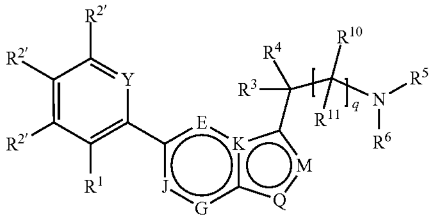

and wherein $R^{2'}$ is selected from the group consisting of fluorine, chlorine, —CN and methyl; and $R^{2''}$ is selected from the group consisting of hydrogen, fluorine, chlorine, —CN and methyl.

In one embodiment the compound has the formula (IA^^^):

(IA^^^)

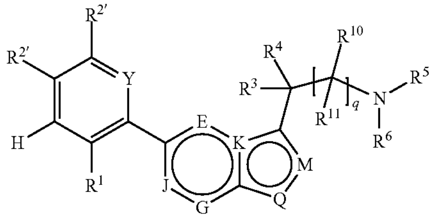

wherein $R^{2'}$ is selected from the group consisting of hydrogen, fluorine, chlorine, —CN and methyl; and $R^{2''}$ is selected from the group consisting of hydrogen, fluorine, chlorine, —CN and methyl.

Suitably E, J and G are each $C(R^7)$, K is carbon, Q is $N(R^8)$, M is nitrogen; and $R^8$ is hydrogen or methyl. Suitably $R^5$ and $R^6$ are each methyl. Suitably, $R^{2'}$ is fluorine; K is carbon; Q is $N(R^8)$; M is nitrogen; E, F and G are each $C(R^7)$; and $R^8$ is methyl.

In one preferred embodiment, the compound has the formula (IA^^):

(IA^^)

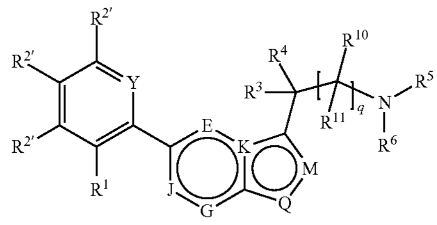

wherein:

$R^1$ is a group of formula —X-L-A;

A is 4-pyrazolyl, said pyrazolyl being optionally substituted with up to 3 substituent groups selected from methyl and $—C(O)N(CH_3)_2$;

X is —O—;

L is $—(CH_2)_m—$;

m is 2;

$R^{2'}$ is selected from the group consisting of fluorine or chlorine (preferably fluorine);

$R^{2''}$ is selected from the group consisting of hydrogen, fluorine or chlorine;

q is 0;

$R^3$ is hydrogen or methyl;

$R^4$ is hydrogen or methyl;

$R^5$ is hydrogen or methyl;

$R^6$ is hydrogen or methyl; or the $R^3$ group and the $R^5$ group and the intervening atoms form a 3 to 7 membered non-aromatic heterocycle composed of the intervening atoms and bonds, (more preferably $R^5$ and $R^6$ are both methyl);

E, J, G, K, Q and M are:

i) E, J and G are each CH, K is carbon, Q is $N(R^8)$, M is nitrogen; and $R^8$ is hydrogen or methyl; or ii) E, J, G and M are each CH, and K and Q are each nitrogen;

with the proviso that A is substituted with no more than one $—C(O)N(CH_3)_2$ group;

or a pharmaceutically acceptable salt and/or solvate thereof.

In one embodiment, the compound of formula (I) is selected from the group consisting of N,N-dimethyl-1-(5-(2-(pyridin-3-ylmethoxy)phenyl)-1H-indazol-3-yl)methanamine;

N,N-dimethyl-1-(5-(2-phenethoxyphenyl)-1H-indazol-3-yl)methanamine;

N,N-dimethyl-1-(5-(2-(quinolin-4-ylmethoxy)phenyl)-1H-indazol-3-yl)methanamine;

N,N-dimethyl-1-(5-(2-(2-(pyridin-3-yl)ethoxy)phenyl)-1H-indazol-3-yl)methanamine 1-(5-(2-(2-(1H-imidazol-1-yl)ethoxy)phenyl)-1H-indazol-3-yl)-N,N-dimethylmethanamine;

N,N-dimethyl-1-(5-(2-benzyloxyphenyl)-1H-indazol-3-yl)methanamine;

1-(5-(4-fluoro-2-(2-(1,3,5-trimethyl-1H-pyrazol-4-yl)ethoxy)phenyl)-1H-indazol-3-yl)-N,N-dimethylmethanamine;

N,N-dimethyl-1-(5-(4-fluoro-2-(2-(pyridin-3-yl)ethoxy)phenyl)-1H-indazol-3-yl)methanamine;

N,N-dimethyl-1-(5-(4-fluoro-2-(pyridin-3-ylmethoxy)phenyl)-1H-indazol-3-yl)methanamine;

1-(5-(2-(4-fluoro-2-(1H-imidazol-1-yl)ethoxy)phenyl)-1H-indazol-3-yl)-N,N-dimethylmethanamine;

1-(5-(2-(2-(1H-benzo[d]imidazol-1-yl)ethoxy)-4-fluorophenyl)-1H-indazol-3-yl)-N,N-dimethylmethanamine;

1-(5-(2-(2-(1H-1,2,4-triazol-1-yl)ethoxy)-4-fluorophenyl)-1H-indazol-3-yl)-N,N-dimethylmethanamine;

1-(5-(2-(2-(2,4-dimethyl-1H-imidazol-1-yl)ethoxy)-4-fluorophenyl)-1H-indazol-3-yl)-N,N-dimethylmethanamine;

1-(5-(4-fluoro-2-(2-(1,3,5-trimethyl-1H-pyrazol-4-yl)ethoxy)phenyl)-1-methyl-1H-indazol-3-yl)-N,N-dimethylmethanamine;

1-(5-(4-fluoro-2-(2-(1,3,5-trimethyl-1H-pyrazol-4-yl)ethoxy)phenyl)-1-methyl-1H-indazol-3-yl)-N-methylmethanamine;

1-(5-(2-(2-(1H-1,2,4-triazol-1-yl)ethoxy)-4-fluorophenyl)-1-methyl-1H-indazol-3-yl)-N,N-dimethylmethanamine 1-(5-(4-fluoro-2-(2-(1,3,5-trimethyl-1H-pyrazol-4-yl)ethoxy)phenyl)-1-methyl-1H-indazol-3-yl)-N,N-dimethylmethanamine HCl salt;

1-(5-(2-(2-(1H-imidazol-1-yl)ethoxy)-4-fluorophenyl)-1-methyl-1H-indazol-3-yl)-N,N-dimethylmethanamine;

1-(5-(2-(2-(2,4-dimethylthiazol-5-yl)ethoxy)-4-fluorophenyl)-1-methyl-1H-indazol-3-yl)-N,N-dimethylmethanamine;

1-(5-(2-(2-(3,5-dimethyl-1H-pyrazol-4-yl)ethoxy)-4-fluorophenyl)-1-methyl-1H-indazol-3-yl)-N,N-dimethylmethanamine;

1-(5-(2-(2-(4-methylthiazol-5-yl)ethoxy)-4-fluorophenyl)-1-methyl-1H-indazol-3-yl)-N,N-dimethylmethanamine;

1-(5-(4-fluoro-2-(2-(4-methylthiazol-5-yl)ethoxy)phenyl)-1-methyl-1H-indazol-3-yl)ethanamine;

1-(5-(4-fluoro-2-(2-(4-methylthiazol-5-yl)ethoxy)phenyl)-1-methyl-1H-indazol-3-yl)-N,N-dimethylethanamine;

(6-(4-fluoro-2-(2-(4-methylthiazol-5-yl)ethoxy)phenyl)-[1,2,4]triazolo[4,3-a]pyridin-3-yl)methanamine;

(6-(4-fluoro-2-(2-(1,3,5-trimethyl-1H-pyrazol-4-yl)ethoxy)phenyl)-[1,2,4]triazolo[4,3-a]pyridin-3-yl)methanamine;

1-(5-(5-fluoro-2-(2-(1,3,5-trimethyl-1H-pyrazol-4-yl)ethoxy)phenyl)-1-methyl-1H-indazol-3-yl)-N,N-dimethylmethanamine;

1-(5-(3-fluoro-2-(2-(1,3,5-trimethyl-1H-pyrazol-4-yl)ethoxy)phenyl)-1-methyl-1H-indazol-3-yl)-N,N-dimethylmethanamine;

(5-(4-fluoro-2-(2-(1,3,5-trimethyl-1H-pyrazol-4-yl)ethoxy)phenyl)-1-methyl-1H-indazol-3-yl)methanamine;

1-(5-(5-fluoro-2-(2-(1,3,5-trimethyl-1H-pyrazol-4-yl)ethoxy)phenyl)-1-methyl-1H-indazol-3-yl)methanamine;

1-(5-(3-fluoro-2-(2-(1,3,5-trimethyl-1H-pyrazol-4-yl)ethoxy)phenyl)-1-methyl-1H-indazol-3-yl)methanamine;

1-(5-(5-fluoro-2-(2-(1,3,5-trimethyl-1H-pyrazol-4-yl)ethoxy)phenyl)-1-methyl-1H-indazol-3-yl)-N-methylmethanamine;

1-(5-(3-fluoro-2-(2-(1,3,5-trimethyl-1H-pyrazol-4-yl)ethoxy)phenyl)-1-methyl-1H-indazol-3-yl)-N-methylmethanamine;

1-(5-(4-fluoro-2-(2-(4-methylthiazol-5-yl)ethoxy)phenyl)-1H-indazol-3-yl)-N,N-dimethylmethanamine;

1-(6-(4-fluoro-2-(2-(1,3,5-trimethyl-1H-pyrazol-4-yl)ethoxy)phenyl)-[1,2,4]triazolo[4,3-a]pyridin-3-yl)-N,N-dimethylmethanamine;
1-(6-(4-fluoro-2-(2-(4-methylthiazol-5-yl)ethoxy)phenyl)-[1,2,4]triazolo[4,3-a]pyridin-3-yl)-N-methylmethanamine;
1-(6-(4-fluoro-2-(2-(1,3,5-trimethyl-1H-pyrazol-4-yl)ethoxy)phenyl)-[1,2,4]triazolo[4,3-a]pyridin-3-yl)-N-methylmethanamine;
1-(6-(4-chloro-2-(2-(4-methylthiazol-5-yl)ethoxy)phenyl)-[1,2,4]triazolo[4,3-a]pyridin-3-yl)-N,N-dimethylmethanamine;
1-(6-(4-chloro-2-(2-(1,3,5-trimethyl-1H-pyrazol-4-yl)ethoxy)phenyl)-[1,2,4]triazolo[4,3-a]pyridin-3-yl)-N,N-dimethylmethanamine;
1-(6-(4-fluoro-2-(2-(3-isobutyl-1,5-dimethyl-1H-pyrazol-4-yl)ethoxy)phenyl)-[1,2,4]triazolo[4,3-a]pyridin-3-yl)-N,N-dimethylmethanamine;
1-(6-(4-fluoro-2-(2-(5-isobutyl-1,3-dimethyl-1H-pyrazol-4-yl)ethoxy)phenyl)-[1,2,4]triazolo[4,3-a]pyridin-3-yl)-N,N-dimethylmethanamine;
4-(2-{5-fluoro-2-[3-(pyrrolidin-2-yl)-[1,2,4]triazolo[4,3-a]pyridin-6-yl]phenoxy}ethyl)-1,3,5-trimethyl-1H-pyrazole;
4-(2-{2-[3-(azetidin-3-yl)-[1,2,4]triazolo[4,3-a]pyridin-6-yl]-5-fluorophenoxy}ethyl)-1,3,5-trimethyl-1H-pyrazole;
[2-(6-{4-fluoro-2-[2-(1,3,5-trimethyl-1H-pyrazol-4-yl)ethoxy]phenyl}-[1,2,4]triazolo[4,3-a]pyridin-3-yl)ethyl](methyl)amine;
N-methyl[(6-{3-[2-(1,3,5-trimethyl-1H-pyrazol-4-yl)ethoxy]pyridin-2-yl}-[1,2,4]triazolo[4,3-a]pyridin-3-yl)methyl]amine;
4-[2-(5-fluoro-2-{3-[(methylamino)methyl]-[1,2,4]triazolo[4,3-a]pyridin-6-yl}phenoxy)ethyl]-N,N,1,5-tetramethyl-1H-pyrazole-3-carboxamide;
1-(5-(3,4-difluoro-2-(2-(1,3,5-trimethyl-1H-pyrazol-4-yl)ethoxy)phenyl)-1-methyl-1H-indazol-3-yl)-N,N-dimethylmethanamine;
1-(5-(3,4-difluoro-2-(2-(1,3,5-trimethyl-1H-pyrazol-4-yl)ethoxy)phenyl)-1-methyl-1H-indazol-3-yl)-N-methylmethanamine;
[(6-{4-fluoro-2-[2-(1,3,5-trimethyl-1H-pyrazol-4-yl)ethoxy]phenyl}imidazo[1,2-a]pyridin-3-yl)methyl](methyl)amine;
{[6-(2-{2-[1-(difluoromethyl)-3,5-dimethyl-1H-pyrazol-4-yl]ethoxy}-4-fluorophenyl)-[1,2,4]triazolo[4,3-a]pyridin-3-yl]methyl}(methyl)amine;
{[6-(2-{2-[1,5-dimethyl-3-(trifluoromethyl)-1H-pyrazol-4-yl]ethoxy}-4-fluorophenyl)-[1,2,4]triazolo[4,3-a]pyridin-3-yl]methyl}(methyl)amine;
{[6-(2-{2-[1,5-dimethyl-3-(morpholine-4-carbonyl)-1H-pyrazol-4-yl]ethoxy}-4-fluorophenyl)-[1,2,4]triazolo[4,3-a]pyridin-3-yl]methyl}(methyl)amine;
{[6-(2-{2-[1,5-dimethyl-3-(pyrrolidine-1-carbonyl)-1H-pyrazol-4-yl]ethoxy}-4-fluorophenyl)-[1,2,4]triazolo[4,3-a]pyridin-3-yl]methyl}(methyl)amine;
[(6-{5-fluoro-3-[2-(1,3,5-trimethyl-1H-pyrazol-4-yl)ethoxy]pyridin-2-yl}-[1,2,4]triazolo[4,3-a]pyridin-3-yl)methyl](methyl)amine;
[2-(5-{4-fluoro-2-[2-(1,3,5-trimethyl-1H-pyrazol-4-yl)ethoxy]phenyl}-1-methyl-1H-indazol-3-yl)ethyl](methyl)amine;
[2-(5-{4-fluoro-2-[2-(1,3,5-trimethyl-1H-pyrazol-4-yl)ethoxy]phenyl}-1H-indazol-3-yl)ethyl](methyl)amine;
[(6-{4-fluoro-2-[2-(1,3,5-trimethyl-1H-pyrazol-4-yl)ethoxy]phenyl}imidazo[1,2-a]pyridin-3-yl)methyl]dimethylamine;
4-(2-{2-[3-(azetidin-3-yl)-[1,2,4]triazolo[4,3-a]pyridin-6-yl]-5-fluorophenoxy}ethyl)-N,N,1,5-tetramethyl-1H-pyrazole-3-carboxamide;
4-[2-(5-fluoro-2-{3-[2-(methylamino)ethyl]-[1,2,4]triazolo[4,3-a]pyridin-6-yl}phenoxy)ethyl]-N,N,1,5-tetramethyl-1H-pyrazole-3-carboxamide;
Ethyl[(6-{4-fluoro-2-[2-(1,3,5-trimethyl-1H-pyrazol-4-yl)ethoxy]phenyl}imidazo[1,2-a]pyridin-3-yl)methyl]amine;
2-(6-{4-fluoro-2-[2-(1,3,5-trimethyl-1H-pyrazol-4-yl)ethoxy]phenyl}imidazo[1,2-a]pyridin-3-yl)ethan-1-amine;
4-(2-{2-[3-(2-aminoethyl)imidazo[1,2-a]pyridin-6-yl]-5-fluorophenoxy}ethyl)-N,N,1,5-tetramethyl-1H-pyrazole-3-carboxamide;
[2-(6-{4-fluoro-2-[2-(1,3,5-trimethyl-1H-pyrazol-4-yl)ethoxy]phenyl}imidazo[1,2-a]pyridin-3-yl)ethyl](methyl)amine;
[2-(6-{4-fluoro-2-[2-(1,3,5-trimethyl-1H-pyrazol-4-yl)ethoxy]phenyl}imidazo[1,2-a]pyridin-3-yl)ethyl]dimethylamine;
4-[2-(5-fluoro-2-{3-[2-(methylamino)ethyl]imidazo[1,2-a]pyridin-6-yl}phenoxy)ethyl]-N,N,1,5-tetramethyl-1H-pyrazole-3-carboxamide;
[(6-{3-fluoro-2-[2-(1,3,5-trimethyl-1H-pyrazol-4-yl)ethoxy]phenyl}imidazo[1,2-a]pyridin-3-yl)methyl](methyl)amine;
[(6-{3-fluoro-2-[2-(1,3,5-trimethyl-1H-pyrazol-4-yl)ethoxy]phenyl}imidazo[1,2-a]pyridin-3-yl)methyl]dimethylamine;
4-[2-(2-{3-[2-(dimethylamino)ethyl]imidazo[1,2-a]pyridin-6-yl}-5-fluorophenoxy)ethyl]-N,N,1,5-tetramethyl-1H-pyrazole-3-carboxamide;
4-[2-(5-fluoro-2-{3-[(methylamino)methyl]imidazo[1,2-a]pyridin-6-yl}phenoxy)ethyl]-N,N,1,5-tetramethyl-1H-pyrazole-3-carboxamide;
4-[2-(2-{3-[(dimethylamino)methyl]imidazo[1,2-a]pyridin-6-yl}-5-fluorophenoxy)ethyl]-N,N,1,5-tetramethyl-1H-pyrazole-3-carboxamide;
2-(6-{3-fluoro-2-[2-(1,3,5-trimethyl-1H-pyrazol-4-yl)ethoxy]phenyl}imidazo[1,2-a]pyridin-3-yl)ethan-1-amine;
[2-(6-{3-fluoro-2-[2-(1,3,5-trimethyl-1H-pyrazol-4-yl)ethoxy]phenyl}imidazo[1,2-a]pyridin-3-yl)ethyl](methyl)amine;
2-(6-{3,4-difluoro-2-[2-(1,3,5-trimethyl-1H-pyrazol-4-yl)ethoxy]phenyl}imidazo[1,2-a]pyridin-3-yl)ethan-1-amine;
[2-(6-{3,4-difluoro-2-[2-(1,3,5-trimethyl-1H-pyrazol-4-yl)ethoxy]phenyl}imidazo[1,2-a]pyridin-3-yl)ethyl](methyl)amine;
4-[2-(5-fluoro-2-{3-[(methylamino)methyl]imidazo[1,2-a]pyridin-6-yl}phenoxy)ethyl]-1,5-dimethyl-1H-pyrazole-3-carboxylic acid;
{4-[2-(5-fluoro-2-{3-[(methylamino)methyl]imidazo[1,2-a]pyridin-6-yl}phenoxy)ethyl]-1,5-dimethyl-1H-pyrazol-3-yl}methanol;
4-[2-(5-fluoro-2-{3-[(methylamino)methyl]imidazo[1,2-a]pyridin-6-yl}phenoxy)ethyl]-1,5-dimethyl-1H-pyrazole-3-carboxamide;
4-[2-(5-fluoro-2-{3-[(methylamino)methyl]imidazo[1,2-a]pyridin-6-yl}phenoxy)ethyl]-N,1,5-trimethyl-1H-pyrazole-3-carboxamide;
4-[2-(5-fluoro-2-{3-[2-(methylamino)ethyl]imidazo[1,2-a]pyridin-6-yl}phenoxy)ethyl]-1,5-dimethyl-1H-pyrazole-3-carboxylic acid;

{4-[2-(5-fluoro-2-{3-[2-(methylamino)ethyl]imidazo[1,2-a]pyridin-6-yl}phenoxy)ethyl]-1,5-dimethyl-1H-pyrazol-3-yl}methanol;

4-[2-(5-fluoro-2-{3-[2-(methylamino)ethyl]imidazo[1,2-a]pyridin-6-yl}phenoxy)ethyl]-1,5-dimethyl-1H-pyrazole-3-carboxamide;

4-[2-(5-fluoro-2-{3-[2-(methylamino)ethyl]imidazo[1,2-a]pyridin-6-yl}phenoxy)ethyl]-N,1,5-trimethyl-1H-pyrazole-3-carboxamide;

4-[2-(5-fluoro-2-{3-[2-(methylamino)ethyl]imidazo[1,2-a]pyridin-6-yl}phenoxy)ethyl]-1,5-dimethyl-1H-pyrazole-3-carbonitrile;

4-[2-(5-fluoro-2-{3-[(methylamino)methyl]imidazo[1,2-a]pyridin-6-yl}phenoxy)ethyl]-1,5-dimethyl-1H-pyrazole-3-carbonitrile;

4-(2-{2-[3-(2-aminoethyl)imidazo[1,2-a]pyridin-6-yl]-5-fluorophenoxy}ethyl)-1,5-dimethyl-1H-pyrazole-3-carboxylic acid;

4-(2-{2-[3-(2-aminoethyl)imidazo[1,2-a]pyridin-6-yl]-5-fluorophenoxy}ethyl)-N,1,5-trimethyl-1H-pyrazole-3-carboxamide;

[4-(2-{2-[3-(2-aminoethyl)imidazo[1,2-a]pyridin-6-yl]-5-fluorophenoxy}ethyl)-1,5-dimethyl-1H-pyrazol-3-yl]methanol;

4-(2-{2-[3-(2-aminoethyl)imidazo[1,2-a]pyridin-6-yl]-5-fluorophenoxy}ethyl)-1,5-dimethyl-1H-pyrazole-3-carboxamide;

2-[6-(2-{2-[3-(aminomethyl)-1,5-dimethyl-1H-pyrazol-4-yl]ethoxy}-4-fluorophenyl)imidazo[1,2-a]pyridin-3-yl]ethan-1-amine;

N-{[4-(2-{2-[3-(2-aminoethyl)imidazo[1,2-a]pyridin-6-yl]-5-fluorophenoxy}ethyl)-1,5-dimethyl-1H-pyrazol-3-yl]methyl}acetamide;

N-{[4-(2-{2-[3-(2-aminoethyl)imidazo[1,2-a]pyridin-6-yl]-5-fluorophenoxy}ethyl)-1,5-dimethyl-1H-pyrazol-3-yl]methyl}methanesulfonamide;

2-[6-(4-fluoro-2-{2-[3-(methoxymethyl)-1,5-dimethyl-1H-pyrazol-4-yl]ethoxy}phenyl)imidazo[1,2-a]pyridin-3-yl]ethan-1-amine;

2-[6-(4-fluoro-2-{2-[3-(methanesulfonylmethyl)-1,5-dimethyl-1H-pyrazol-4-yl]ethoxy}phenyl)imidazo[1,2-a]pyridin-3-yl]ethan-1-amine;

{[6-(4-fluoro-2-{2-[3-(methanesulfonylmethyl)-1,5-dimethyl-1H-pyrazol-4-yl]ethoxy}phenyl)imidazo[1,2-a]pyridin-3-yl]methyl}(methyl)amine;

{[6-(4-fluoro-2-{2-[3-(methoxymethyl)-1,5-dimethyl-1H-pyrazol-4-yl]ethoxy}phenyl)imidazo[1,2-a]pyridin-3-yl]methyl}(methyl)amine;

2-[6-(2-{2-[1,5-dimethyl-3-(morpholine-4-carbonyl)-1H-pyrazol-4-yl]ethoxy}-4-fluorophenyl)imidazo[1,2-a]pyridin-3-yl]ethan-1-amine;

4-(2-{2-[3-(2-aminoethyl)imidazo[1,2-a]pyridin-6-yl]-5-fluorophenoxy}ethyl)-N-(2-methoxyethyl)-1,5-dimethyl-1H-pyrazole-3-carboxamide;

2-{6-[2-(2-{1,5-dimethyl-3-[(methylamino)methyl]-1H-pyrazol-4-yl}ethoxy)-4-fluorophenyl]imidazo[1,2-a]pyridin-3-yl}ethan-1-amine;

N-{[4-(2-{2-[3-(2-aminoethyl)imidazo[1,2-a]pyridin-6-yl]-5-fluorophenoxy}ethyl)-1,5-dimethyl-1H-pyrazol-3-yl]methyl}-N-methylacetamide;

N-{[4-(2-{2-[3-(2-aminoethyl)imidazo[1,2-a]pyridin-6-yl]-5-fluorophenoxy}ethyl)-1,5-dimethyl-1H-pyrazol-3-yl]methyl}-N-methylmethanesulfonamide;

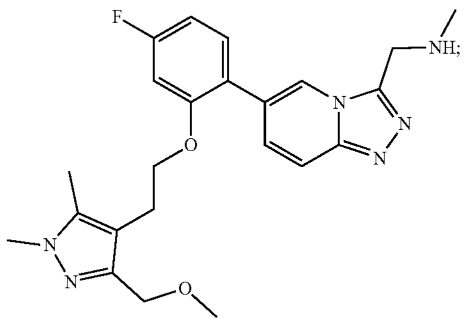

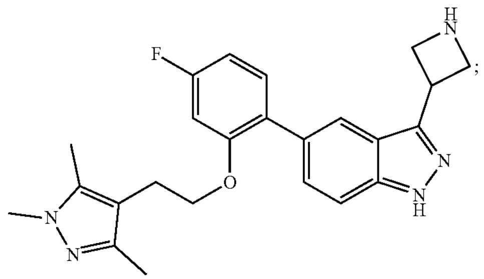

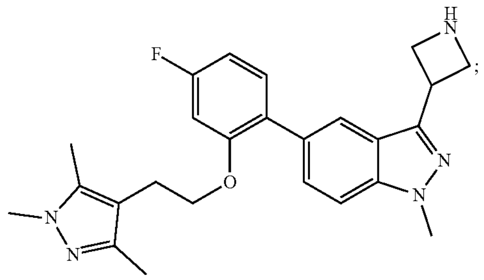

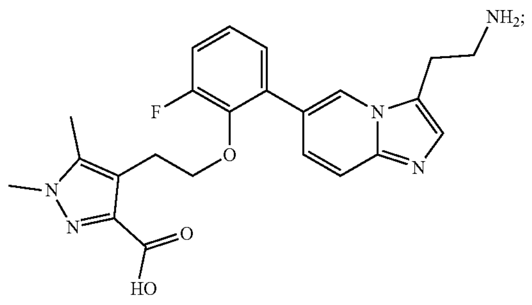

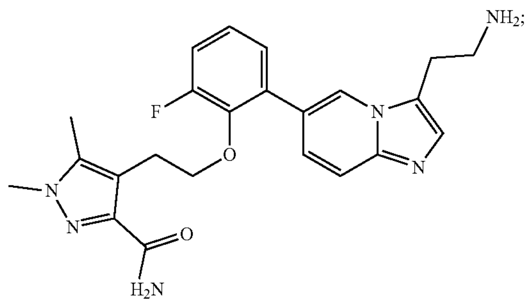

-continued
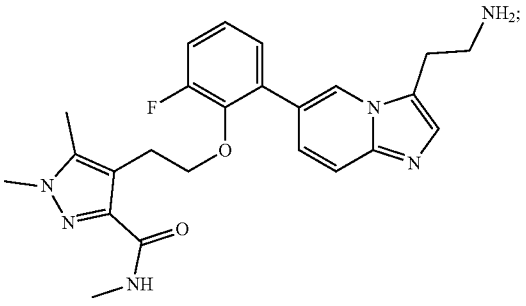
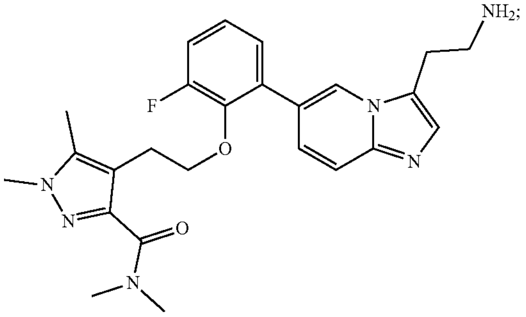
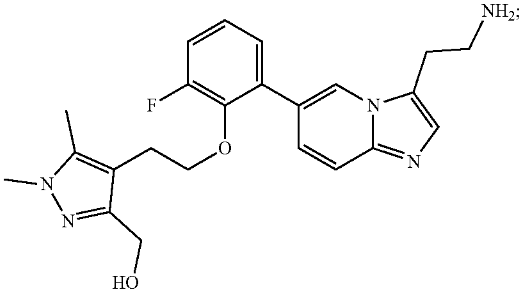
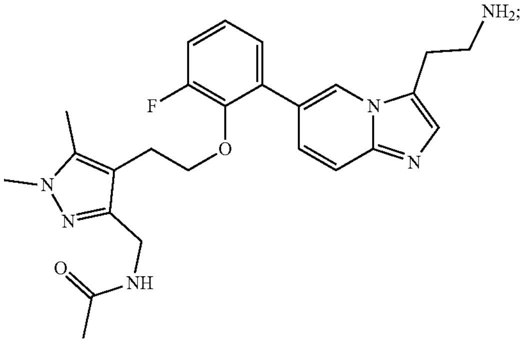
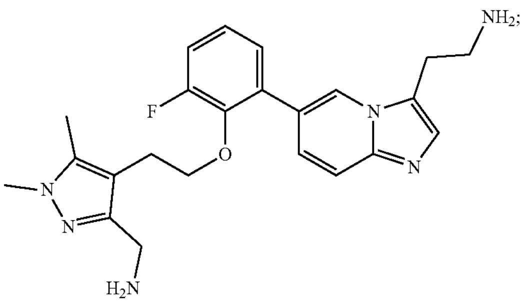
-continued
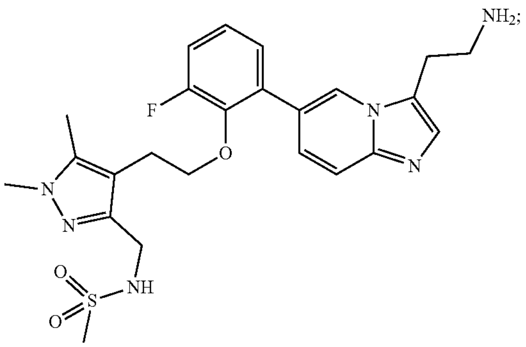
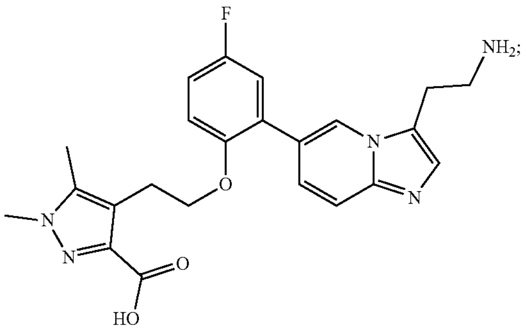
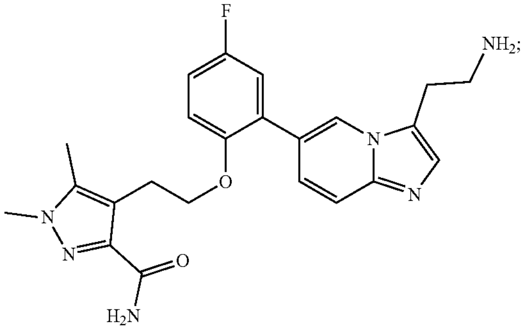
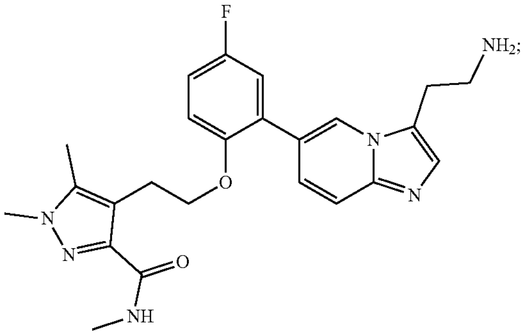
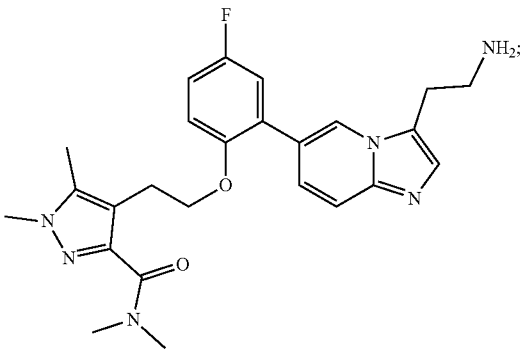

-continued
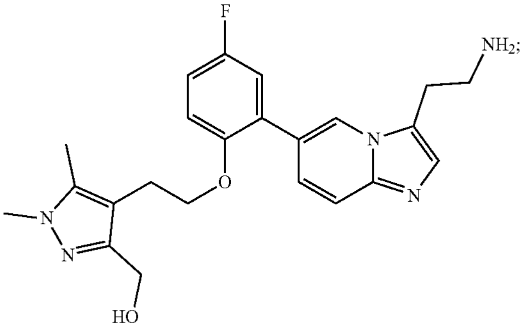
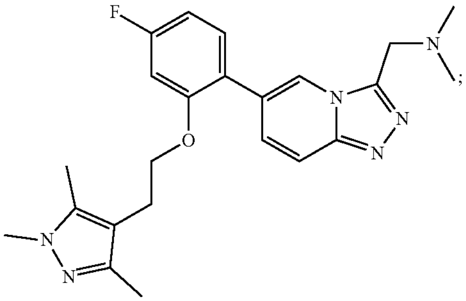
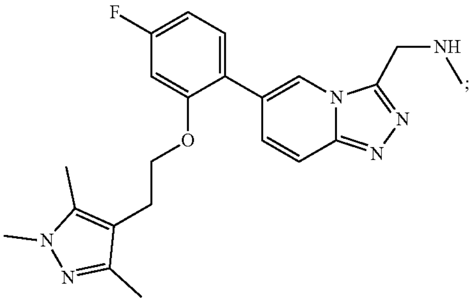
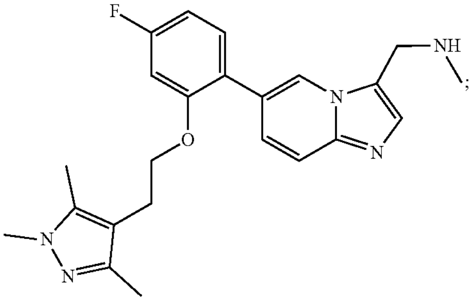
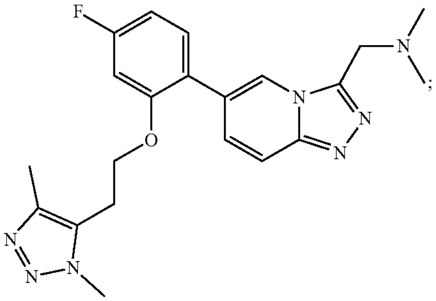
-continued
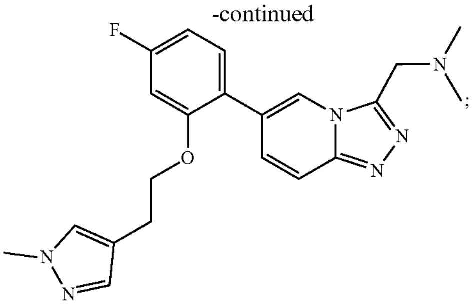
and
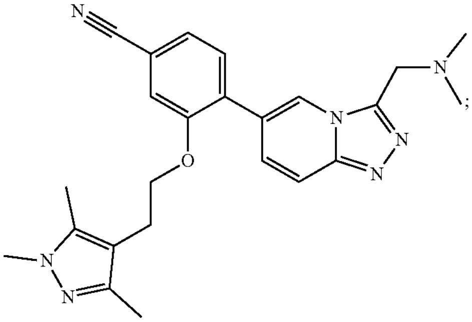
or a pharmaceutically acceptable salt and/or solvate thereof.
In one embodiment, the NMT inhibitor is any one of the following compounds:
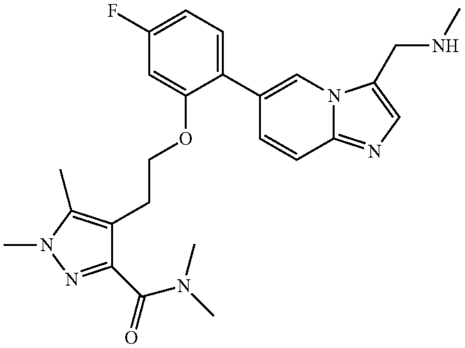
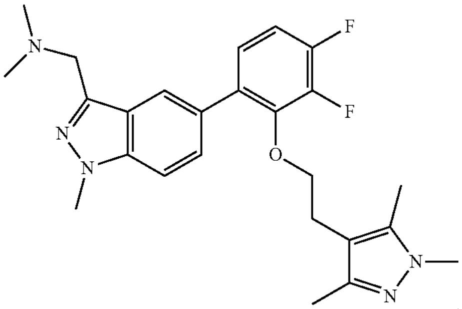
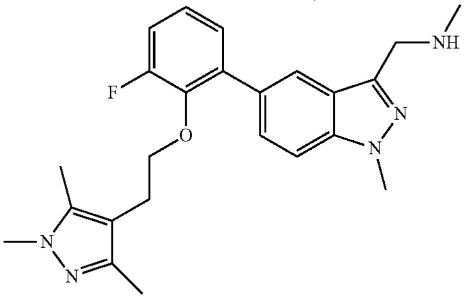

-continued

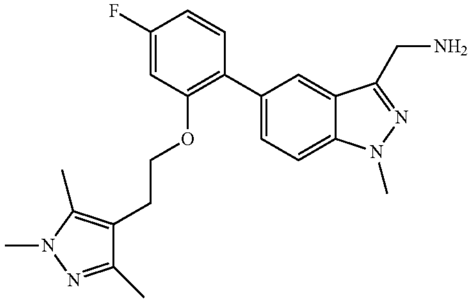

or a pharmaceutically acceptable salt and/or solvate thereof.

In one embodiment, the NMT inhibitor is any one of the following compounds:

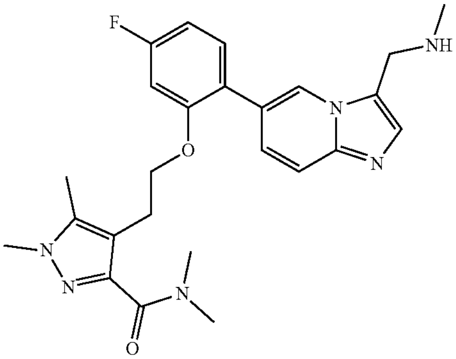

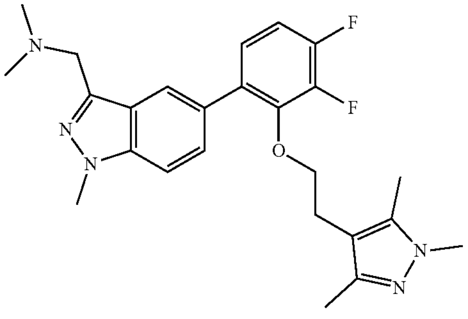

or a pharmaceutically acceptable salt and/or solvate thereof.

In one highly preferred embodiment, the NMT inhibitor is 1-(5-(3,4-difluoro-2-(2-(1,3,5-trimethyl-1H-pyrazol-4-yl)ethoxy)phenyl)-1-methyl-1H-indazol-3-yl)-N,N-dimethyl-methanamine:

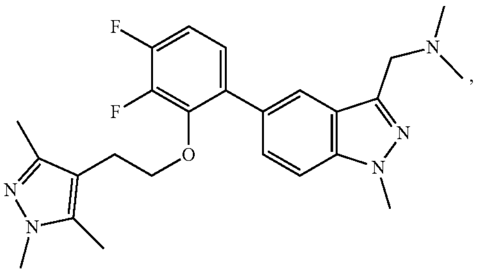 [SMILES: Cc1nn(C)c(C)c1CCOc1c(-c2ccc3c(c2)c(CN(C)C)nn3C)ccc(F)c1F]

or a pharmaceutically acceptable salt and/or solvate thereof.

NMT inhibitors of Formula (II)

In one embodiment, the NMT inhibitor is a compound of formula (II):

(II)

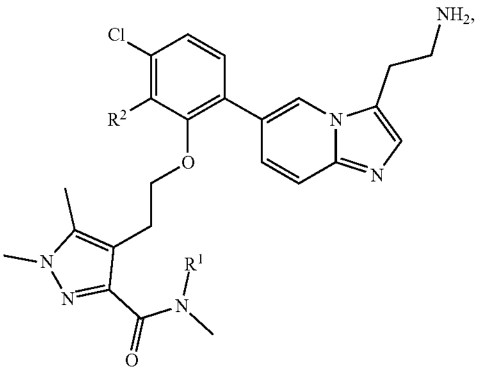

wherein:

$R^1$ is H or —$CH_3$; and $R^2$ is H or F;

or a pharmaceutically acceptable salt and/or solvate thereof.

NMT inhibitors of formula (II) are further described in WO2020/128473. It will be understood that suitable and preferred NMT inhibitors of Formula (II) of the present invention may therefore include any of the compounds disclosed in WO2020/128473.

In another particular embodiment, the NMT inhibitor is selected from any one of the following compounds:

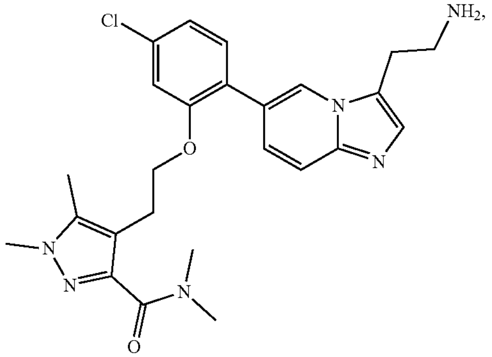

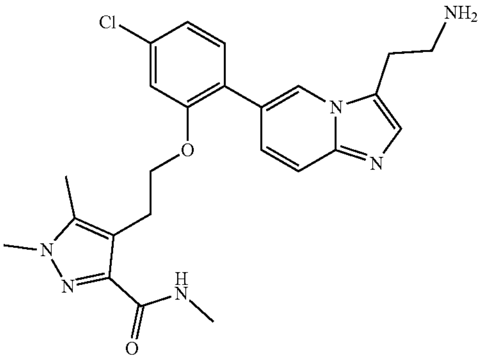

-continued

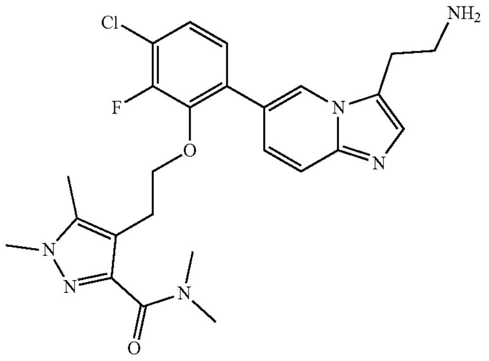

and

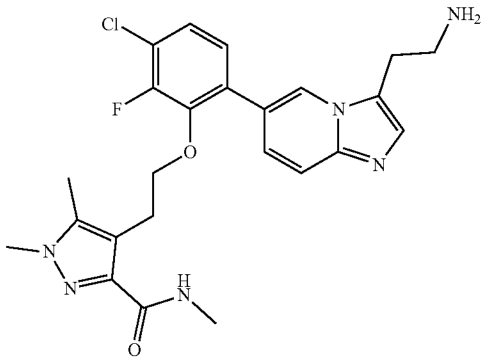

(i.e. 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide, 4-(2-{2-[3-(2-aminoethyl)imidazo[1,2-a]pyridin-6-yl]-5-chlorophenoxy}ethyl)-N,1,5-trimethyl-1H-pyrazole-3-carboxamide, 4-(2-{6-[3-(2-aminoethyl)imidazo[1,2-a]pyridin-6-yl]-3-chloro-2-fluorophenoxy}ethyl)-N,N,1,5-tetramethyl-1H-pyrazole-3-carboxamide and 4-(2-{6-[3-(2-aminoethyl)imidazo[1,2-a]pyridin-6-yl]-3-chloro-4-fluorophenoxy}ethyl)-N,1,5-trimethyl-1H-pyrazole-3-carboxamide respectively) or a pharmaceutically acceptable salt and/or solvate thereof.

In another particular embodiment, the NMT inhibitor is selected from any one of the following compounds:

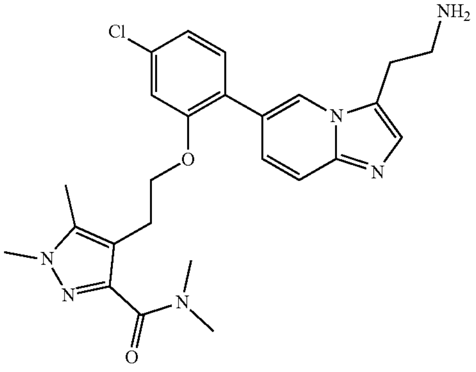

and

-continued

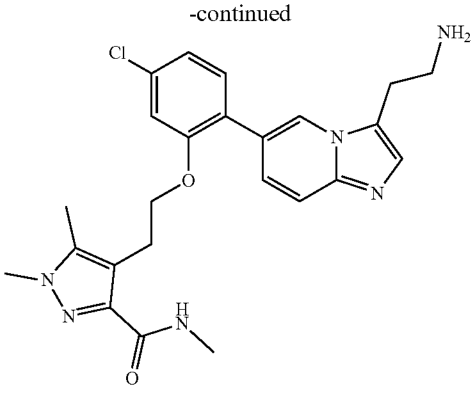

(i.e. 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide and 4-(2-{2-[3-(2-aminoethyl)imidazo[1,2-a]pyridin-6-yl]-5-chlorophenoxy}ethyl)-N,1,5-trimethyl-1H-pyrazole-3-carboxamide) or a pharmaceutically acceptable salt and/or solvate thereof.

In another particular embodiment, the NMT inhibitor is the following compound:

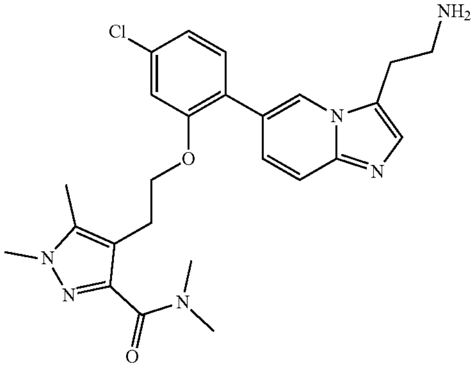 [SMILES: Cc1c(CCOc2cc(Cl)ccc2-c2ccc3ncc(CCN)n3c2)c(C(=O)N(C)C)nn1C]

(i.e. 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide) or a pharmaceutically acceptable salt and/or solvate thereof.

NMT Inhibitors of Formula (III) and (IV)

In certain embodiments, the NMT inhibitor is a compound of Formula (III) or Formula (IV) shown below, or a pharmaceutically acceptable salt and/or solvate thereof:

Formula (III)

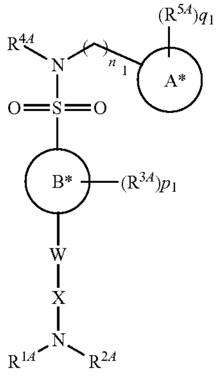

-continued

Formula (IV)

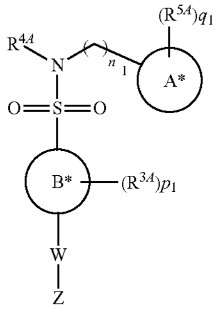

wherein:

$n_1$ is 0, 1, 2, 3, 4, 5 or 6;

Ring A*, is an optionally substituted nitrogen containing aryl group wherein each substitutable carbon or nitrogen in Ring A* is optionally and independently substituted by one or more $R^{5A}$ and wherein if Ring A* contains an —NH— moiety that nitrogen may be optionally substituted by $C_{1-6}$alkyl (e.g. methyl); and wherein $R^{4A}$ and Ring A* together with the atoms to which they are attached may form a cyclic group, Ring B* is an optionally substituted aryl or heteroaryl group wherein each substitutable carbon or heteroatom in Ring B* is optionally and independently substituted by one or more $R^{3A}$.

W and X, one of which may be absent, are independently selected from $R^{11A}$, hydrocarbyl (e.g. $C_{1-8}$ alkyl, alkenyl, alkynyl, or haloalkyl) optionally substituted with $R^{11A}$, and —$(CH_2)_{k1}$-heterocyclyl optionally substituted with $R^{12A}$; $k_1$ is 0, 1, 2, 3, 4, 5 or 6;

$R^{1A}$, $R^{2A}$, $R^{3A}$, $R^{4A}$ and $R^{5A}$ are independently selected from hydrogen, $R^{12A}$, hydrocarbyl (e.g. $C_{1-6}$ alkyl, alkenyl, alkynyl, or haloalkyl) optionally substituted with $R^{12A}$, and a —$(CH_2)_{L1}$— heterocyclyl optionally substituted with one or more $R^{12A}$; wherein $R^{1A}$ and $R^{2A}$ taken together with the atoms to which they are attached may form a heterocycle, optionally substituted with one or more $R^{12A}$, wherein $R^{1A}$ and/or $R^{2A}$ taken together with W or X may form a heterocycle optionally substituted with one or more $R^{12A}$; and wherein one or more of $R^{3A}$ and $R^{5A}$ taken together with the atoms to which they are attached may form a carbocycle, for example heterocyclyl, optionally substituted with $R^{12A}$; $L_1$ is 0, 1, 2, 3, 4, 5 or 6;

wherein:

each $R^{11A}$ and $R^{12A}$ is independently selected from halogen, trifluoromethyl, cyano, thio, nitro, oxo, $=NR^{13A}$, $-OR^{13A}$, $-SR^{13A}$, $-C(O)R^{13A}$, $-C(O)OR^{13A}$, $-OC(O)R^{13A}$, $-NR^{13A}COR^{14A}$, $-NR^{13A}CON(R^{14A})_2$, $-NR^{13a}COR^{14a}$, $-NR^{13a}CO_2R^{14A}$, $-(O)R^{13A}$, $-S(O)_2R^{13A}$, $-SON(R^{13A})_2$, $-NR^{13A}S(O)_2R^{14A}$; $-CSR^{13A}$, $-N(R^{13A})R^{14A}$, $-C(O)N(R^{13A})R^{14A}$, $-SO_2N(R^{13A})R^{14A}$ and $R^{15A}$;

$R^{13A}$ and $R^{14A}$ are each independently selected from hydrogen or $R^{15A}$.

$R^{15A}$ is selected from hydrocarbyl (e.g. $C_{1-6}$alkyl, alkenyl, alkynyl, or haloalkyl), carbocyclyl and —$(CH_2)_{m1}$-heterocyclyl, and each $R^{15A}$ is optionally and independently substituted with one or more of halogen, cyano, amino, hydroxy, $C_{1-6}$alkyl or cycloalkyl and $C_{1-6}$alkoxy;

$m_1$ is 0, 1, 2, 3, 4, 5 or 6;

$p_1$ is 0, 1, 2, 3 or 4; the values of $R^{4A}$ may be the same or different; and $q_1$ is 0, 1, 2, 3 or 4; wherein the values of $R^{5A}$ may be the same or different;

Y and Z, one or both of which may be absent, are independently selected from hydrogen, $R^{16A}$, hydrocarbyl (e.g.$C_{1-6}$alkyl, alkenyl, alkynyl, or haloalkyl) optionally substituted with $R^{16A}$, and —$(CH_2)_{r1}$-heterocyclyl optionally substituted with $R^{16A}$, wherein each $R^{16A}$ is independently selected from halogen, trifluoromethyl, cyano, thio, nitro, oxo, $=NR^{17A}$, $-OR^{17A}$, $-SR^{17A}$, $-C(O)R^{17A}$, $-C(O)OR^{17A}$, $-OC(O)R^{17A}$, $-NR^{17A}COR^{18A}$, $-NR^{17A}CON(R^{18A})_2$, $-NR^{17A}COR^{18A}$, $NR^{17A}CO_2R^{18A}$, $-S(O)R^{17A}$, $-S(O)_2R^{17A}$, $-SON(R^{17A})_2$, $-NR^{17A}S(O)_2R^{18A}$; $-CSR^{17A}$, $-N(R^{17A})R^{18A}$, $-C(O)N(R^{17A})R^{18A}$, $-SO_2N(R^{17A})R^{18A}$ and $R^{19A}$; $r_1$ is 0, 1, 2, 3, 4, 5 or 6;

wherein:

$R^{17A}$ and $R^{18A}$ are each independently selected from hydrogen or $R^{19A}$.

$R^{19A}$ is selected from hydrocarbyl (e.g. $C_{1-6}$alkyl, alkenyl, alkynyl, or haloalkyl), carbocyclyl and —$(CH_2)_{s1}$-heterocyclyl, and each $R^{19A}$ is optionally and independently substituted with one or more of halogen, cyano, amino, hydroxy, $C_{1-6}$alkyl and $C_{1-6}$alkoxy; and $s_1$ is 0, 1, 2, 3, 4, 5 or 6.

NMT inhibitors of Formula (III) and (VI) are further described in WO2010/026365. It will be understood that suitable and preferred NMT inhibitors of Formula (III) and (IV) of the present invention may therefore include any of the compounds disclosed in WO2010/026365.

Suitably, the NMT inhibitor is a compound of Formula (IIIa) shown below, or a pharmaceutically acceptable salt and/or solvate thereof:

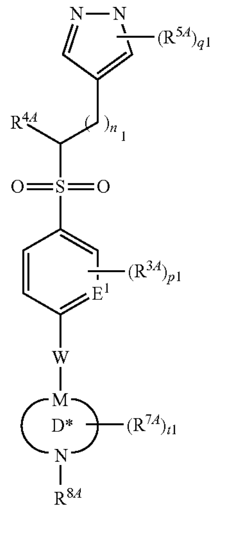

Formula (IIIa)

wherein:

$n_1$ is 0, 1, 2, 3, 4, 5 or 6;

$E^1$ is independently selected from C and N;

W is selected from a hydrocarbyl optionally substituted with $R^{11A}$, an optionally substituted aryl or heteroaryl group and a carbocyclyl optionally substituted with one or more of halogen, cyano, amino, hydroxy, $C_{1-6}$alkyl and $C_{1-6}$alkoxy groups;

M is selected from C and N;

$R^{3A}$, $R^{4A}$ and $R^{5A}$ are independently selected from hydrogen, $R^{12A}$, hydrocarbyl optionally substituted with $R^{12A}$, and $-(CH_2)_{L1}$-heterocyclyl optionally substituted with $R^{12A}$;

$L_1$ is 0, 1, 2, 3, 4, 5 or 6;

wherein each $R^{11A}$ and $R^{12A}$ is independently selected from halogen, trifluoromethyl, cyano, thio, nitro, oxo, $=NR^{13A}$, $-OR^{13A}$, $-SR^{13A}$, $-C(O)R^{13A}$, $-C(O)OR^{13A}$, $-OC(O)R^{13A}$, $-NR^{13A}COR^{14A}$, $-NR^{13A}CON(R^{13A})_2$, $-NR^{13A}COR^{14A}$, $-NR^{13A}CO_2R^{14A}$, $-S(O)^{13A}$, $-S(O)_2$, $R^{13A}$, $-SO_2N(R^{13A})_2$, $-NR^{13A}S(O)_2R^{14A}$; $-CSR^{13A}$, $-N(R^{13A})R^{14A}$, $-C(O)N(R^{13A})R^{14A}$, $-SO_2N(R^{13A})R^{14A}$ and $R^{15A}$;

$R^{13A}$ and $R^{14A}$ are each independently selected from hydrogen or $R^{15A}$;

wherein $R^{15A}$ is selected from hydrocarbyl, carbocyclyl and $-(CH_2)_{m1}$-heterocyclyl, and each $R^{15A}$ is optionally and independently substituted with one or more of halogen, cyano, amino, hydroxy, $C_{1-6}$alkyl and $C_{1-6}$alkoxy;

Ring D* is an optionally substituted nitrogen containing 6 or 7 membered heterocycle, wherein each substitutable carbon or nitrogen in Ring D* is optionally and independently substituted by one or more $R^{7A}$;

$R^{7A}$ is independently selected from hydrogen, $R^{20A}$, hydrocarbyl optionally substituted with $R^{20A}$, and $-(CH_2)_{V1}-$ heterocyclyl optionally substituted with $R^{20A}$;

$v_1$ is 0, 1, 2, 3, 4, 5 or 6;

wherein each $R^{20A}$ is independently selected from halogen, trifluoromethyl, cyano, thio, nitro, oxo, $=NR^{21A}$, $-OR^{21A}$, $-SR^{21A}$, $-C(O)R^{21A}$, $-C(O)OR^{21A}$, $-OC(O)R^{21A}$, $-NR^{21A}COR^{22A}$, $-NR^{21A}CON(R^{22A})_2$, $-NR^{21A}COR^{22A}$, $-NR^{21A}CO_2R^{22A}$, $-S(O)R^{21A}$, $-S(O)_2R^{21A}$, $-SON(R^{21A})_2$, $-NR^{21A}S(O)_2R^{22A}$; $-CSR^{21A}$, $N(R^{21A})R^{22A}$, $-C(O)N(R^{21A})R^{22A}$, $-SO_2N(R^{21A})R^{22A}$ and $R^{23A}$; wherein $R^{21A}$ and $R^{22A}$ are each independently selected from hydrogen or $R^{23A}$; wherein $R^{23A}$ is selected from hydrocarbyl, carbocyclyl and $-(CH_2)_{w1}$-heterocyclyl, and each $R^{23A}$ is optionally and independently substituted with one or more of halogen, cyano, amino, hydroxy, $C_{1-6}$alkyl and $C_{1-6}$alkoxy;

$w_1$ is 0, 1, 2, 3, 4, 5 or 6;

$R^{8A}$ is selected from the list of optional substituents represented by the group $R^{4A}$;

$m_1$ is 0, 1, 2, 3, 4, 5 or 6;

$p^1$ is 0, 1, 2, 3 or 4, wherein the values of $R^{4A}$ may be the same or different;

$q_1$ is 0, 1, 2, 3 or 4, wherein the values of $R^{5A}$ may be the same or different; and $t_1$ is 0, 1, 2, 3, 4, 5 or 6, wherein the values of $R^{7A}$ may be the same or different.

More suitably, the NMT inhibitor is a compound of Formula (IIIa) shown below, or a pharmaceutically acceptable salt and/or solvate thereof:

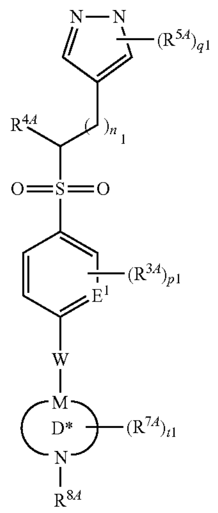

Formula (IIIa)

wherein:

$n_1$ is 0 or 1;

$E^1$ is C;

W is a (1-4C)hydrocarbyl, an aryl (e.g. phenyl) or heteroaryl group (e.g. pyridinyl);

M is selected from C and N;

$R^{3A}$, $R^{4A}$ and $R^{5A}$ are independently selected from hydrogen, $R^{12A}$, and (1-3C)hydrocarbyl optionally substituted with $R^{12A}$;

$R^{12A}$ is independently selected from halogen, trifluoromethyl, cyano, thio, nitro, oxo, $-OR^{13A}$, $-SR^{13A}$, $-C(O)R^{13A}$, $-C(O)OR^{13A}$, $-OC(O)R^{13A}$, $-NR^{13A}COR^{14A}$ and $R^{15A}$;

$R^{13A}$ and $R^{14A}$ are each independently selected from hydrogen or a (1-4C)hydrocarbyl (e.g. methyl);

Ring D* is an optionally substituted nitrogen containing 6 or 7 membered heterocycle, wherein each substitutable carbon or nitrogen in Ring D* is optionally and independently substituted by one or more $R^{7A}$;

$R^{7A}$ is independently selected from hydrogen, (1-4C) hydrocarbyl, halogen, trifluoromethyl, cyano, thio, nitro or oxo;

$R^{8A}$ is a hydrogen or a (1-4C)hydrocarbyl (e.g. methyl);

$p_1$ is 0, 1 or 2, wherein the values of $R^{4A}$ may be the same or different;

$q_1$ is 3, wherein the values of $R^{5A}$ may be the same or different; and $t_1$ is 0, 1 or 2, wherein the values of $R^{7A}$ may be the same or different.

In a particular embodiment, the NMT inhibitor is any one of the compounds shown in Table 1 of WO2010/026365.

In a further embodiment, the NMT inhibitor is a compound selected from:

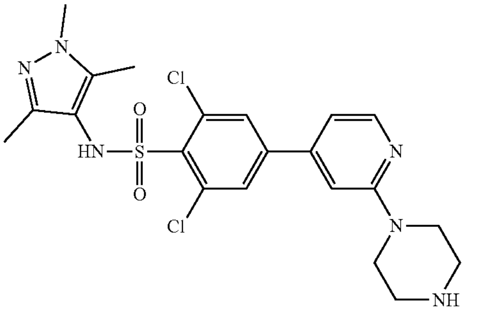
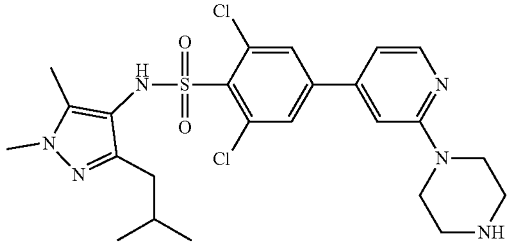
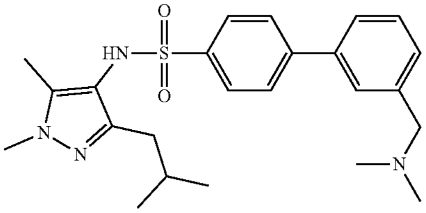
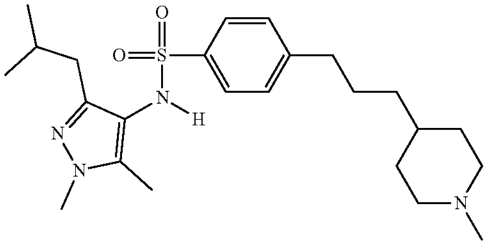
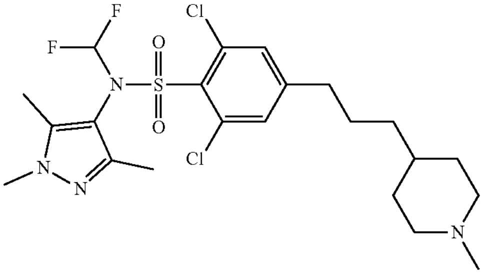
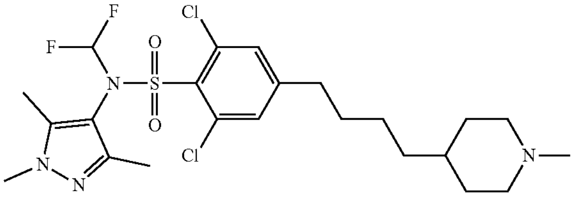
-continued
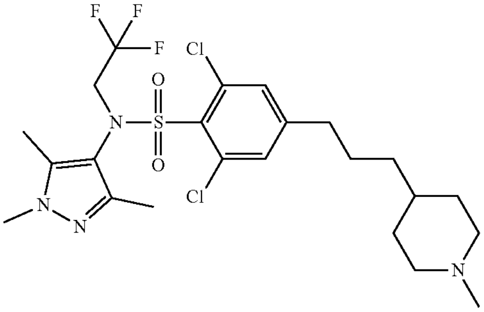
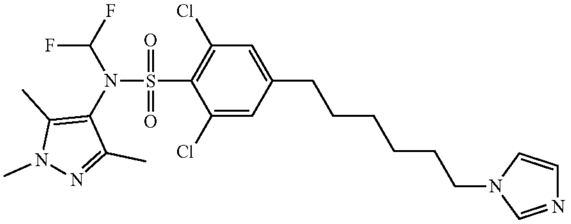
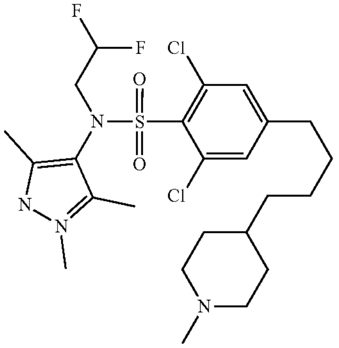
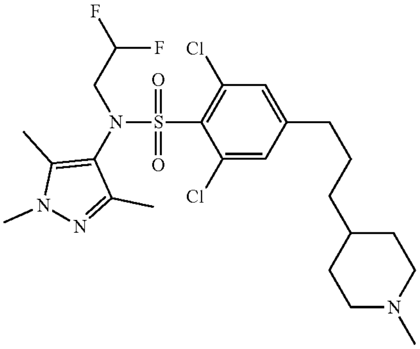
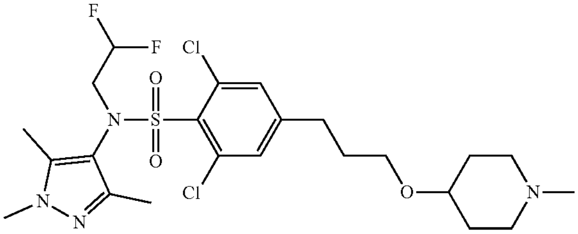
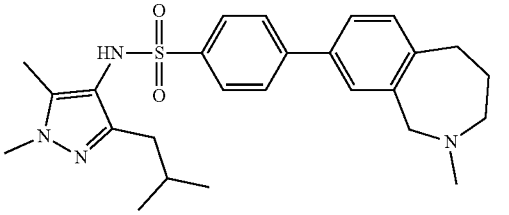 [SMILES: Cc1c(NS(=O)(=O)c2ccc(-c3ccc4c(c3)CN(C)CCC4)cc2)c(CC(C)C)nn1C]

or a pharmaceutically acceptable salt and/or solvate thereof.

In a further embodiment, the NMT inhibitor is a compound selected from:

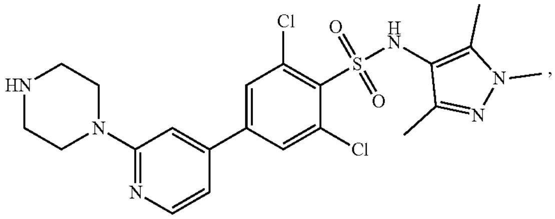
,

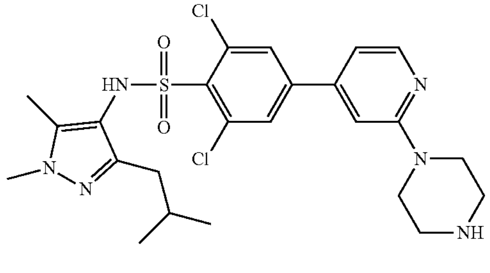

or a pharmaceutically acceptable salt and/or solvate thereof.

In a highly preferred embodiment, the NMT inhibitor is (2,6-dichloro-4-(2-piperazin-1-yl-pyridin-4-yl)-N-(1,3,5-trimethyl-1H-pyraxol-4-yl)-benzenesulfonamide):

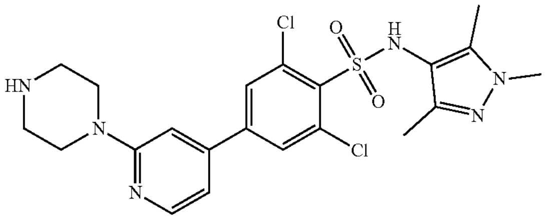 [SMILES: Cc1nn(C)c(C)c1NS(=O)(=O)c1c(Cl)cc(-c2ccnc(N3CCNCC3)c2)cc1Cl]

or a pharmaceutically acceptable salt and/or solvate thereof.

In another highly preferred embodiment, the NMT inhibitor is 2,6-dichloro-N-(5-isobutyl-1,3-dimethyl-1H-pyrazol-4-yl(-4-(2-piperazin-1-yl-pyridin-4-yl)-benzenesulfonamide:

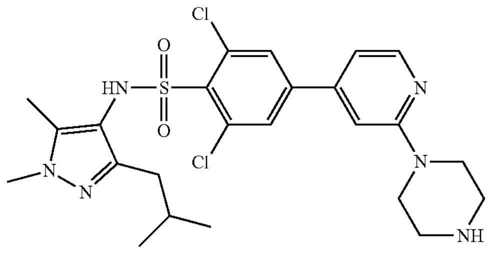 [SMILES: Cc1c(NS(=O)(=O)c2c(Cl)cc(-c3ccnc(N4CCNCC4)c3)cc2Cl)c(CC(C)C)nn1C]

or a pharmaceutically acceptable salt and/or solvate thereof.

Other Possible NMT Inhibitors

Other suitable NMT inhibitors may include, for example, any one of the compounds displaying activity as an inhibitor of N-myristoyl transferase (NMT) described in WO00/37464 (Roche) or WO2013/083991 (Imperial Innovations Limited).

In certain embodiments, the NMT inhibitor is any one of the compounds displaying activity as an inhibitor of N-myristoyl transferase (NMT) described in WO2013/083991. It will be appreciated that this embodiment encompasses both generic and specific compounds described in WO2013/083991.

In a particular embodiment, the NMT inhibitor of the present invention is any one of compounds 1-140 disclosed in WO2013/083991.

More generally, compounds may be identified as being NMT inhibitors, in particular inhibitors of human NMT1 (HsNMT1), and thus being of use according to the invention, using a sensitive fluorescence-based assay based on detection of CoA by 7-diethylamino-3-(4-maleimido-phenyl)-4-methylcoumarin, as described in Goncalves, V., et al., *Analytical Biochemistry,* 2012, 421, 342-344 and Goncalves, V., et al., *J. Med. Chem,* 2012, 55, 3578.

Suitably, the NMT inhibitors of use according to the invention may have inhibitory activity against NMT e.g. HsNMT1 in the above assay in terms of $IC_{50}$ value of less than 100 μM, such as less than 10 μM, for example less than 1 μM, in particular less than 0.1 μM, especially less than 0.01 μM.

Salts of the NMT inhibitors for use in the invention are those wherein a counter-ion is pharmaceutically acceptable. Suitable pharmaceutically acceptable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicar-boxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. For example, it may be the hydrochloric (HCl) salt.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The NMT inhibitor may possess one or more asymmetric centers; such compounds can therefore be produced as individual (R)- or (S)-stereoisomers or as mixtures thereof. It is to be understood that the NMT inhibitors for use in the present invention encompasses all optical, diastereoisomers and geometric isomers and mixtures thereof that possess NMT inhibition activity.

The present invention also encompasses NMT inhibitors as defined herein which comprise one or more isotopic substitutions. For example, H may be in any isotopic form, including 1H, 2H(D), and 3H (T); C may be in any isotopic form, including 12C, 13C, and 14C; and O may be in any isotopic form, including 16O and 18O; and the like.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al., Pharmaceutical Research, 1995. 12(7): p. 954-954, and Water-Insoluble Drug Formulation, $2^{nd}$ ed. R. Liu, CRC Press, page 553, which are incorporated herein by reference. Accordingly, it will be understood by the skilled person that the NMT inhibitors for use in the present invention may be present in the form of solvates, wherein the associated solvent is a pharmaceutically acceptable solvent. For example, a hydrate is an example of a pharmaceutically acceptable solvate.

It is also to be understood that the NMT inhibitors may exhibit polymorphism, and that the invention encompasses all such forms that possess the herein described activity.

The NMT inhibitors for use in the present invention may also exist in a number of different tautomeric forms and references to NMT inhibitors for use in the present invention include all such forms. For the avoidance of doubt, where a compound can exist in one of several tautomeric forms, and only one is specifically described or shown, all others are nevertheless embraced. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

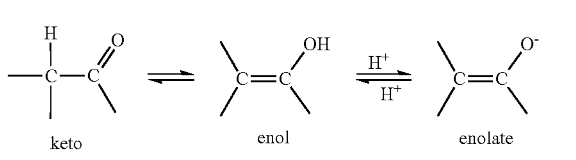

The NMT inhibitor for use in the present invention may be administered in the form of a pro-drug which is broken down in the human or animal body to release the NMT inhibitor for use in the present invention. A pro-drug may be used to alter the physical properties and/or the pharmacokinetic properties of the NMT inhibitor. A pro-drug can be formed when the NMT inhibitor contains a suitable group or substituent to which a property-modifying group can be attached. Examples of pro-drugs include in vivo cleavable ester derivatives that may be formed at a carboxy group or a hydroxy group in an NMT inhibitor for use in the present invention, and in-vivo cleavable amide derivatives that may be formed at a carboxy group or an amino group in an NMT inhibitor for use in the present invention.

Clauses

The invention may be further defined by the following clauses:

Clause 1. A NMT inhibitor for use in the prophylaxis or treatment of a senescence-associated disease or disorder.

Clause 2. Use of a NMT inhibitor in the manufacture of a medicament for the prophylaxis or treatment of a senescence-associated disease or disorder.

Clause 3. A method of prophylaxis or treatment of a senescence-associated disease or disorder by administering to a subject in need thereof, a therapeutically effective amount of a NMT inhibitor.

Clause 4. A pharmaceutical composition comprising a NMT inhibitor for use in the prophylaxis or treatment of a senescence-associated disease or disorder.

Clause 5. The pharmaceutical composition according to clause 4, wherein the composition comprises one or more therapeutic agents and/or one or more pharmaceutically acceptable excipients.

Clause 6. The NMT inhibitor, use, method or composition according to any one of clauses 1 to 5, wherein the senescence-associated disease or disorder is cancer, wherein said cancer comprises senescent cells.

Clause 7. The NMT inhibitor, use, method or composition according to clause 6, wherein cells of the cancer have been induced into senescence by treatment with a chemotherapeutic agent or radiotherapy.

Clause 8. The NMT inhibitor, use, method or composition according to clause 7, wherein the chemotherapeutic agent or radiotherapy is administered in an amount which induces senescence which is less than a therapeutically effective amount.

Clause 9. The NMT inhibitor, use, method or composition according to clause 7 or 8, wherein the chemotherapeutic agent is selected from aphidicolin, bleomycin, carboplatin, docetaxel, cisplatin, cyclophosphamide, 5-fluorouracil diaziquone, epigallocatechin gallate, etoposide, hydroxyurea, K858, lovastatin, MLN4924, pyrithione, resveratrol, retinols, TPA, PEP005, PEP008 and VO—OHpic.

Clause 10. The NMT inhibitor, use, method or composition according to clause 7 or 8, wherein the chemotherapeutic agent is a CDK4/6 inhibitor, such as ribociclib, abemaciclib, SHR6390, trilaciclib, lerociclib, palbociclib, PF-06873600, FCN-437c, BPI-16350, XZP-3287, HS-10342 and CS3002.

Clause 11. The NMT inhibitor, use, method or composition according to clause 8, wherein the chemotherapeutic agent is an aurora kinase inhibitor, such as barasertib, alisertib, danusertib, AT9283, PF-03814735, MLN8054 and AMG 900.

Clause 12. The NMT inhibitor, use, method or composition according to clause 8, wherein the chemotherapeutic agent is a Topo I or Topo II inhibitor, such as irinotecan, topotecan, camptothecin, diflomotecan, lamellarin D, etoposide, teniposide, doxorubicin, daunorubicin, mitoxantrone, amsacrine, ellipticines, aurintricarboxylic acid, and HU-331.

Clause 13. The NMT inhibitor, use method or composition according to any one of clauses 1 to 8, wherein the chemotherapeutic agent is bleomycin, doxorubicin, etoposide, palbociclib or cisplatin.

Clause 14. The NMT inhibitor, use, method or composition according to clause 6, wherein the cancer is a recurrent cancer or a metastatic cancer.

Clause 15. The NMT inhibitor, use, method or composition according to any one of clauses 1 to 5, wherein the senescence-associated disease or disorder is one or more side effects of chemotherapy or radiotherapy, wherein said chemotherapy or radiotherapy induce senescence.

Clause 16. The NMT inhibitor according to clause 15, wherein the one or more side effects are selected from weight loss, endocrine changes, hormone imbalance, changes in hormone signaling, cardiotoxicity, changes in body composition, a reduced ability to be physically active, gastrointestinal toxicity, nausea, vomiting, constipation, anorexia, diarrhea, peripheral neuropathy, fatigue, malaise, low physical activity, hematological toxicity, anemia, hepatotoxicity, alopecia, pain, infection, mucositis, fluid retention, dermatological toxicity, rashes, dermatitis, hyperpigmentation, urticaria, photosensitivity, nail changes, and mouth, gum and throat problems.

Clause 17. The NMT inhibitor, use, method or composition according to any one of clauses 1 to 5, wherein the senescence-associated disease or disorder is precancerous lesions.

Clause 18. A NMT inhibitor, or a pharmaceutically acceptable salt and/or solvate thereof, for use in combination with a chemotherapeutic agent or radiotherapy in the treatment of a cancer comprising senescent cells, wherein the NMT inhibitor and the chemotherapeutic agent or radiotherapy are administered simultaneously, sequentially or separately.

Clause 19. The NMT inhibitor, use, method or composition according to any one of clauses 1 to 5, wherein the senescence-associated disease or disorder is selected from a metabolic disease, an inflammatory or autoimmune disease or disorder, a cardiovascular disease or disorder, a pulmonary disease or disorder, a neurological disease or disorder, an eye disease or disorder, and a dermatological disease or disorder.

Clause 20. The NMT inhibitor, use, method or composition according to clause 19, wherein the senescence-associated disease or disorder is a metabolic disease.

Clause 21. The NMT inhibitor, use, method or composition according to clause 20, wherein the metabolic disease is selected from diabetes, diabetic ulcer, metabolic syndrome, and obesity.

Clause 22. The NMT inhibitor, use, method or composition according to clause 19, wherein the senescence-associated disease or disorder is an inflammatory or autoimmune disease or disorder.

Clause 23. The NMT inhibitor, use, method or composition according to clause 22, wherein the inflammatory or autoimmune disease or disorder is selected from osteoarthritis, osteoporosis, oral mucositis, inflammatory bowel disease, kyphosis, herniated intervertebral disc, systemic lupus erythematosus and lupus nephritis.

Clause 24. The NMT inhibitor, use, method or composition according to clause 19, wherein the senescence-associated disease or disorder is a cardiovascular disease or disorder.

Clause 25. The NMT inhibitor, use, method or composition according to clause 24, wherein the cardiovascular disease or disorder is selected from atherosclerosis, angina, arrhythmia, cardiomyopathy, congestive heart failure, coronary artery disease, carotid artery disease, endocarditis, coronary thrombosis, myocardial infarction, hypertension, aortic aneurysm, cardiac diastolic dysfunction, hypercholesterolemia, hyperlipidemia, mitral valve prolapse, peripheral vascular disease, cardiac stress resistance, cardiac fibrosis, brain aneurysm, and stroke.

Clause 26. The NMT inhibitor, use, method or composition according to clause 19, wherein the senescence-associated disease or disorder is a pulmonary disease or disorder.

Clause 27. The NMT inhibitor, use, method or composition according to clause 26, wherein the pulmonary disease or disorder is selected from pulmonary fibrosis, idiopathic pulmonary fibrosis, chronic obstructive pulmonary disease, asthma, cystic fibrosis, emphysema, bronchiectasis and age-related loss of pulmonary function.

Clause 28. The NMT inhibitor, use, method or composition according to clause 19, wherein the senescence-associated disease or disorder is a neurological disease or disorder.

Clause 29. The NMT inhibitor, use, method or composition according to clause 28, wherein the neurological disease or disorder is selected from Alzheimer's disease, Parkinson's disease, Huntington's disease, dementia, mild cognitive impairment, macular degeneration, and motor neuron dysfunction.

Clause 30. The NMT inhibitor, use, method or composition according to clause 19, wherein the senescence-associated disease or disorder is an eye disease or disorder.

Clause 31. The NMT inhibitor, use, method or composition according to clause 30, wherein the eye disease or disorder is selected from macular degeneration, glaucoma, cataracts, presbyopia, and vision loss.

Clause 32. The NMT inhibitor, use, method or composition according to clause 19, wherein the senescence-associated disease or disorder is dermatological disease or disorder.

Clause 33. The NMT inhibitor, use, method or composition according to clause 32, wherein the dermatological disease or disorder is selected from eczema, psoriasis, hyperpigmentation, nevi, rashes, atopic dermatitis, urticaria, diseases and disorders related to photosensitivity or photoaging, rhytides, pruritis, dysesthesia, eczematous eruptions, eosinophilic dermatosis, reactive neutrophilic dermatosis, pemphigus, pemphigoid, immunobullous dermatosis, fibrohistocytic proliferations of skin, cutaneous lymphomas, and cutaneous lupus.

Clause 34. The NMT inhibitor, use, method or composition according to any one of clauses 1 to 5, wherein the senescence-associated disease or disorder is an aging-related disease or disorder.

Clause 35. The NMT inhibitor, use, method or composition according to clause 34, wherein the aging-related disease or disorder is selected from renal disease, renal failure, chronic kidney disease, frailty, hearing loss, muscle fatigue, skin conditions, skin wound healing, liver fibrosis, non-alcoholic fatty liver disease, hepatic steatosis, pancreatic fibrosis, oral submucosa fibrosis, and sarcopenia.

Clause 36. A NMT inhibitor for use in prolonging the lifespan of a subject.

Clause 37. The NMT inhibitor according to clause 36, wherein the NMT inhibitor reduces the number of senescent cells in the subject.

Clause 38. A NMT inhibitor for use as a vaccine adjuvant.

Clause 39. The NMT inhibitor, use, method or composition according to any one of clauses 1 to 38, wherein the NMT inhibitor is a compound of formula (I):

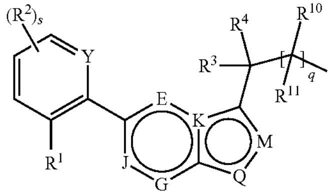

(I)

wherein:

Y is selected from the group consisting of —CH—, —C($R^2$)— and —N—;

$R^1$ is a group of formula —X-L-A;

X represents —O—;

L represents —$(CH_2)_m$—;

m is 1, 2 or 3;

A is a 6-10-membered aromatic carbocycle or a 5-10-membered aromatic heterocycle, said aromatic carbocycle or heterocycle being optionally substituted with 1, 2, or 3 substituents each independently selected from the group consisting of —F, —Cl, —Br, —$OCH_3$, —$OCF_3$, —CN, —$C_{1-6}$alkyl optionally substituted by up to 3 halogen, hydroxyl, or —$OC_{1-4}$alkyl groups, —S(O)$C_{1-4}$alkyl, —$S(O)_2C_{1-4}$alkyl, —C(O)N$(R^9)_2$, —C(O)N($R^{13}$)$C_{1-4}$alkyl$OC_{1-4}$alkyl, —C(O)N($C_{1-4}$alkyl$OC_{1-4}$alkyl$)_2$, —CH-2C(O)N$(R^9)_2$, —$CH_2$C(O)N($R^{13}$)$C_{1-4}$alkyl$OC_{1-4}$alkyl, —$CH_2$C(O)N($C_{1-4}$alkyl$OC_{1-4}$alkyl$)_2$, —$S(O)_2NHC_{1-4}$alkyl, —$S(O)_2$N($C_{1-4}$alkyl$)_2$, —$NHC_{1-4}$alkyl, —N($C_{1-4}$alkyl$)_2$, —NHC(O)$C_{1-4}$alkyl, —NHC(O)$CF_3$, —NHS$(O)_2$$C_{1-4}$alkyl, $CH_2N(R^{13})_2$, $CH_2N(R^{13})C(O)C_{1-4}$alkyl, $CH_2N(R^{13})S(O)_2C_{1-4}$alkyl, —$CH_2S(O)_2C_{1-4}$alkyl, and $CO_2H$;

s is 0, 1, 2, or 3;

each $R^2$ is independently selected from the group consisting of —F, —C, —Br, —$OCH_3$, —$OCF_3$, —CN, —$C_{1-4}$alkyl optionally substituted by up to 3 halogen or hydroxyl groups, —S(O)$C_{1-4}$alkyl, —$S(O)_2C_{1-4}$alkyl, —$S(O)_2NHC_{1-4}$alkyl, —$S(O)_2$N($C_{1-4}$alkyl$)_2$, —$NHC_{1-4}$alkyl, —N($C_{1-4}$alkyl$)_2$, —NHC(O)$C_{1-4}$alkyl, —NHC(O)$CF_3$, and —$NHS(O)_2C_{1-4}$alkyl;

q is 0 or 1;

$R^3$ is hydrogen or methyl; $R^4$ is hydrogen or methyl;

$R^5$ is hydrogen or $C_{1-6}$alkyl optionally substituted by up to 3 —F, —Cl, —Br, —OH, —$OCH_3$, —$OCF_3$ or —CN groups; $R^6$ is hydrogen or $C_{1-6}$alkyl optionally substituted by up to 3 —F, —Cl, —Br, —OH, —$OCH_3$, —$OCF_3$ or —CN groups; or the $R^5$ and $R^6$ groups and the N they are bonded to form a 4 to 7 membered non-aromatic heterocycle, the heterocycle optionally comprising 1 or 2 further heteroatoms selected from N, O and S, optionally substituted by up to 3 —F, —Cl, —Br, —OH, —$OCH_3$, —$OCF_3$ or —CN groups;

when present $R^{10}$ is hydrogen or methyl;

when present $R^{11}$ is hydrogen or methyl;

or the $R^3$ group and the $R^5$ group and the intervening atoms form a 3 to 7 membered non-aromatic heterocycle composed of the intervening atoms and bond, or the intervening atoms and —$(CHR^a)_r$—; or the $R^{10}$ group and the $R^5$ group and the intervening atoms form a 3 to 7 membered non-aromatic heterocycle composed of the intervening atoms and —$(CHR^a)_r$;

r is 1, 2, 3, 4 or 5; $R^a$ is hydrogen or methyl;

each $R^7$ is independently selected from the group consisting of hydrogen, halogen, $C_{1-4}$alkoxy, and $C_{1-4}$alkyl optionally substituted with 1, 2 or 3 halogens; and $R^8$ is selected from the group selected from hydrogen and $C_{1-4}$alkyl;

each $R^9$ is independently selected from the group consisting of hydrogen and $C_{1-4}$alkyl, or two $R^9$ groups and the N they are bonded to form a 4 to 7 membered non-aromatic heterocycle, the heterocycle optionally comprising 1 or 2 further heteroatoms selected from N, O and S;

each $R^{13}$ is independently selected from the group consisting of hydrogen and $C_{1-4}$alkyl; and wherein i) E, J and G are each C($R^7$), K is carbon, Q is N($R^8$), and M is nitrogen;

ii) E, J and G are each C($R^7$), and K, Q and M are each nitrogen; or iii) E, J, G and M are each C($R^7$), and K and Q are each nitrogen;

or a pharmaceutically acceptable salt and/or solvate thereof.

Clause 40. The NMT inhibitor, use, method or composition according to clause 39, wherein the NMT inhibitor is a compound of formula (IA^^):

(IA^^)

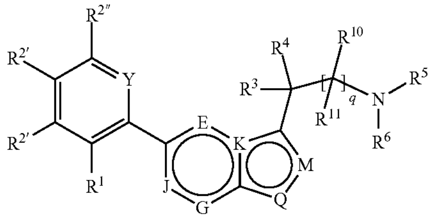

wherein:

$R^1$ is a group of formula —X-L-A;

A is 4-pyrazolyl, said pyrazolyl being optionally substituted with up to 3 substituent groups selected from methyl and —C(O)N$(CH_3)_2$;

X is —O—;

L is —$(CH_2)_m$—;

m is 2;

$R^{2'}$ is selected from the group consisting of fluorine or chlorine (preferably fluorine);

$R^{2''}$ is selected from the group consisting of hydrogen, fluorine or chlorine;

q is 0;

$R^3$ is hydrogen or methyl;

$R^4$ is hydrogen or methyl;

$R^5$ is hydrogen or methyl;

$R^6$ is hydrogen or methyl; or the $R^3$ group and the $R^5$ group and the intervening atoms form a 3 to 7 membered non-aromatic heterocycle composed of the intervening atoms and bonds, (more preferably $R^5$ and $R^6$ are both methyl);

E, J, G, K, Q and M are:

i) E, J and G are each CH, K is carbon, Q is N($R^8$), M is nitrogen; and $R^8$ is hydrogen or methyl; or ii) E, J, G and M are each CH, and K and Q are each nitrogen;

with the proviso that A is substituted with no more than one —C(O)N$(CH_3)_2$ group;

or a pharmaceutically acceptable salt and/or solvate thereof.

Clause 41. The NMT inhibitor, use, method or composition according to clause 40, wherein the NMT inhibitor is 1-(5-(3,4-difluoro-2-(2-(1,3,5-trimethyl-1H-pyrazol-4-yl)ethoxy)phenyl)-1-methyl-1H-indazol-3-yl)-N,N-dimethylmethanamine:

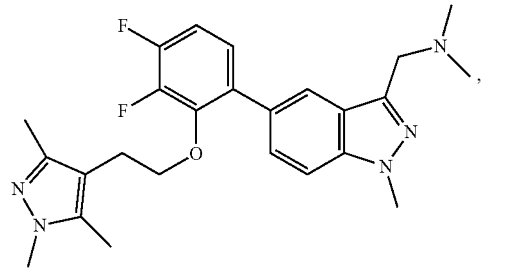 [SMILES: Cc1nn(C)c(C)c1CCOc1c(-c2ccc3c(c2)c(CN(C)C)nn3C)ccc(F)c1F]

or a pharmaceutically acceptable salt and/or solvate thereof.

Clause 42. The NMT inhibitor, use, method or composition according to any one of clauses 1 to 38, wherein the NMT inhibitor is a compound of formula (II):

(II)

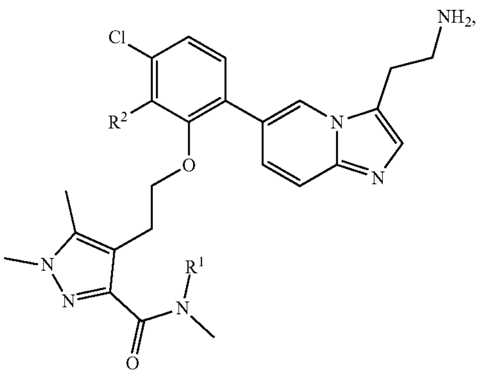

wherein:

$R^1$ is H or —$CH_3$; and $R^2$ is H or F;

or a pharmaceutically acceptable salt and/or solvate thereof.

Clause 43. The NMT inhibitor, use, method or composition according to clause 42, wherein the NMT inhibitor is 4-(2-{2-[3-(2-aminoethyl)imidazo[1,2-a]pyridin-6-yl]-5-chlorophenoxy}ethyl)-N,N,1,5-tetramethyl-1H-pyrazole-3-carboxamide:

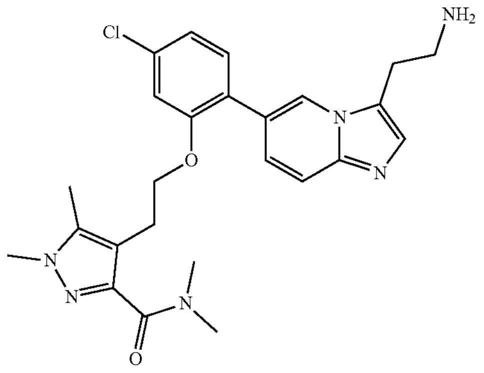 [SMILES: Cc1c(CCOc2cc(Cl)ccc2-c2ccc3ncc(CCN)n3c2)c(C(=O)N(C)C)nn1C]

or a pharmaceutically acceptable salt and/or solvate thereof.

Clause 44. The NMT inhibitor, use, method or composition any one of clauses 1 to 38, wherein the NMT inhibitor is a compound of formula (III) or (IV):

(III)

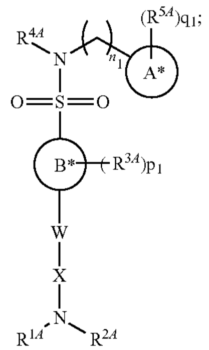

or (IV)

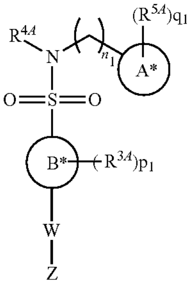

wherein:

$n_1$ is 0, 1, 2, 3, 4, 5 or 6;

Ring A*, is an optionally substituted nitrogen containing aryl group wherein each substitutable carbon or nitrogen in Ring A* is optionally and independently substituted by one or more $R^{5A}$ and wherein if Ring A* contains an —NH— moiety that nitrogen may be optionally substituted by $C_{1-6}$alkyl (e.g. methyl); and wherein $R^{4A}$ and Ring A* together with the atoms to which they are attached may form a cyclic group, Ring B* is an optionally substituted aryl or heteroaryl group wherein each substitutable carbon or heteroatom in Ring B* is optionally and independently substituted by one or more $R^{3A}$.

W and X, one of which may be absent, are independently selected from $R^{11A}$, hydrocarbyl (e.g. $C_{1-8}$ alkyl, alkenyl, alkynyl, or haloalkyl) optionally substituted with $R^{11A}$, and —$(CH_2)_{k1}$-heterocyclyl optionally substituted with $R^{12A}$; $k_1$ is 0, 1, 2, 3, 4, 5 or 6;

$R^{1A}$, $R^{2A}$, $R^{3A}$, $R^{4A}$ and $R^{5A}$ are independently selected from hydrogen, $R^{12A}$, hydrocarbyl (e.g. $C_{1-6}$ alkyl, alkenyl, alkynyl, or haloalkyl) optionally substituted with $R^{12A}$, and a —$(CH_2)_{L1}$— heterocyclyl optionally substituted with one or more $R^{12A}$; wherein $R^{1A}$ and $R^{2A}$ taken together with the atoms to which they are attached may form a heterocycle, optionally substituted with one or more $R^{12A}$wherein $R^{1A}$ and/or $R^{2A}$ taken together with W or X may form a heterocycle optionally substituted with one or more $R^{12A}$; and wherein one or more of $R^{3A}$ and $R^{5A}$ taken together with the atoms to which they are attached may form a carbocycle, for example heterocyclyl, optionally substituted with $R^{12A}$; $L_1$ is 0, 1, 2, 3, 4, 5 or 6;

wherein:

each $R^{11A}$ and $R^{12A}$ is independently selected from halogen, trifluoromethyl, cyano, thio, nitro, oxo, $=NR^{13A}$, $—OR^{13A}$, $—SR^{13A}$, $—C(O)R^{13A}$, $—C(O)OR^{13A}$, $—OC(O)R^{13A}$, $—NR^{13A}COR^{14A}$, $—NR^{13A}CON(R^{13A})_2$, $—NR^{13a}COR^{14a}$, $—NR^{13a}CO_2R^{14A}$, $—S(O)R^{13A}$, $—S(O)_2R^{13A}$, $—SON(R^{13A})_2$, $—NR^{13A}S(O)_2R^{14A}$; $—CSR^{13A}$, $—N(R^{13A})R^{14A}$, $—C(O)N(R^{13A})R^{14A}$, $—SO_2N(R^{13A})R^{14A}$ and $R^{15A}$;

$R^{13A}$ and $R^{14A}$ are each independently selected from hydrogen or $R^{15A}$;

$R^{15A}$ is selected from hydrocarbyl (e.g. $C_{1-6}$alkyl, alkenyl, alkynyl, or haloalkyl), carbocyclyl and $—(CH_2)_{m1}$-heterocyclyl, and each $R^{15A}$ is optionally and independently substituted with one or more of halogen, cyano, amino, hydroxy, $C_{1-6}$alkyl or cycloalkyl and $C_{1-6}$alkoxy;

$m_1$ is 0, 1, 2, 3, 4, 5 or 6;

$p_1$ is 0, 1, 2, 3 or 4; the values of $R^{4A}$ may be the same or different; and $q_1$ is 0, 1, 2, 3 or 4; wherein the values of $R^{5A}$ may be the same or different;

Y and Z, one or both of which may be absent, are independently selected from hydrogen, $R^{16A}$, hydrocarbyl (e.g. $C_{1-6}$alkyl, alkenyl, alkynyl, or haloalkyl) optionally substituted with $R^{16A}$, and $—(CH_2)_{r1}$-heterocyclyl optionally substituted with $R^{16A}$, wherein each $R^{16A}$ is independently selected from halogen, trifluoromethyl, cyano, thio, nitro, oxo, $=NR^{17A}$, $—OR^{17A}$, $—SR^{17A}$, $—C(O)R^{17A}$, $—C(O)OR^{17A}$, $—OC(O)R^{17A}$, $—NR^{17A}COR^{18A}$, $—NR^{17A}CON(R^{18A})_2$, $—NR^{17A}COR^{18A}$, $—NR^{17A}CO_2R^{18A}$, $—S(O)R^{17A}$, $—S(O)_2R^{17A}$, $—SON(R^{17A})_2$, $—NR^{17A}S(O)_2R^{18A}$; $—CSR^{17A}$, $—N(R^{17A})R^{18A}$, $—C(O)N(R^{17A})R^{18A}$, $—SO_2N(R^{17A})R^{18A}$ and $R^{19A}$; $r_1$ is 0, 1, 2, 3, 4, 5 or 6;

wherein:

$R^{17A}$ and $R^{18A}$ are each independently selected from hydrogen or $R^{19A}$;

$R^{19A}$ is selected from hydrocarbyl (e.g. $C_{1-6}$alkyl, alkenyl, alkynyl, or haloalkyl), carbocyclyl and $—(CH_2)_{s1}$-heterocyclyl, and each $R^{19A}$ is optionally and independently substituted with one or more of halogen, cyano, amino, hydroxy, $C_{1-6}$alkyl and $C_{1-6}$alkoxy; and $s_1$ is 0, 1, 2, 3, 4, 5 or 6;

or a pharmaceutically acceptable salt and/or solvate thereof.

Clause 45. The NMT inhibitor, use, method or composition according to clause 44, wherein the NMT inhibitor is a compound of formula (IIIa):

(IIIa)

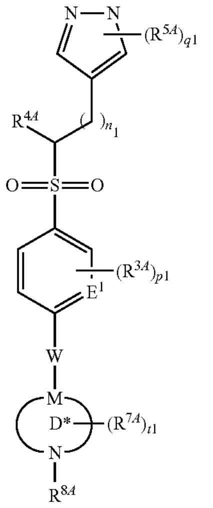

wherein:

$n_1$ is 0 or 1;

$E^1$ is C;

W is a (1-4C)hydrocarbyl, an aryl (e.g. phenyl) or heteroaryl group (e.g. pyridinyl);

M is selected from C and N;

$R^{3A}$, $R^{4A}$ and $R^{5A}$ are independently selected from hydrogen, $R^{12A}$, and (1-3C)hydrocarbyl optionally substituted with $R^{12A}$;

$R^{12A}$ is independently selected from halogen, trifluoromethyl, cyano, thio, nitro, oxo, $—OR^{13A}$, $SR^{13A}$, $—C(O)R^{13A}$, $—C(O)OR^{13A}$, $—OC(O)R^{13A}$, $—NR^{13A}COR^{14A}$ and $R^{15A}$;

$R^{13A}$ and $R^{14A}$ are each independently selected from hydrogen or a (1-4C)hydrocarbyl (e.g. methyl);

Ring D* is an optionally substituted nitrogen containing 6 or 7 membered heterocycle, wherein each substitutable carbon or nitrogen in Ring D* is optionally and independently substituted by one or more $R^{7A}$;

$R^{7A}$ is independently selected from hydrogen, (1-4C) hydrocarbyl, halogen, trifluoromethyl, cyano, thio, nitro or oxo;

$R^{8A}$ is a hydrogen or a (1-4C)hydrocarbyl (e.g. methyl);

$p_1$ is 0, 1 or 2, wherein the values of $R^{4A}$ may be the same or different;

$q_1$ is 3, wherein the values of $R^{5A}$ may be the same or different; and $t_1$ is 0, 1 or 2, wherein the values of $R^{7A}$ may be the same or different.

Clause 46. The NMT inhibitor, use, method or composition according to clause 45, wherein the NMT inhibitor is (2,6-dichloro-4-(2-piperazin-1-yl-pyridin-4-yl)-N-(1,3,5-trimethyl-1H-pyraxol-4-yl)-benzenesulfonamide):

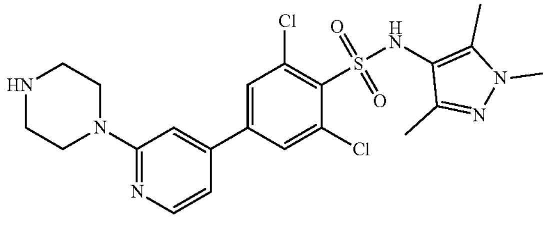 [SMILES: Cc1nn(C)c(C)c1NS(=O)(=O)c1c(Cl)cc(-c2ccnc(N3CCNCC3)c2)cc1Cl]

or a pharmaceutically acceptable salt and/or solvate thereof.

Clause 47. The NMT inhibitor, use, method or composition according to clause 45, wherein the NMT inhibitor is 2,6-dichloro-N-(5-isobutyl-1,3-dimethyl-1H-pyrazol-4-yl(-4-(2-piperazin-1-yl-pyridin-4-yl)-benzenesulfonamide:

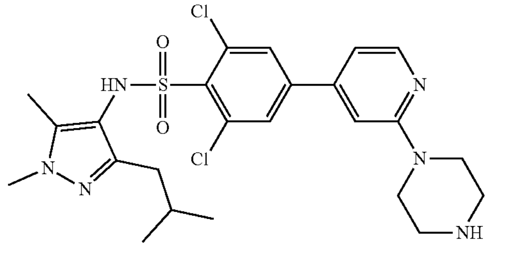 [SMILES: Cc1c(NS(=O)(=O)c2c(Cl)cc(-c3ccnc(N4CCNCC4)c3)cc2Cl)c(CC(C)C)nn1C]

Synthesis of NMT Inhibitors

The NMT inhibitors for use in the present invention can be prepared by any suitable technique known in the art. Particular processes for the preparation of the NMT inhibitors described herein may be found in WO00/37464 (Roche), WO2010/026365 (University of Dundee), WO2013/083991 (Imperial Innovations Limited), WO2017/001812 (Imperial Innovations Limited), WO2020/128473 (Imperial College Innovations Limited), and WO2020/128475 (Imperial College Innovations Limited).

In the description of the synthetic methods described herein and in any of the references noted above, it is to be understood that all proposed reaction conditions, including choice of solvent, reaction atmosphere, reaction temperature, duration of the experiment and workup procedures, can be selected by a person skilled in the art.

Numerous synthetic routes to the NMT inhibitors described herein can be devised by a person skilled in the art and the exemplified synthetic routes described in the above references do not limit the invention. Many methods exist in the literature for the synthesis of heterocycles, for example: Joule, J. A.; Mills, K., Heterocyclic Chemistry, 2010, 5th Edition, Pub. Wiley.

Synthesis of Example Compounds 1 to 3

Throughout the accompanying Examples section and throughout the specification as a whole, reference to Compounds 1, 2 and/or 3 will be understood to be a reference to the compound(s) shown below:

Compound 1

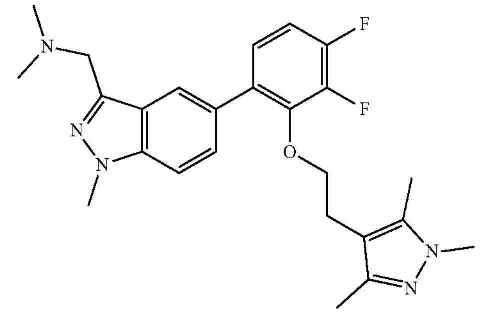

(1-(5-(3,4-difluoro-2-(2-(1,3,5-trimethyl-1H-pyrazol-4-yl)ethoxy)phenyl)-1-methyl-1H-indazol-3-yl)-N,N-dimethylmethanamine)

-continued

Compound 2

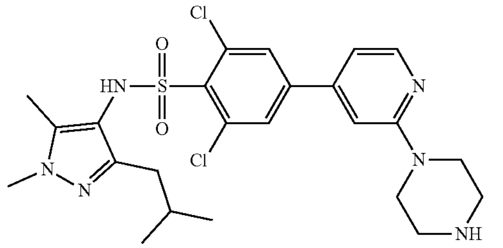

2,6-dichloro-N-(5-isobutyl-1,3-dimethyl-1H-pyrazol-4-yl(-4-(2-piperazin-1-yl-pyridin-4-yl)-benzenesulfonamide Compound 3

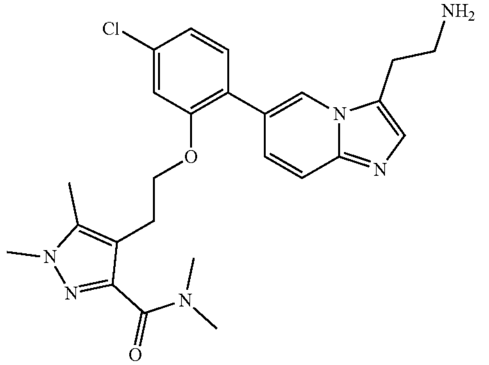 [SMILES: Cc1c(CCOc2cc(Cl)ccc2-c2ccc3ncc(CCN)n3c2)c(C(=O)N(C)C)nn1C]

(4-(2-{2-[3-(2-aminoethyl)imidazo[1,2-a]pyridin-6-yl]-5-chlorophenoxy}ethyl)-N,N,1,5-tetramethyl-1H-pyrazole-3-caboxamide)

Compound 1 may be prepared using the synthetic procedures described in WO2017/001812. For the avoidance of doubt, Compound 1 of the present invention corresponds to Example 49 of WO2017/001812. Compound 2 may be prepared using the synthetic procedure described in WO2010/026365. For the avoidance of doubt, Compound 2 of the present invention corresponds to the compound DDD86481 of WO2010/026365. Compound 3 may be prepared using the synthetic procedure described in WO2020/128473. For the avoidance of doubt, Compound 3 corresponds to Example 1 of WO2020/128473.

Biological Data

Abbreviations

4OHT 4-hydroxy-tamoxifen
ATCC American Type Culture Collection
BrdU 5-Bromo-2'-deoxyuridine
COPI coat protein complex I
DAPI 4',6-Diamidino-2-Phenylindole
DMEM Dulbecco's modified eagle medium
FBS Foetal bovine serum
FFPE Formalin-fixed paraffin-embedded
FITC Fluorescein Isothiocyanate
Gluc Gaussia luciferase
HDTVI Hydrodynamic tail vein injection
i.p. intraperitoneally
NMT N-Myristoyltransferase
NMTi N-Myristoyltransferase inhibitors
OCT Optimal cutting temperature
OIS Oncogene induced senescence
PBS Phosphate Buffer Solution
PFA Paraformaldehyde
TIS Therapy induced senescence
UPR unfolded protein response Materials and Methods Culturing Mammalian Cell Lines IMR90 human diploid fibroblasts (ATCC CCL-186), SK-HEP-1 hepatic adenocarcinoma (ATCC HTB-52), MCF7 (ATCC HTB-22) and HCT-116 colorectal carcinoma (ATCC CCL-247) cell lines were obtained from American Type Culture Collection (ATCC®). Under normal culture conditions the above cell lines were maintained on Dulbecco's modified eagle medium (DMEM) (Gibco®) supplemented 1% 100× Gibco® Antimycotic-antibiotic and 10% (v/v) Foetal bovine serum (FBS) (Labtech—Batch 41213, South American Origin) hereinafter referred to as DM10 media.

Passaging of cells was performed by enzymatic detachment using 0.05% Trypsin-EDTA (Gibco®) on cells for 5 minutes followed by inactivation in DM10 media and centrifugation at 200 g for 5 min. Supernatant was aspirated to remove dead cells and debris and pellet resuspended in fresh DM10. Cell viability and counts were determined by flow cytometry on a Guava EasyCyte platform (Millipore®) using Guava ViaCount Reagent to provide stains of dying and nucleated cells. In-built GuavaSoft software was used to gate live cells and remove cell debris/dead cells from final cell count. Experiments using IMR90 cells or cell lines generated from them were carried out using cells between passage 10 to 14 with viability above 90%.

Primary cells and cell lines underwent cryopreservation for long term storage. To cryopreserve cells were detached, pelleted and resuspended in DM10 media supplemented with 10% DMSO as a cryoprotectant and immediately transferred to cryovials placed in a Nalgene® MrFrosty™ freezing container at −80° C. Freezing container would then provide cooling at 1° C./min allowing for gradual temperature reduction of the cells. After 24 hours, cryovials were transferred to liquid nitrogen storage tanks for long term storage. Revival of cells from −80° C. or liquid nitrogen was performed by thawing in a 37° C. water bath and diluting in DM10 media, followed by centrifugation and resuspension again in fresh DM10 media to remove DMSO. After 24 hours, media was replaced and cells allowed to rest an additional 48-72 h before plating experiments.

Generation of Cell Stocks & Senescence Induction

Figure 4A:
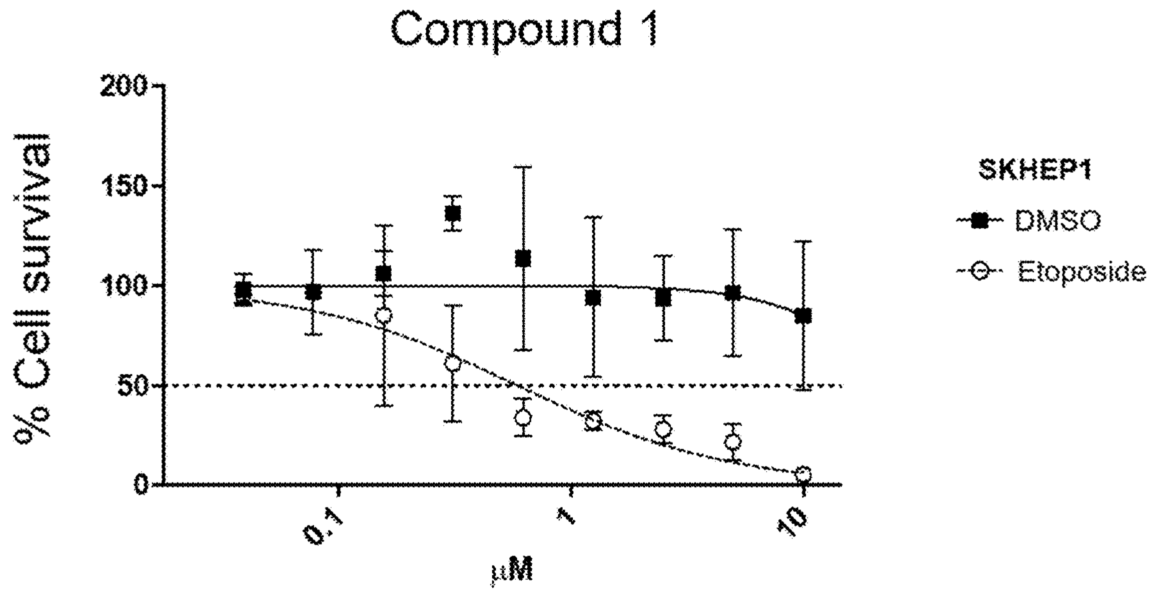
FIGS. 4A-C: Illustrate that Compounds 1 to 3 selectively eliminate SKHEP1 cells induced to senescence by etoposide over non-senescent cells (DMSO control).
Figure 4B:
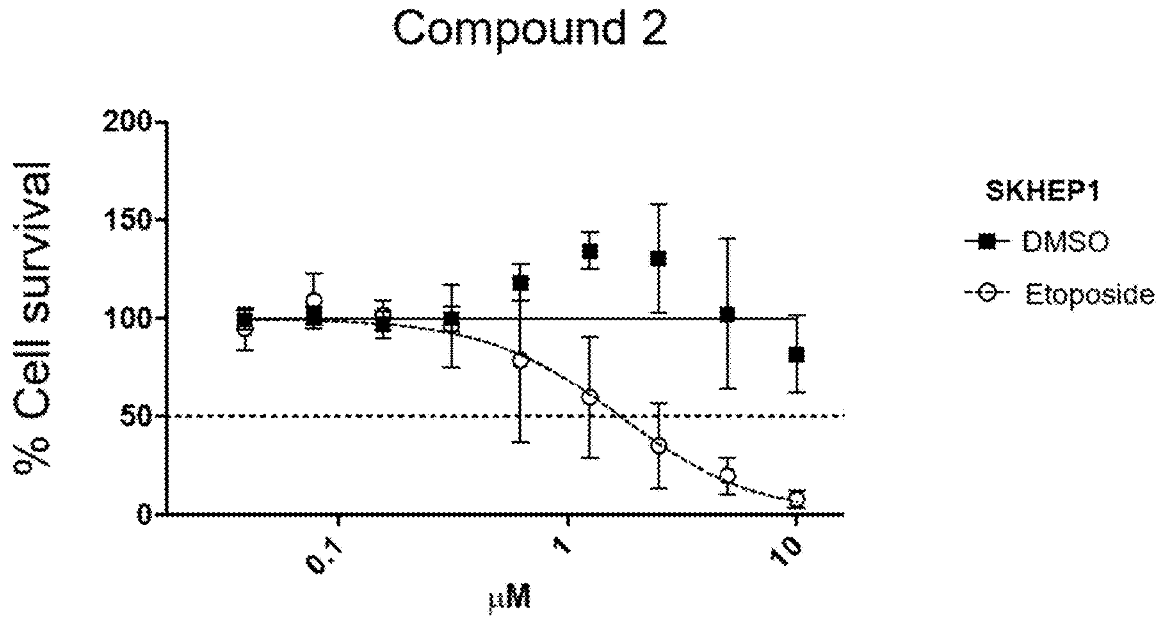
Figure 4C:
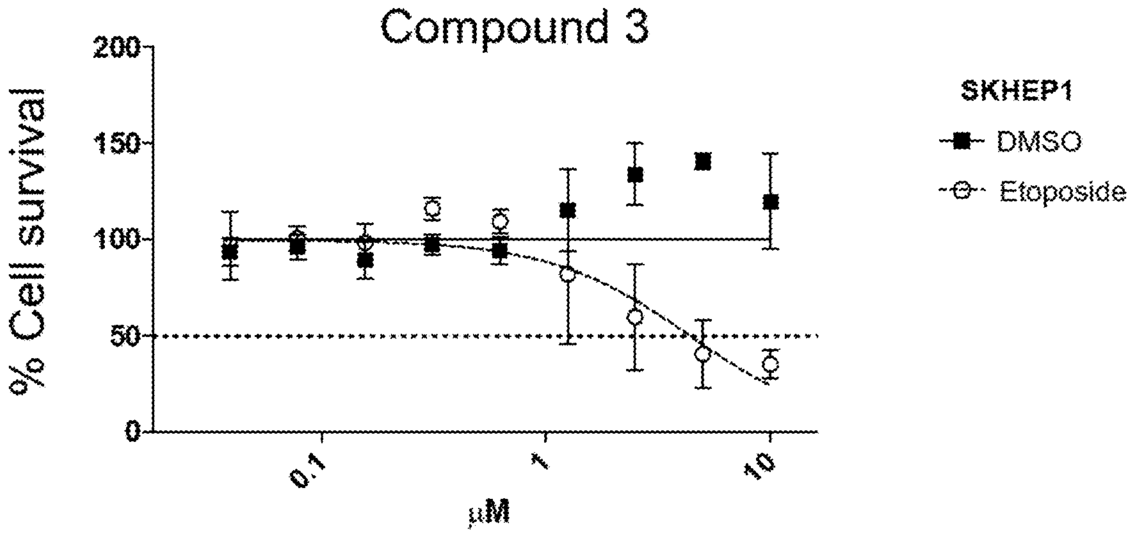

IMR90 cells were used to generate inducible ER:RAS (hereinafter iRAS) cells to model Oncogene induced senescence (OIS), through retroviral infection of pLNC-ER:RAS-neo into IMR90 cells followed by selection with Neomycin. IMR90 cells containing the pLNC-ER:RAS plasmid backbone pLXSN were infected in parallel to assess leakiness in the pLNC-ER:RAS system. Treatment with 100 nM 4OHT (Sigma, in DMSO) was used to induce IMR90 ER:RAS cells to undergo oncogene induced senescence (OIS). Therapy induced senescence (TIS) was induced in IMR90 cells by treatment with 33 μM (50 ug/ml) bleomycin sulphate (Generon, HY-17565) for 24 hours, 20 μM palbociclib (Selleckchem, S1116) for 7 days or 100 nM doxorubicin (Cayman chemical, 15007) for 7 days. Senescence was induced in SK-HEP-1 cells by treatment with 2 μM etoposide (Sigma-Aldrich, E1383) for 7 days (FIGS. 4A-C). HCT-116 senescence was induced by 250 nM treatment with doxorubicin (Cayman chemical, 15007) for 48 hours followed by 5 days culture in media without chemotherapy (FIG. 5), or by treatment with 100 nM doxorubicin, 2 μM etoposide or 100 μM cisplatin for 3 days followed by 4 days culture in media without chemotherapy (FIGS. 6A-7C). Senescence was induced in MCF7 by 200 nM treatment with doxorubicin for 7 days, 2 μM etoposide for 7 days or 10 μM cisplatin for 7 days (FIGS. 8A-9C).

Growth/Survival Assays

Colony formation assays—to assess senescence induction were performed by seeding 0.08-0.12×$10^6$ IMR90 or IMR90 ER:RAS cells in 10 cm dishes, cells were then induced to senescence and cultured for 10-14 days or until DMSO treated—proliferating cells had reached 80-90% confluency. To assess senolysis, cells were seeded in 10 cm plates at high density; 0.5-0.8×$10^6$ for IMR90 or ER:RAS, 0.015×$10^6$ for DMSO treated or 0.08×$10^6$ for etoposide treated SK-HEP-1 cell lines and 0.0075×$10^6$ for DMSO or treated 0.08×$10^6$ for doxorubicin treated HCT-116 cell lines. Plates were cultured for 7 days and then media changed to low serum media with 0.5% FBS (hereinafter DM0.5) to induce quiescence in DMSO treated cells and to not underestimate potential non-senescent cell toxicity. Senolytic drugs were added at their indicated concentration in DMSO (<5% v/v final concentration) and cultured for a further 3 days. If longer drug treatment was required fresh drug and media was added on day 3 and cultured for a further 4 days. Upon experiment endpoint plates were then fixed with 0.5% (w/v, PBS) glutaraldehyde (Sigma) for 1 hour, washed twice with $dH_2O$ and left to dry overnight. Dried plates were then stained with a 0.2% (w/v, PBS) solution of crystal violet for 1 hour, washed 3 times with $dH_2O$ and left to air dry overnight. Plates were then imaged using HP Scanjet4850 photo scanner.

BrdU Incorporation—Cell proliferation was assessed through incorporation of nucleotide analogue 5-Bromo-2'-deoxyuridine (BrdU) into cells. 2×$10^3$ or 8×$10^3$ IMR90 cells were seeded into 96-well plates in duplicate for DMSO/palbociclib treated and bleomycin/doxorubicin treated cells respectively. 10 μM BrdU was added to cells 18 h before desired time point and wells were then washed in PBS and fixed using 4% paraformaldehyde (w/v, PBS) for 45 minutes to 1 hour before removal and washing 3 times with PBS. BrdU incorporation was assessed via immunofluorescence and high-content analysis (see section 'Immunofluorescence & High throughput microscopy').

High-throughput microscopy survival assay—To assess senolytic effect of drugs, cells were cultured for 7 days, culture media was changed to DM0.5 media and drugs in DMSO were added (<5% v/v final concentration), drugs were replenished after 3 days if assay length was longer than 72 h. Wells were fixed in 4% PFA for 1 hour at day 10 to 14, washed 3 times with PBS and then stained with 1 μg/mL DAPI (w/v, PBS) for 10 minutes. Wells were then washed 3 times with PBS. Optionally plates could be stored at 4° C. for up to 2 weeks and DAPI stained. Image acquisition of DAPI stained cells was performed on an automated InCell Analyser 2000 (GE Healthcare®) and high-content analysis on the InCell Investigator 2.7.3 software used to quantify number of DAPI positive cells per well. A top-hat method was used to segment cell-nuclei based on DAPI stained area and a minimum nuclear area threshold of 80 μm used to exclude debris. For cancer cell lines, nuclear area threshold was reduced to 40 μm. Survival was measured as cell counts relative to DMSO treated quiescent or senescent cells.

Immunofluorescence & High Throughput Microscopy

Immunofluorescence staining was carried out by first fixing wells of 96 well plate at desired timepoint for 1 hour using 4% PFA (w/v, in PBS) followed by washing 3 times with PBS. Wells were then permeabilized using 0.2% Triton® X-100 (v/v, PBS) for 10 min or with 0.5% Triton® X-100 (v/v, PBS) for COPI staining. Wells were then washed twice with PBS to halt permeabilization and then non-specific antibody binding blocked by incubation with a blocking solution for 1 hour at RT. Blocking solution contained 1% BSA (w/v, PBS) supplemented with 0.4% Fish Skin Gelatin (v/v, PBS). Primary antibodies were diluted in respective blocking solution (see 'Antibodies' for dilutions), blocking solution removed from well and incubated with primary antibody solution for 1 hour at RT. For BrdU staining primary antibody solution is supplemented with 0.5 U/ul DNase (Sigma) and 1 mM $MgCl_2$ and incubation times reduced to 30 minutes. Following incubation, primary antibody was then removed by washing 3 times with PBS. Secondary antibodies conjugated to Alexa-594 or Alexa-488 fluorophores were then diluted in blocking solution added to wells to be incubated in dark for 1 hour. Secondary antibody was then removed by washing 3 times with PBS and nuclei counterstaining with 1 μg/mL DAPI (w/v, PBS) for 10 minutes. Wells were then washed with PBS three times.

Immunofluorescence image acquisition was performed using an automated InCell Analyzer 2000 high-throughput microscope. Multiple 96-well plates were placed into stacks from which a KiNEDx Robotic arm (PAA) running Overlord™ software so that plates could be sequentially loaded, imaged and removed with the InCell microscope. Wells were imaged using a 20× objective except for wells stained only with DAPI or Golgi-related staining, which were performed at 10× and 40× respectively. 2×2 binning of images were used to reduce image file sizes. Fluorophores were imaged using pre-set 'DAPI', 'Texas Red' & 'FITC' wavelengths on microscope for DAPI stain, AlexaFluor® 594 and AlexaFluor® 488 respectively. 8, 24 & 18 fields per well were captured for 10×, 20× and 40× objectives respectively.

High content image analysis was carried out using the InCell Investigator 2.7.3 software (GE Healthcare®). DAPI nuclear counterstain was used to segment cells using a Top-hat method and used to provide a mask for nuclear localized stains. For cytoplasmic stains a 6 μm collar was applied around the cell and for detection of cytoplasmic organelles such as Golgi, a 'region growing' collar was used. Quantification for nuclear staining was measured as average pixel intensity (grey scale) for the wavelength of fluorophore across the area of the nuclear mask. Cytoplasmic staining quantification was of either the average pixel intensity or the coefficient of variance of pixel intensities within collar area. Golgi structural analysis utilized a multiscale top-hat segmentation method to detect organelle structures between 1 and 3 pixels in size within a region growing collar.

Mouse Models & Treatments

All mice were purchased from Charles River UK, Ltd. For Hydrodynamic tail vein injection (HDTVI) experiments female C57BL/6J mice aged 5-6 weeks were given 20 μg of $Nras^{G12V}$ & *gaussia* luciferase (Gluc) expressing plasmid and 5 μg of SB13 transposase-expressing plasmid. Plasmids were prepared using GeneElute HP Endotoxin-free Plasmid Maxiprep kit (Sigma). Purified plasmids were diluted in sterile-filtered PBS to a total volume of 10% mouse body weight and injected into mouse lateral tail vein within a 10 s window. 4 days after HDTVI, mice were bled to assess presence of *gaussia* luciferase signal in the blood serum and used to randomize/equalize groupings for vehicle and drug treated groups. On day 5 mice were given 25 mg/kg of Compound 3 (n=9) or Vehicle (n=9) (10 mM Na2HPO4-7H2O & NaH2PO4H2O buffer, 0.2% Tween-80, pH 7.4) intraperitoneally (i.p.) daily for 4 days and every 48 hours' blood collected for assessment of serum *gaussia* signal. 24 hours after last drug injection mice were culled and livers collected for paraffin embedding and frozen in Optimal cutting temperature (OCT) using liquid $N_2$.

For aging experiments C57BL/6J female mice aged 109-111 weeks were injected with 10 mg/kg of Compound 2 (n=6; 4 $p16^{+/+}$ and 2 $p16^{+/luc}$ (Burd et al., Cell. 2013 Jan. 17; 152(1-2):340-51.) (dissolved by cold water bath sonication in vehicle) or Vehicle (n=6; 4, $p16^{+/+}$ and 2, $p16^{+/luc}$) (5% DMSO, 20% PEG400, 10 mM $Na_2HPO_4$-$7H_2O$ & $NaH_2PO_4H_2O$ buffer, 0.5% Tween-80, pH 7.3) i.p. daily for 5 days, then given three rounds of 2 day rest period and 3 day daily i.p. Mice were then allowed to rest for 6 days before physiological assessments (see 'blood chemistry & immune cell composition analysis') and then culled, collecting organs for freezing in OCT, paraffin embedding and collecting blood for serum-isolation.

For follow-up aging experiments C57BL/6JRccHsd female mice aged 63-67 weeks old were injected with Vehicle (n=20) (10 mM $Na_2HPO_4$-$7H_2O$ & $NaH_2PO_4H_2O$ buffer, 0.2% Tween-80, pH 7.4), 10 mg/kg Compound 2 (n=20) (5% DMSO, 20% PEG400, 10 mM $Na_2HPO_4$-$7H_2O$) & $NaH_2PO_4H_2O$ buffer, 0.5% Tween-80, pH 7.3, dissolved by cold water bath sonication), or Compound 3 (n=20) (10 mM $Na_2HPO_4$-$7H_2O$ & $NaH_2PO_4H_2O$ buffer, 0.2% Tween-80, pH 7.4) i.p. daily for 3 days, then given four rounds of 4 week rest period and 3 day daily i.p. injection. Blood was collected prior to each round of injection for physiological assessments. Mice were allowed to rest 4 weeks prior to being culled and organs collected for freezing in OCT, paraffin embedding and snap-freezing for RNA extraction.

For high-fat diet experiments C57BL/6J male mice aged 8-weeks old were placed on Chow or high-fat diet (kcal 40% fat (non-trans-fat Primex Shortening), kcal 20% fructose, 2% cholesterol, D1602230i) for 4 weeks prior to first round of injections. Mice were then injected with Vehicle (Chow diet, n=15) (high-fat diet, n=15) (10 mM $Na_2HPO_4$-$7H_2O$ & $NaH_2PO_4H_2O$ buffer, 0.2% Tween-80, pH 7.4) or 10 mg/kg Compound 2 (high-fat diet, n=15) (5% DMSO, 20% PEG400, 10 mM $Na_2HPO_4$-$7H_2O$) & $NaH_2PO_4H_2O$ buffer, 0.5% Tween-80, pH 7.3, dissolved by cold water bath sonication) i.p. daily for 3 days, then given 2 rounds of 4 week rest period and 3 day daily i.p. injection. Blood was collected prior to each round of injection for physiological assessments. Mice were allowed to rest 4 weeks prior to being culled and organs collected for freezing in OCT, paraffin embedding, blood collection for physiological measurements and tissue snap-freezing for RNA extraction.

All mouse procedures were performed under licence, according to UK Home Office Animals (Scientific Procedures) Act 1986 and local institutional guidelines (Imperial College ethical review committee).

Blood Chemistry & Immune Cell Composition Analysis

For analysis of immune cell composition in whole blood, tail-vein blood was collected 2 days after last treatment. Whole blood was diluted in saline to a volume of 200 mL and ran on a Sysmex XE2100 automated cell counter. Blood glucose levels were determined by collecting whole-blood from tail vein into heparinised tubes (Abraxis), 120-140 μL of whole-blood to be loaded onto a comprehensive diagnostic profile reagent rotor (Abraxis) and run on a VetScan VS2 Chemistry Analyzer (Abraxis: 500-7123).

Immunohistochemistry (IHC)

Tissue Processing—Organs/specimens were fixed in 4% PFA overnight before being transferred to 70% Ethanol. Tissue processing prior to paraffin-embedding was performed on a Sakura Tissue-Tek VIP®6 automated tissue processor. Briefly, specimens in embedding cassettes were dehydrated by progressing through steps of 70% Ethanol for 45 min at 37° C., 80% Ethanol for 45 min at 37° C., 90% Ethanol for 30 min at 37° C., 96% Ethanol for 45 min at 37° C., 100% Ethanol for 30 min at 37° C., 100% Ethanol for 1 hr at 37° C., 100% Ethanol for 1 hr at 37° C. Dehydrated samples are then cleared by three washes in Xylene for 30 min, 45 min and 1 hr at 37° C. Finally, specimens are infiltrated by two immersions in 62° C. paraffin wax for 45 min and 1 hr, followed by two immersions in 62° C. paraffin wax for 30 min. Specimen was then embedded in paraffin-block on an embedding centre (Leica EG1160 Embedding Center) and 4 μm sections made using ThermoFisher scientific Microtome Microm HM355S and attached to slides.

Immunohistochemical staining—Slides were deparaffinised by washing slides twice in Histoclear™ for 5 min each, followed by 5 min washes in decreasing concentrations of ethanol with 100%, 75%, 50% & 25% ethanol washes before a final wash 5 min in $dH_2O$. Heat induced epitope retrieval (HIER) was then performed in pressure cooker for 20 min using either antigen-unmasking solution, Citrate-based at pH 6.0 (VectorLab H-3300-250) or antigen-unmasking solution, Tris-based at pH 9.0 (VectorLab H-3301-250) depending on antibody manufacturers' instructions. Following HIER, slides were cooled on ice for 10 min and then washed in PBS for 5 min. For intracellular stains, sections were permeabilized with 0.2% Triton X-100 in PBS for 10 min and washed twice in PBS for 5 min. For NRAS staining in liver slides were washed in 0.1% $H_2O_2$ in PBS for 15 min followed by washing twice in PBS to reduce endogenous peroxide activity. Sections were marked using hydrophobic pen and Non-specific antigen binding was blocked by incubating slides with CAS-Block™ Histochemical reagent (ThermoFisher, 008120) for 30-45 min in a humidified chamber. Slides were then incubated with primary antibody overnight in a humidified chamber at 4° C. For experiments utilising p21 antibody, slides were incubated with primary p21 antibody (p21 [EPR18021], Abcam, 1:200) overnight in a humidified chamber at 4° C. Slides were washed twice in PBS for 5 min and incubated with secondary antibody SignalStain® Boost IHC detection reagent Mouse/Rabbit, HRP (Cell Signalling Technology, 8125) for 30-45 min. Next, slides were washed twice in PBS for 5 min and incubated for 2-10 min with SignalStain® DAB substrate kit (CST, 8059) to detect HRP signal. Signal development was stopped when visible positive cells could be detected on a microscope, by washing slides in $dH_2O$. To counterstain DAB signal, slides were incubated for 30 s in Modified Mayer's Hematoxylin (Lillie's Modification) (DAKO), washed in $dH_2O$, and incubated for 30 s in 0.05% Ammonium solution (PBS) followed by washing in $dH_2O$. Prior to mounting coverslips with VectaMount aqueous mounting media (VectorLab, H-5501-60) slides were dehydrated by washing 1 min in 75% Ethanol, 5 min in 100% Ethanol and 5 min in Histoclear®.

Slide image acquisition & analysis—Slides were acquired using a 20× brightfield objective on a Zeiss Axio Scan Z.1 slide scanner and analysis performed using QuPath version 0.2.0-m9 using in built positive cell detection tool to segment Haematoxylin stained nuclei and quantify mean intensity of DAB.

Cytochemical Senescence Associated-β-Galactosidase Assay

Lung and liver samples frozen in optimal cutting temperature (OCT) were cryosectioned (15 μM) and frozen sections fixed in ice-cold 0.5% Glutaraldehyde (w/v, PBS) for 15 min and washed 1 mM $MgCl_2$/PBS (pH 6.0) for 5 min. β-galactosidase activity was stained for with X-gal staining solution (1 mg $ml^{-1}$ X-gal, ThermoFisher Scientific, 5 mM $K_3(Fe(CN)_6)$, 5 mM $K_4(Fe(CN)_6)$) for 18 h at 37° C. Slides were dehydrated and coverslips mounted prior to being imaged using 20× brightfield objective on Zeiss AxioScan Z.1 slide scanner. ImageJ was used to quantify staining by measuring the β-gal stained area as a percentage of the total tissue area excluding luminal spaces.

Oil Red O Staining

Oil Red O staining for lipids was carried out on liver tissue in OCT was snap-frozen in liquid $N_2$ and cryosectioned (15 μM). Sections were equilibrated to RT for 10 min and then stained with 0.5% Oil Red O solution (w/v, in isopropanol, Sigma, O1391) for 5 min, rinsed in tap water and counterstained with Mayer's hematoxylin for 30 s. Then sections were again rinsed in tap water for 30 min and coverslips mounted. Images were acquired on Zeiss AxioScan Z.1 and ImageJ quantification of Oil-red stain area relative to background tissue area performed for 3 fields per section.

Sirius red staining was carried out for collagen I/III fibre containing connective tissue on paraffin embedded sections using Pico-Sirius Red Stain Kit (Abcam, ab150681). Priorto staining, sections were deparaffinised in Histoclear and graded ethanol washes as described above (see Immunohistochemical staining) and hydrated in distilled water. Sections were then incubated with Pico-Sirius red solution for 60 min at Rt and then rinsed twice with 0.5% glacial acetic acid solution (in dH2O). Excess water was then removed by shaking slides and then rinsing in 100% ethanol. Sections were then dehydrated by two washes 100% ethanol for 2 min each and two washes in Histoclear for 2 min each. Coverslips were mounted and slides imaged on Zeiss AxioScan Z.1. Staining was quantified across 3 random fields from each tissue slide by thresholding collagen-stained area for detection of fibres (red) and measuring this area relative to the total cytoplasmic area (yellow).

For extraction of total RNA from cells, 6-well plates were scraped in 800 μL of TRIzol® reagent (Invitrogen), mixed with 160 μL of Chloroform (Sigma), vortexed and centrifuged as stated above. Aqueous phase was then transferred to a new tube and processed from step 2 onwards of manufacturer's instructions for RNAeasy® Mini Kit (Qiagen).

RNA-Seq and GSEA

Total RNA from tissues was bulk extracted by way of bead disruption in 800 μL of TRIzol® reagent (Invitrogen) using TissueLyser (Qiagen) followed by further homogenization using QIAshredder kit (Qiagen) according to manufacturer's instructions. Homogenized tissue in TRIzol® was then mixed with 160 μL of Chloroform (Sigma) and vortexed for 15 s, then centrifuged at 15,000 rpm at 4° C. for 30-45 min. Top aqueous phase containing RNA was then column purified using RNAeasy® Mini Kit (Qiagen) and subjected to DNase treatment as per manufacturer's instructions. RNA concentration was determined using NanoDrop® ND-1000 UV-Vis spectrophotometer at 260 nm wavelength.

Total RNA extracted and purified from tissues or from cell extraction was analysed on a 2100 Bioanalyzer (Agilent) using RNA 6000 Nano Kit (Agilent) to verify RNA purity and integrity prior to library preparation. RNA from tissue samples with an RNA integrity number (RIN) corresponding to the ratio of 18S to 28S rRNA peaks on bioanalyzer trace of less than 3 were not submitted for library processing. Library preparation to generate cDNA was performed by MRC-LMS genomics core facility with 200 ng of starting RNA using the NEBNext® Poly(A) mRNA magnetic isolation kit (NEB, E7490) to isolate mRNA from total RNA sample. Purified samples were then processed using the NEBNext® Ultra™ II. Directional RNA Library Prep Kit for illumina (NEB, E7760). Libraries were then assessed on a 2100 Bioanalyzer and concentration determined using a Qubit® Fluorometer and the Qubit dsDNA HS Assay kit (Thermo Scientific™) Indexed libraries were then run on 2 lanes of a NextSeq 2000 sequencer (Illumina) with >10 million single end 75 bp reads being generated per sample.

Human RNA-seq reads were assessed for quality using FASTQC and then aligned to human genome hg19 by Tophat (v. 2.0.11) using '-library-type-fr-firststrand' parameters along with gene annotation from Ensembl (v.67). Mouse RNA-seq reads were assessed for quality using FASTQC and then aligned to mouse genome mm9 by Tophat (v. 2.0.11) using '-library-type-fr-firststrand' parameters along with gene annotation from Ensembl (v.67). Expression levels were determined Gene set enrichment analysis (GSEA) was carried out on the differential expression between vehicle and drug treated aged tissues using "wald statistics" parameters in DESeq2 and all curated gene sets in MSigDB.

RNA Extraction and Quantitative Real Time-PCR

Total RNA from lung or liver tissue was extracted by mechanical disruption in 800 μL of TRIzol® reagent (Invitrogen) using a microsample homogenizer (Precellys) according to manufacturer's instructions. RNA concentration was determined using NanoDrop® ND-1000 UV-Vis spectrophotometer at 260 nm wavelength. cDNA was synthesized using the SuperScript™ III Reverse Transcriptase (Thermo Fisher, Waltham, MA, USA). mRNA expression analysis was performed using real-time quantitative PCR (RT-qPCR) (PowerUp™ SYBR® Green Master Mix, Applied Biosystems, Foster City, CA, USA) run on a CFX96™ Real-Time PCR Detection system (Bio-Rad). Relative gene expression was determined using ΔΔCt method by measuring RT-qPCR signal relative to signal of housekeeping gene, Actb for lung or Hrpt for liver tissue.

mouse monoclonal anti-DNA damage-inducible transcript 3 protein (CHOP) (L63F7, Cell Signalling Technology) 1:1000, rabbit polyclonal anti-X-box-binding protein 1 (XBP1) (Abcam, ab37152) 1:200, rabbit monoclonal anti-p21 (EPR18021, Abcam) 1:700, rabbit polyclonal anti-Cyclic AMP-dependent transcription factor ATF-6 alpha (ATF6) (Abcam, ab37149) 1:500, goat polyclonal anti-interleukin-6 (IL-6) (R&D systems, AF-206-NA) 1:200 (1:40 for Therapy-induced senescence), mouse monoclonal anti-interleukin-8 (IL-8) (6217, R&D systems), goat anti-mouse immunoglobulin (Ig)G (heavy plus light (H+L)), AlexaFluor 594 conjugated, Thermo Fisher Scientific, A11029) 1:2000, goat anti-mouse IgG (H+L), AlexaFluor 594 conjugated, Thermo Fisher Scientific, A11032) 1:2000, goat anti-rabbit IgG (H+L, AlexaFluor 594 conjugated, Thermo Fisher Scientific, A11037), donkey anti-sheep IgG (H+L), AlexaFluor 594 conjugated, Thermo Fisher Scientific, A11016) 1:2000, goat anti-rabbit IgG-horseradish peroxidase (Santa Cruz, sc-2004) 1:5000, goat anti-mouse IgG-horseradish peroxidase (Santa Cruz, sc-2005) 1:5000.

Biological Example 1: Determining the Senolytic Activity of NMT Inhibitors in Primary Cells Oncogene-Induced Senescence To understand whether N-myristoylation could be a liability of senescent cells, IMR90 ER:RAS cells were treated with 100 nM 4OHT (to activate ER:RAS and induce OIS), or DMSO (as a control). 7 days after induction, the indicated concentrations of Compounds 1 to 3 were added. To determine senolytic activity of NMT inhibitors, 7 days after adding the drugs with replenishment after 3 days, cells were fixed, imaged and cells numbers were quantified using high throughput microscopy. Survival is shown as a measure of Sequence of qRT-PCR primers

| Target | Species | Forward primer | SEQ ID NO: | Reverse primer | SEQ ID NO: |
|---|---|---|---|---|---|
| Actin b | Mouse | ATGGAGGGGAATACAGCCC | 1 | TTCTTTGCAGCTCCTTCGTT | 2 |
| Col3a1 | Mouse | ACAGCAAATTCACTTACACAG TTC | 3 | CTCATTGCCTTGCGTGTTT | 4 |
| Col6a3 | Mouse | ACTGGAACCACGGAAGTTCA | 5 | GTCACTTCCAACATCGAGGC | 6 |
| CXCL5 | Mouse | TGATCGCTAATTTGGAGGTGA | 7 | TGGATCCAGACAGACCTCCT | 8 |
| MMP3 | Mouse | TGATGAACGATGGACAGAG | 9 | TTGGCTGAGTGGTAGAGTCC | 10 |
| MMP12 | Mouse | CACTTCCCAGGAATCAAGCCT | 11 | TTTGGTGACACGACGGAACA | 12 |
| Tgf-β | Mouse | CGGAGAGCCCTGGATACCA | 13 | ACTTCCAACCCAGGTCCTTC | 14 |
| Pai-1 | Mouse | CCAACATCTTGGATGCTGAA | 15 | GCCAGGGTTGCACTAAACAT | 16 |
| α-SMA | Mouse | CCCAAAGCTAACCGGGAGAAG | 17 | CCAGAATCCAACACGATGCC | 18 |
| Hprt | Mouse | CACAGGACTAGAACACCTGC | 19 | GCTGGTGAAAAGGACCTCT | 20 |
| Col1a1 | Mouse | GAGAGGTGAACAAGGTCCCG | 21 | AAACCTCTCTCGCCTCTTGC | 22 |
| Col4a1 | Mouse | CTGGCACAAAAGGGACGAG | 23 | ACGTGGCCGAGAATTTCACC | 24 |

Antibodies

Figure 1B:
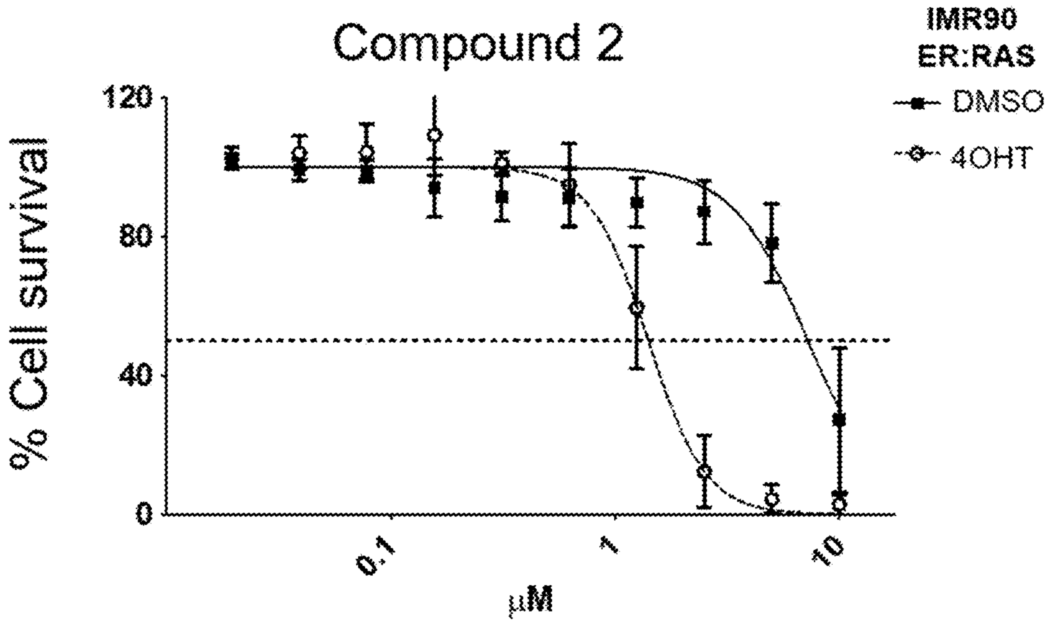
Figure 1C:
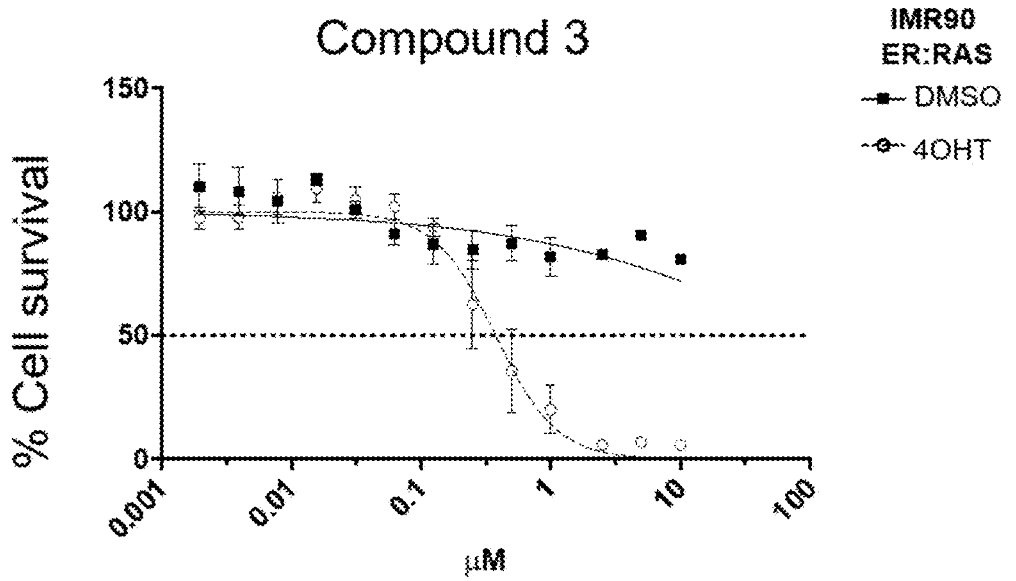

The following antibodies were used in this study: rabbit polyclonal anti-p21 (M-19; Santa Cruz, sc-471) 1:200, mouse monoclonal anti-N-Ras (F155, Santa Cruz, sc-31) 1:100, sheep polyclonal anti-Trans-Golgi network integral membrane protein 2 (TGN46) (BioRad, AHP500G) 1:400, cell counts relative to drug vehicle (DMSO) treated 4OHT cells (n=8) and control cells (n=8). Data is shown as mean±SD, n represents independent biological experiments. The results indicate that Compounds 1 to 3 preferentially kill cells undergoing OIS, therefore behaving as senolytics (FIGS. 1A-C).

Bleomycin- and Doxorubicin-Induced Senescence

To understand whether the senolytic effect of NMT inhibitors was only observed in cells undergoing OIS, NMT inhibitors were tested in cells undergoing senescence in response to other stresses.

Bleomycin-Induced Senescence

Figure 2A:
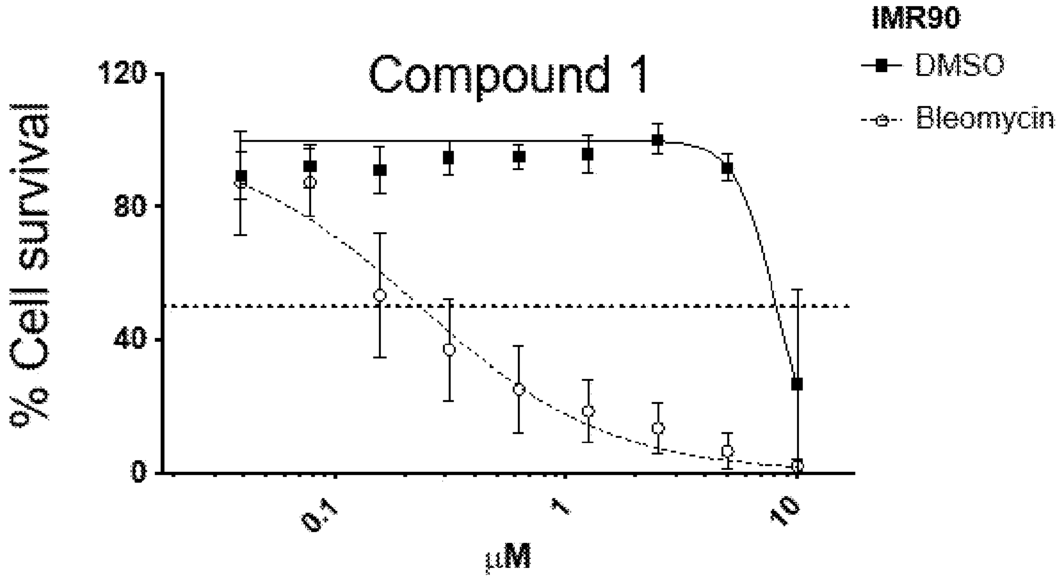
FIGS. 2A-C: Illustrate that Compounds 1 to 3 selectively eliminate IMR90 ER:RAS cells induced to senescence by bleomycin over non-senescent cells (DMSO control).
Figure 2B:
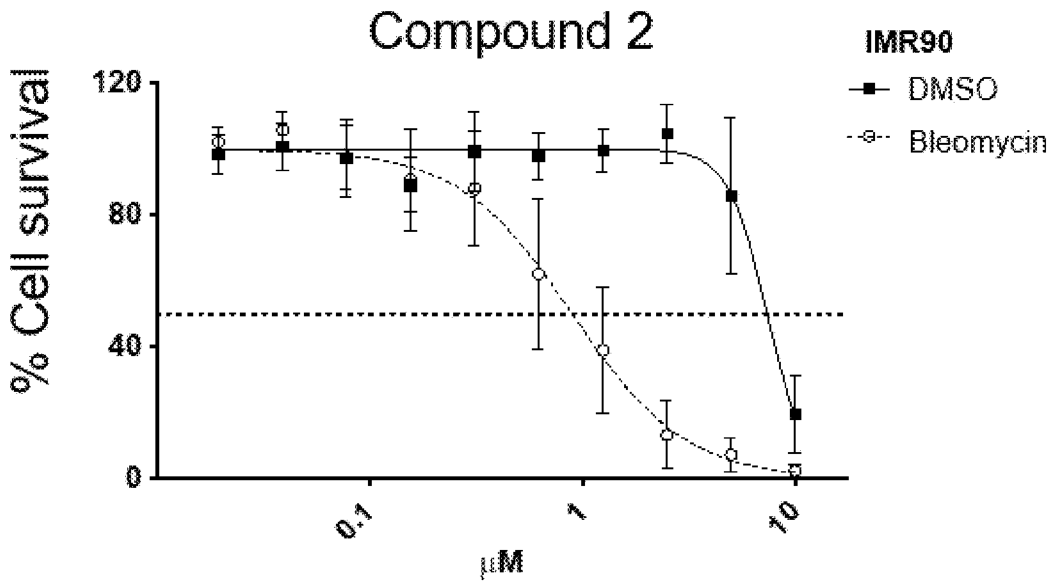
Figure 2C:
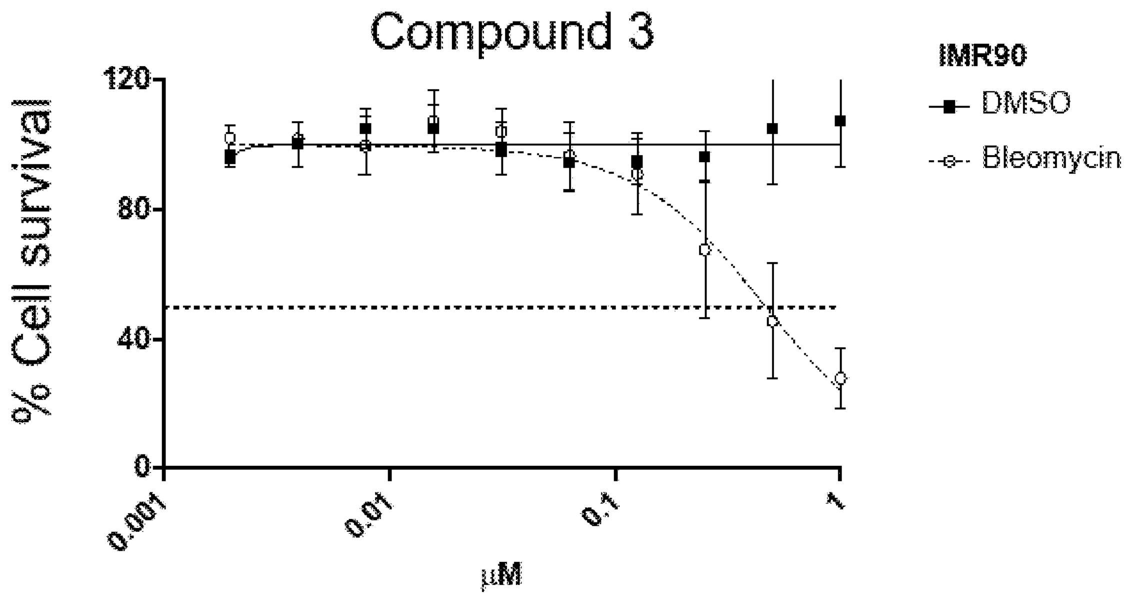

IMR90 cells were treated with bleomycin (to induce senescence), or DMSO (as a control). 7 days after induction, the indicated concentrations of Compounds 1 to 3 were added. Senolytic activity of inhibitors was determined 7 days after adding the drugs with replenishment after 3 days, cells were fixed, imaged and cells numbers were quantified using high throughput microscopy. Survival shown as a measure of cell counts relative to drug vehicle (DMSO) treated bleomycin-treated cells (n=7) and control cells (n=7). Data is shown as mean+SD, n represents independent biological experiments. The results indicate that NMT inhibitors can selectively kill senescent cells induced to senescence by bleomycin (FIGS. 2A-C).

Doxorubicin-Induced Senescence

Figure 3A:
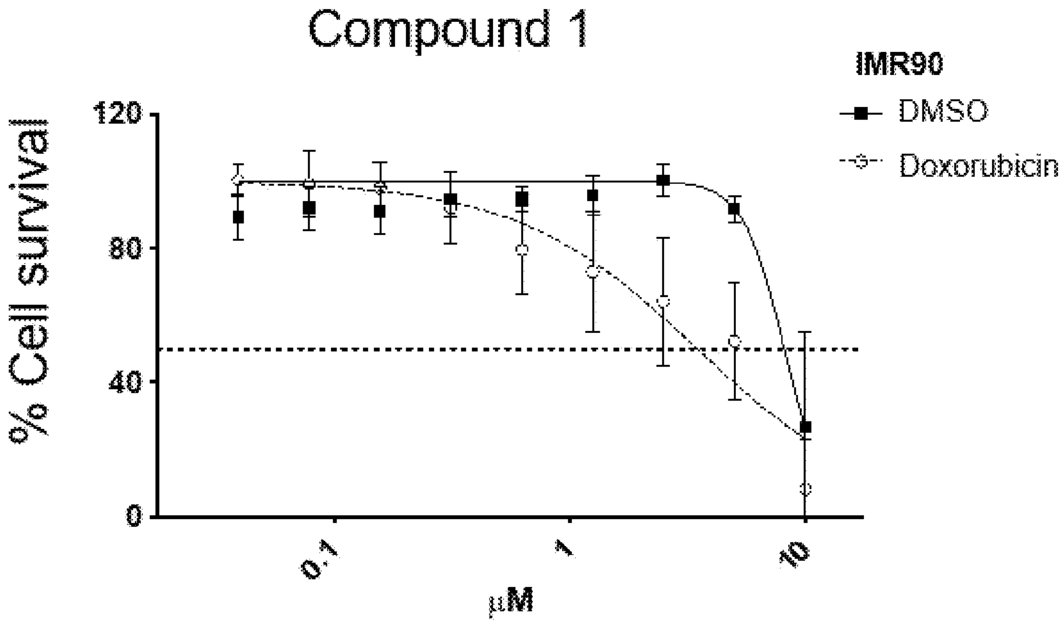
FIGS. 3A-B: Illustrate that Compounds 1 and 2 selectively eliminate IMR90 ER:RAS cells induced to senescence by doxorubicin over non-senescent cells (DMSO control).
Figure 3B:
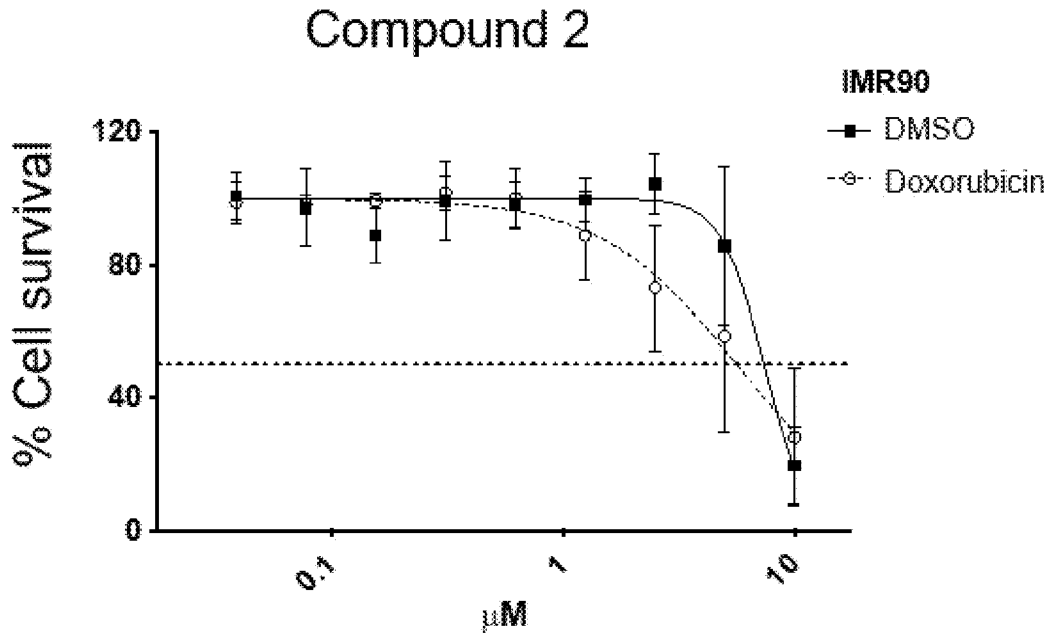

IMR90 cells were treated with doxorubicin (to induce senescence), or DMSO (as a control). 7 days after induction, the indicated concentrations of Compounds 1 or 2 were added. Senolytic activity of inhibitors was determined 7 days after adding the drugs with replenishment after 3 days, cells were fixed, imaged and cells numbers were quantified using high throughput microscopy. Survival shown as a measure of cell counts relative to drug vehicle (DMSO) treated doxorubicin-treated cells (Compound 1 n=6, Compound 2, n=4) and control cells (Compound 1 n=6, Compound 2, n=5). Data is shown as mean±SD, n represents independent biological experiments. The results indicate that NMT inhibitors can selectively kill senescent cells induced to senescence by doxorubicin (FIGS. 3A-B).

Biological Example 2: Determining the Senolytic Activity of NMT Inhibitors in Cancer Cells Given that irradiation, chemotherapy and many targeted therapies work as anticancer agents by inducing senescence, sequential treatment of that treatment followed by treatment with a senolytic compound (termed as "one-two punch" approach) has been suggested as a way to improve cancer therapies.

SKHEP1 Cancer Cells

SKHEP1 liver cancer cells were treated with etoposide (to induce senescence), or DMSO (as a control). 6 days after induction, the indicated concentrations Compounds 1 to 3 were added. Senolytic activity was measured of NMT inhibitors, 7 days after adding the drugs with replenishment after 3 days, cells were fixed, imaged and cells numbers were quantified using high throughput microscopy. Survival shown as a measure of cell counts relative to drug vehicle (DMSO) treated etoposide-senescent cells (n=3) and control cells (n=3). Data is shown as mean±SD, n represents independent biological experiments. The results indicate that Compounds 1 to 3 preferentially kill cancer cells that undergo senescence after being induced to senescence with etoposide, therefore behaving as senolytics in cancer cells (FIGS. 4A-C).

HCT116 Cancer Cells

Figure 5:
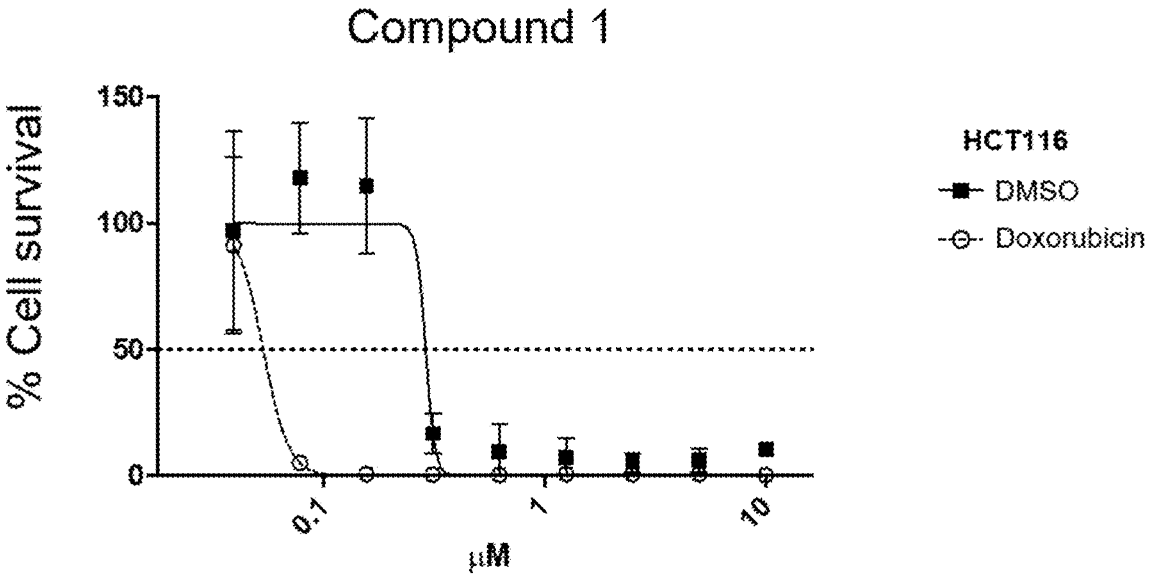
FIG. 5: Illustrates that Compound 1 selectively eliminates HCT116 cells induced to senescence by doxorubicin over non-senescent cells (DMSO control).
Figure 6A:
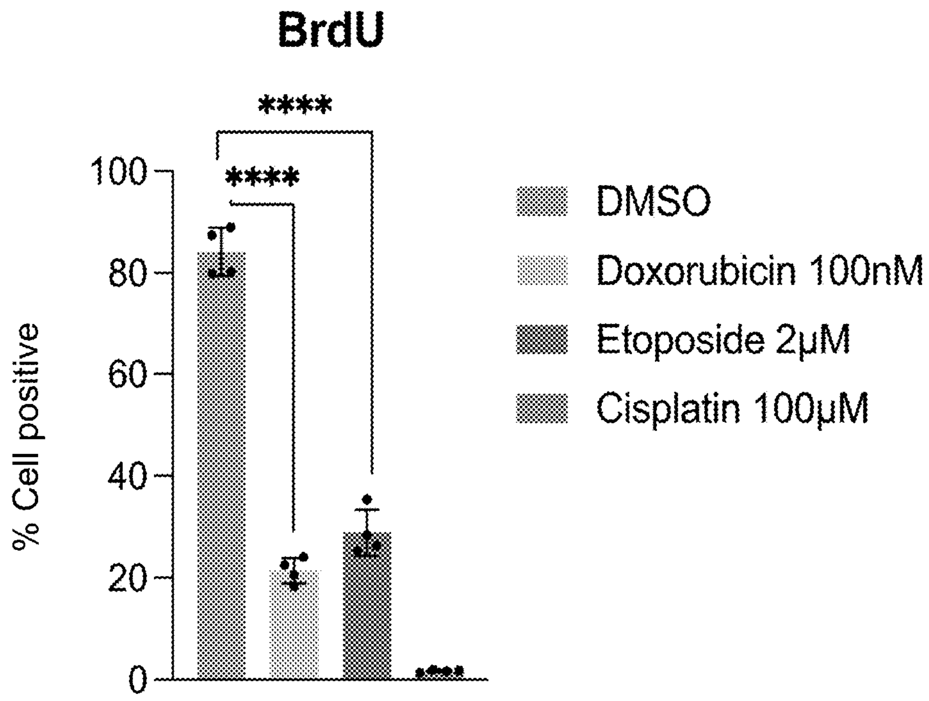
FIGS. 6A-C: Illustrate that treatment of HCT116 cells with doxorubicin, etoposide or cisplatin induces senescence (DMSO control). The bars from left to right are: DMSO, Doxorubicin 100 nM, Etoposide 2 μM and Cisplatin 100 μM.
Figure 6B:
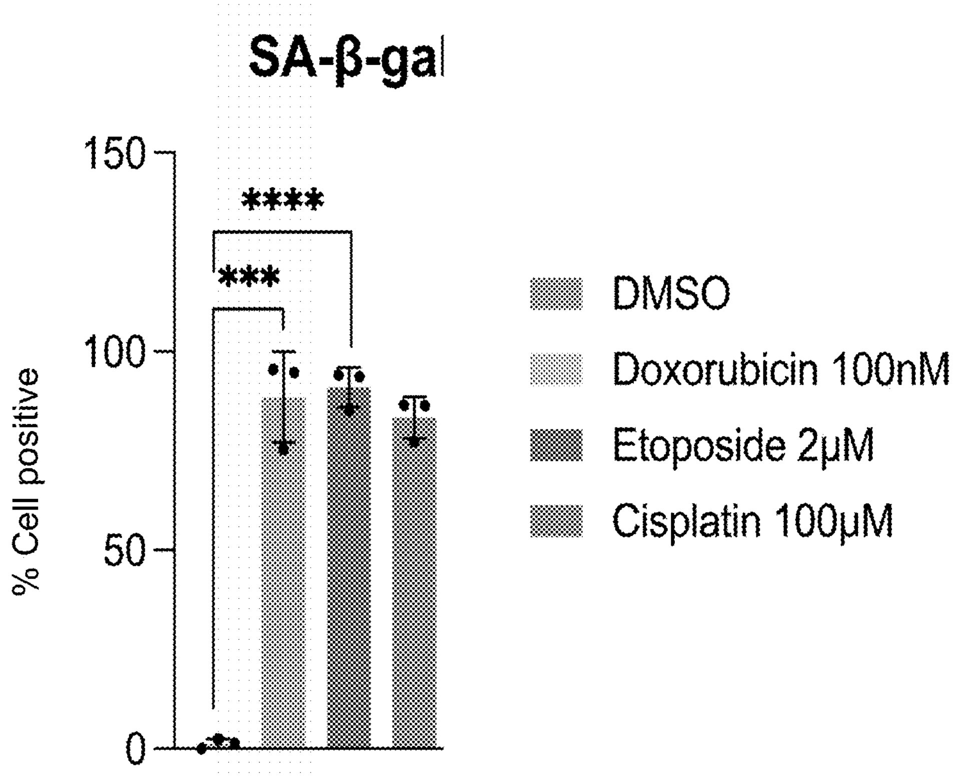
Figure 6C:
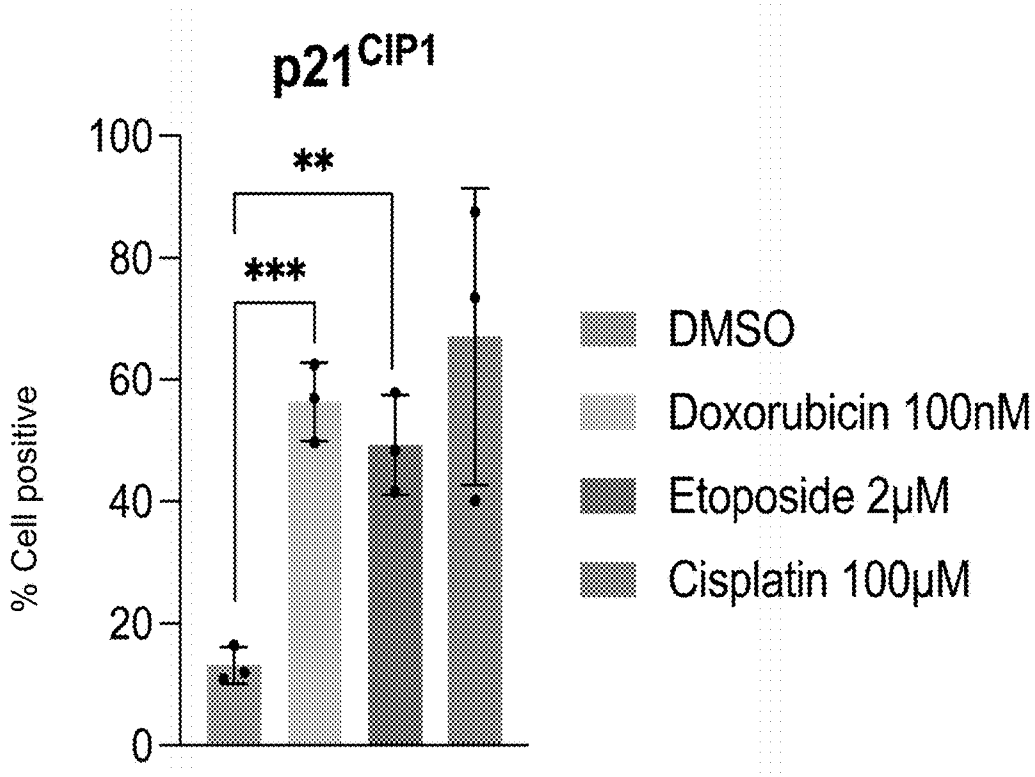

In a first experiment, HCT116 colon cancer cells were treated with doxorubicin (to induce senescence), or DMSO (as a control). 7 days after induction, the indicated concentrations of Compound 1 were added. 7 days after adding the drugs with replenishment after 3 days, cells were fixed, imaged and cells numbers were quantified using high throughput microscopy. Survival shown as a measure of cell counts relative to drug vehicle (DMSO) treated doxorubicin-senescent cells (n=2) and control cells (n=2). The results indicate that Compound 1 preferentially kills cancer cells that undergo senescence after being treated with doxorubicin, therefore behaving as a senolytic in cancer cells (FIG. 5).

Figure 7A:
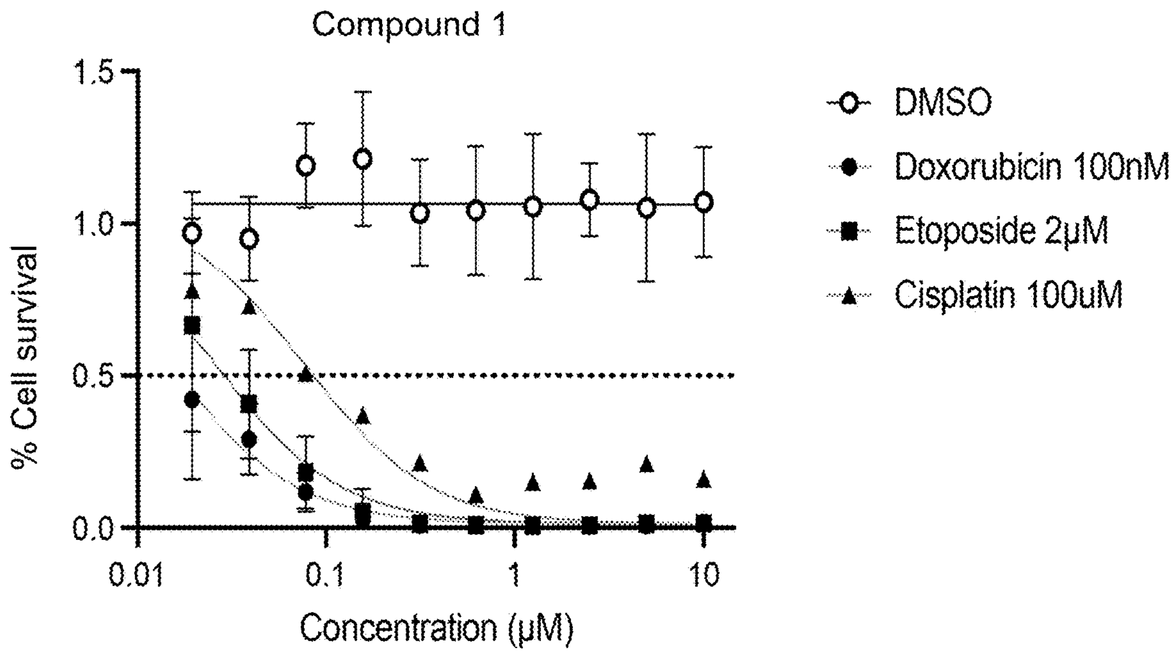
FIGS. 7A-C: Illustrate that Compounds 1 to 3 selectively eliminate HCT116 cells induced to senescence by doxorubicin, etoposide or cisplatin over non-senescent cells (DMSO control). The bars from left to right are: DMSO, Doxorubicin 100 nM, Etoposide 2 μM and Cisplatin 100 μM.
Figure 7B:
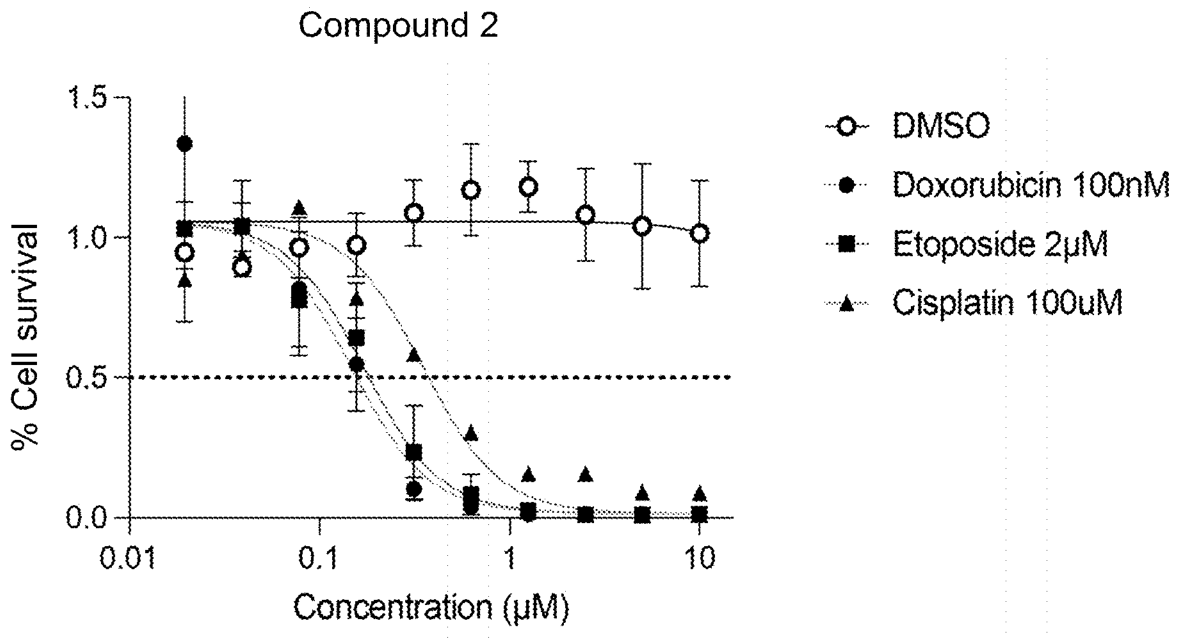
Figure 7C:
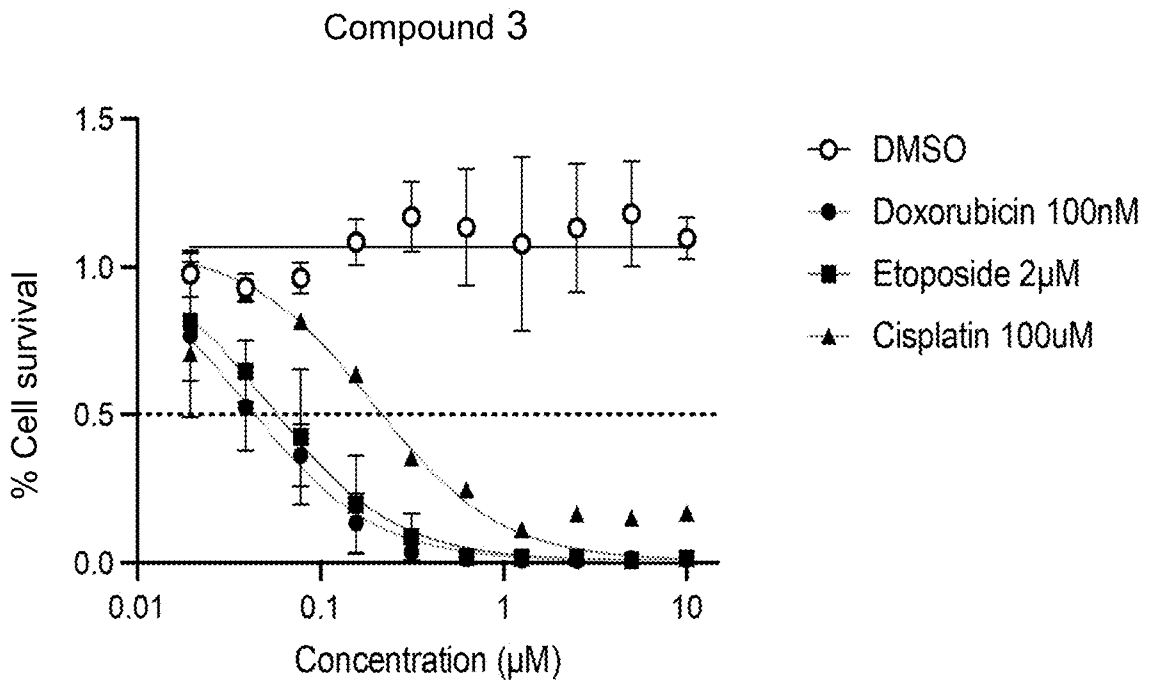
Figure 8A:
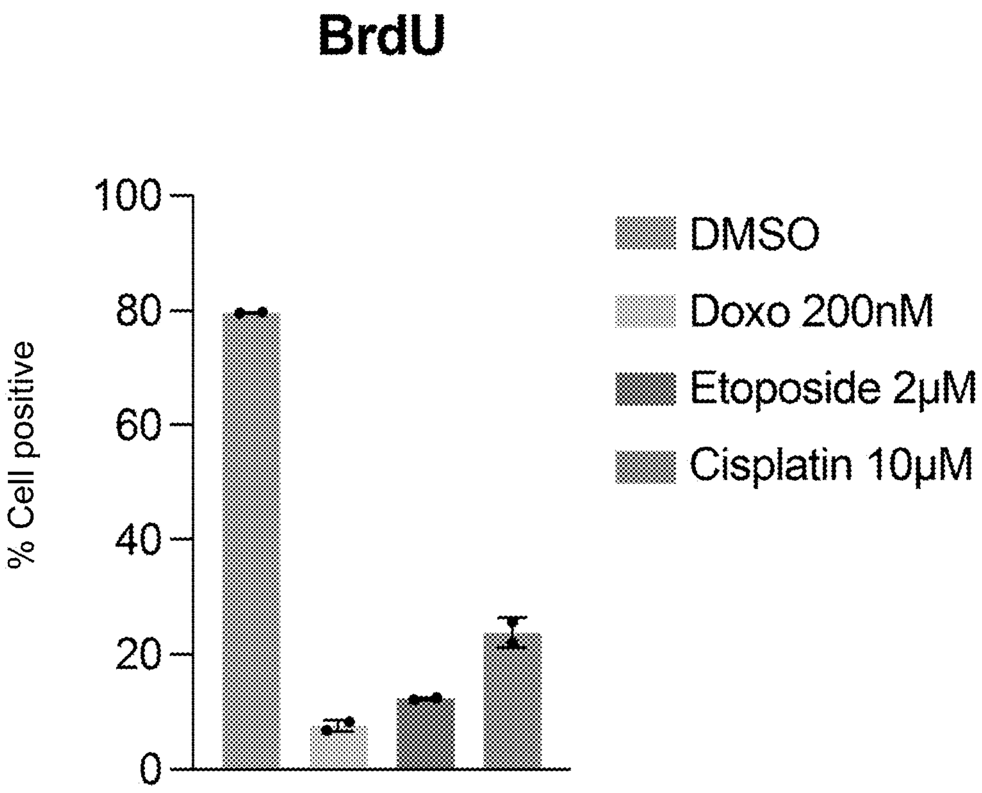
FIGS. 8A-C: Illustrate that treatment of MCF7 cells with doxorubicin, etoposide or cisplatin induces senescence (DMSO control). The bars from left to right are: DMSO, Doxorubicin 200 nM, Etoposide 2 μM and Cisplatin 10 μM.
Figure 8B:
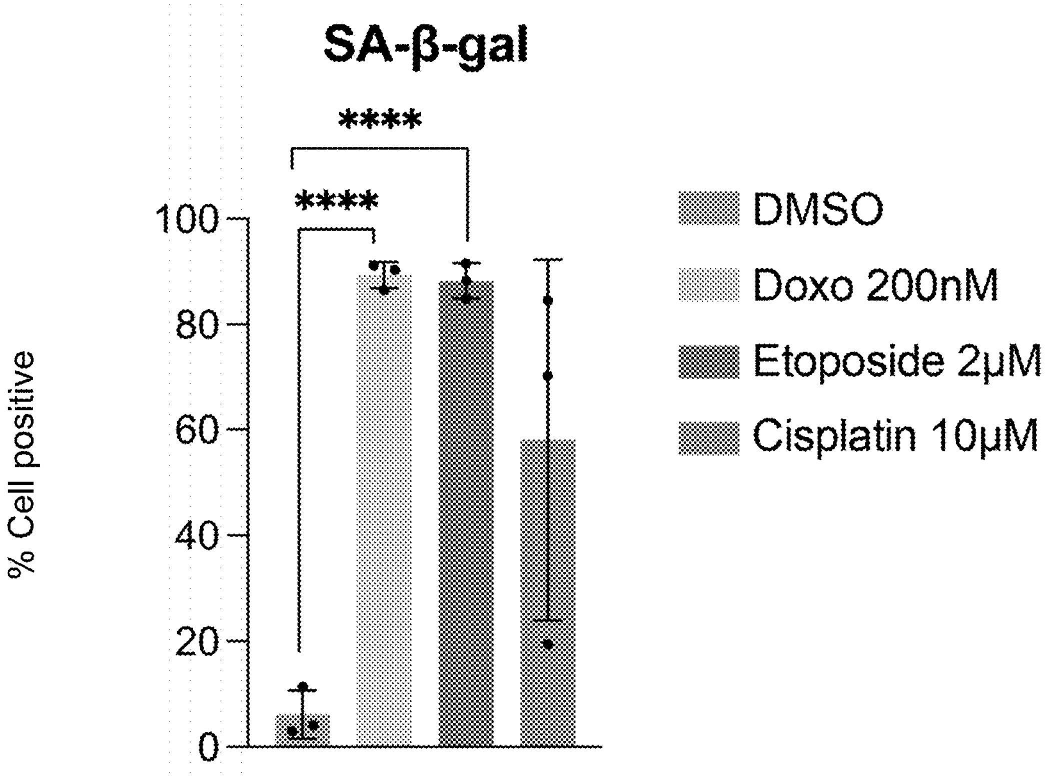
Figure 8C:
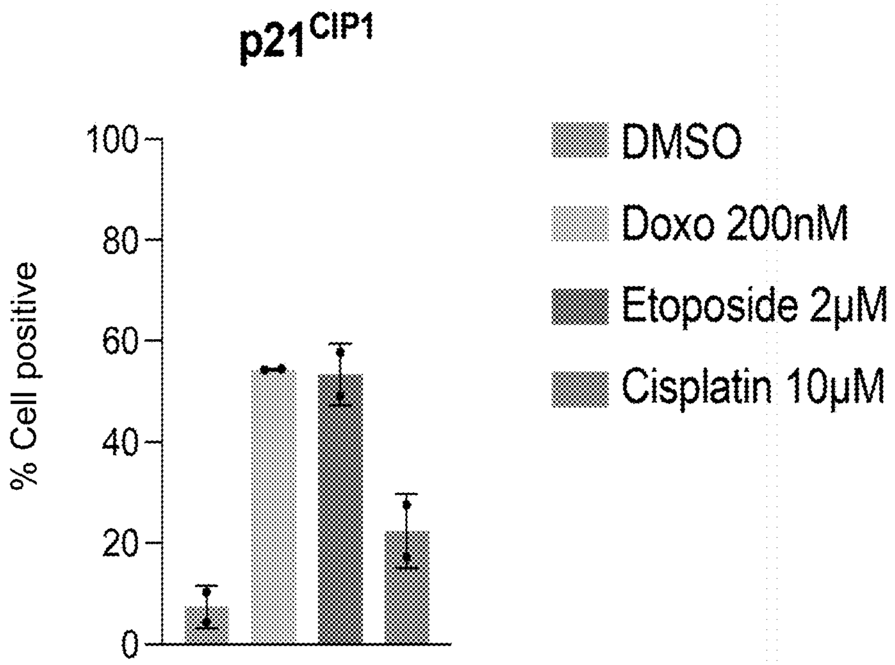

In a second experiment, HCT116 were treated with doxorubicin, etoposide or cisplatin (to induce senescence) or DMSO (as a control). 7 days after treatment, BrdU incorporation (to assess cell division), SA-β-Galactosidase activity and $p21^{CIP1}$ expression (as markers of senescence) were analysed. HCT116 cells treated with any of the three drugs, stopped proliferating (FIG. 6A) and upregulated SA-β-Galactosidase activity and $p21^{CIP1}$ expression (FIGS. 6B-C) confirming that were senescent. HCT116 cells that underwent senescence (after treatment with doxorubicin, etoposide or cisplatin) or the corresponding controls (treated with DMSO) were treated with the indicated concentrations of Compound 1 (FIG. 7A), Compound 2 (FIG. 7B) or Compound 3 (FIG. 7C). Media and compounds were replenished after 72 h of treatment and cultured for 48 h more before fixation and measurement of survival via high-throughput microscopy. DMSO/Doxorubicin/Etoposide (n=4), Cisplatin (n=1). The results indicate that NMT inhibitors preferentially kill cancer cells that undergo senescence after being treated with doxorubicin, etoposide or cisplatin, therefore behaving as senolytics in cancer cells.

MCF7 Cancer Cells

Figure 9A:
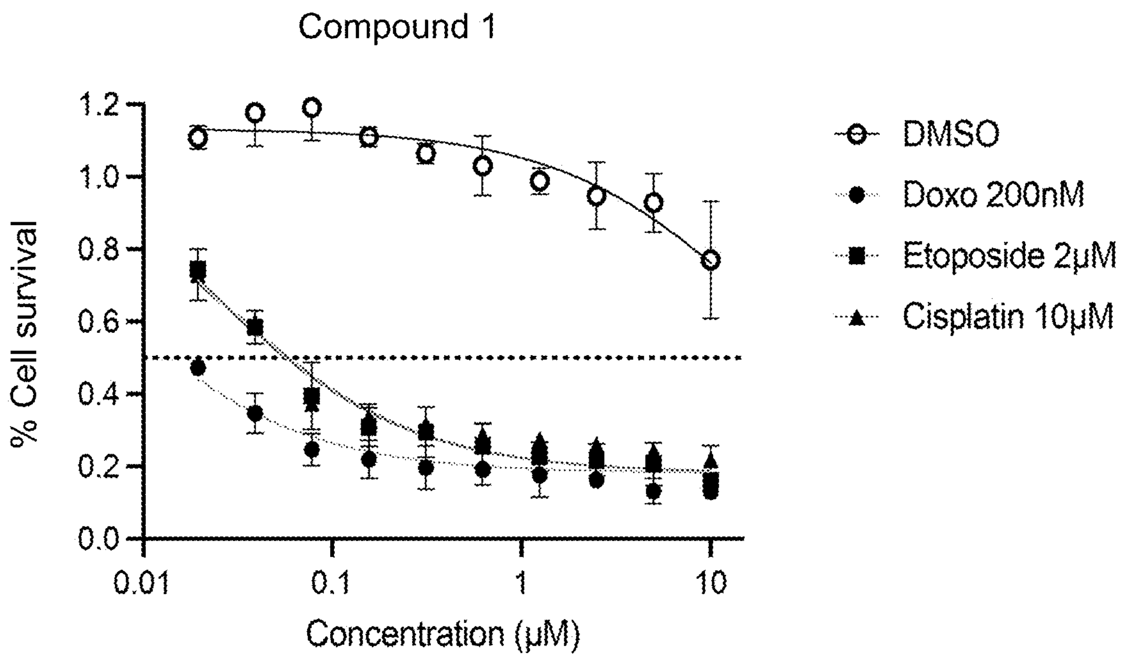
FIGS. 9A-C: Illustrate that Compounds 1 to 3 selectively eliminate MCF7 cells induced to senescence by doxorubicin, etoposide or cisplatin over non-senescent cells (DMSO control). The bars from left to right are: DMSO, Doxorubicin 200 nM, Etoposide 2 μM and Cisplatin 10 μM.
Figure 9B:
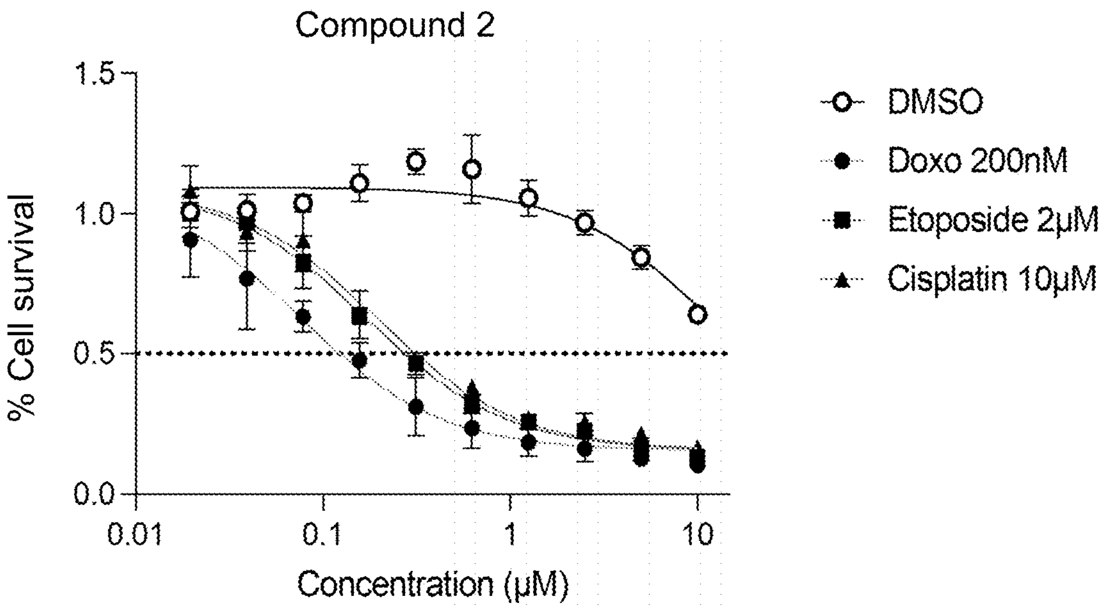
Figure 9C:
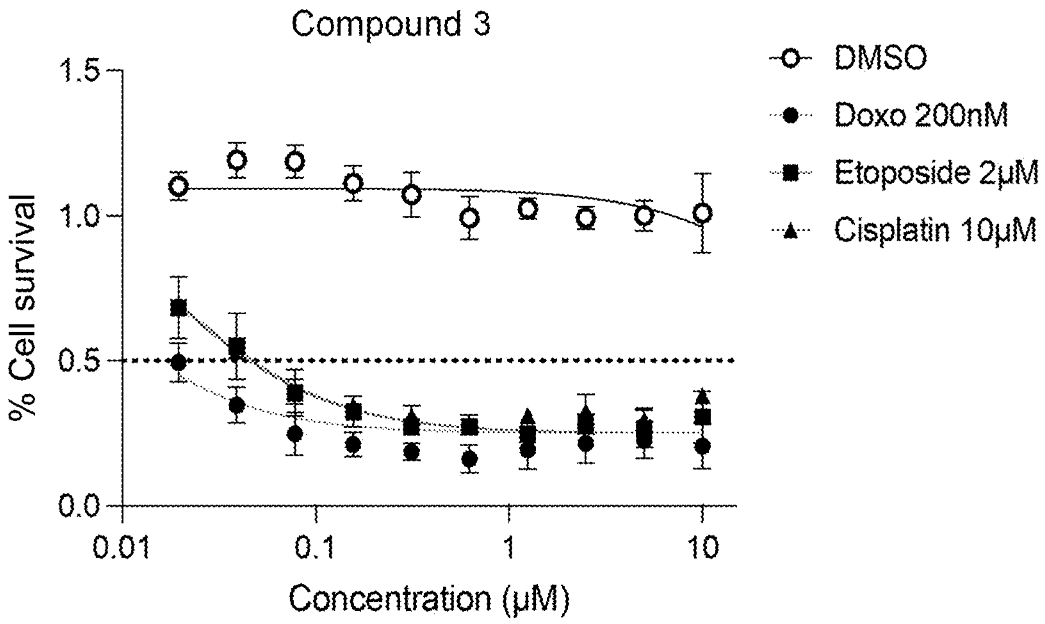

MCF7 cancer cells were treated with doxorubicin, etoposide or cisplatin (to induce senescence) or DMSO (as a control). 7 days after treatment, analysed BrdU incorporation (to assess cell division), SA-β-Galactosidase activity and $p21^{CIP1}$ expression (as markers of senescence) were analysed. MCF7 cells treated with any of the three drugs, stopped proliferating (FIG. 8A) and upregulated SA-β-Galactosidase activity and $p21^{CIP1}$ expression (FIGS. 8B-C) confirming that were senescent. MCF7 cells that underwent senescence (after treatment with doxorubicin, etoposide or cisplatin) or the corresponding controls (treated with DMSO) were treated with the indicated concentrations of Compound 1 (FIG. 9A), Compound 2 (FIG. 9B) or Compound 3 (FIG. 9C). Media and compounds were replenished after 72 h of treatment and cultured for 48 h more before fixation and measurement of survival via high-throughput microscopy. DMSO/Doxorubicin/Etoposide (n=3), Cisplatin (n=2).

The results of these experiments suggest that NMT inhibitors are senolytic against different cancer cells, irrespective of how senescence was induced in these cancer cells.

Figure 10A:
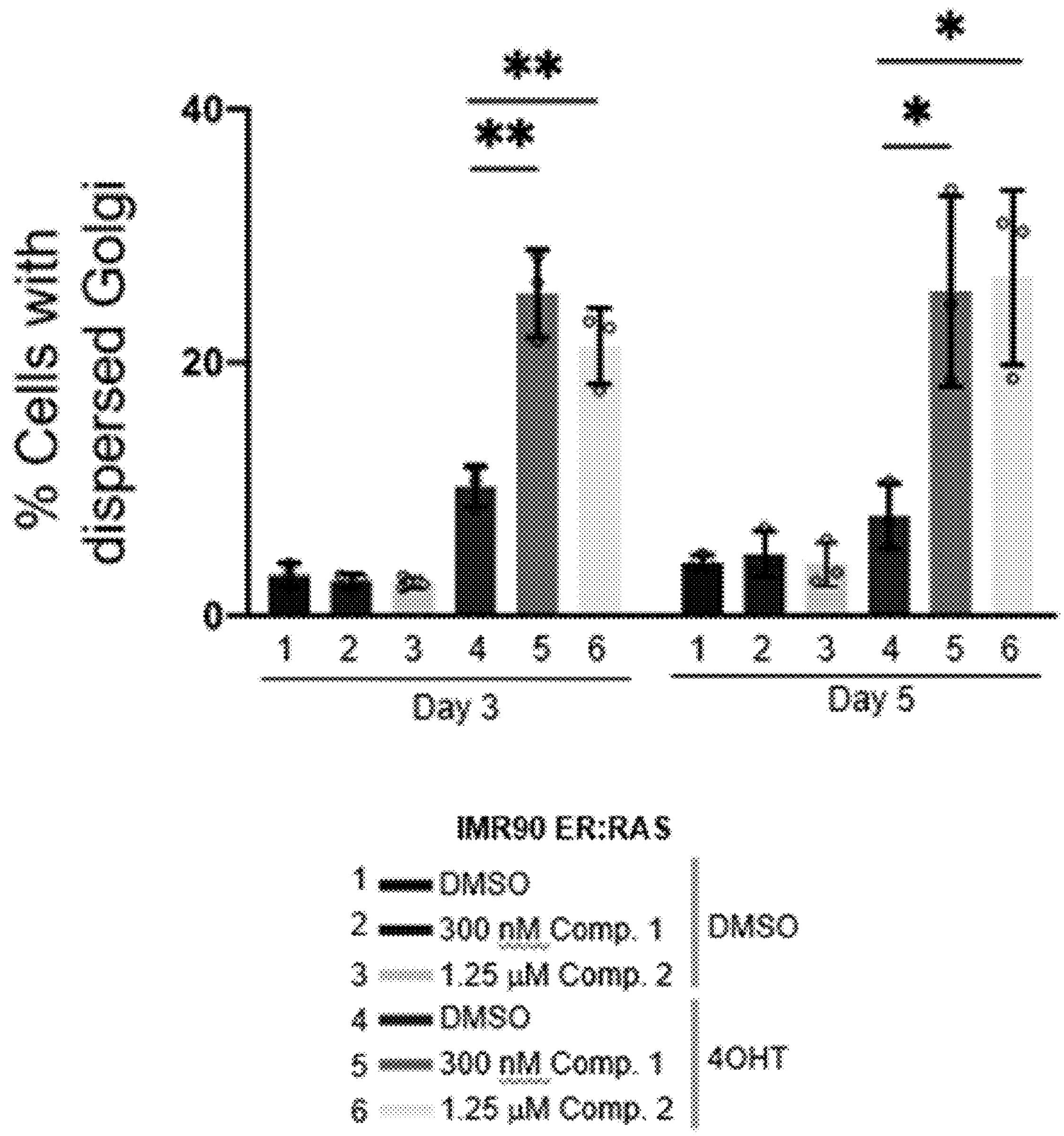
FIGS. 10A-B: Illustrate that treatment of IMR90 ER:RAS cells undergoing senescence with Compounds 1 and 2 induces Golgi dispersal.
Figure 10B:
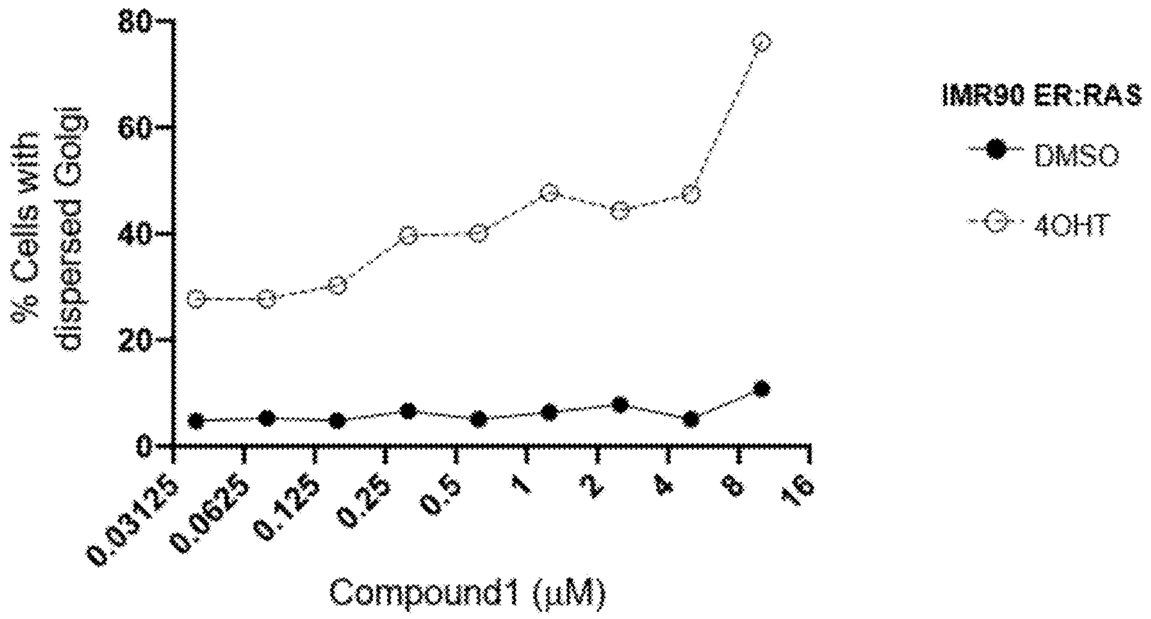

Biological Example 3: Determining the Effect of NMT Inhibitors on Golgi Dispersal and Cytokine Levels Effect on NMT Inhibitors on Golgi Dispersal Arf GTPases that are involved in vesicle formation in the Golgi apparatus are known to undergo N-myristoylation in mammalian cells. A well-known effect associated with inhibition of Arf GTPases is Golgi disruption. Senescent cells have a hyperactive secretory apparatus that is necessary for processing components of the SASP. Therefore, to understand whether treatment with NMT inhibitors could cause Golgi disruption, distribution of the trans-Golgi protein TGN46 was imaged using high throughput automated microscopy. IMR90 ER:RAS cells undergoing senescence (after induction with 4OHT), were treated with the indicated concentrations of Compounds 1 or 2. Assessment of Golgi dispersal was carried out 7 days after addition of the drugs by staining with TGN46 antibodies. The results indicate that treatment with NMT inhibitors selectively caused Golgi dispersal on senescent cells (FIGS. 10A-B).

Figure 11:
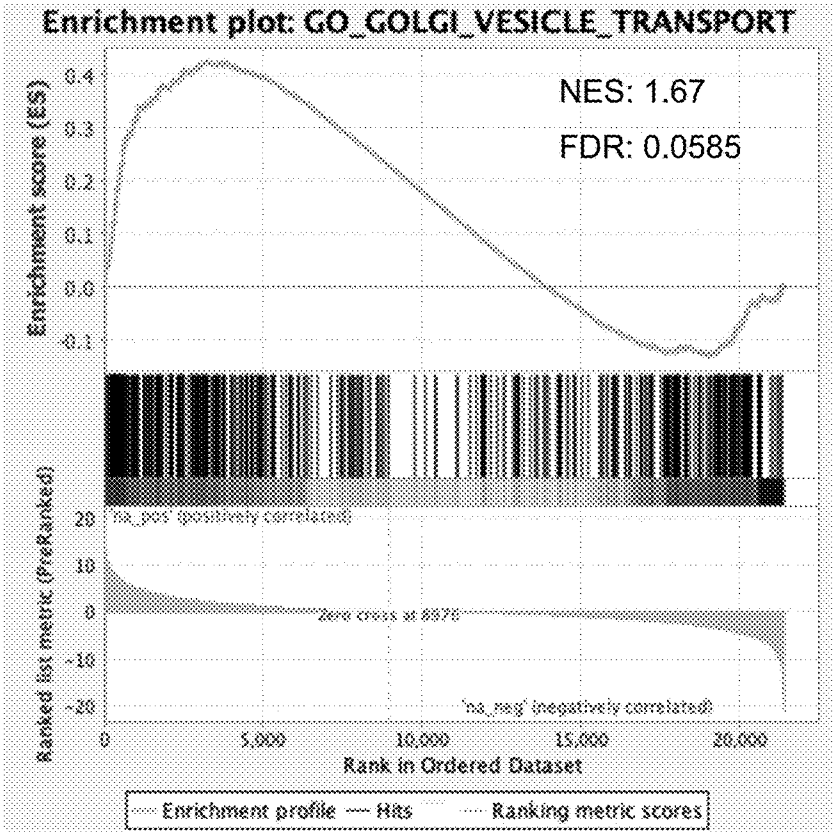
FIG. 11: Illustrates that transcriptional signatures for Golgi transport are enriched in senescent cells treated with NMT inhibitors.
Figure 11:
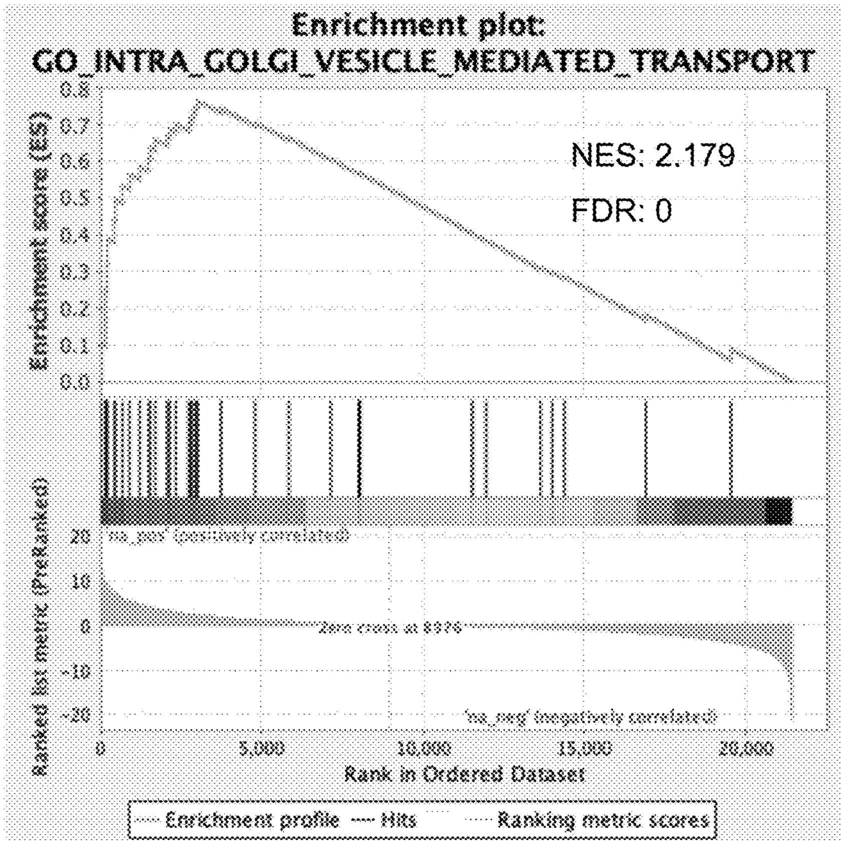
Figure 11:
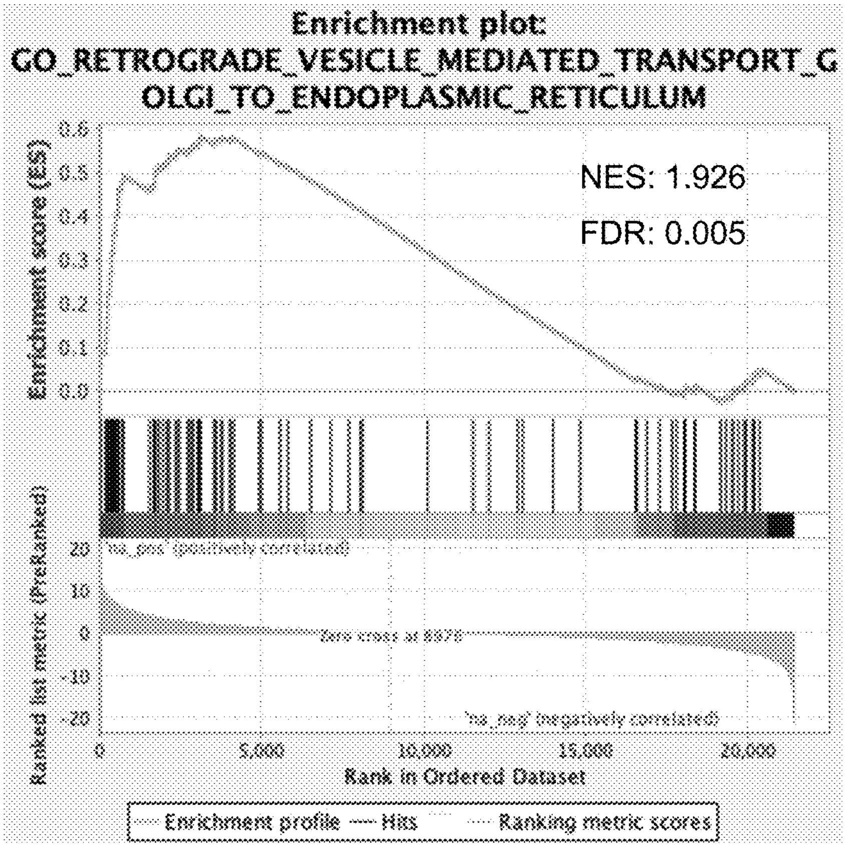
Figure 11:
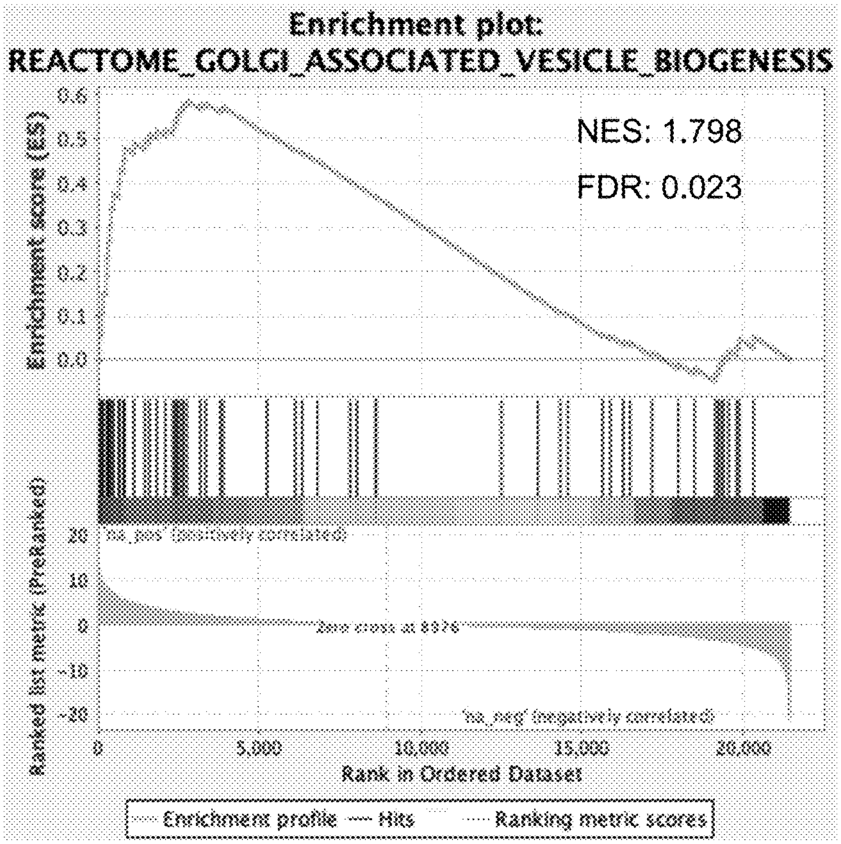
Figure 11:
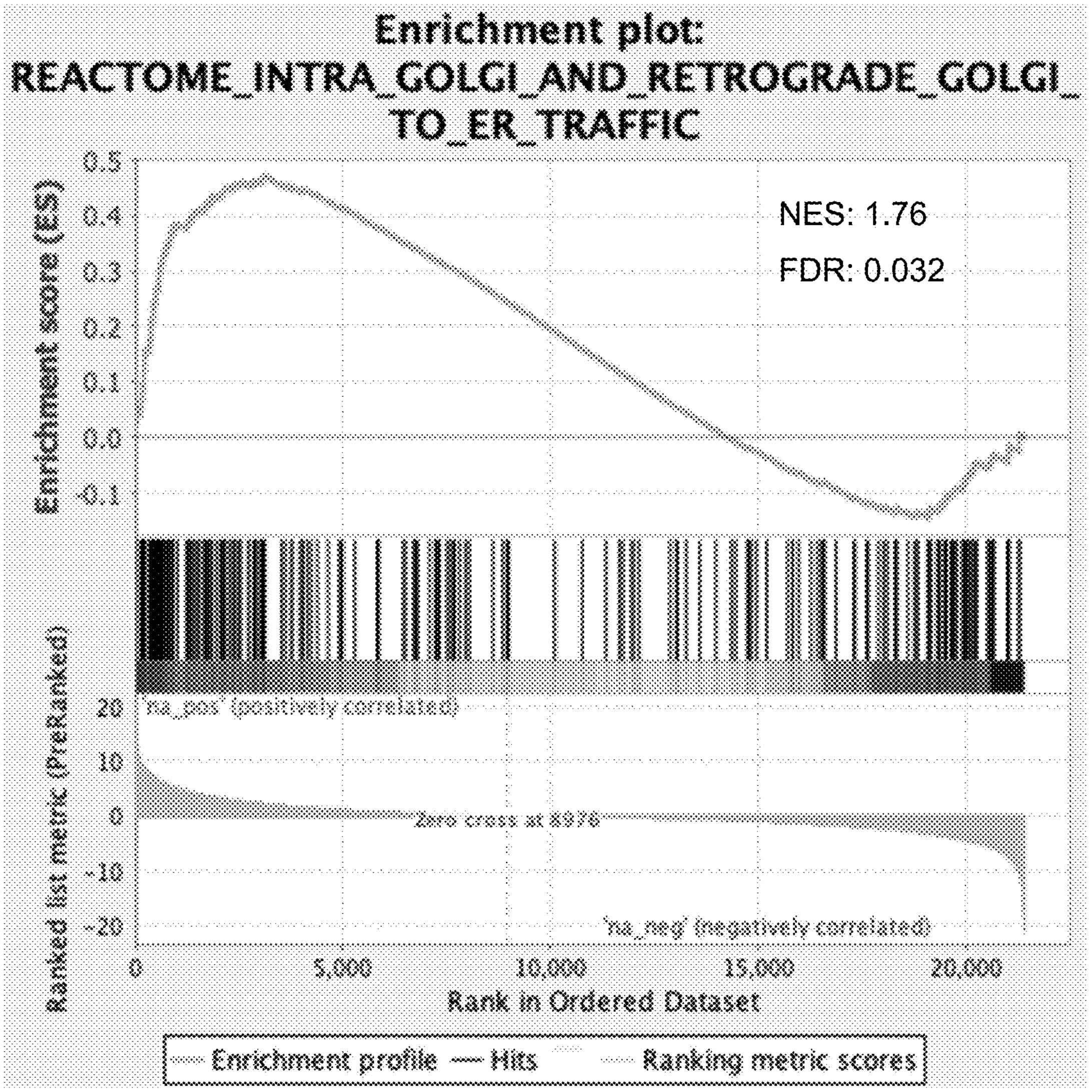

To further investigate the effect of NMT inhibitors in the Golgi apparatus, RNA-Seq of IMR90 ER:RAS cells undergoing senescence (after induction with 4OHT) was performed, followed by treatment with the indicated concentrations of Compound 2. Taking advantage of gene set enrichment analysis (GSEA), enrichment of Golgi and trafficking signatures in senescent cells treated with NMT inhibitors was observed (FIG. 11). These results further suggest that treatment of senescent cells with NMT inhibitors affect the Golgi apparatus.

Since a functional Golgi apparatus is required to process secreted proteins and senescent cells are characterized by the production of a bioactive secretome, known as the SASP, it is possible that Golgi disruption could hamper protein processing and secretion, resulting in aberrant intracellular accumulation of proteins destined to secretion that could activate proteotoxic responses (such as the unfolded protein response). This could result in the selective killing of senescent cells after treatment with NMT inhibitors.

Effect of NMT Inhibitors on Cytokine Levels

Figure 12A:
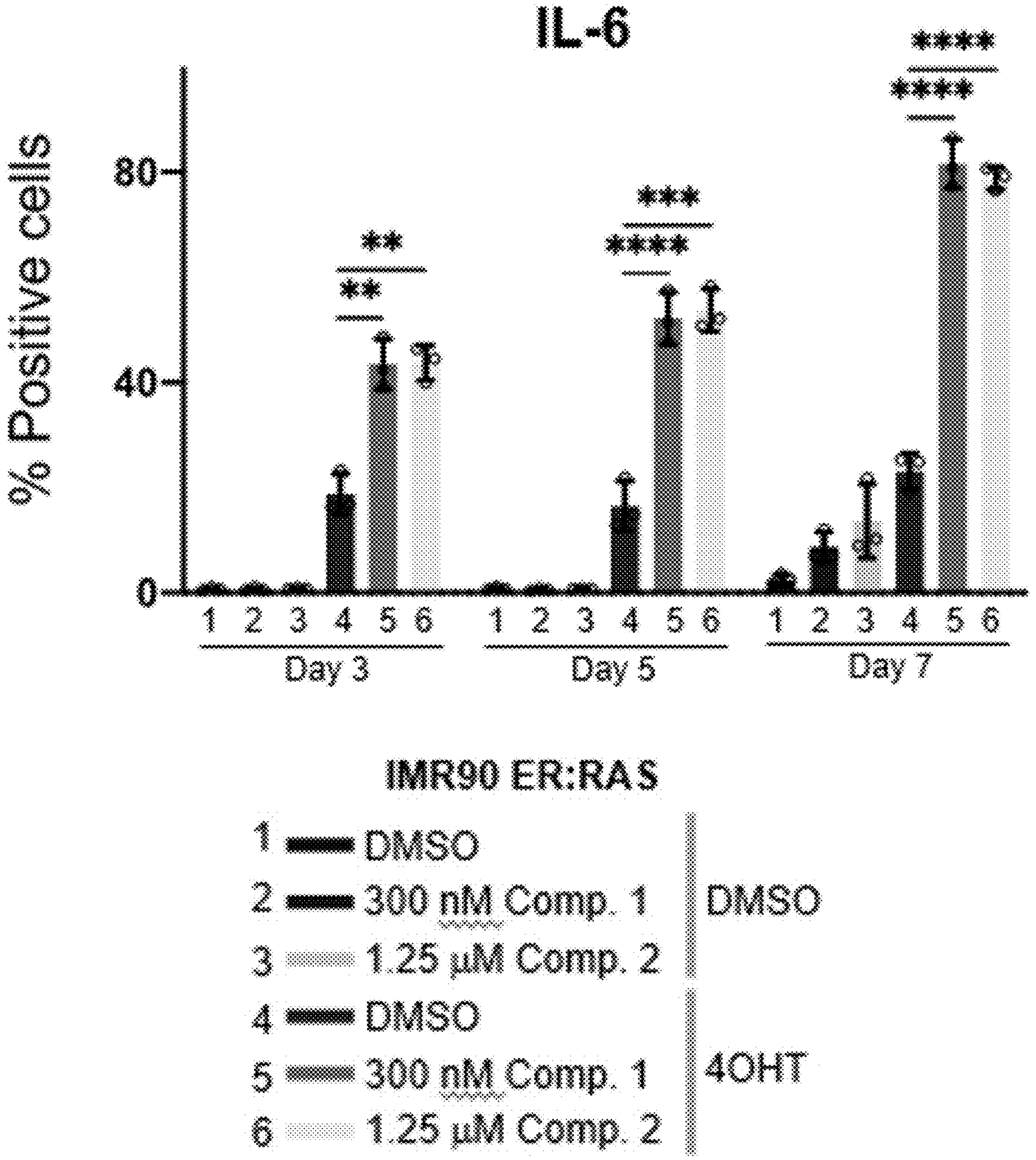
FIGS. 12A-C: Illustrate that treatment with Compounds 1 and 2 results in intracellular accumulation of cytokines in senescent cells.
Figure 12B:
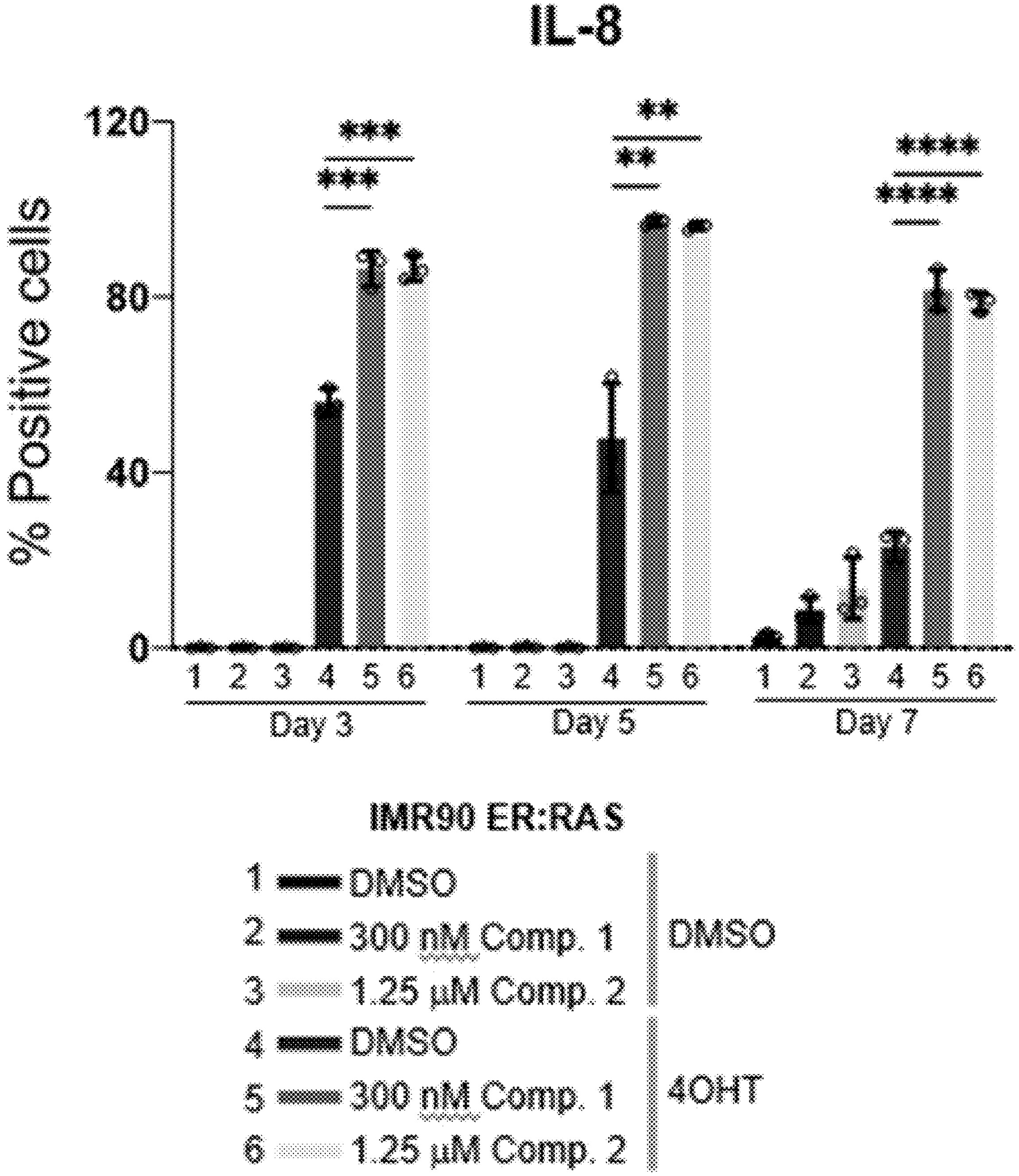
Figure 12C:
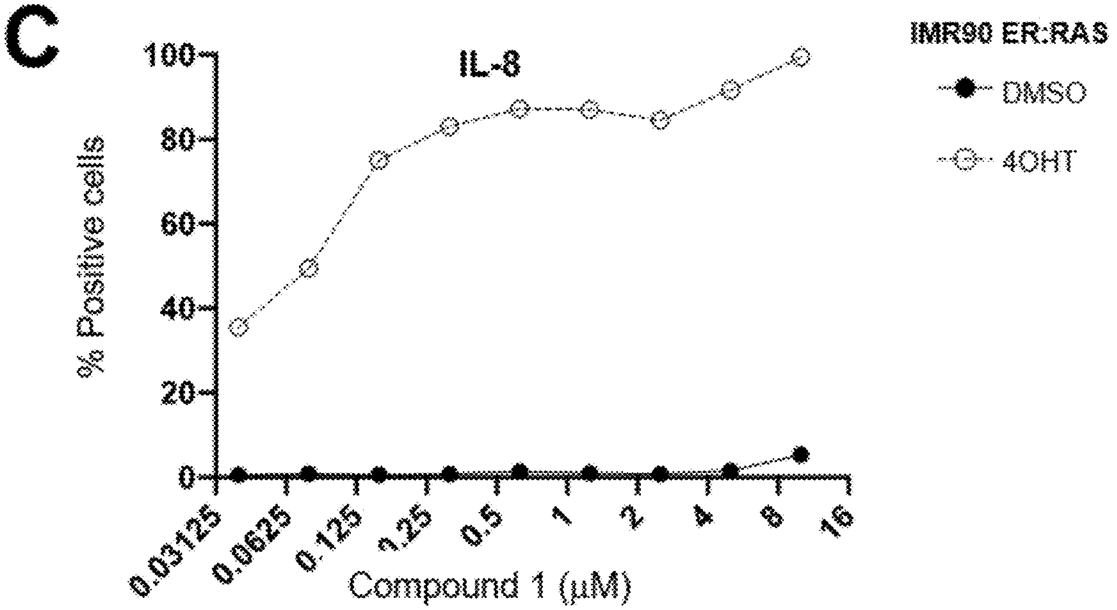

The intracellular levels of two SASP components, IL-6 and IL-8 were assessed using stained cells. IMR90 ER:RAS cells undergoing senescence (after induction with 4OHT), were treated with the indicated concentrations of Compounds 1 or 2. Assessment of intracellular levels of cytokines was carried out 7 days after addition of the drugs by staining with antibodies recognizing IL-6 or IL-8. The results indicate that treatment with NMT inhibitors selectively resulted in an intracellular accumulation of these cytokines on senescent cells (FIGS. 12A-C).

Figure 13A:
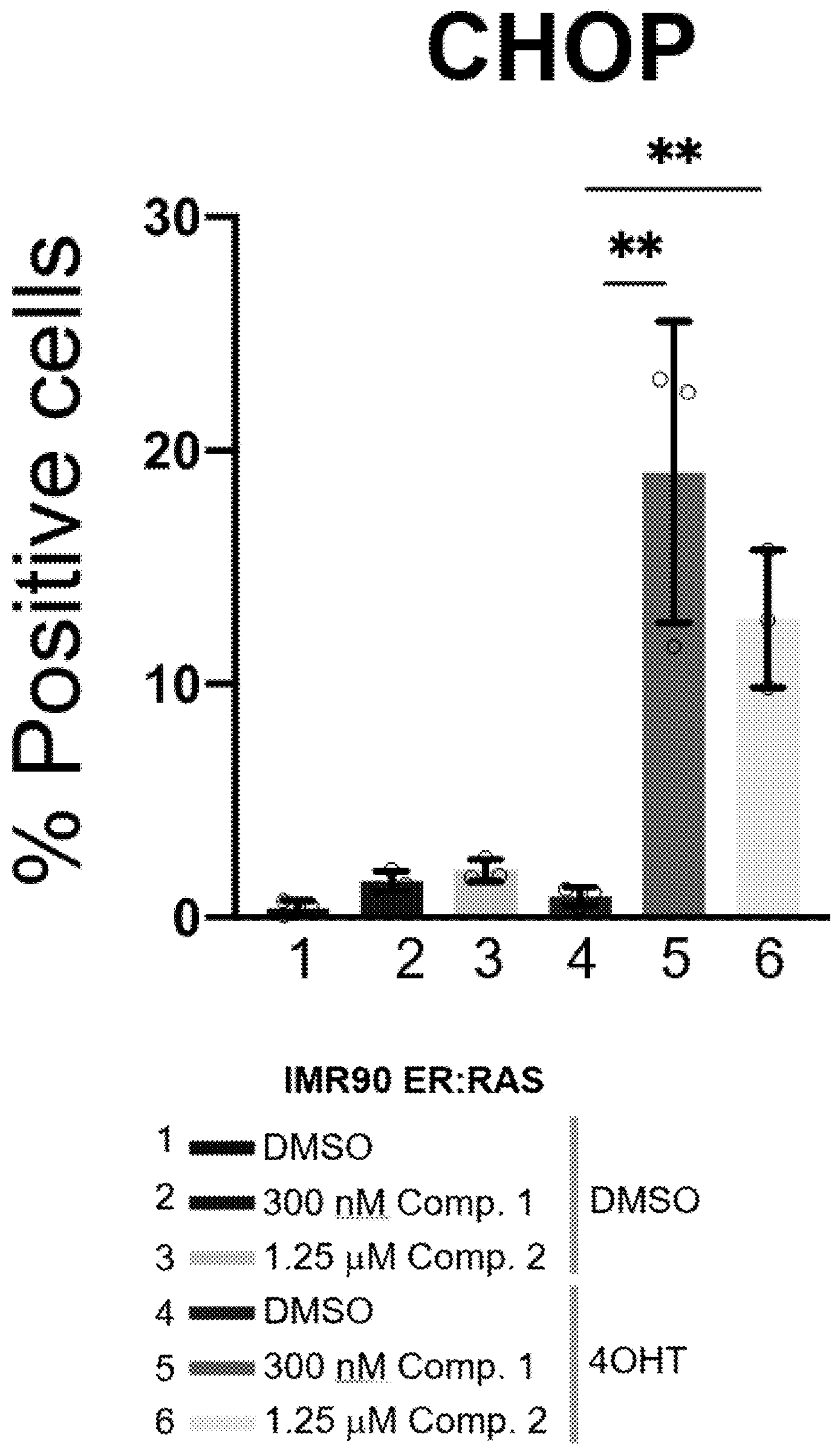
FIGS. 13A-C: Illustrate that treatment with Compounds 1 and 2 induces the unfolded protein response (UPR) in senescent cells.
Figure 13B:
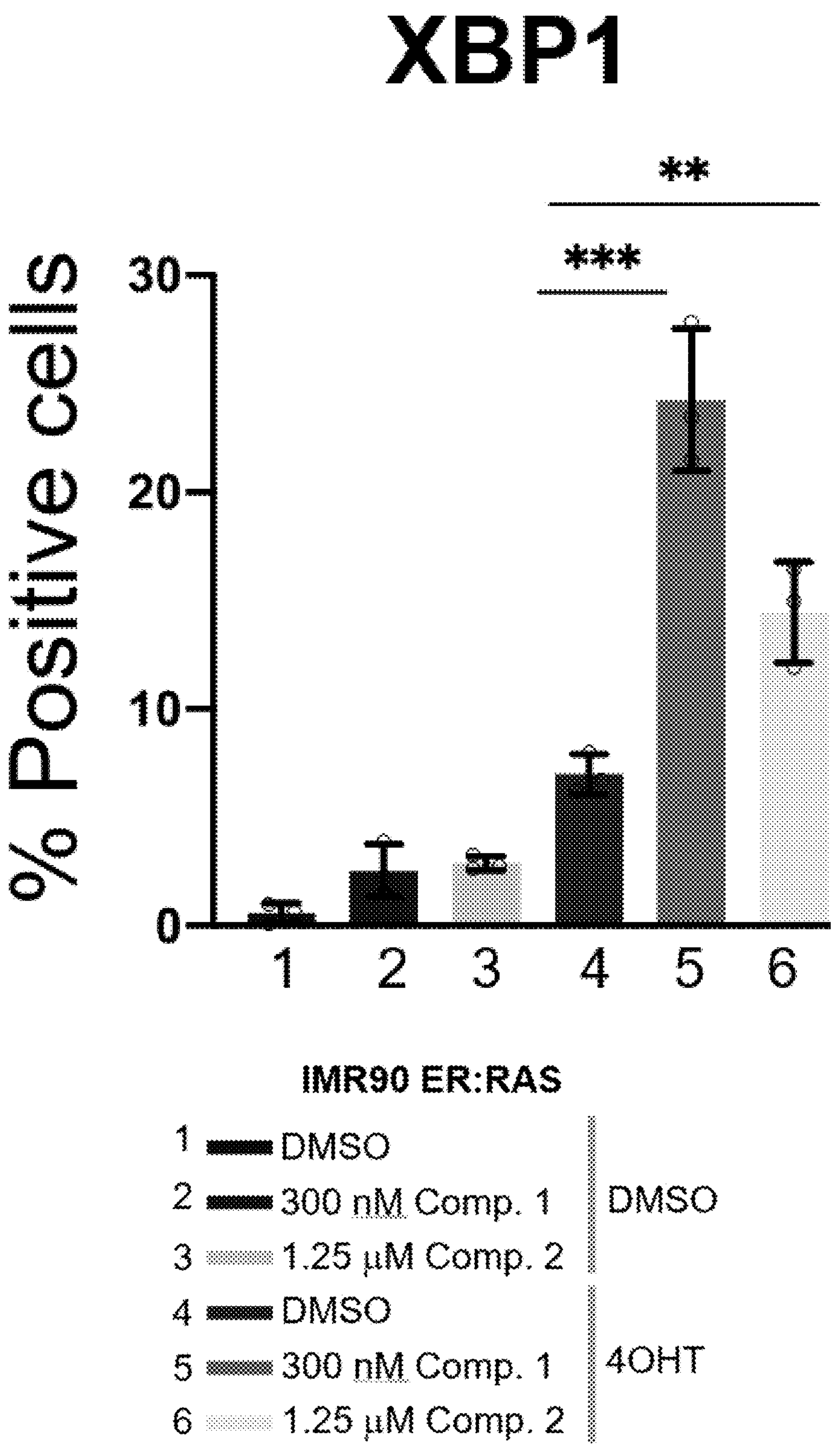
Figure 13C:
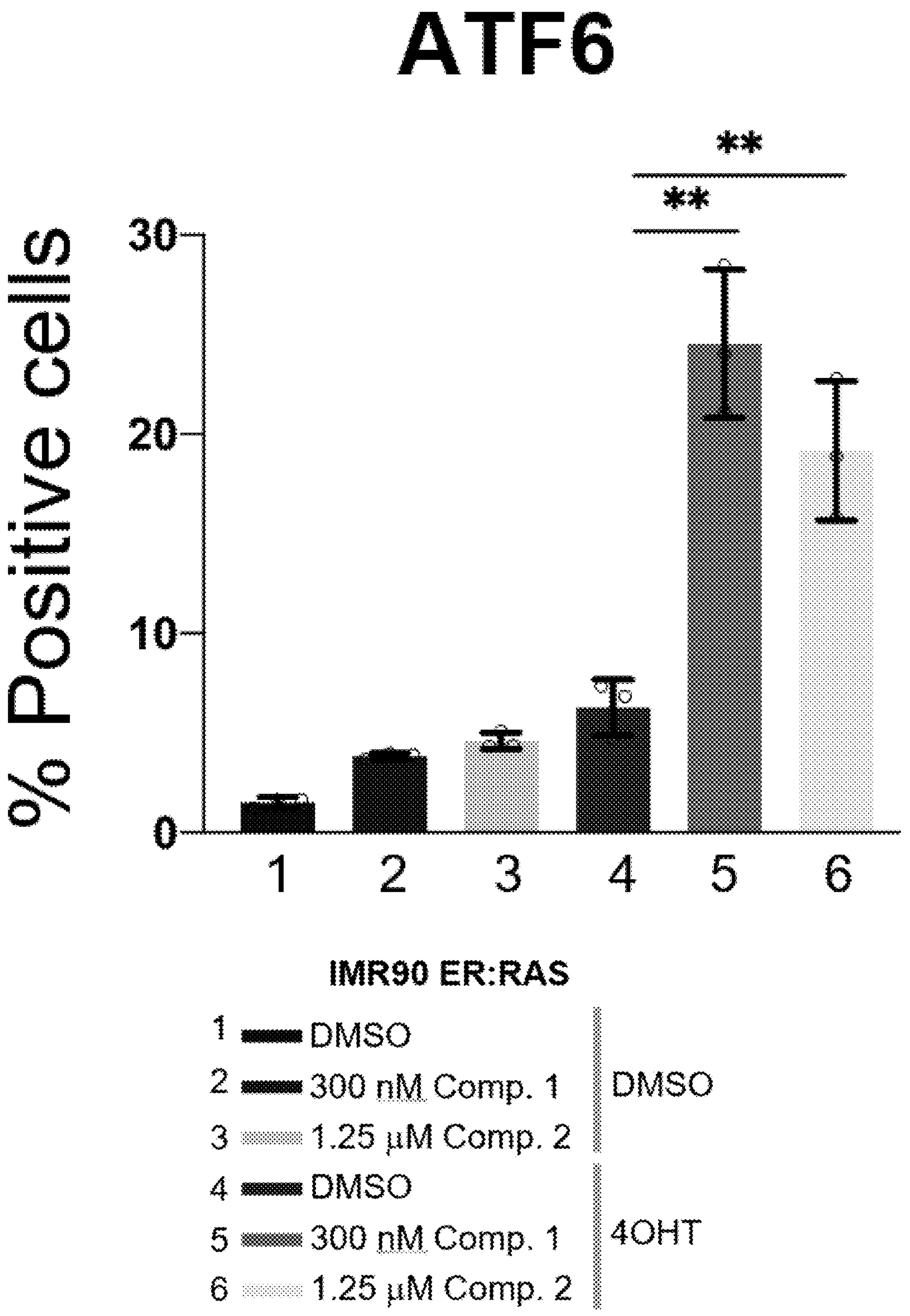
Figure 13D:
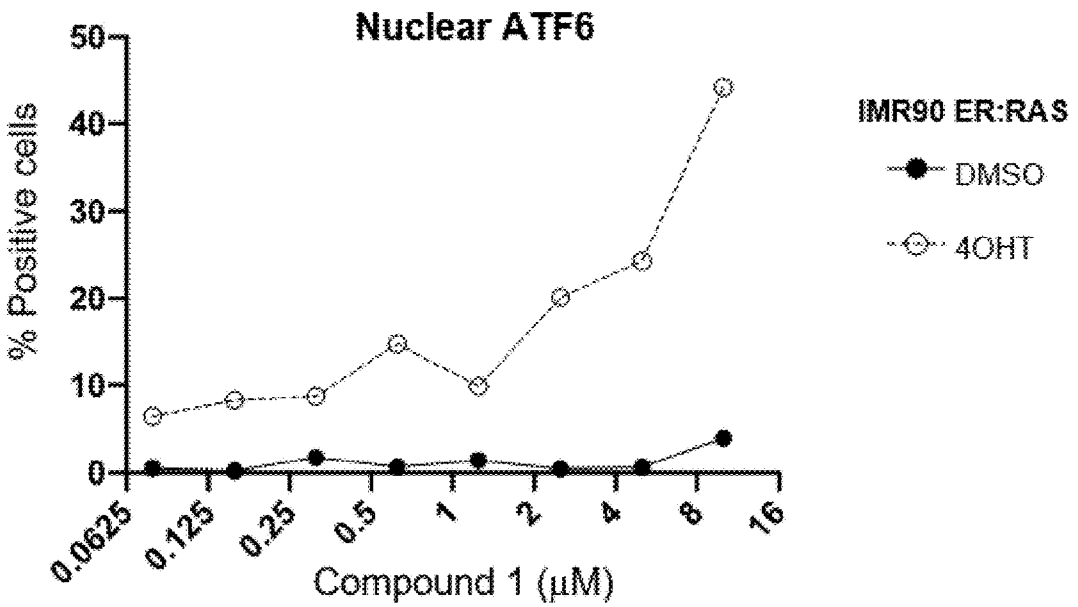
FIG. 13D: Illustrates the effect of the concentration of Compound 1 on nuclear ATF6 levels in senescent and non-senescent cells.

Biological Example 4: Determining the Effect of NMT Inhibitors on the Unfolded Protein Response, and the Effect of Inhibition of the Unfolded Protein Response Effect of NMT Inhibitors on the Unfolded Protein Response To investigate whether aberrant intracellular accumulation of secreted proteins could cause activation of the UPR on senescent cells treated with NMT inhibitors, components of the UPR (CHOP, XBP1 and ATF6) were imaged using high throughput automated microscopy. IMR90 ER:RAS cells undergoing senescence (after induction with 4OHT), were treated with the indicated concentrations of Compounds 1 or 2. Assessment of UPR activation was carried out 7 days after addition of the drugs by staining with antibodies recognizing CHOP (FIG. 13A), XBP1 (FIG. 13B) or ATF6 (FIG. 13C) on day 5. Quantification of levels of UPR markers shown as percentage of cells above nuclear intensity threshold for 4OHT treated (n=3) and control cells (n=3). Data is shown as mean±SD, n represents independent biological experiments. FIG. 13D shows the effect of the indicated concentrations of Compound 1 on nuclear ATF6 levels (a marker of UPR activation), in control and senescent cells. The results indicate that treatment with NMT inhibitors causes the induction of the unfolded protein response on senescent cells (FIGS. 13A-D).

Figure 14:
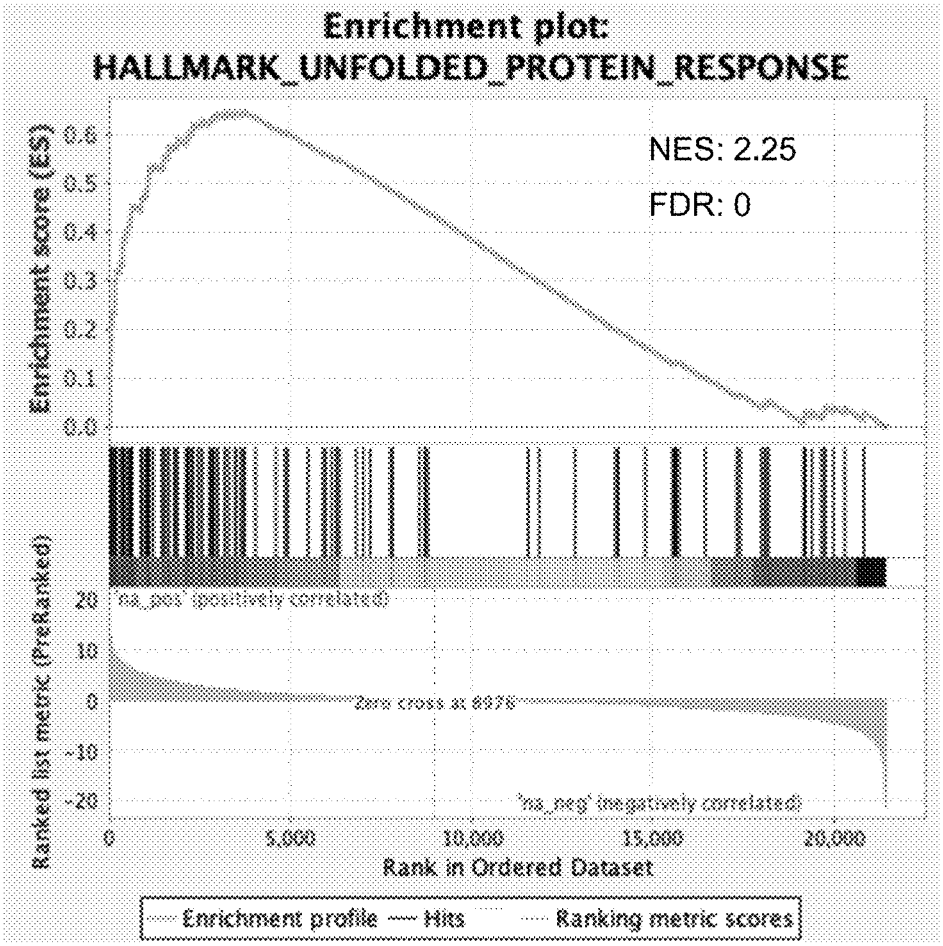
FIG. 14: Illustrates that transcriptional signatures for UPR are enriched in senescent cells treated with NMT inhibitors.
Figure 14:
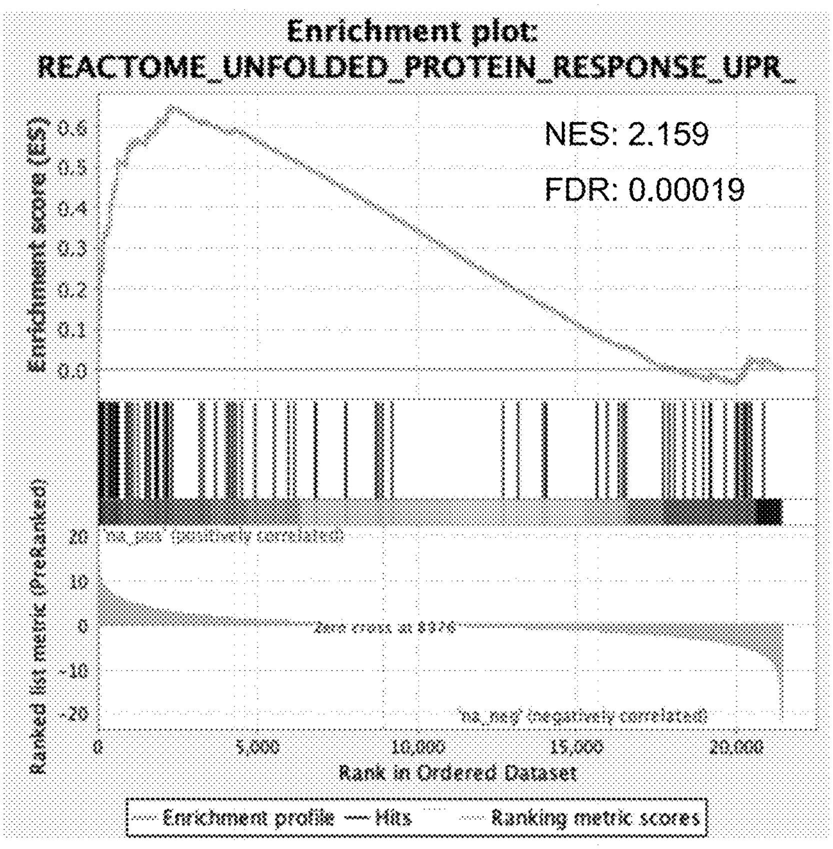
Figure 14:
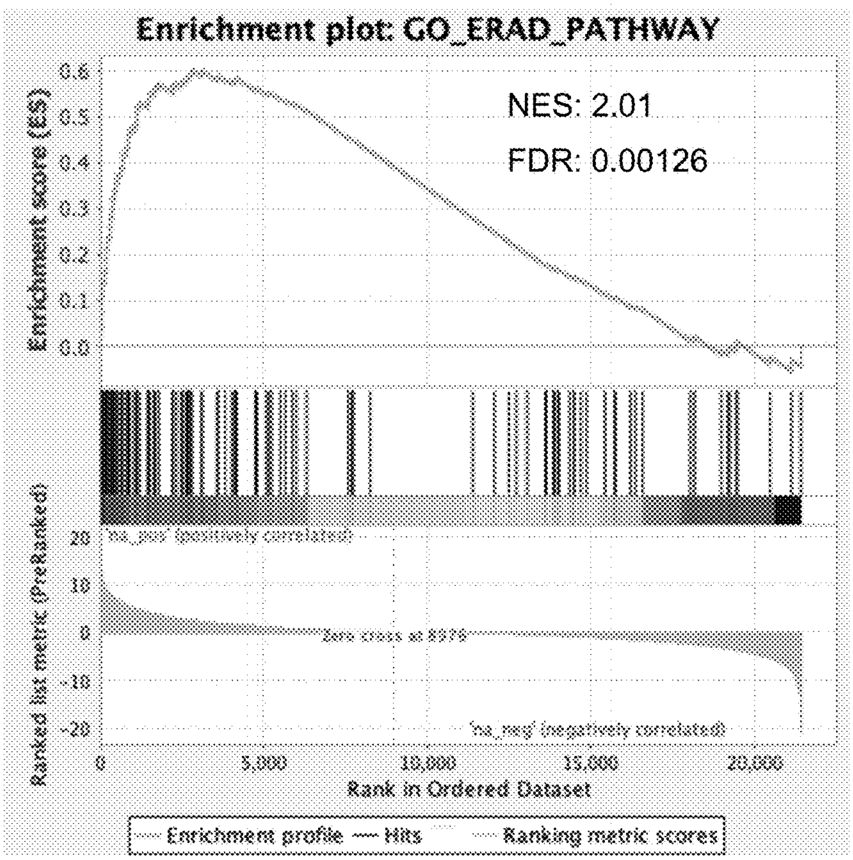
Figure 14:
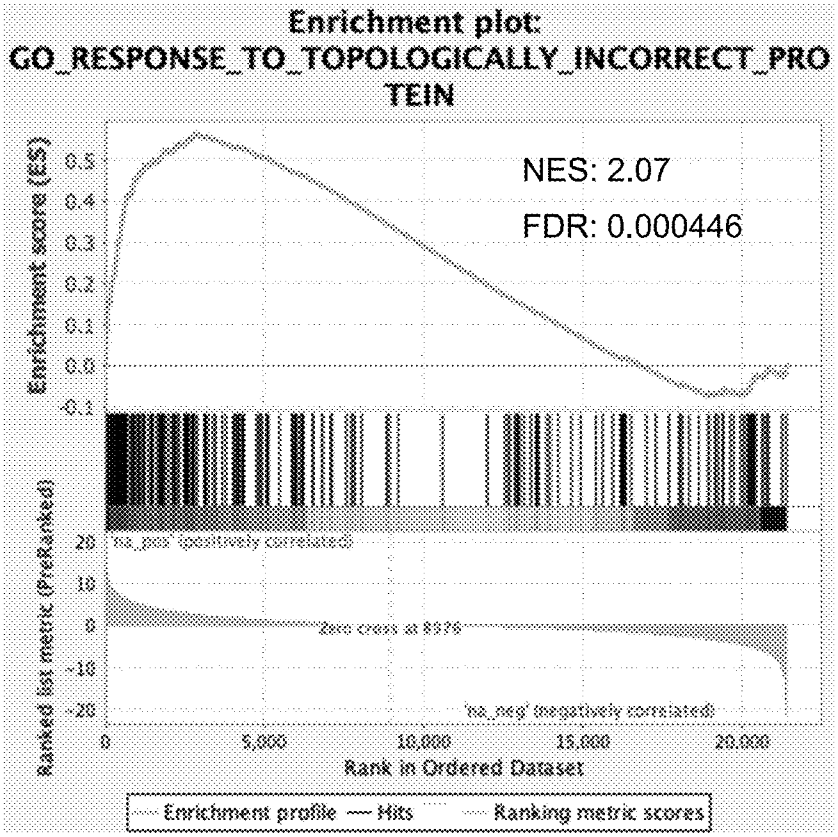
Figure 14:
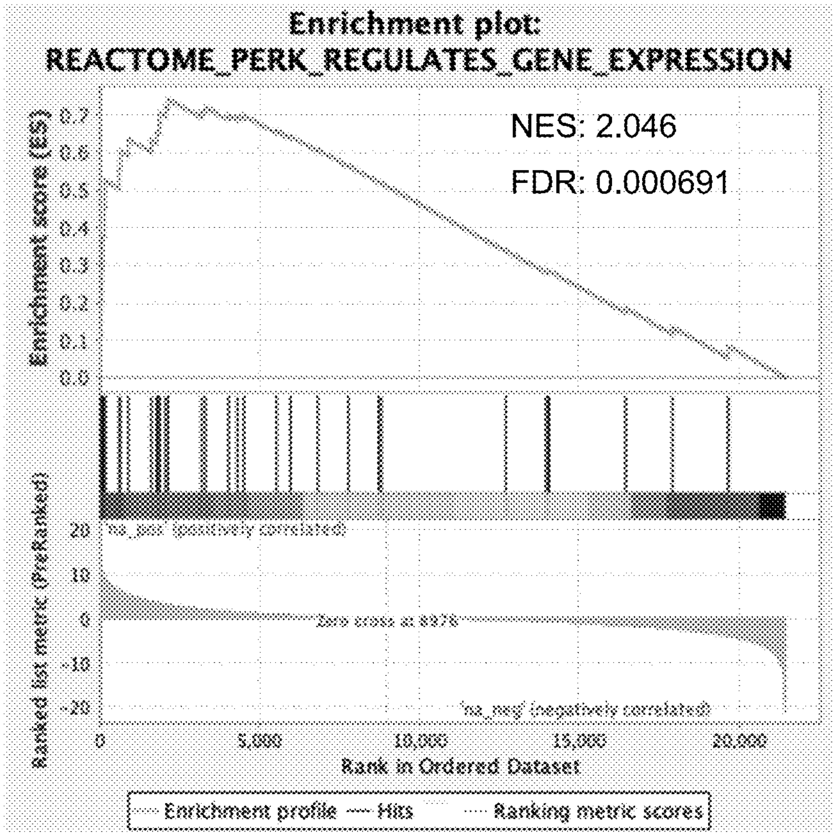
Figure 15A:
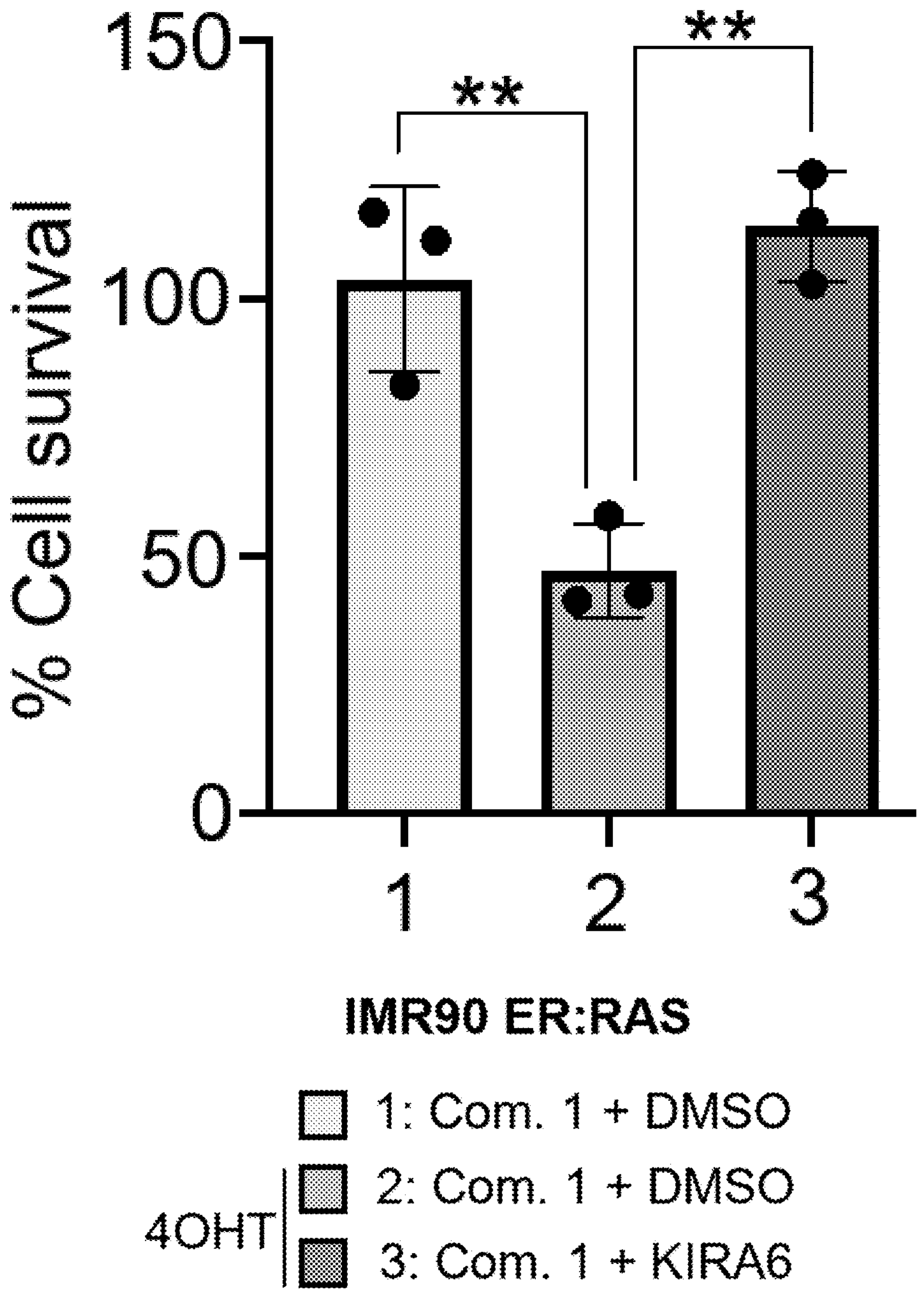
FIGS. 15A-B: Illustrate that the senolytic activity of Compounds 1 and 2 is dependent on IRE1 and the unfolded protein response.
Figure 15B:
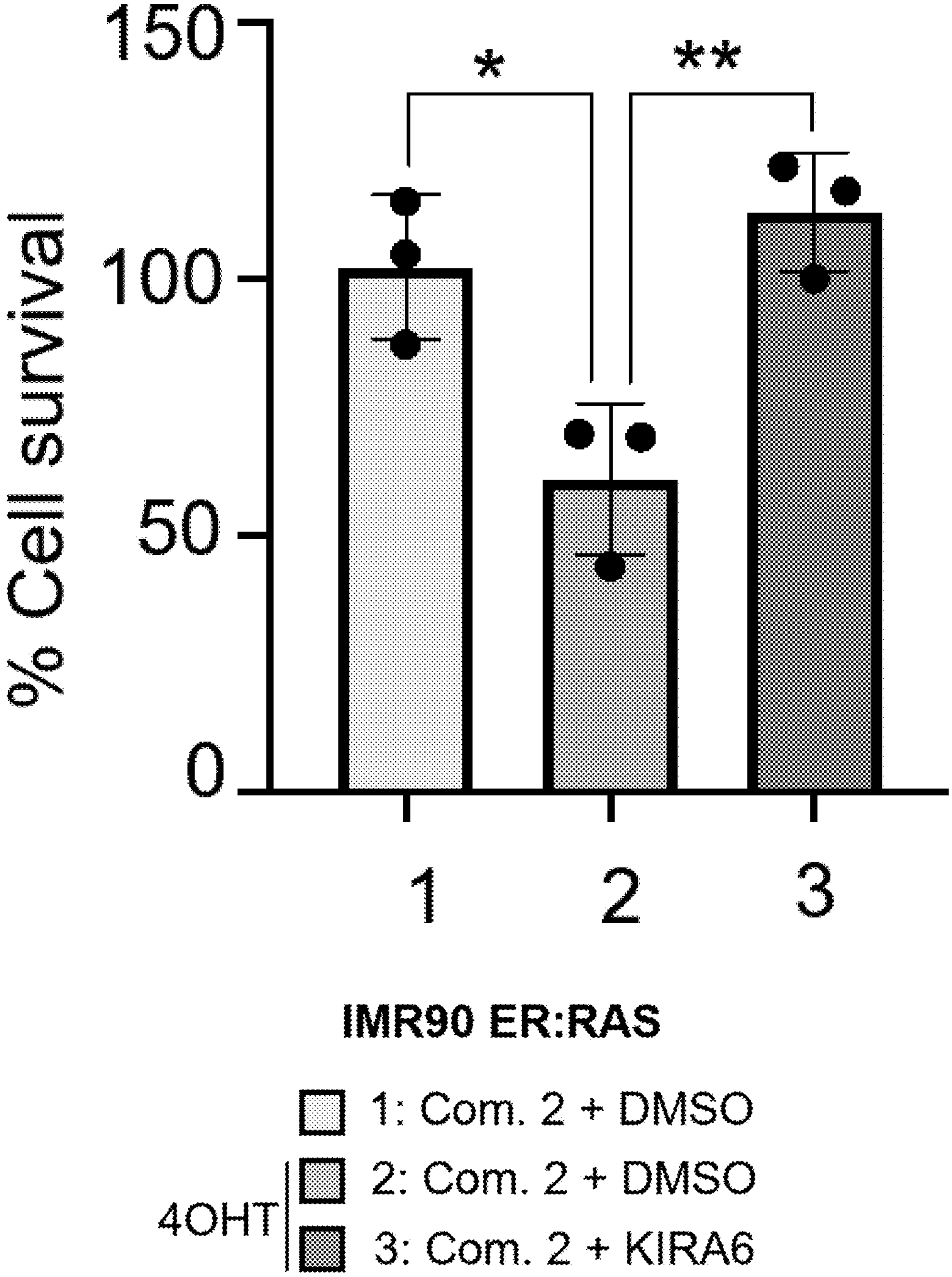

Moreover, using GSEA, enrichment of signatures of UPR in senescent cells treated with NMT inhibitors was observed (FIG. 14). These results further suggest that treatment of senescent cells with NMT inhibitors activate the UPR, Effect of Inhibition of the Unfolded Protein Response To investigate whether the activation of UPR caused by NMT inhibition in senescent cells was responsible for the senolytic potential of NMT inhibitors, cells were treated with KIRA6, a selective inhibitor of IRE1, a kinase necessary for the UPR. IMR90 ER:RAS cells undergoing senescence (after induction with 4OHT), were treated with 600 nM KIRA6 (an IRE1 inhibitor) on day 4 post-induction. On day 7 post-induction, cells were treated with Compound 1 or 2 and 600 nM KIRA6. Treatment with KIRA6, an inhibitor of the unfolded protein response protein IRE1, prevented the senolytic activity of NMT inhibitors in 4OHT treated cells (n=3) fixed, imaged and quantified 5 days after NMT inhibitor treatment (at day 12 post-induction). Both NMT inhibitor and Kira6 were replenished 3 days after addition of NMT inhibitor (at day 10 post-induction). Data is shown as mean±SD, n represents independent biological experiments. As treatment with KIRA6 prevented the senolytic activity of NMT inhibitors (FIGS. 15A-B). This result suggests that activation of the UPR mediates the senolytic potential of NMT inhibitors.

Figure 16A:
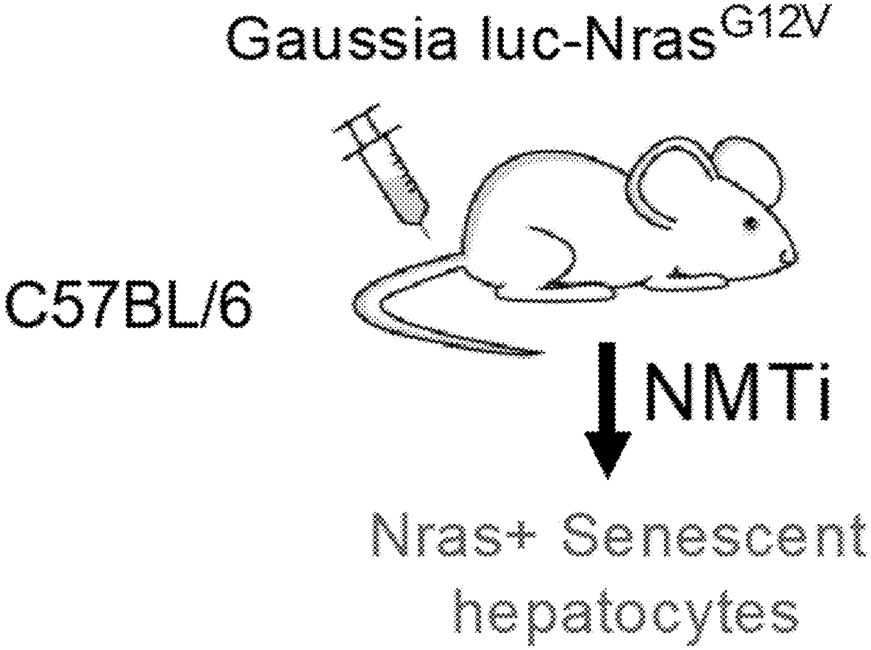
FIGS. 16A-B: Illustrate the treatment regime for 26-month old mice.
Figure 16B:
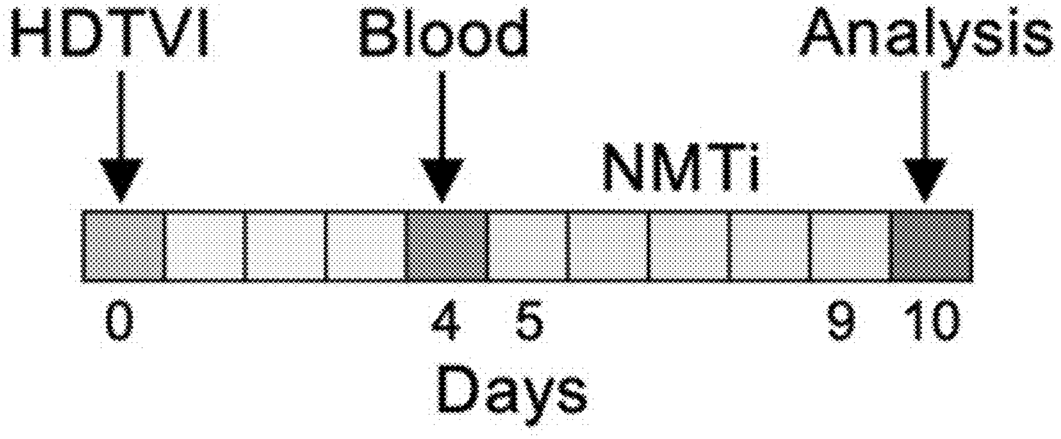
Figure 16C:
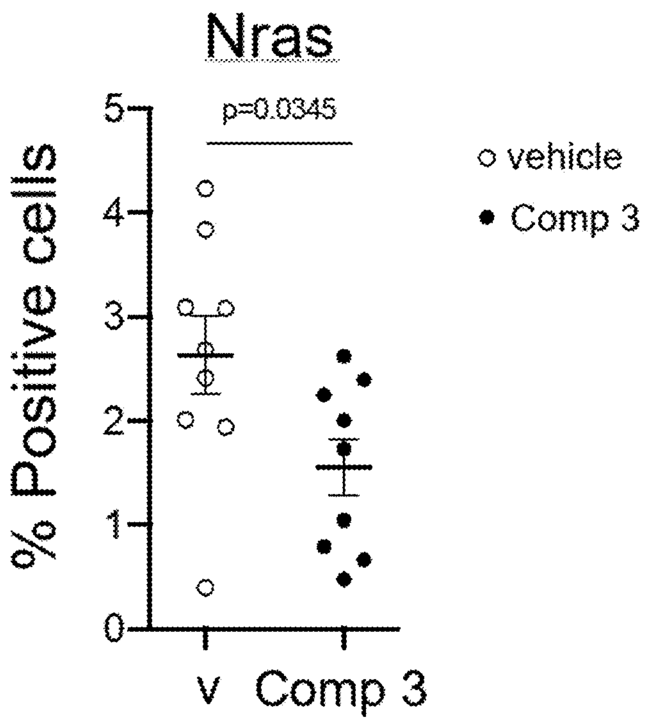
FIGS. 16C-E: Illustrate that treatment with Compound 3 reduces the number senescent preneoplastic hepatocytes in a model of liver cancer initiation.
Figure 16D:
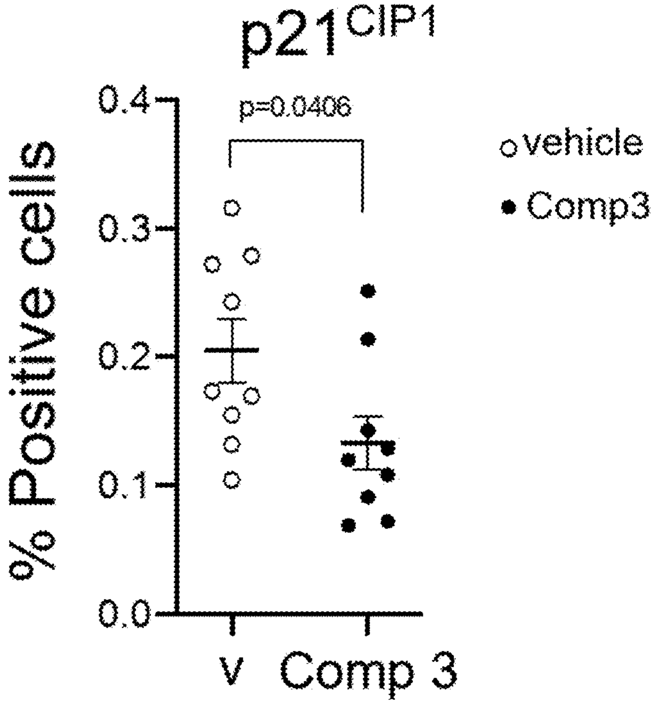
Figure 16E:
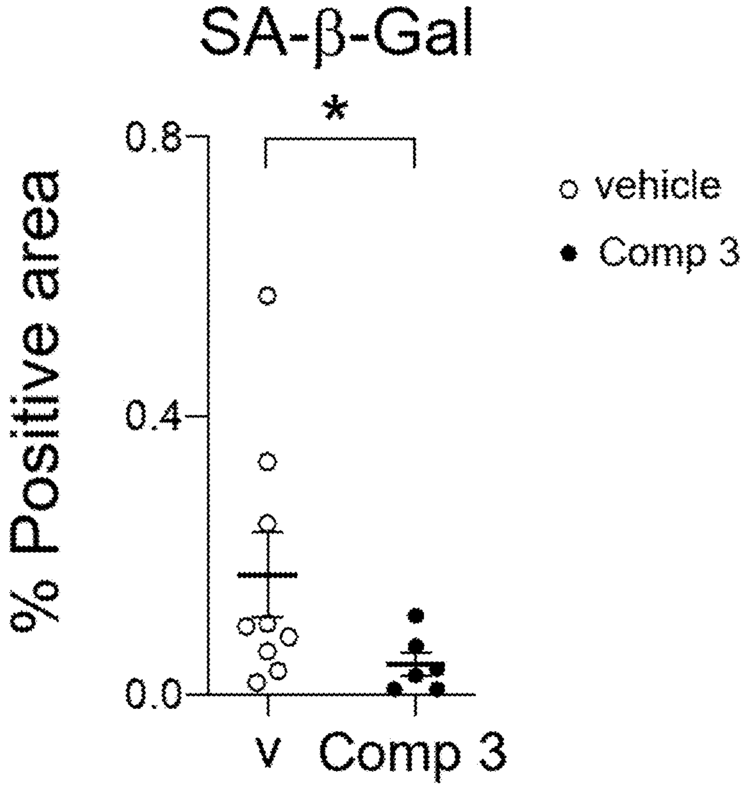

Biological Example 5: Determining the Effects of NMT Inhibitors in a Model of Liver Cancer Initiation In Vivo To investigate the senolytic potential of NMT inhibitors in vivo, OIS was triggered in hepatocytes via transposon-mediated transfer of oncogenic Nras ($Nras^{G12v}$) delivered by hydrodynamic tail vein injection (FIG. 16A). 5 days after transduction, a randomised group of mice were treated daily with an NMT inhibitor as indicated (FIG. 16B). Staining of liver section showed a reduction on Nras+ hepatocytes in the liver of NMT inhibitor treated mice (FIG. 16C), suggesting that NMT inhibitors are able to eliminate senescent cells in vivo. A reduction of $p21^{CIP1}$+ hepatocytes in the liver of NMT inhibitor treated mice was also observed (FIG. 16D). Furthermore, senescent-associated β-galactosidase staining was reduced in the livers of mice treated with NMTi (FIG. 16E). These results suggest that treatment with NMT inhibitors can kill senescent preneoplastic cells in a model of liver cancer initiation.

Figure 17A:
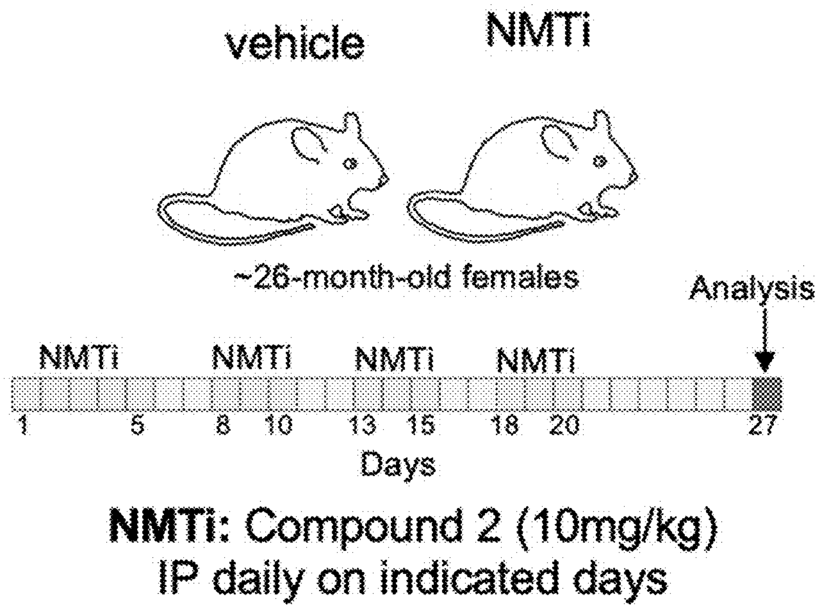
FIG. 17A: Illustrates the treatment regime for 26-month old mice.
Figure 17B:
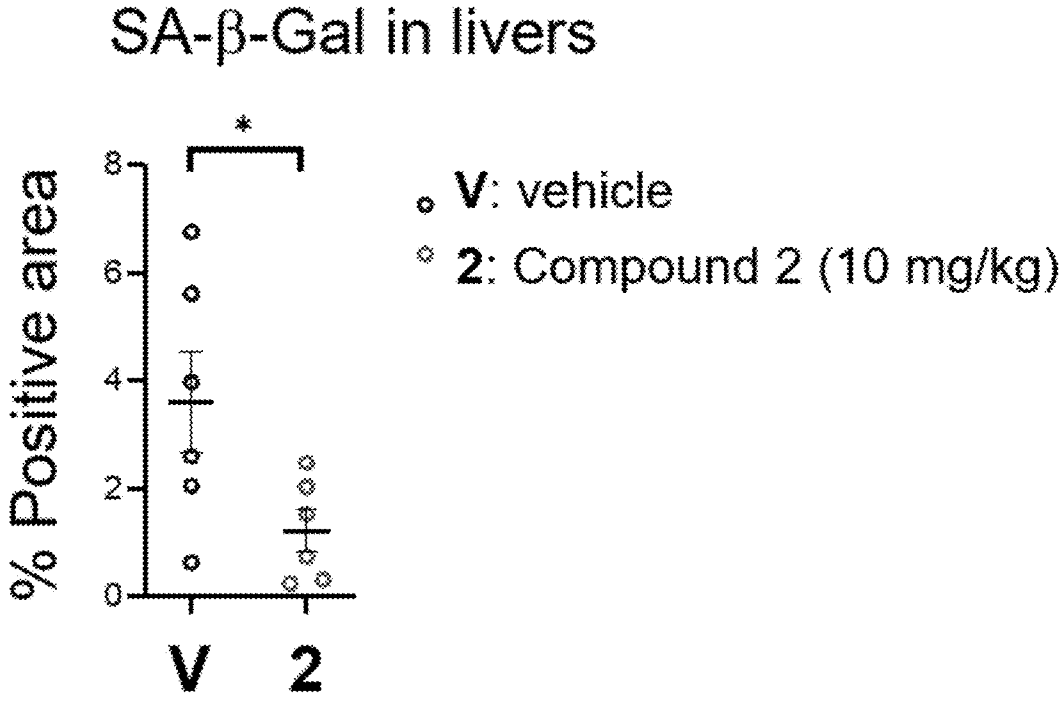
FIGS. 17B-C: Illustrate that treatment with Compound 2 results in reduced cellular senescence, with the reduced presence of senescent cell in the liver (FIG. 17B) and in the lungs (FIG. 17C).
Figure 17C:
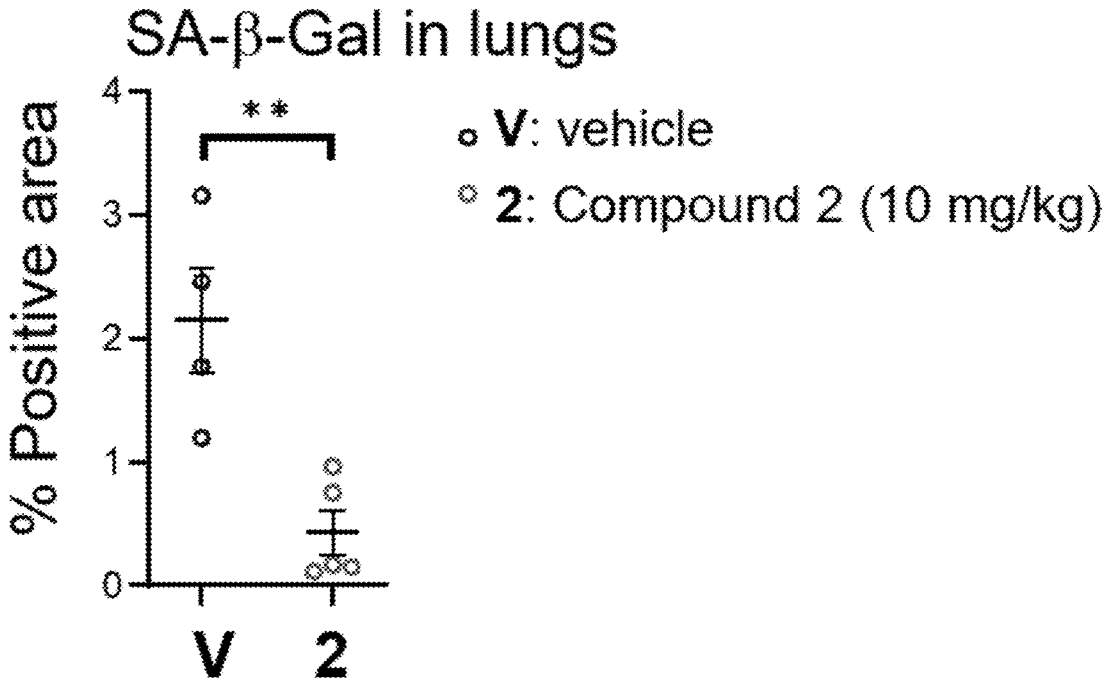

Biological Example 6: Determining the Senolytic Activity of NMT Inhibitors in Old Mice To evaluate the senolytic potential of NMT inhibitors in vivo, a group of ~26 month female mice were treated with Compound 2 (FIG. 17A). Reduced number of senescent cells were observed in mice treated with NMT inhibitors when compared with vehicle treated mice (FIG. 17B-C). The presence of senescent cells was analysed in livers (FIG. 17B) and lungs (FIG. 17C) of old mice treated with Compound 2 by performing senescent-associated β-galactosidase staining. In both cases, we observed that mice treated with compound 2 have lower levels of senescent cells (FIGS. 17B-C). This result suggests that NMT inhibitors can behave as effective senolytic compounds eliminating senescent cells in different tissues in vivo.

Figure 18A:
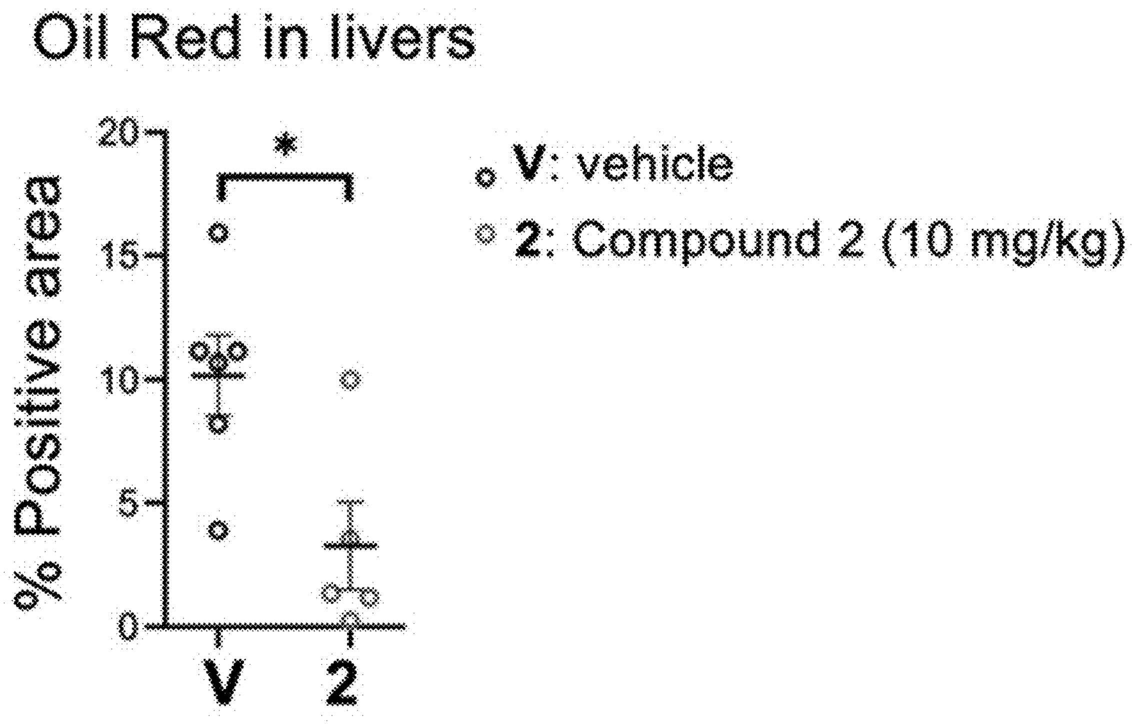
FIG. 18A: Illustrates that treatment with Compound 2 results in reduced accumulation of lipids in the liver.

Biological Example 7: Determining the Effects of NMT Inhibitors in Senescence-Associated Pathologies To understand what effects are associated with the treatment with NMT inhibitors in vivo, we analysed different parameters in the same cohort of old mice described in FIG. 17A. First, we looked into the accumulation of lipid droplets in the liver using Oil Red O staining. These are an indication of hepatic steatosis, and importantly, elimination of senescent cells has been previously shown capable to reduce steatosis. We observed a reduced accumulation of lipids in the livers of mice treated with NMTi (FIG. 18A). This result suggests that treatment with NMTi could impact senescence-associated pathologies such as steatosis, liver disease and other metabolic disorders.

Figure 18B:
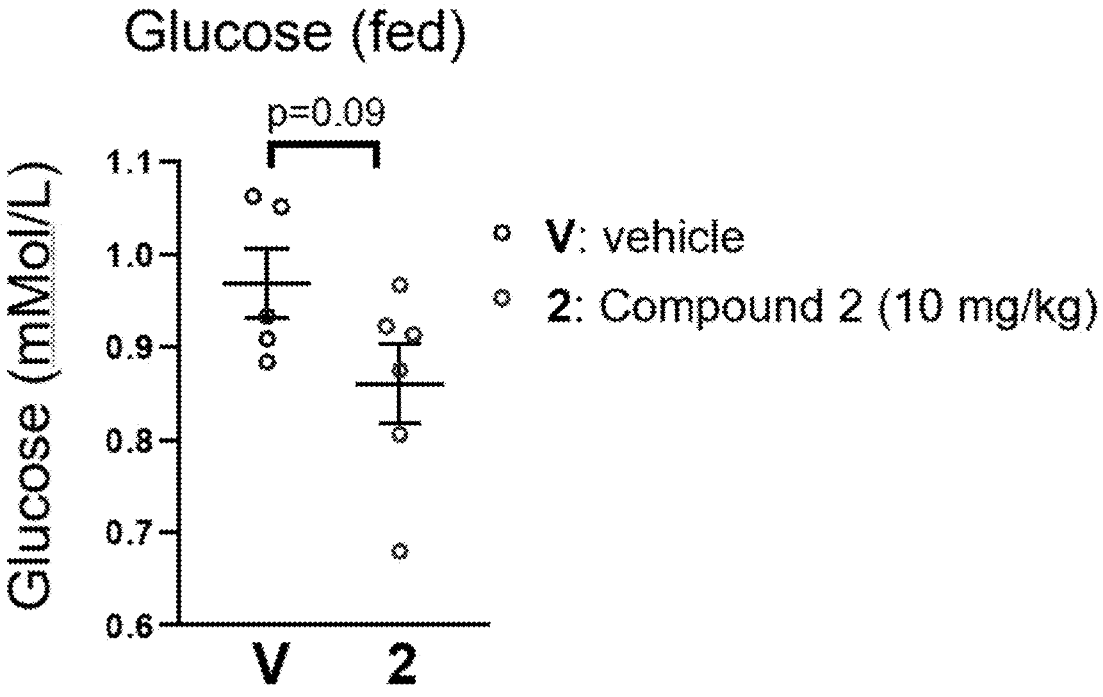
FIGS. 18B-C: Illustrate that treatment with Compound 2 results in reduced glucose in fed and fasted old mice.
Figure 18C:
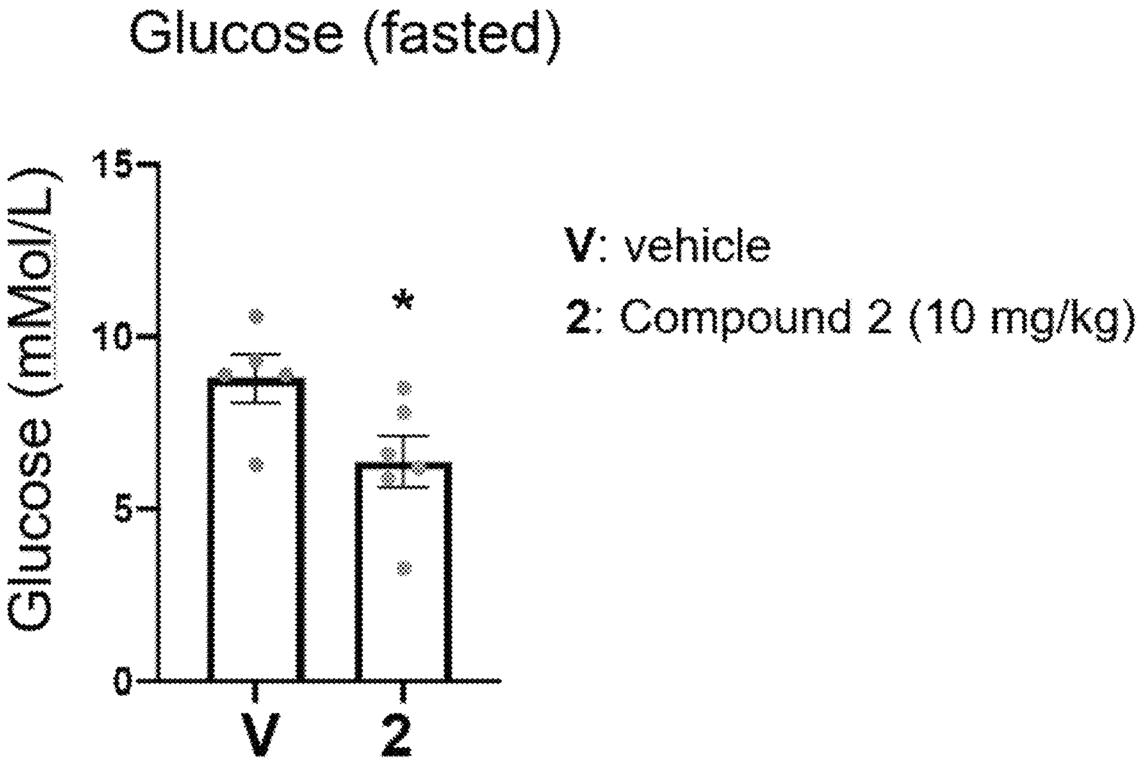

Other pathological change observed in old mice is the presence of increased levels of glucose in blood. This can be related with diabetes or metabolic disease. Importantly, both pathologies have been associated with the presence of senescent cells. We analyse the concentration of glucose in blood from mice treated with Compound 2 that were kept fed (FIG. 18B) or had been fasted (FIG. 18C. Mice treated with NMTi presented lower levels of glucose than their old mice counterparts (FIGS. 18B-C). This result suggests that treatment with NMTi could normalise the high levels of glucose in blood associated with diabetes or metabolic disease.

Figure 19:
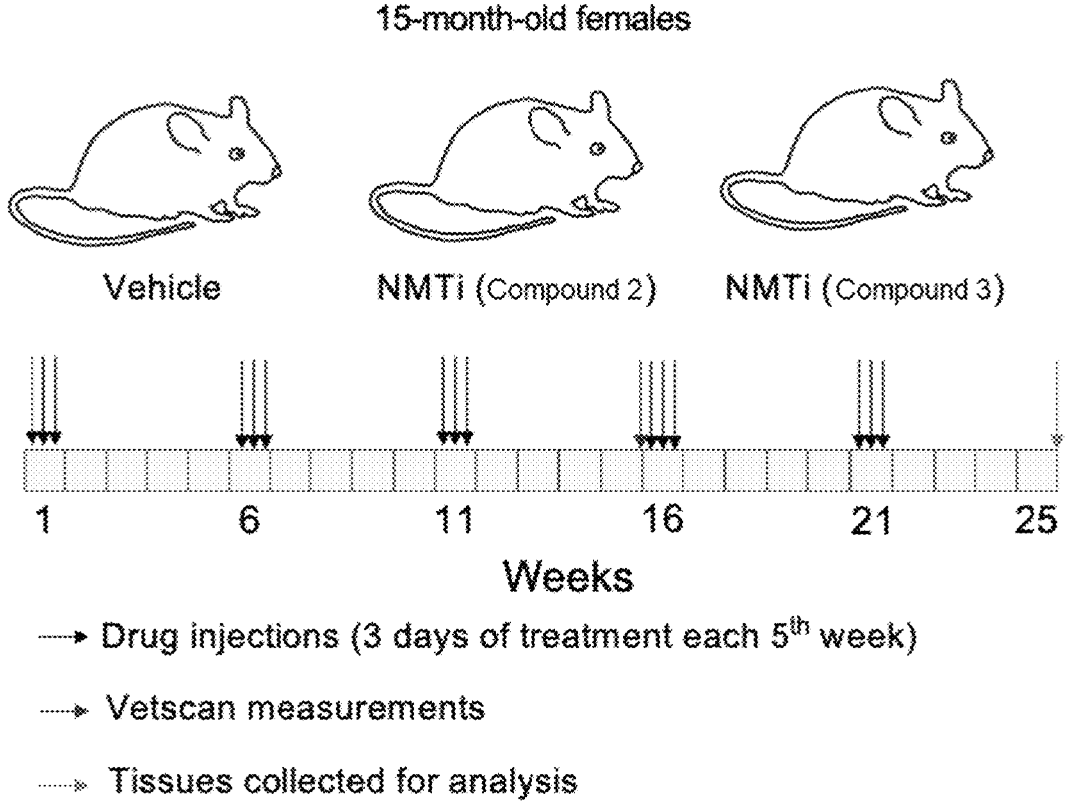
FIG. 19: Illustrates the experimental design for assessing the effect of treating aged mice with NMT inhibitors.
Figure 20A:
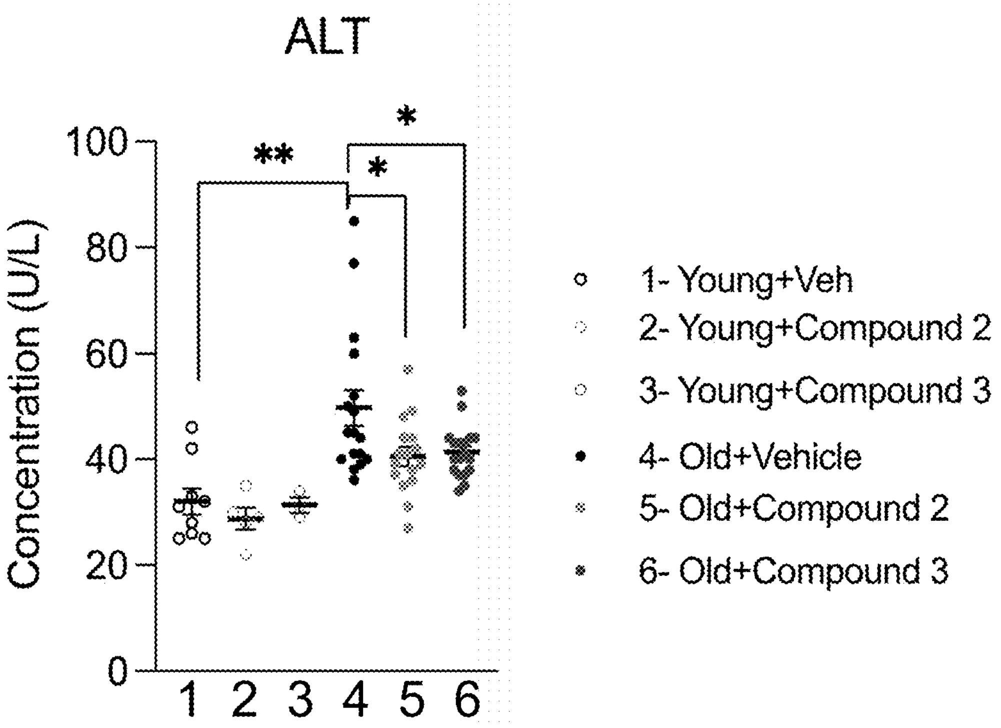
FIGS. 20A-C: Illustrate that aged mice treated with a NMT inhibitor showed lower levels of ALT, amylase and glucose in blood.
Figure 20B:
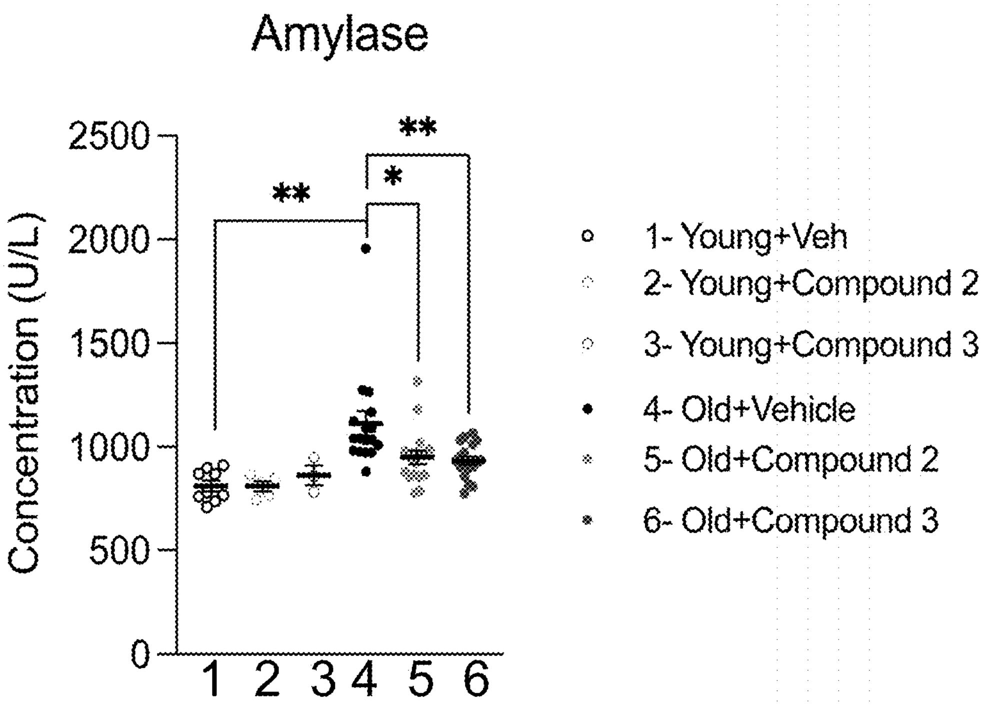
Figure 20C:
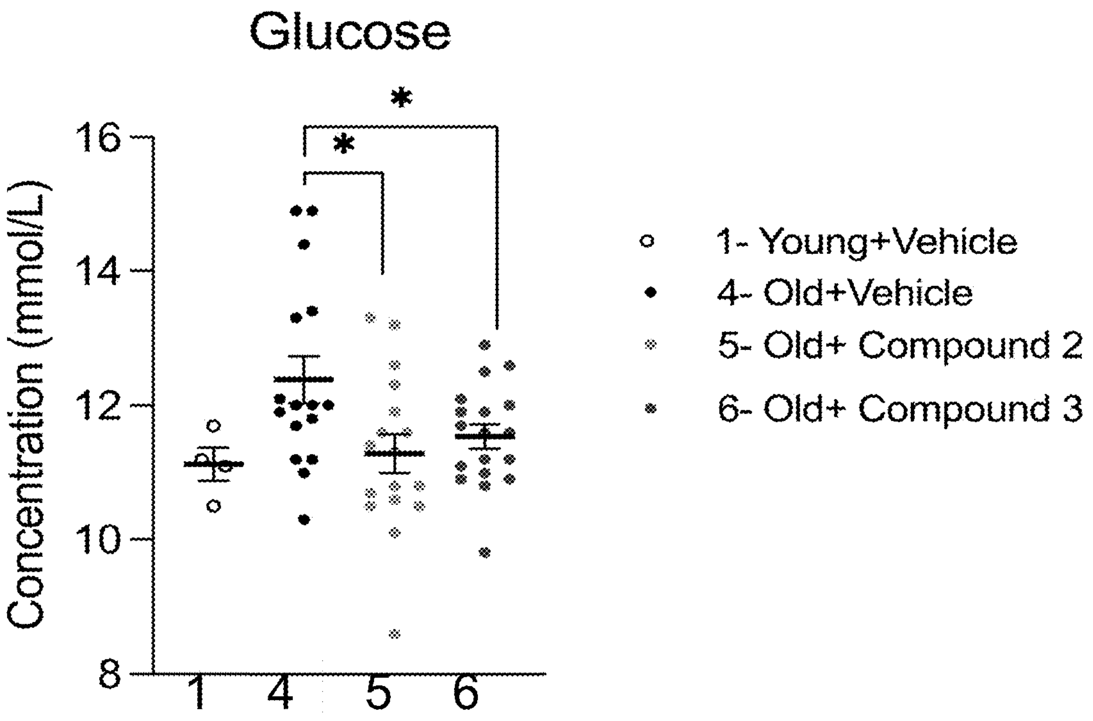

Further experiments were performed on a separate cohort of old mice. 15-month old (mo) female C57/BL6 mice were subjected to 1 week of 3 daily treatments with either Vehicle, Compound 2 (10 mg/kg) or Compound 3 (25 mg/kg) followed by a 4 week treatment holiday. This regimen was repeated 4 more times and blood was collected for Vetscan measurements prior to the $4^{th}$ round of treatment (FIG. 19). At that stage, ~19 mo females presented elevated levels of ALT, amylase and glucose in blood when compared with young mice (FIG. 20A). Old mice treated with Compound 2 or 3 showed lower level that vehicle-treated controls of ALT (indicative of liver damage, FIG. 20A), amylase (indicative of pancreatic damage, FIG. 20B) and glucose in blood (FIG. 20C). These results suggest that treatment with NMTi could normalize the levels in blood of different markers associated with disease e.g. pancreatic, liver and metabolic disease.

Figure 21:
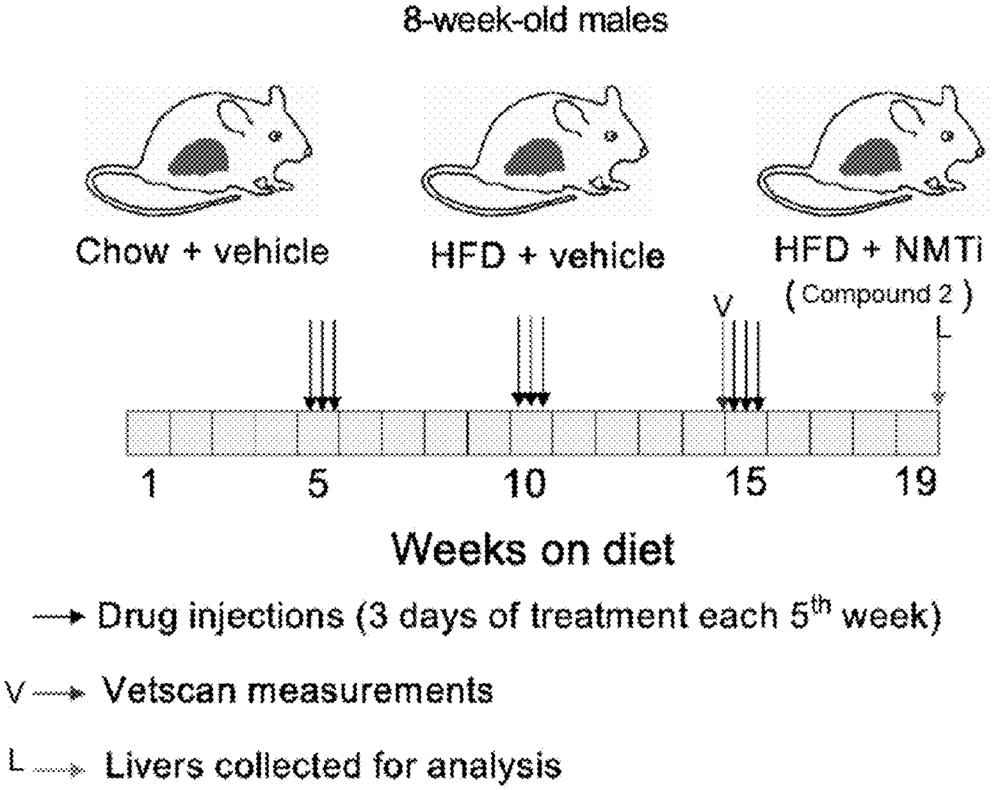
FIG. 21: Illustrates the experimental design of treating mice fed with a high fat diet with a NMT inhibitor.

Further experiments were performed using a high fat diet model of nonalcoholic steatohepatitis (NASH, FIG. 21). 8-week old (wo) male C57/BL6 mice were placed on either chow or a high fat diet (HFD; Kcal 40% fat—Non trans fat Primex Shortening, Kcal 20%—fructose, Kcal 2%-cholesterol) for 5 weeks, on week 5 mice were give 3 daily injections of either Vehicle or Compound 2 (10 mg/kg). This regimen was repeated twice more as indicated in FIG. 21. Blood was collected for suPAR and Vetscan measurements prior to $3^{rd}$ round of treatment. Mice were subsequently allowed to rest for 4 weeks before collection of tissues.

Figure 22A:
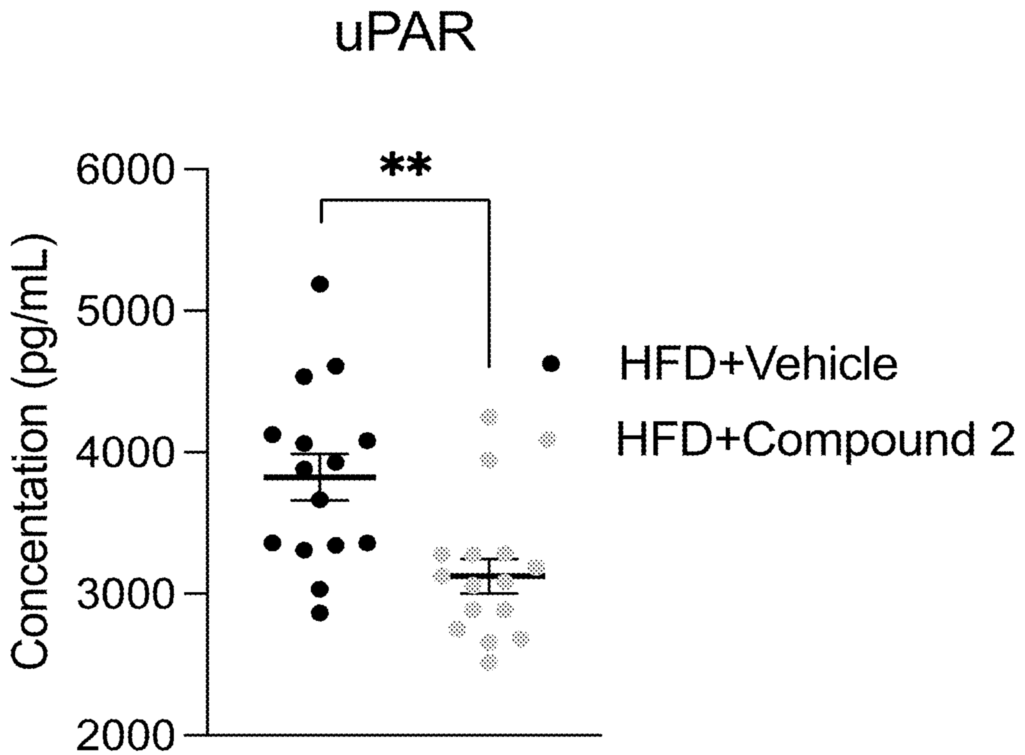
FIG. 22A: Illustrates that high fat diet fed mice treated with a NMT inhibitor showed lower levels of suPAR in blood.
Figure 22B:
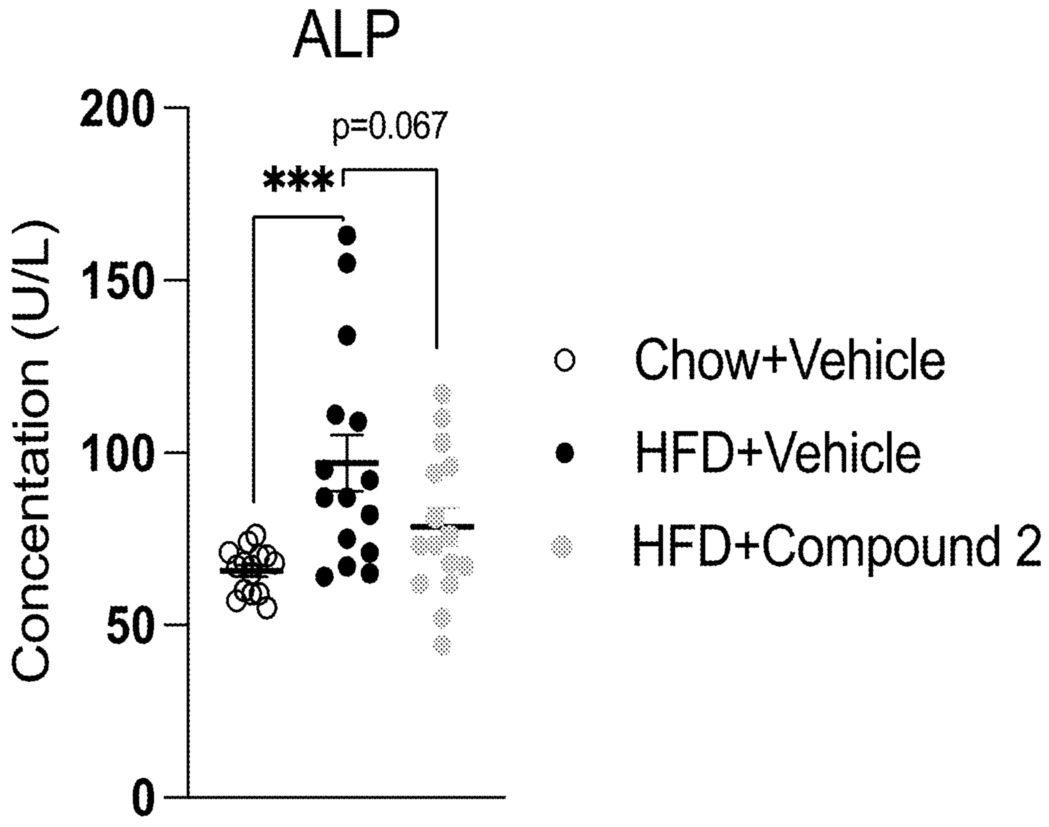
FIGS. 22B-D: Illustrate that treatment of high fat diet fed mice with a NMT inhibitor normalized the levels of ALT, ALP and albumin in blood.
Figure 22C:
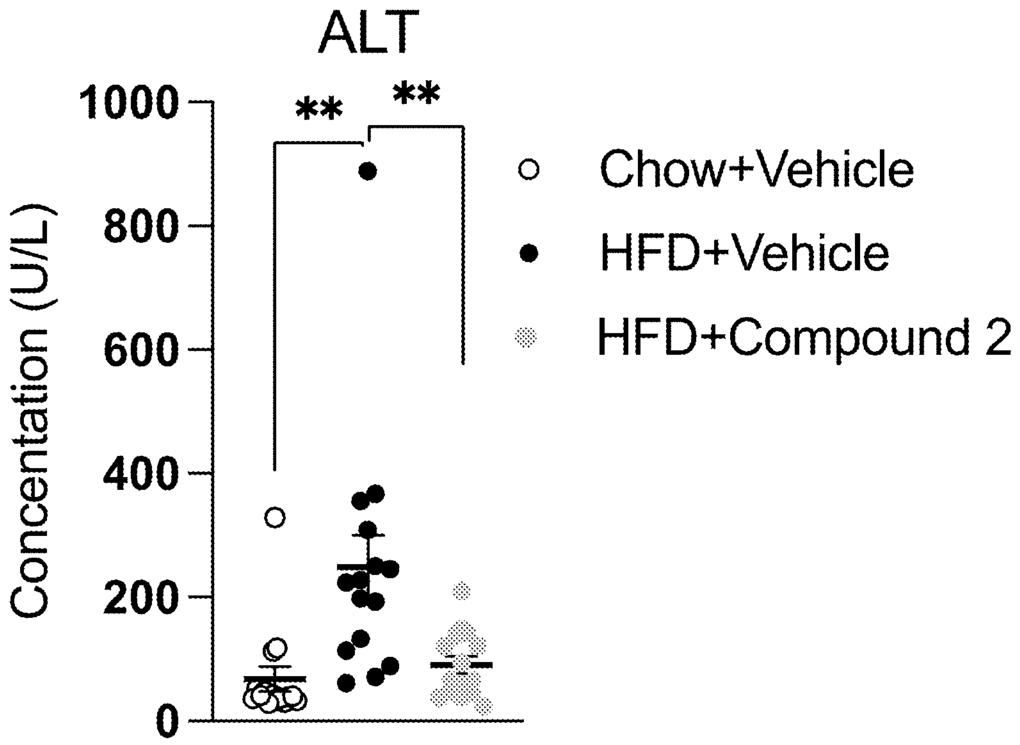
Figure 22D:
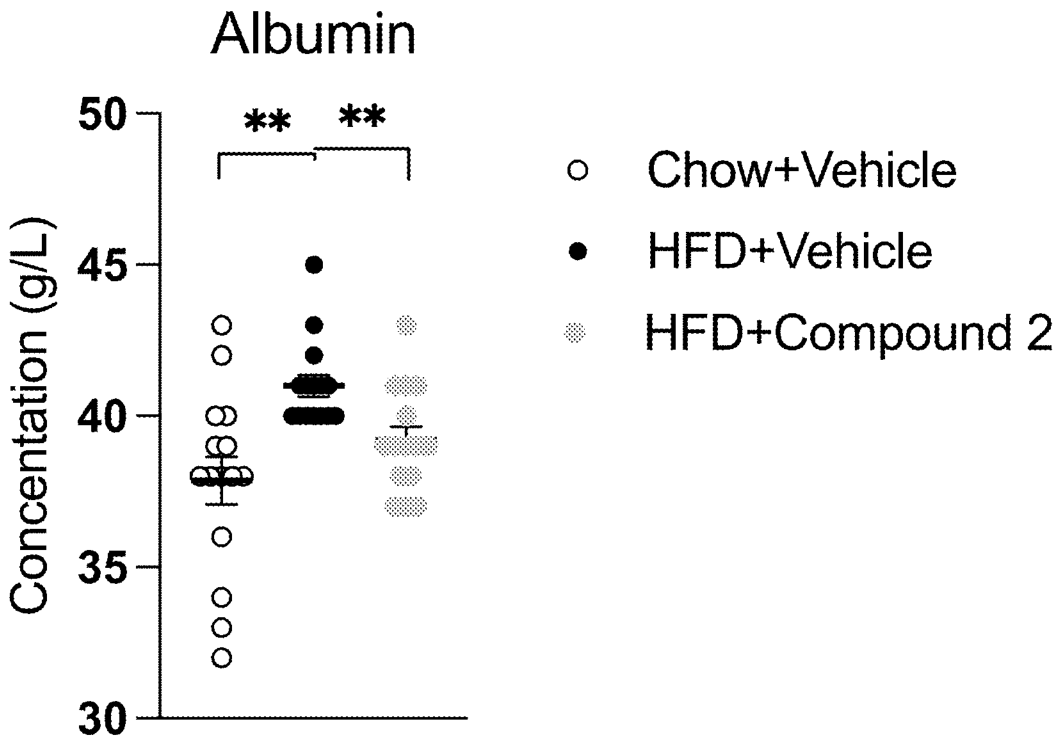
Figure 23:
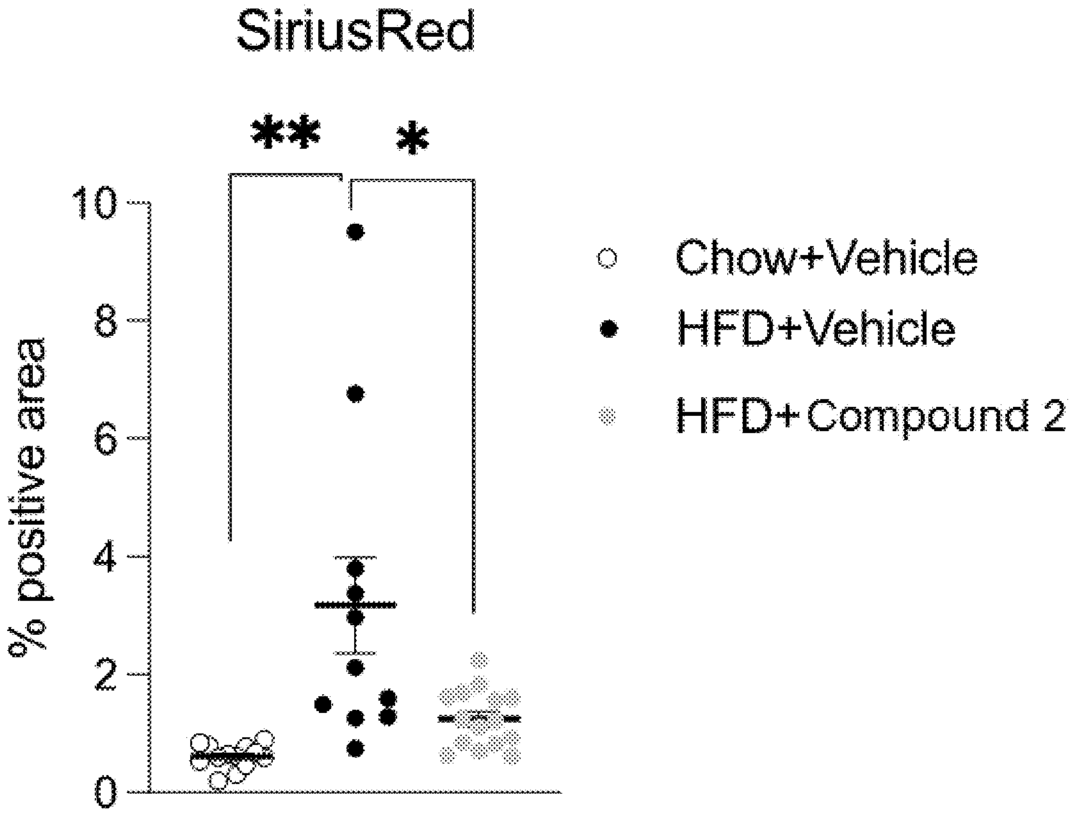
FIG. 23: Illustrates that treatment of high fat diet fed mice with a NMT inhibitor normalized liver fibrosis.
Figure 24A:
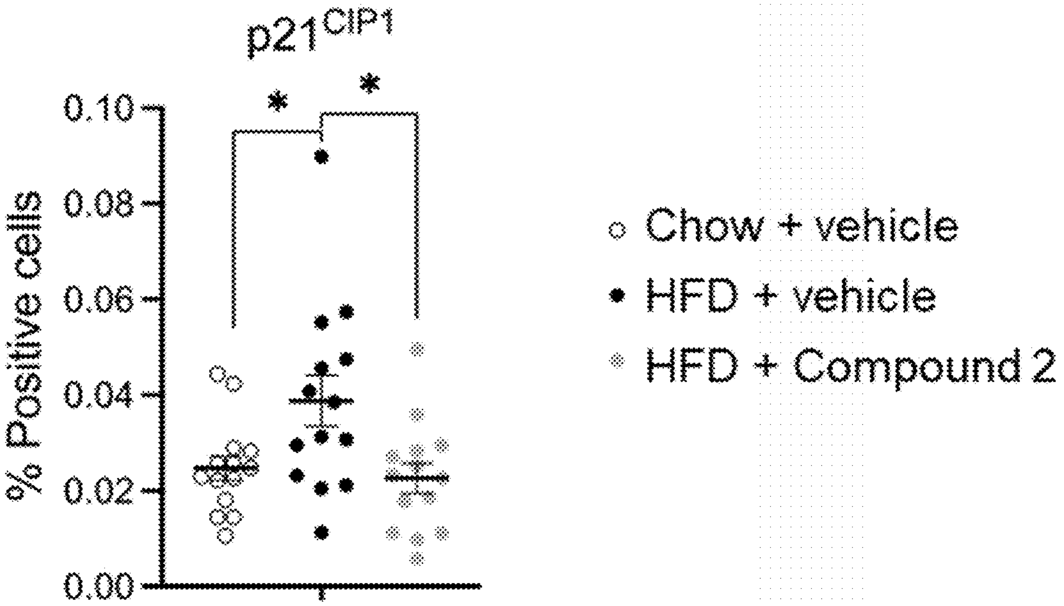
FIG. 24A: Illustrates that treatment of high fat diet fed mice with a NMT inhibitor normalized the levels of $p21^{CIP1}$ in livers.
Figure 24B:
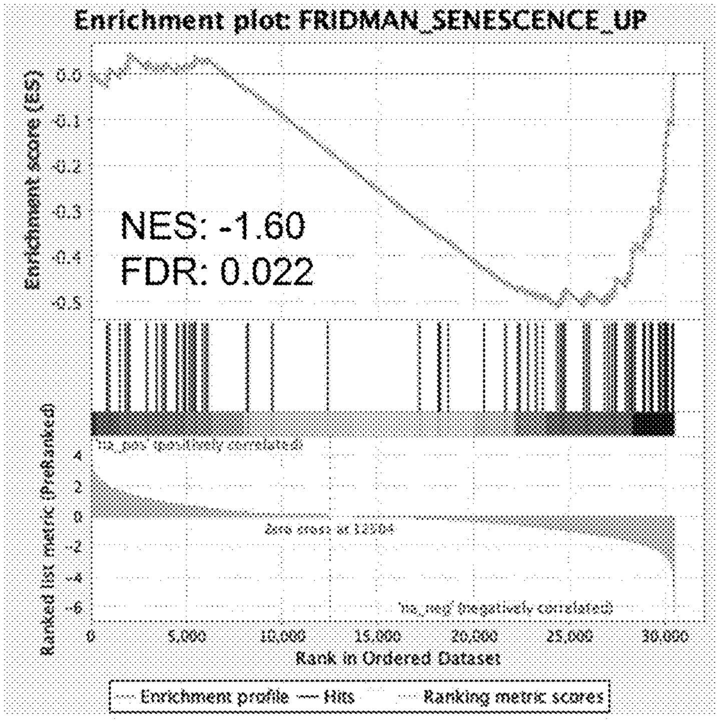
FIG. 24B-C: Illustrate that transcriptional signatures for Fridman senescence and senescence-associated secretory phenotype are downregulated in the livers of mice treated with a NMT inhibitor.
Figure 24C:
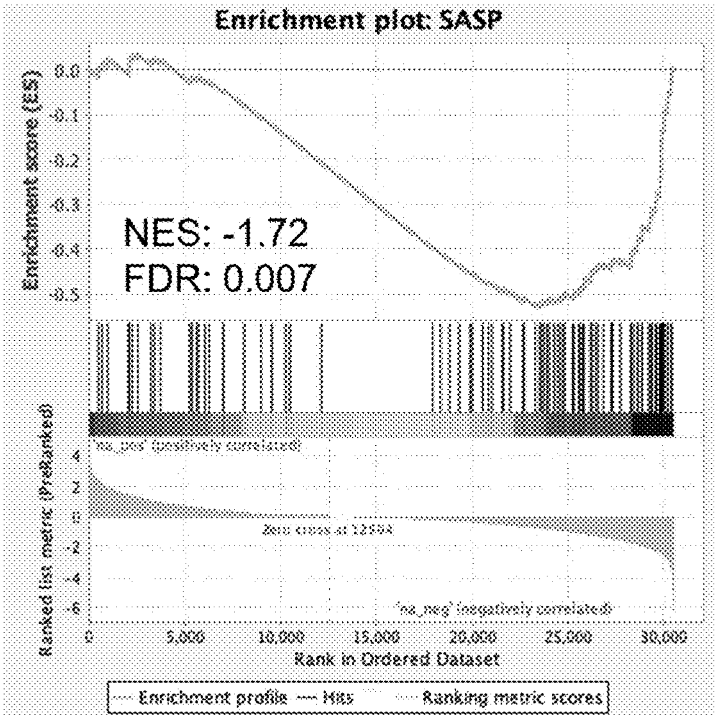
Figure 24D:
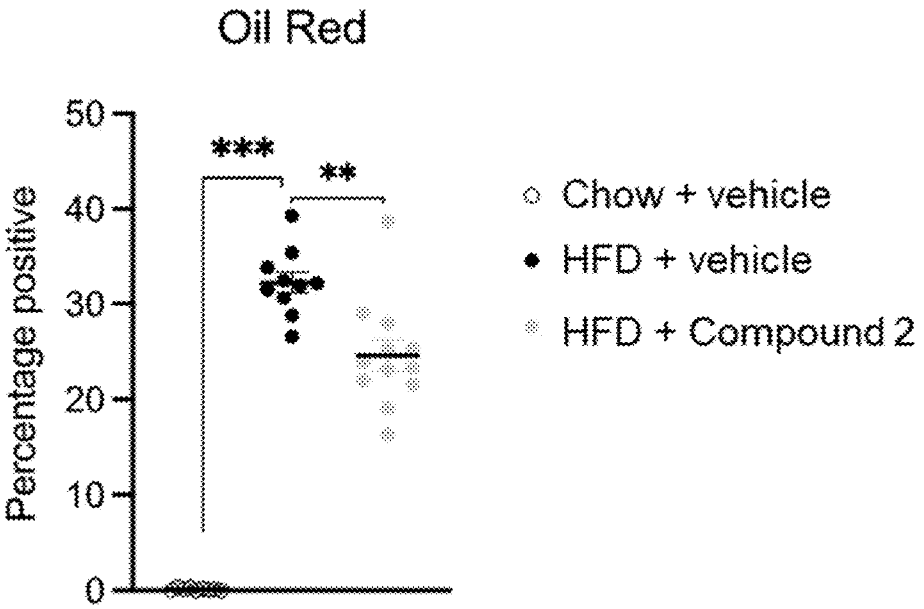
FIG. 24D: Illustrates that treatment with a NMT inhibitor results in reduced accumulation of lipids in the liver.
Figure 24E:
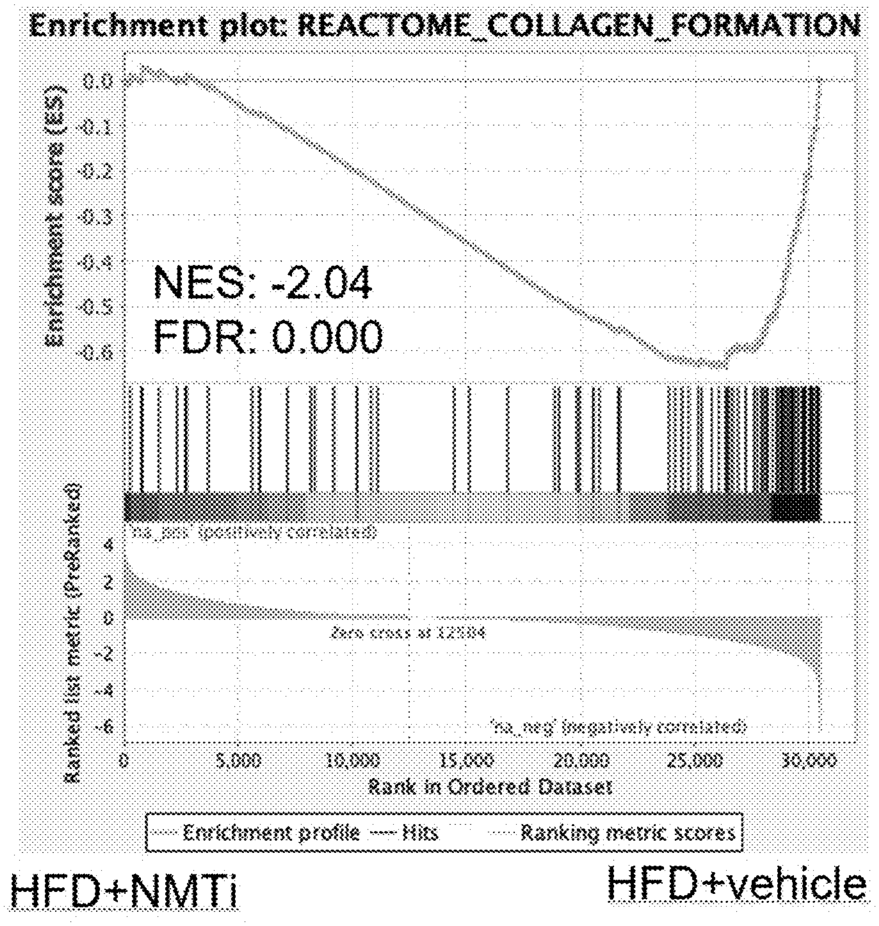
FIG. 24E: Illustrates that transcriptional signatures for collagen formation are downregulated in the livers of mice treated with a NMT inhibitor.
Figure 24F:
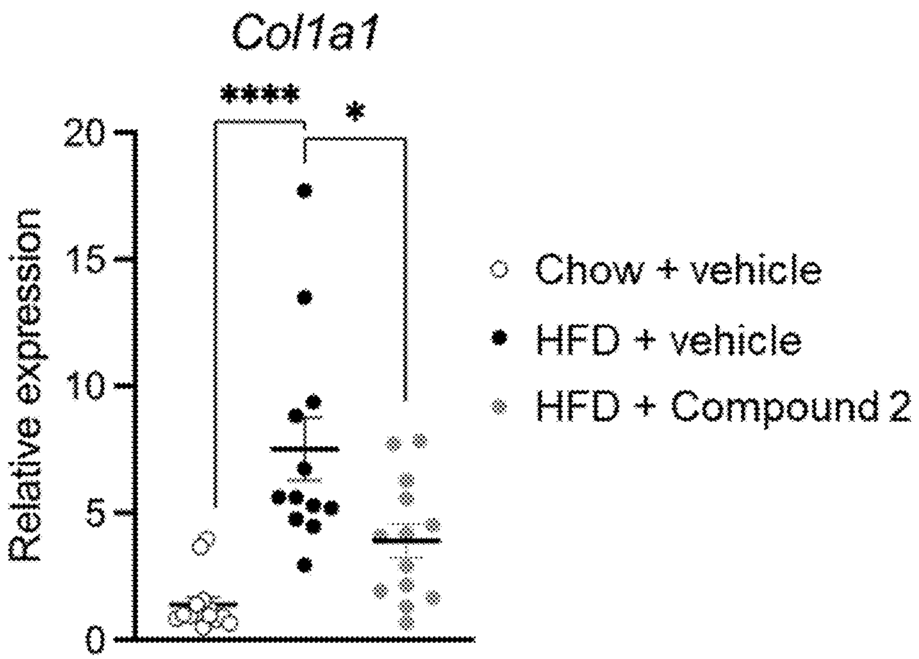
FIGS. 24F-G: Illustrate that treatment of high fat diet fed mice with a NMT inhibitor normalized the levels of Collal and Col4a1 in the liver.
Figure 24G:
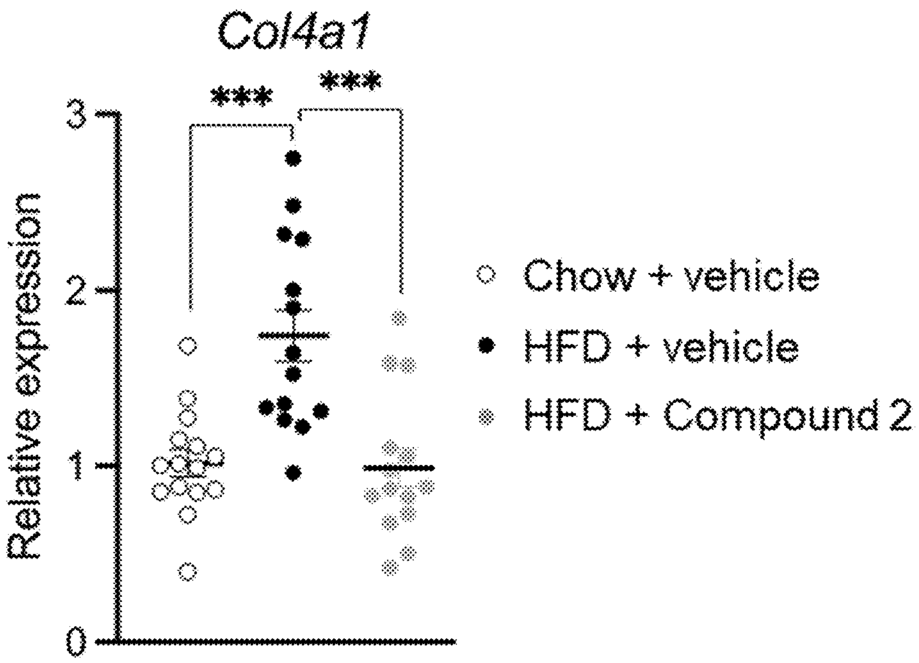

Mice fed in HFD treated with compound presented lower levels of suPAR in blood that vehicle-treated controls (FIG. 22A). suPAR has been suggested as a surrogate marker of senescence, and therefore this result suggest that treatment with Compound 2 reduced the levels of senescent cells in mice fed with HFD. To evaluate the liver damage associated with these mice, we measured the levels of ALT, ALP and albumin in blood (FIGS. 22B-D), in all cases the levels increased in mice fed with HFD when compared to chow-fed mice. Moreover, treatment with Compound 2 normalised the levels of ALT, ALP and albumin in blood of mice fed with HFD (FIGS. 22B-D).

of the consequences associated with a high fat diet liver fibrosis. Sirius red staining showed increased liver fibrosis in mice fed on HFD. This increased fibrosis was normalized in mice treated with Compound 2 (FIG. 23). Collagen deposition is involved in the development of liver fibrosis. Treatment with a NMTi led to an downregulation of transcriptional signatures of collagen formation in the transcriptome of livers of mice (FIG. 24E). Levels of mRNA encoding collagen genes Col1a1 and Col4a1 (markers of liver fibrosis) were lower in the livers of mice which were treated with a NMTi (FIGS. 24F-G). Another consequence of HFD is the abnormal accumulation of lipids (steatosis). A reduction in this lipid accumulation in the livers of mice treated with NMTi was also observed (FIG. 24D). Accumulation of senescent cells has been shown to be a contributor factor to NASH. A reduction of $p21^{CIP1}$-positive hepatocytes (used as a marker of senescence) in the liver of NMTi treated mice was also observed (FIG. 24A), and treatment with NMTi lead to downregulation of transcriptional signatures of Fridman senescence and the senescence-associated secretory phenotype in the transcriptome of livers of mice (FIGS. 24B-C).

Figure 25:
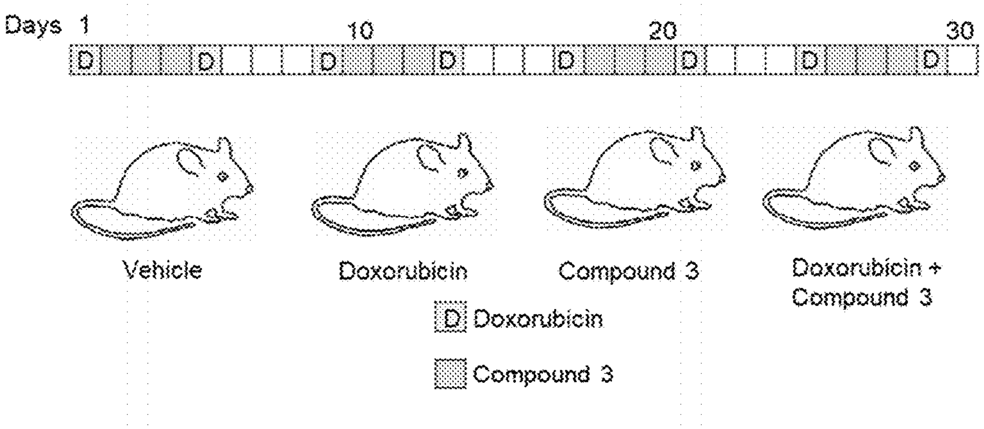
FIG. 25: Illustrates the experimental design of the effect of treatment with a NMT inhibitor in a mouse xenograft model.

Biological Example 8: Determining the Effect of Co-Operative Chemotherapy and NMT Inhibitor Treatment in a Cancer Xenograft Study To study the effects of combination therapy of Compound 3 and doxorubicin, human colon cancer cell line HCT116 was subcutaneously xenografted onto BALB/c nude mice. Mice were inoculated with $5\times10^6$ viable HCT116 cells resuspended in 0.1 mL of PBS. Over the course of 30 days, mice were dosed with vehicle ($Na_2HPO_4$ buffer (10 mM) (pH 7.4)+0.2% Tween 80), doxorubicin, intravenous, 3 mg/kg (0.9% NaCl, $dH_2O$), Compound 3, intraperitoneal, 10 mg/kg (on days 2, 3, 4, 10, 11 and 12 of the study) or 20 mg/kg (on days 18, 19, 20 and 26, 27, 28 of the study) ($Na_2HPO_4$buffer (10 mM) (pH 4.5)+0.2% Tween 80) or combination of doxorubicin and Compound 3. To avoid possible toxicity due to additive effects of drugs, mice were treated with both drugs non-contemporaneously, with doxorubicin doses being given 3 days apart and Compound 3 within a 3-day gap, with dosing holiday provided for 3 days between dosing rounds. Mice were sacrificed when tumour volume exceeded 2000 $mm^3$ (FIG. 25).

Figure 26A:
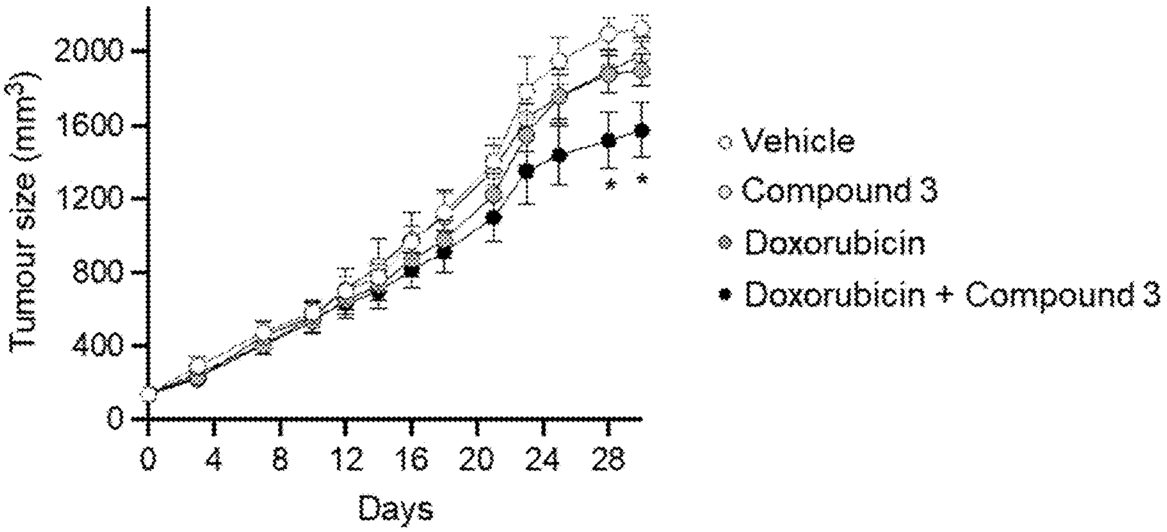
FIGS. 26A-B: Illustrate the effect of treatment with a NMT inhibitor on the tumor size throughout the study and the final tumor size.
Figure 26B:
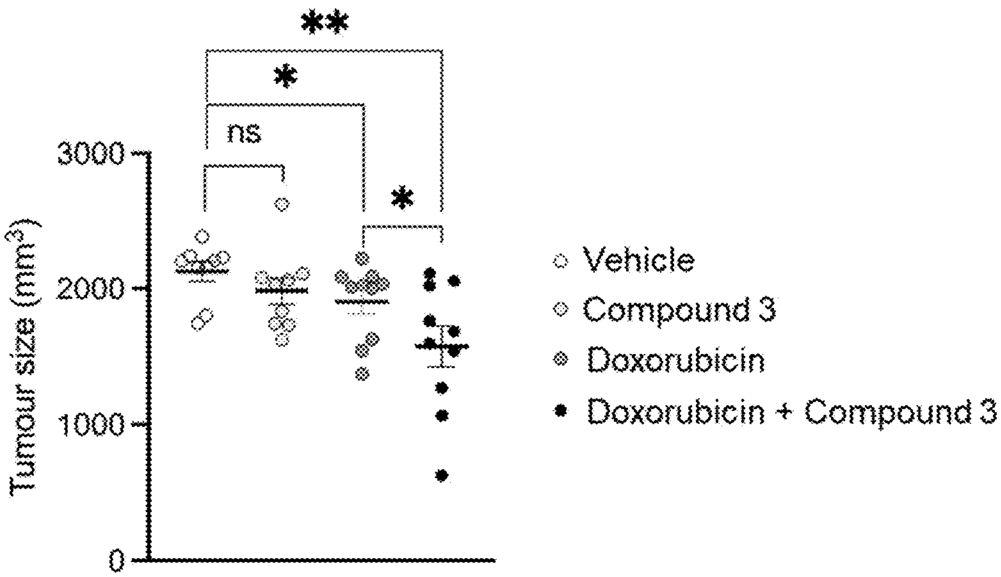

The tumour size in the different treatment groups during the duration of the experiment is shown in FIG. 26A, whilst the final tumour size at day 30 is shown in FIG. 26B. The results indicate that the tumour size in the treatment group utilising doxorubicin and Compound 3 was significantly smaller from day 22 of the study (FIG. 26A), and the final tumour size of this treatment group was smaller compared to vehicle, Compound 3 alone or doxorubicin alone (FIG. 26B). Therefore, the results suggest that co-operative therapy with a chemotherapeutic agent and a NMT inhibitor reduces tumour growth in vivo.

Figure 27:
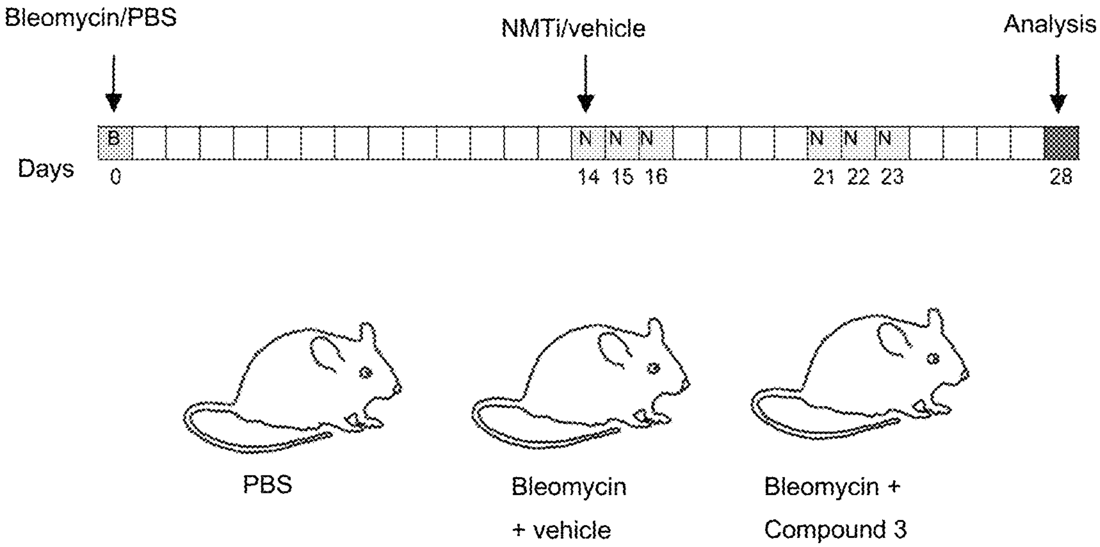
FIG. 27: Illustrates the experimental design of assessing the effect of treatment with a NMT inhibitor in a model of pulmonary fibrosis induced with bleomycin.

Biological Example 9: Determining the Activity of NMT Inhibitors in a Pulmonary Fibrosis Model The use of the murine intratracheal bleomycin model in animals of both genders, using hydroxyproline measurements for collagen accumulation along with histologic assessments, is considered to be the best-characterized animal model available for preclinical testing of pulmonary fibrosis (Jenkins et al., 2017). Therefore, the effect of treatment of NMTi in this model was investigated. Mice were intratracheally inoculated with Bleomycin at 0.75 U/kg of body weight in PBS (or with PBS only as a control) on day 0. Mice were treated daily on days 14 to 16 and 21 to 23 with Compound 3 (25 mg/kg of body weight, intraperitoneal, or vehicle. Mice were then sacrificed at day 28 for further analysis (FIG. 27).

The results indicate that treatment with NMTi reduces the accumulation of hydroxyproline in the lungs of mice (FIG.

Figure 28A:
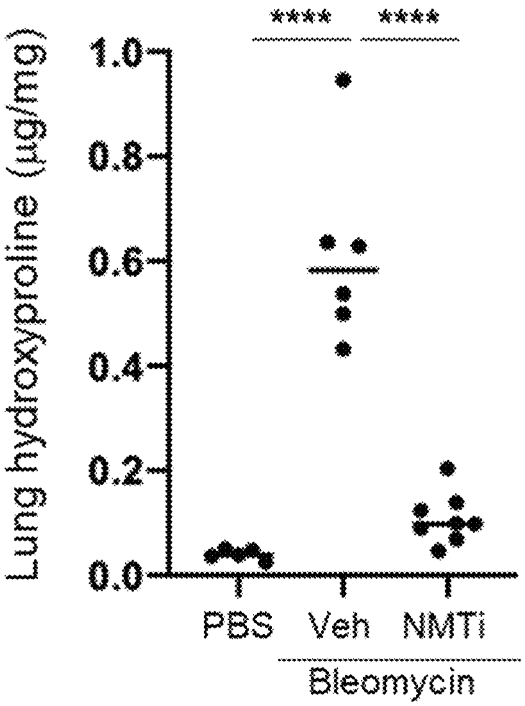
FIG. 28A: Illustrates that treatment with a NMT inhibitor results in reduced accumulation of hydroxyproline in the lung.
Figure 28B:
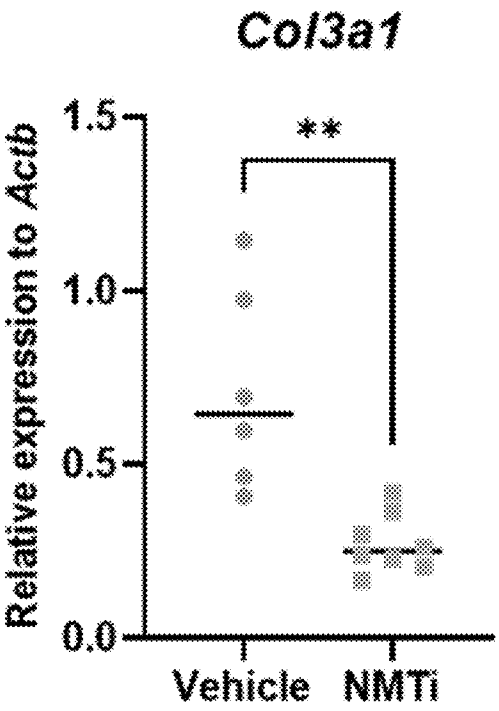
FIGS. 28B-I: Illustrate that treatment with a NMT inhibitor results in reduced lung expression of collagen, pro-fibrotic factors, matrix metalloproteinases, CXCL5 and α-SMA.
Figure 28C:
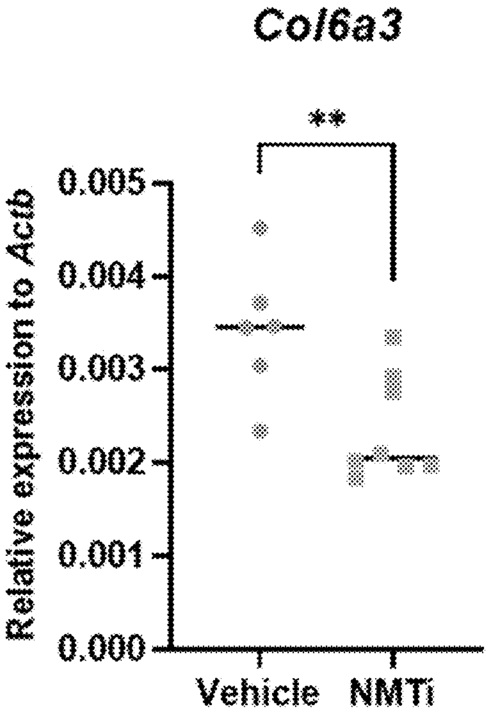
Figure 28D:
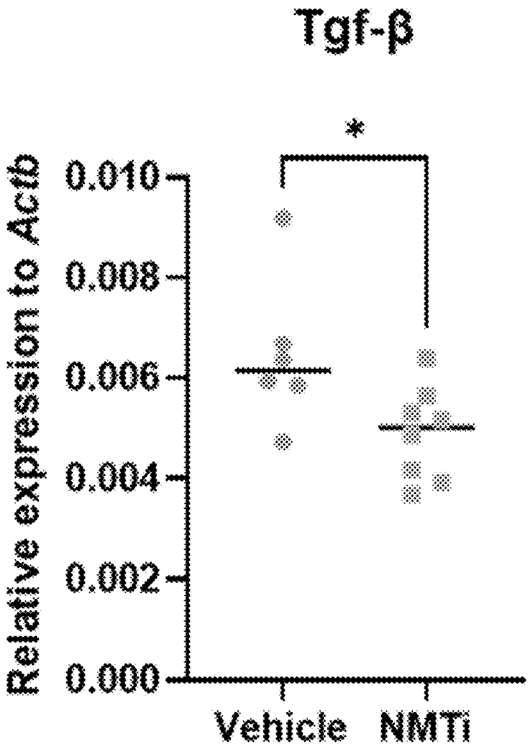
Figure 28E:
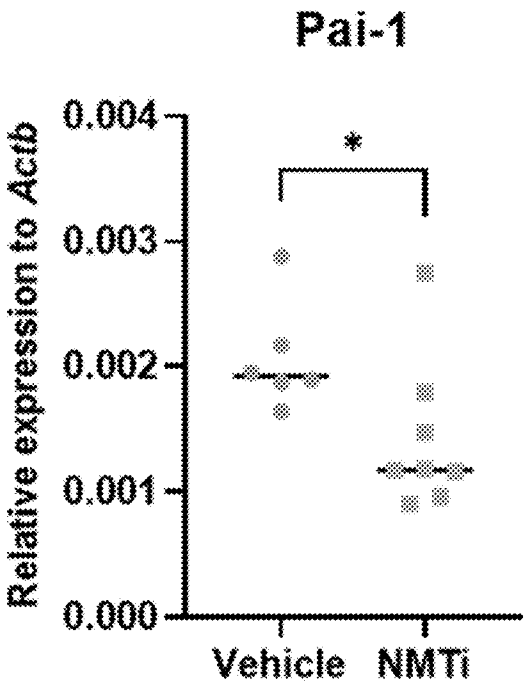
Figure 28F:
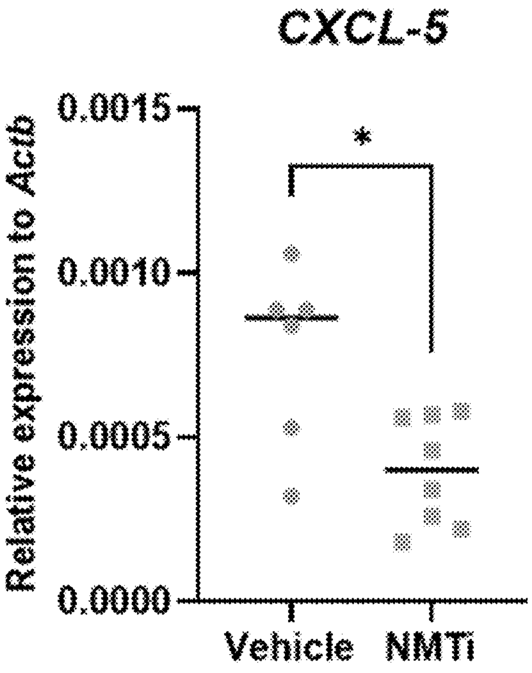
Figure 28G:
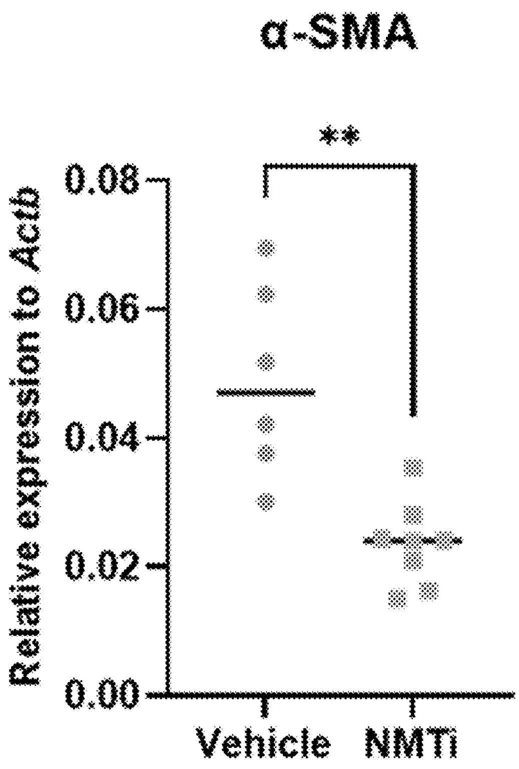
Figure 28H:
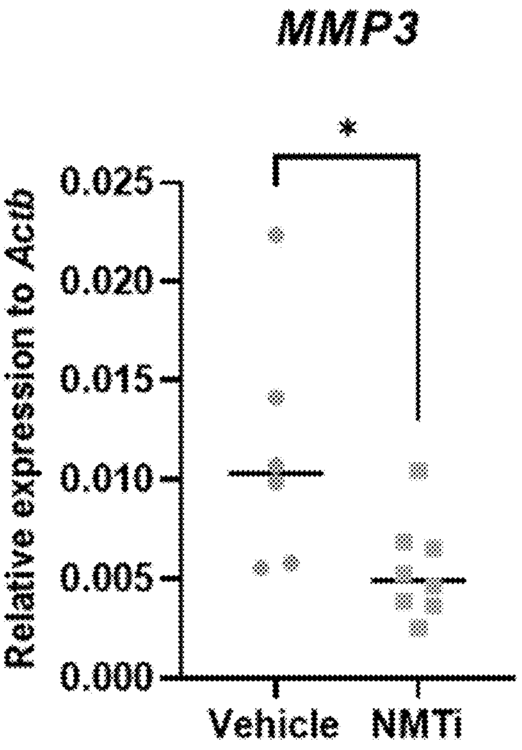
Figure 28I:
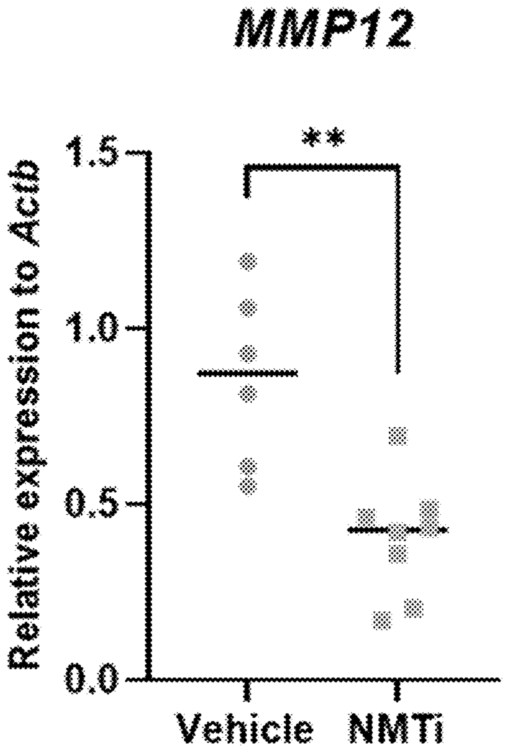

28A). The expression of collagen genes (Col3a1 and Col6a3; FIGS. 28C-C), pro-fibrotic factors (Tgf-b and Pai-1; FIGS. 28D-E), the inflammatory cytokine CXCL-5 (FIG. 28F), α-SMA (FIG. 28G), and markers of activated fibroblasts and matrix metalloproteinases (MMP3 and MMP12; FIGS. 28H-1) were also reduced in the lungs of mice treated with a NMTi. These results indicate that NMTi may be useful in the treatment of fibrosis such as pulmonary fibrosis.

Conclusion:

In summary, the above Biological Examples indicate that treatment with multiple NMT inhibitors results in the selective killing of senescent cells. NMT inhibitors are able to kill different types of cells undergoing senescence (either normal or cancerous) and are able to kill senescent cells irrespective of how the cells were induced to go into senescence. The results also indicate that NMT inhibitors are efficacious in killing senescent cells in vivo. The results also indicate that NMT inhibitors normalise the levels of different markers of disease (e.g. liver or pancreatic damage) in blood. The results also suggest that senescent cells are more sensitive to Golgi dispersal than normal cells when treated with NMT inhibitors. Therefore, processing and secretion of proteins is disrupted on senescent cells what activates the unfolded protein response (UPR). Selective induction of the UPR by NMT inhibitors in senescent cells is responsible for their senolytic properties. The results also indicate that NMT inhibitors reduce the levels of senescent cells in vivo. The results also indicate that NMT inhibitors reduce the levels of markers of liver damage in vivo, and of liver fibrosis. The results also indicate that NMT inhibitors reduce the levels of markers of pulmonary fibrosis. The results also indicate that NMT inhibitors reduce the levels of steatosis markers (accumulation of lipid droplets) in liver. The results also indicate that co-operative treatment with a chemotherapeutic agent and a NMT inhibitor reduces tumour growth in vivo. The results also indicate that the NMT inhibitors of the invention demonstrate senolytic potential in vivo. Therefore, the NMT inhibitors are expected to be useful medicaments for use in the treatment of senescence-associated diseases and disorders.

All publications, including but not limited to patents and patent applications, cited in this specification are herein incorporated by reference as if each individual publication were specifically and individually indicated to be incorporated by reference herein as though fully set forth.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims which follow.

REFERENCES

Baker, D. J., B. G. Childs, M. Durik, M. E. Wijers, C. J. Sieben, J. Zhong, R. A. Saltness, K. B. Jeganathan, G. C. Verzosa, A. Pezeshki, K. Khazaie, J. D. Miller and J. M. van Deursen (2016). "Naturally occurring p16(Ink4a)-positive cells shorten healthy lifespan." Nature 530 (7589): 184-189.

Baker, D. J., T. Wijshake, T. Tchkonia, N. K. LeBrasseur, B. G. Childs, B. van de Sluis, J. L. Kirkland and J. M. van Deursen (2011). "Clearance of p16Ink4a-positive senescent cells delays ageing-associated disorders." Nature 479(7372): 232-236.

Collado, M., J. Gil, A. Efeyan, C. Guerra, A. J. Schuhmacher, M. Barradas, A. Benguria, A. Zaballos, J. M. Flores, M. Barbacid, D. Beach and M. Serrano (2005). "Tumour biology: senescence in premalignant tumours." Nature 436(7051): 642.

Demaria, M., N. Ohtani, S. A. Youssef, F. Rodier, W. Toussaint, J. R. Mitchell, R. M. Laberge, J. Vijg, H. Van Steeg, M. E. Dolle, J. H. Hoeijmakers, A. de Bruin, E. Hara and J. Campisi (2014). "An essential role for senescent cells in optimal wound healing through secretion of PDGF-AA." Dev Cell 31(6): 722-733.

Fuhrmann-Stroissnigg, H., Y. Y. Ling, J. Zhao, S. J. McGowan, Y. Zhu, R. W. Brooks, D. Grassi, S. Q. Gregg, J. L. Stripay, A. Dorronsoro, L. Corbo, P. Tang, C. Bukata, N. Ring, M. Giacca, X. Li, T. Tchkonia, J. L. Kirkland, L. J. Niedernhofer and P. D. Robbins (2017). "Identification of HSP90 inhibitors as a novel class of senolytics." Nat Commun 8(1): 422.

Gorgoulis, V., P. D. Adams, A. Alimonti, D. C. Bennett, O. Bischof, C. Bishop, J. Campisi, M. Collado, K. Evangelou, G. Ferbeyre, J. Gil, E. Hara, V. Krizhanovsky, D. Jurk, A. B. Maier, M. Narita, L. Niedernhofer, J. F. Passos, P. D. Robbins, C. A. Schmitt, J. Sedivy, K. Vougas, T. von Zglinicki, D. Zhou, M. Serrano and M. Demaria (2019). "Cellular Senescence: Defining a Path Forward." Cell 179(4): 813-827.

Guerrero, A., R. Guiho, N. Herranz, A. Uren, D. J. Withers, J. P. Martinez-Barbera, L. F. Tietze and J. Gil (2020). "Galactose-modified duocarmycin prodrugs as senolytics." Aging Cell 19(4): e13133.

Guerrero, A., N. Herranz, B. Sun, V. Wagner, S. Gallage, R. Guiho, K. Wolter, J. Pombo, E. E. Irvine, A. J. Innes, J. Birch, J. Glegola, S. Manshaei, D. Heide, G. Dharmalingam, J. Harbig, A. Olona, J. Behmoaras, D. Dauch, A. G. Uren, L. Zender, S. Vernia, J. P. Martinez-Barbera, M. Heikenwalder, D. J. Withers and J. Gil (2019). "Cardiac glycosides are broad-spectrum senolytics." Nat Metab 1(11): 1074-1088.

Herranz, N. and J. Gil (2018). "Mechanisms and functions of cellular senescence." J Clin Invest 128(4): 1238-1246.

Krishnamurthy, J., C. Torrice, M. R. Ramsey, G. I. Kovalev, K. AI-Regaiey, L. Su and N. E. Sharpless (2004). "Ink4a/Arf expression is a biomarker of aging." J Clin Invest 114(9): 1299-1307.

Krizhanovsky, V., M. Yon, R. A. Dickins, S. Hearn, J. Simon, C. Miething, H. Yee, L. Zender and S. W. Lowe (2008). "Senescence of activated stellate cells limits liver fibrosis." Cell 134(4): 657-667.

Munoz-Espin, D. and M. Serrano (2014). "Cellular senescence: from physiology to pathology." Nat Rev Mol Cell Biol 15(7): 482-496.

Ovadya, Y. and V. Krizhanovsky (2018). "Strategies targeting cellular senescence." J Clin Invest 128(4): 1247-1254.

Sieben, C. J., I. Sturmlechner, B. van de Sluis and J. M. van Deursen (2018). "Two-Step Senescence-Focused Cancer Therapies." Trends Cell Biol 28(9): 723-737.

Wagner, V. and J. Gil (2020). "Senescence as a therapeutically relevant response to CDK4/6 inhibitors." Oncogene.

Wang, L., R. Leite de Oliveira, C. Wang, J. M. Fernandes Neto, S. Mainardi, B. Evers, C. Lieftink, B. Morris, F. Jochems, L. Willemsen, R. L. Beijersbergen and R. Bernards (2017). "High-Throughput Functional Genetic and Compound Screens Identify Targets for Senescence Induction in Cancer." Cell Rep 21(3): 773-783.

Wilson, W. H., O. A. O'Connor, M. S. Czuczman, A. S. LaCasce, J. F. Gerecitano, J. P. Leonard, A. Tulpule, K. Dunleavy, H. Xiong, Y. L. Chiu, Y. Cui, T. Busman, S. W. Elmore, S. H. Rosenberg, A. P. Krivoshik, S. H. Enschede and R. A. Humerickhouse (2010). "Navitoclax, a targeted high-affinity inhibitor of BCL-2, in lymphoid malignancies: a phase 1 dose-escalation study of safety, pharmacokinetics, pharmacodynamics, and antitumour activity." Lancet Oncol 11(12): 1149-1159.

Barnes, P. J., Baker, J., and Donnelly, L. E. (2019). Cellular Senescence as a Mechanism and Target in Chronic Lung Diseases. Am J Respir Crit Care Med 200, 556-564. Schafer, M. J., White, T. A., Iijima, K., Haak, A. J., Ligresti, G., Atkinson, E. J., Oberg, A. L., Birch, J., Salmonowicz, H., Zhu, Y., et al. (2017). Cellular senescence mediates fibrotic pulmonary disease. Nat Commun 8, 14532.

Zhu, Y., Tchkonia, T., Pirtskhalava, T., Gower, A. C., Ding, H., Giorgadze, N., Palmer, A. K., Ikeno, Y., Hubbard, G. B., Lenburg, M., et al. (2015). The Achilles' heel of senescent cells: from transcriptome to senolytic drugs. Aging Cell 14, 644-658.

Katsuumi G, Shimizu I, Yoshida Y, Minamino T. Vascular Senescence in Cardiovascular and Metabolic Diseases. Front Cardiovasc Med. 2018 Mar. 5; 5:18. doi: 10.3389/fcvm.2018.00018. Gevaert A B, Shakeri H, Leloup A J, Van Hove C E, De Meyer G R Y, Vrints C J, Lemmens K, Van Craenenbroeck E M. Endothelial Senescence Contributes to Heart Failure With Preserved Ejection Fraction in an Aging Mouse Model. Circ Heart Fail. 2017 June; 10(6):e003806. doi: 10.1161/CIRCHEARTFAILURE.116.003806.

Wang J, Uryga A K, Reinhold J, Figg N, Baker L, Finigan A, Gray K, Kumar S, Clarke M, Bennett M. Vascular Smooth Muscle Cell Senescence Promotes Atherosclerosis and Features of Plaque Vulnerability. Circulation. 2015 Nov. 17; 132(20):1909-19. doi: 10.1161/CIRCULATIONAHA.115.016457.

Childs B G, Baker D J, Wijshake T, Conover C A, Campisi J, van Deursen J M. Senescent intimal foam cells are deleterious at all stages of atherosclerosis. Science. 2016 Oct. 28; 354(6311):472-477. doi: 10.1126/science.aaf6659. Epub 2016 Oct. 27.

Walaszczyk A, Dookun E, Redgrave R, Tual-Chalot S, Victorelli S, Spyridopoulos I, Owens A, Arthur H M, Passos J F, Richardson G D. Pharmacological clearance of senescent cells improves survival and recovery in aged mice following acute myocardial infarction. Aging Cell. 2019 June; 18(3):e12945.

Baker D J, Petersen R C. Cellular senescence in brain aging and neurodegenerative diseases: evidence and perspectives. J Clin Invest. 2018 Apr. 2; 128(4):1208-1216. doi: 10.1172/JC195145. Epub 2018 Feb. 19.

Chinta S J, Woods G, Demaria M, Rane A, Zou Y, McQuade A, Rajagopalan S, Limbad C, Madden D T, Campisi J, Andersen J K. Cellular Senescence Is Induced by the Environmental Neurotoxin Paraquat and Contributes to Neuropathology Linked to Parkinson's Disease. Cell Rep. 2018 Jan. 23; 22(4):930-940. doi: 10.1016/j.celrep.2017.12.092. Epub 2018 Jan. 28.

Zhang P, Kishimoto Y, Grammatikakis I, Gottimukkala K, Cutler R G, Zhang S, Abdelmohsen K, Bohr V A, Misra Sen J, Gorospe M, Mattson M P. Senolytic therapy alleviates Aβ-associated oligodendrocyte progenitor cell senescence and cognitive deficits in an Alzheimer's disease model. Nat Neurosci. 2019 May; 22(5):719-728. doi: 10.1038/s41593-019-0372-9. Epub 2019 Apr. 1.

Ogrodnik M, Zhu Y, Langhi L G P, Tchkonia T, Kruger P, Fielder E, Victorelli S, Ruswhandi R A, Giorgadze N, Pirtskhalava T, Podgorni O, Enikolopov G, Johnson K O, Xu M, Inman C, Palmer A K, Schafer M, Weigl M, Ikeno Y, Burns T C, Passos J F, von Zglinicki T, Kirkland J L, Jurk D. Obesity-Induced Cellular Senescence Drives Anxiety and Impairs Neurogenesis. Cell Metab. 2019 May 7; 29(5):1061-1077.e8. doi: 10.1016/j.cmet.2018.12.008. Epub 2019 Jan. 3. Erratum in: Cell Metab. 2019 May 7; 29(5):1233.

Pradat P F, Barani A, Wanschitz J, Dubourg O, Lombbs A, Bigot A, Mouly V, Bruneteau G, Salachas F, Lenglet T, Meininger V, Butler-Browne G. Abnormalities of satellite cells function in amyotrophic lateral sclerosis. Amyotroph Lateral Scler. 2011 July; 12(4):264-71. doi: 10.3109/17482968.2011.566618. Epub 2011 Apr. 8.

Sreekumar P G, Hinton D R, Kannan R. The Emerging Role of Senescence in Ocular Disease. Oxid Med Cell Longev. 2020 Mar. 9; 2020:2583601. doi: 10.1155/2020/2583601.

Binet F, Cagnone G, Crespo-Garcia S, Hata M, Neault M, Dejda A, Wilson A M, Buscarlet M, Mawambo G T, Howard J P, Diaz-Marin R, Parinot C, Guber V, Pilon F, Juneau R, Laflamme R, Sawchyn C, Boulay K, Leclerc S, Abu-Thuraia A, Côté J F, Andelfinger G, Rezende F A, Sennlaub F, Joyal J S, Mallette F A, Sapieha P. Neutrophil extracellular traps target senescent vasculature for tissue remodeling in retinopathy. Science. 2020 Aug. 21; 369 (6506):eaay5356. doi: 10.1 126/science.aay5356.

Gao L, Slack M, Barnas J L, McDavid A, Anolik J, Looney R J. Cell Senescence in Lupus. Curr Rheumatol Rep. 2019 Jan. 14; 21(2):1. doi: 10.1007/s11926-019-0800-6. Erratum in: Curr Rheumatol Rep. 2019 May 23; 21(7):32. Barnas, Jennifer L [added].

Gu Z, Cao X, Jiang J, Li L, Da Z, Liu H, Cheng C. Upregulation of p16INK4A promotes cellular senescence of bone marrow-derived mesenchymal stem cells from systemic lupus erythematosus patients. Cell Signal. 2012 December; 24(12):2307-14. doi:10.1016/j.cellsig.2012.07.012. Epub 2012 Jul. 20.

Bellei B, Picardo M. Premature cell senescence in human skin: Dual face in chronic acquired pigmentary disorders. Ageing Res Rev. 2020 January; 57:100981. doi: 10.1016/j.arr.2019.100981. Epub 2019 Nov. 14.

Michaloglou C, Vredeveld L C, Soengas M S, Denoyelle C, Kuilman T, van der Horst C M, Majoor D M, Shay J W, Mooi W J, Peeper D S. BRAFE600-associated senescence-like cell cycle arrest of human naevi. Nature. 2005 Aug. 4; 436(7051):720-4. doi: 10.1038/nature03890.

Ogrodnik M, Miwa S, Tchkonia T, Tiniakos D, Wilson C L, Lahat A, Day C P, Burt A, Palmer A, Anstee Q M, Grellscheid S N, Hoeijmakers J H J, Barnhoorn S, Mann D A, Bird T G, Vermeij W P, Kirkland J L, Passos J F, von Zglinicki T, Jurk D. Cellular senescence drives age-dependent hepatic steatosis. Nat Commun. 2017 Jun. 13; 8:15691. doi: 10.1038/ncomms15691.

Ogrodnik M, Jurk D. Senescence explains age- and obesity-related liver steatosis. Cell Stress. 2017 Sep. 19; 1(1):70-72. doi: 10.15698/cst2017.10.108.

Burd C E, Sorrentino J A, Clark K S, Darr D B, Krishnamurthy J, Deal A M, Bardeesy N, Castrillon D H, Beach D H, Sharpless N E. Monitoring tumorigenesis and senescence in vivo with a p16(INK4a)-luciferase model. Cell. 2013 Jan. 17; 152(1-2):340-51.

Mehr R, Melamed D. Reversing B cell aging. Aging (Albany NY). 2011 April; 3(4):438-43. doi: 10.18632/aging.100313.

Frasca D. Senescent B cells in aging and age-related diseases: Their role in the regulation of antibody responses. Exp Gerontol. 2018 Jul. 1; 107:55-58. doi: 10.1016/j.exger.2017.07.002. Epub2017 Jul. 4.

Ma S., Wang C., Mao X., Hao Y., B Cell Dysfunction Associated With Aging and Autoimmune Diseases, 10, 2019, 318.

Thompson P J, Shah A, Ntranos V, Van Gool F, Atkinson M, Bhushan A. Targeted Elimination of Senescent Beta Cells Prevents Type 1 Diabetes. Cell Metab. 2019 May 7; 29(5):1045-1060.e10.

Yang C, Xue J, An N, Huang X J, Wu Z H, Ye L, Li Z H, Wang S J, Pan Q J, Liang D, Liu H F. Accelerated Glomerular Cell Senescence in Experimental Lupus Nephritis. Med Sci Monit. 2018 Sep. 28; 24:6882-6891.

Goncalves V, Brannigan J A, Thinon E, Olaleye T O, Serwa R, Lanzarone S, Wilkinson A J, Tate E W, Leatherbarrow R J. A fluorescence-based assay for N-myristoyltransferase activity. Anal Biochem. 2012 Feb. 1; 421(1):342-4.

Goncalves V, Brannigan J A, Whalley D, Ansell K H, Saxty B, Holder A A, Wilkinson A J, Tate E W, Leatherbarrow R J. Discovery of *Plasmodium vivax* N-myristoyltransferase inhibitors: screening, synthesis, and structural characterization of their binding mode. J Med Chem. 2012 Apr. 12; 55(7):3578-82.

Jenkins R G, Moore B B, Chambers R C, Eickelberg O, Konigshoff M, Kolb M, Laurent G J, Nanthakumar C B, Olman M A, Pardo A, Selman M, Sheppard D, Sime P J, Tager A M, Tatler A L, Thannickal V J, White E S; ATS Assembly on Respiratory Cell and Molecular Biology. An Official American Thoracic Society Workshop Report: Use of Animal Models for the Preclinical Assessment of Potential Therapies for Pulmonary Fibrosis. Am J Respir Cell Mol Biol. 2017 May; 56(5):667-679.

The invention claimed is:

1. A method of treatment of a senescence-associated disease or disorder by administering to a subject in need thereof, a therapeutically effective amount of a NMT inhibitor, wherein the senescence-associated disease or disorder is a liver-related disease or disorder, wherein the senescence-associated disease or disorder is not cancer.

2. The method according to claim 1, wherein the liver-related disease or disorder is selected from non-alcoholic steatohepatitis, liver fibrosis, non-alcoholic fatty liver disease, hepatic steatosis, and liver cirrhosis.

3. The method according to claim 2, wherein the liver-related disease or disorder is selected from non-alcoholic steatohepatitis, liver fibrosis, non-alcoholic fatty liver disease, and hepatic steatosis.

4. The method according to claim 1, wherein the NMT inhibitor is a compound of formula (I):

(I)

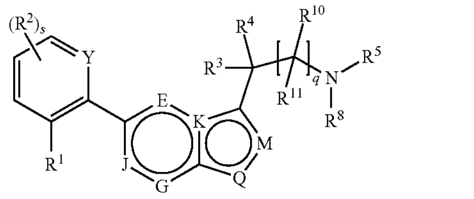

wherein:

Y is selected from the group consisting of —CH—, —$C(R^2)$— and —N—;

$R^1$ is a group of formula —X-L-A;

X represents —O—;

L represents —$(CH_2)_m$—;

m is 1, 2 or 3;

A is a 6-10-membered aromatic carbocycle or a 5-10-membered aromatic heterocycle, said aromatic carbocycle or heterocycle being optionally substituted with 1, 2, or 3 substituents each independently selected from the group consisting of —F, —Cl, —Br, —$OCH_3$, —$OCF_3$, —CN, —$C_{1-6}$alkyl optionally substituted by up to 3 halogen, hydroxyl, or —$OC_{1-4}$alkyl groups, —$S(O)C_{1-4}$alkyl, —$S(O)_2C_{1-4}$alkyl, —$C(O)N(R^9)_2$, —$C(O)N(R^{13})$ $C_{1-4}$alkyl$OC_{1-4}$alkyl, —$C(O)N(C_{1-4}$alkyl$OC_{1-4}$alkyl$)_2$, —$CH_2C(O)N(R^9)_2$, —$CH_2C(O)N(R^{13})C_{1-4}$alkyl $OC_{1-4}$alkyl, —$CH_2C(O)N(C_{1-4}$alkyl$OC_{1-4}$alkyl$)_2$, —$S(O)_2NHC_{1-4}$alkyl, —$S(O)_2N(C_{1-4}$alkyl$)_2$, —$NHC_{1-4}$alkyl, —$N(C_{1-4}$alkyl$)_2$, —$NHC(O)C_{1-4}$alkyl, —$NHC(O)CF_3$, —$NHS(O)_2C_{1-4}$alkyl, $CH_2N(R^{13})_2$, $CH_2N(R^{13})$ $C(O)C_{1-4}$alkyl, $CH_2N(R^{13})$ $S(O)_2C_{1-4}$alkyl, —$CH_2S(O)_2C_{1-4}$alkyl, and $CO_2H$;

s is 0, 1, 2, or 3;

each $R^2$ is independently selected from the group consisting of —F, —Cl, —Br, —$OCH_3$, —$OCF_3$, —CN, —$C_{1-4}$alkyl optionally substituted by up to 3 halogen or hydroxyl groups, —$S(O)C_{1-4}$alkyl, —$S(O)_2C_{1-4}$alkyl, —$S(O)_2NHC_{1-4}$alkyl, —$S(O)_2N(C_{1-4}$alkyl$)_2$, —$NHC_{1-4}$alkyl, —$N(C_{1-4}$alkyl$)_2$, —$NHC(O)C_{1-4}$alkyl, —$NHC(O)CF_3$, and —$NHS(O)_2C_{1-4}$alkyl;

q is 0 or 1;

$R^3$ is hydrogen or methyl; $R^4$ is hydrogen or methyl;

$R^5$ is hydrogen or $C_{1-6}$alkyl optionally substituted by up to 3 —F, —Cl, —Br, —OH, —$OCH_3$, —$OCF_3$ or —CN groups; $R^6$ is hydrogen or $C_{1-6}$alkyl optionally substituted by up to 3 —F, —Cl, —Br, —OH, —$OCH_3$, —$OCF_3$ or —CN groups; or the $R^5$ and $R^6$ groups and the N they are bonded to form a 4 to 7 membered non-aromatic heterocycle, the heterocycle optionally comprising 1 or 2 further heteroatoms selected from N, O and S, optionally substituted by up to 3 —F, —Cl, —Br, —OH, —$OCH_3$, —$OCF_3$ or —CN groups;

when present $R^{10}$ is hydrogen or methyl;

when present $R^{11}$ is hydrogen or methyl;

or the $R^3$ group and the $R^5$ group and the intervening atoms form a 3 to 7 membered non-aromatic heterocycle composed of the intervening atoms and bond, or the intervening atoms and —$(CHR^a)_r$—; or the $R^{10}$ group and the $R^5$ group and the intervening atoms form a 3 to 7 membered non-aromatic heterocycle composed of the intervening atoms and —$(CHR^a)_r$—;

r is 1, 2, 3, 4 or 5; $R^a$ is hydrogen or methyl;

each $R^7$ is independently selected from the group consisting of hydrogen, halogen, $C_1$-4alkoxy, and $C_{1-4}$alkyl optionally substituted with 1, 2 or 3 halogens; and $R^8$ is selected from the group selected from hydrogen and $C_{1-4}$alkyl;

each $R^9$ is independently selected from the group consisting of hydrogen and $C_{1-4}$alkyl, or two $R^9$ groups and the N they are bonded to form a 4 to 7 membered non-aromatic heterocycle, the heterocycle optionally comprising 1 or 2 further heteroatoms selected from N, O and S;

each $R^{13}$ is independently selected from the group consisting of hydrogen and $C_{1-4}$alkyl; and wherein i) E, J and G are each $C(R^7)$, K is carbon, Q is $N(R^8)$, and M is nitrogen;

ii) E, J and G are each $C(R^7)$, and K, Q and M are each nitrogen; or iii) E, J, G and M are each $C(R^7)$, and K and Q are each nitrogen;

or a pharmaceutically acceptable salt and/or solvate thereof.

5. The method according to claim 1, wherein the NMT inhibitor is a compound of formula (II):

(II)

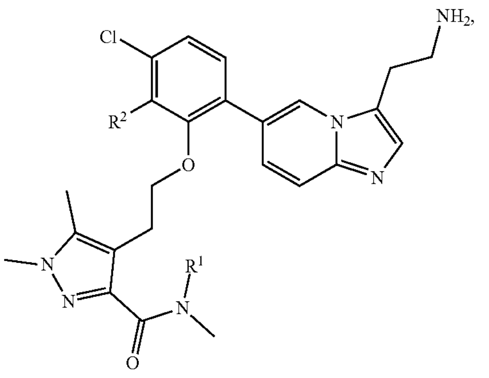

wherein:

$R^1$ is H or —$CH_3$; and $R^2$ is H or F;

or a pharmaceutically acceptable salt and/or solvate thereof.

6. The method according to claim 5, wherein the NMT inhibitor is 4-(2-{2-[3-(2-aminoethyl) imidazo[1,2-a]pyridin-6-yl]-5-chlorophenoxy}ethyl)-N,N,1,5-tetramethyl-1H-pyrazole-3-carboxamide:

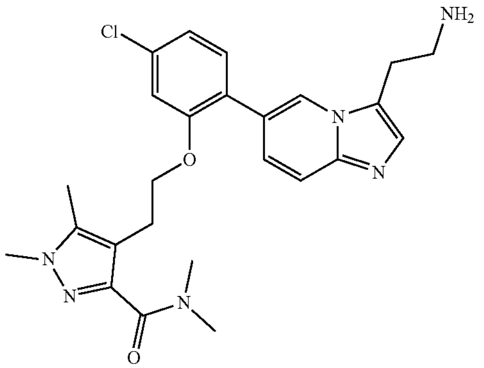

or a pharmaceutically acceptable salt and/or solvate thereof.

7. A method of treatment of a senescence-associated disease or disorder by administering to a subject in need thereof, a therapeutically effective amount of a pharmaceutical composition comprising a NMT inhibitor or a pharmaceutically acceptable salt and/or solvate thereof, wherein the senescence-associated disease or disorder is a liver-related disease or disorder, wherein the senescence-associated disease or disorder is not cancer.

8. The method according to claim 7, wherein the pharmaceutical composition comprises one or more therapeutic agents and/or one or more pharmaceutically acceptable excipients.

9. The method according to claim 7, wherein the liver-related disease or disorder is selected from non-alcoholic steatohepatitis, liver fibrosis, non-alcoholic fatty liver disease, hepatic steatosis, and liver cirrhosis.

10. The method according to claim 9, wherein the liver-related disease or disorder is selected from non-alcoholic steatohepatitis, liver fibrosis, non-alcoholic fatty liver disease, and hepatic steatosis.

11. The method according to claim 7, wherein the NMT inhibitor is a compound of formula (I):

(I)

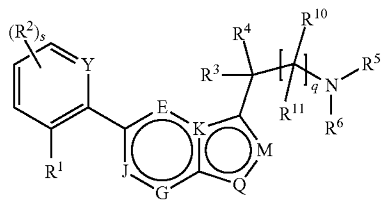

wherein:

Y is selected from the group consisting of —CH—, —C($R^2$)— and —N—;

$R^1$ is a group of formula —X-L-A;

X represents —O—;

L represents —$(CH_2)_m$—;

m is 1, 2 or 3;

A is a 6-10-membered aromatic carbocycle or a 5-10-membered aromatic heterocycle, said aromatic carbocycle or heterocycle being optionally substituted with 1, 2, or 3 substituents each independently selected from the group consisting of —F, —Cl, —Br, —$OCH_3$, —$OCF_3$, —CN, —$C_{1-6}$alkyl optionally substituted by up to 3 halogen, hydroxyl, or —$OC_{1-4}$alkyl groups, —S(O)$C_{1-4}$alkyl, —$S(O)_2C_{1-4}$alkyl, —C(O)N$(R^9)_2$, —C(O)N($R^{13}$) $C_{1-4}$alkyl$OC_{1-4}$alkyl, —C(O)N($C_{1-4}$alkyl$OC_{1-4}$alkyl$)_2$, —$CH_2$C(O)N$(R^9)_2$, —$CH_2$C(O)N($R^{13}$)$C_{1-4}$alkyl $OC_{1-4}$alkyl, —$CH_2$C(O)N($C_{1-4}$alkyl$OC_{1-4}$alkyl$)_2$, —$S(O)_2NHC_{1-4}$alkyl, —$S(O)_2N(C_{1-4}$alkyl$)_2$, —$NHC_{1-4}$alkyl, —N($C_{1-4}$alkyl$)_2$, —NHC(O)$C_{1-4}$alkyl, —NHC(O)$CF_3$, —$NHS(O)_2C_{1-4}$alkyl, $CH_2N(R^{13})_2$, $CH_2N(R^{13})$ C(O)$C_{1-4}$alkyl, $CH_2N(R^{13})$ $S(O)_2C_{1-4}$alkyl, —$CH_2S(O)_2C_{1-4}$alkyl, and $CO_2H$;

s is 0, 1, 2, or 3;

each $R^2$ is independently selected from the group consisting of —F, —Cl, —Br, —$OCH_3$, —$OCF_3$, —CN, —$C_{1-4}$alkyl optionally substituted by up to 3 halogen or hydroxyl groups, —S(O)$C_{1-4}$alkyl, —$S(O)_2C_{1-4}$alkyl, —$S(O)_2NHC_{1-4}$alkyl, —$S(O)_2N(C_{1-4}$alkyl$)_2$, —$NHC_{1-4}$alkyl, —N($C_{1-4}$alkyl$)_2$, —NHC(O)$C_{1-4}$alkyl, —NHC(O)$CF_3$, and —$NHS(O)_2C_{1-4}$alkyl;

q is 0 or 1;

$R^3$ is hydrogen or methyl; $R^4$ is hydrogen or methyl;

$R^5$ is hydrogen or $C_{1-6}$alkyl optionally substituted by up to 3 —F, —Cl, —Br, —OH, —$OCH_3$, —$OCF_3$ or —CN groups; $R^6$ is hydrogen or $C_{1-6}$alkyl optionally substituted by up to 3 —F, —Cl, —Br, —OH, —$OCH_3$, —$OCF_3$ or —CN groups; or the $R^5$ and Re groups and the N they are bonded to form a 4 to 7 membered non-aromatic heterocycle, the heterocycle optionally comprising 1 or 2 further heteroatoms selected from N, O and S, optionally substituted by up to 3 —F, —Cl, —Br, —OH, —$OCH_3$, —$OCF_3$ or —CN groups;

when present $R^{10}$ is hydrogen or methyl;

when present $R^{11}$ is hydrogen or methyl;

or the $R^3$ group and the $R^5$ group and the intervening atoms form a 3 to 7 membered non-aromatic heterocycle composed of the intervening atoms and bond, or the intervening atoms and —$(CHR^a)_r$—; or the $R^{10}$ group and the $R^5$ group and the intervening atoms form a 3 to 7 membered non-aromatic heterocycle composed of the intervening atoms and —$(CHR^a)_r$—;

r is 1, 2, 3, 4 or 5; $R^a$ is hydrogen or methyl;

each $R^7$ is independently selected from the group consisting of hydrogen, halogen, $C_{1-4}$alkoxy, and $C_{1-4}$alkyl optionally substituted with 1, 2 or 3 halogens; and $R^8$ is selected from the group selected from hydrogen and $C_{1-4}$alkyl;

each $R^9$ is independently selected from the group consisting of hydrogen and $C_{1-4}$alkyl, or two $R^9$ groups and the N they are bonded to form a 4 to 7 membered non-aromatic heterocycle, the heterocycle optionally comprising 1 or 2 further heteroatoms selected from N, O and S;

each $R^{13}$ is independently selected from the group consisting of hydrogen and $C_{1-4}$alkyl; and wherein i) E, J and G are each C($R^7$), K is carbon, Q is N($R^8$), and M is nitrogen;

ii) E, J and G are each C($R^7$), and K, Q and M are each nitrogen; or iii) E, J, G and M are each C($R^7$), and K and Q are each nitrogen;

or a pharmaceutically acceptable salt and/or solvate thereof.

12. The method according to claim 7, wherein the NMT inhibitor is a compound of formula (II):

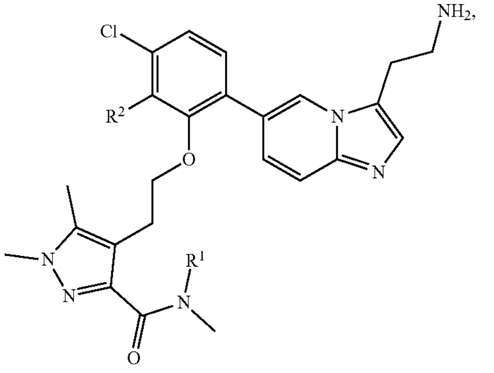
(II)
wherein:
$R^1$ is H or $-CH_3$; and
$R^2$ is H or F;
or a pharmaceutically acceptable salt and/or solvate thereof.
13. The method according to claim 12, wherein the NMT inhibitor is 4-(2-{2-[3-(2-aminoethyl) imidazo[1,2-a]pyridin-6-yl]-5-chlorophenoxy}ethyl)-N,N,1,5-tetramethyl-1H-pyrazole-3-carboxamide:
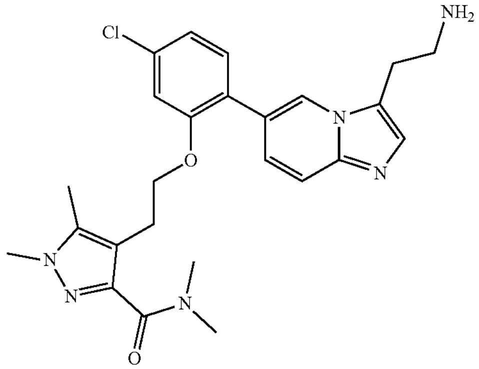 [SMILES: Cc1c(CCOc2cc(Cl)ccc2-c2ccc3ncc(CCN)n3c2)c(C(=O)N(C)C)nn1C]
or a pharmaceutically acceptable salt and/or solvate thereof.
* * * * *

SEQUENCE LISTING

```
<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: qRT-PCR Primer

<400> SEQUENCE: 1

atggagggga atacagccc                                                    19


<210> SEQ ID NO 2
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 2

ttctttgcag ctccttcgtt                                                   20


<210> SEQ ID NO 3
<211> LENGTH: 24
<212> TYPE: DNA
<213> ORGANISM: Artificial Sequence
<220> FEATURE:
<223> OTHER INFORMATION: qRT-PCR primer

<400> SEQUENCE: 3

acagcaaatt cacttacaca gttc                                              24


<210> SEQ ID NO 4
<211> LENGTH: 19
<212> TYPE: DNA
<213> ORGANISM: Artificial Sequence
<220> FEATURE:
<223> OTHER INFORMATION: qRT-PCR primer

<400> SEQUENCE: 4

ctcattgcct tgcgtgttt                                                    19


<210> SEQ ID NO 5
<211> LENGTH: 20
```

<212> TYPE: DNA
<213> ORGANISM: Artificial Sequence
<220> FEATURE:
<223> OTHER INFORMATION: qRT-PCR primer

<400> SEQUENCE: 5
actggaacca cggaagttca 20

<210> SEQ ID NO 6
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 6
gtcacttcca acatcgaggc 20

<210> SEQ ID NO 7
<211> LENGTH: 21
<212> TYPE: DNA
<213> ORGANISM: Artificial Sequence
<220> FEATURE:
<223> OTHER INFORMATION: qRT-PCR primer

<400> SEQUENCE: 7
tgatcgctaa tttggaggtg a 21

<210> SEQ ID NO 8
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 8
tggatccaga cagacctcct 20

<210> SEQ ID NO 9
<211> LENGTH: 19
<212> TYPE: DNA
<213> ORGANISM: Artificial Sequence
<220> FEATURE:
<223> OTHER INFORMATION: qRT-PCR primer

<400> SEQUENCE: 9
tgatgaacga tggacagag 19

<210> SEQ ID NO 10
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 10
ttggctgagt ggtagagtcc 20

<210> SEQ ID NO 11
<211> LENGTH: 21
<212> TYPE: DNA
<213> ORGANISM: Artificial Sequence
<220> FEATURE:
<223> OTHER INFORMATION: qRT-PCR primer

<400> SEQUENCE: 11

-continued cacttcccag gaatcaagcc t 21

<210> SEQ ID NO 12
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 12
tttggtgaca cgacggaaca 20

<210> SEQ ID NO 13
<211> LENGTH: 19
<212> TYPE: DNA
<213> ORGANISM: Artificial Sequence
<220> FEATURE:
<223> OTHER INFORMATION: qRT-PCR primer

<400> SEQUENCE: 13
cggagagccc tggatacca 19

<210> SEQ ID NO 14
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 14
acttccaacc caggtccttc 20

<210> SEQ ID NO 15
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 15
ccaacatctt ggatgctgaa 20

<210> SEQ ID NO 16
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 16
gccagggttg cactaaacat 20

<210> SEQ ID NO 17
<211> LENGTH: 21
<212> TYPE: DNA
<213> ORGANISM: Artificial Sequence
<220> FEATURE:
<223> OTHER INFORMATION: qRT-PCR primer

<400> SEQUENCE: 17
cccaaagcta accgggagaa g 21

<210> SEQ ID NO 18
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 18
ccagaatcca acacgatgcc 20

<210> SEQ ID NO 19
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 19
cacaggacta gaacacctgc 20

<210> SEQ ID NO 20
<211> LENGTH: 19
<212> TYPE: DNA
<213> ORGANISM: Artificial Sequence
<220> FEATURE:
<223> OTHER INFORMATION: qRT-PCR primer

<400> SEQUENCE: 20
gctggtgaaa aggacctct 19

<210> SEQ ID NO 21
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 21
gagaggtgaa caaggtcccg 20

<210> SEQ ID NO 22
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 22
aaacctctct cgcctcttgc 20

<210> SEQ ID NO 23
<211> LENGTH: 19
<212> TYPE: DNA
<213> ORGANISM: Artificial Sequence
<220> FEATURE:
<223> OTHER INFORMATION: qRT-PCR primer

<400> SEQUENCE: 23
ctggcacaaa agggacgag 19

<210> SEQ ID NO 24
<211> LENGTH: 20
<212> TYPE: DNA
<213> ORGANISM: Artificial Sequence
<220> FEATURE:
<223> OTHER INFORMATION: qRT-PCR primer

<400> SEQUENCE: 24
acgtggccga gaatttcacc 20